United States Patent
Chen et al.

(10) Patent No.: US 8,420,655 B2
(45) Date of Patent: Apr. 16, 2013

(54) BENZIMIDAZOLE INHIBITORS OF LEUKOTRIENE PRODUCTION

(75) Inventors: Zhidong Chen, New Milford, CT (US); Ming-Hong Hao, Ridgefield, CT (US); Weimin Liu, Beijing (CN); Ho-Yin Lo, Bethel, CT (US); Pui Leng Loke, Oxfordshire (GB); Chuk Chui Man, Ridgefield, CT (US); Tina Marie Morwick, New Milford, CT (US); Peter Allen Nemoto, Southbury, CT (US); Hidenori Takahashi, LaGrangeville, NY (US); Heather Tye, Oxfordshire (GB); Lifen Wu, New Milford, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/957,766

(22) Filed: Dec. 1, 2010

(65) Prior Publication Data

US 2011/0301161 A1    Dec. 8, 2011

Related U.S. Application Data

(60) Provisional application No. 61/266,562, filed on Dec. 4, 2009.

(51) Int. Cl.
*A61K 31/506* (2006.01)
*C07D 403/14* (2006.01)

(52) U.S. Cl.
USPC ........ 514/256; 544/333; 546/113; 546/273.4; 514/299; 514/338

(58) Field of Classification Search .................. 514/275, 514/256, 299, 338; 544/297, 333; 546/125, 546/113, 273.4
See application file for complete search history.

(56) References Cited

U.S. PATENT DOCUMENTS

| 6,911,444 | B2 | 6/2005 | Lacrampe et al. | |
| 7,138,420 | B2 * | 11/2006 | Bentzien et al. | 514/388 |
| 7,319,108 | B2 | 1/2008 | Schwink et al. | |

FOREIGN PATENT DOCUMENTS

| EP | 0193013 A2 | 9/1986 |
| WO | 9961020 A1 | 12/1999 |
| WO | 2005012288 A1 | 2/2005 |
| WO | 2006044602 A2 | 4/2006 |
| WO | 2007056228 A2 | 5/2007 |
| WO | 2007120574 A2 | 10/2007 |
| WO | 2008030369 A1 | 3/2008 |
| WO | 2008067644 A1 | 6/2008 |
| WO | 2008128335 A1 | 10/2008 |
| WO | 2008156721 A1 | 12/2008 |
| WO | 2009048547 A1 | 4/2009 |
| WO | 2011068821 A1 | 6/2011 |
| WO | 2011143466 A1 | 11/2011 |

OTHER PUBLICATIONS

International Search Report for PCT/US2010/058479 mailed Feb. 25, 2011.
International Search Report for PCT/US20111057786 mailed on Dec. 19, 2011.
International Search Report for PCT/US20111057787 mailed Mar. 21, 2012.
U.S. Appl. No. 13/281,685, filed Oct. 26, 2011. Zhidong Chen.
U.S. Appl. No. 13/281,687, filed Oct. 26, 2011. Stephane De Lombaert.
Werz, Oliver et al. "Pharmacological intervention with 5-lipoxygenase: new insights and novel compounds" Expert Opin. Ther. Patents (2005) 15(5) pp. 505-519.

* cited by examiner

*Primary Examiner* — Charanjit Aulakh
(74) *Attorney, Agent, or Firm* — Michael P. Morris; Usha R. Patel

(57) ABSTRACT

The present invention relates to compounds of formula (I):

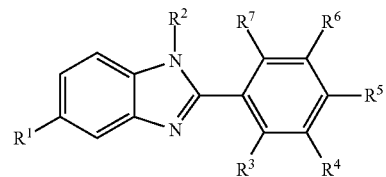

and pharmaceutically acceptable salt thereof, wherein $R^1$-$R^7$ are as defined herein. The invention also relates to pharmaceutical compositions comprising these compounds, methods of using these compounds in the treatment of various diseases and disorders, processes for preparing these compounds and intermediates useful in these processes.

10 Claims, No Drawings

BENZIMIDAZOLE INHIBITORS OF LEUKOTRIENE PRODUCTION

FIELD OF THE INVENTION

This invention relates to benzimidazoles that are useful as inhibitors of five lipoxygenase activating protein (FLAP) and are thus useful for treating a variety of diseases and disorders that are mediated or sustained through the activity of leukotrienes including asthma, allergy, rheumatoid arthritis, multiple sclerosis, inflammatory pain, acute chest syndrome and cardiovascular diseases including atherosclerosis, myocardial infarction and stroke. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Leukotrienes (LTs) and the biosynthetic pathway from arachidonic acid leading to their production have been the targets of drug discovery efforts for over twenty years. LTs are produced by several cell types including neutrophils, mast cells, eosinophils, basophils monocytes and macrophages. The first committed step in the intracellular synthesis of LTs involves oxidation of arachidonic acid by 5-lipoxygenase (5-LO) to LTA4, a process requiring the presence of the 18 kD integral membrane protein 5-lipoxygenase-activating protein (FLAP) (D. K. Miller et al., Nature, 1990, 343, 278-281; R. A. F. Dixon et al., Nature, 1990, 343, 282-284). Subsequent metabolism of $LTA_4$ leads to $LTB_4$, and the cysteinyl LTs- $LTC_4$, $LTD_4$ and $LTE_4$ (B. Samuelsson, Science, 1983, 220, 568-575). The cysteinyl LTs have potent smooth muscle constricting and bronchoconstricting effects and they stimulate mucous secretion and vascular leakage. $LTB_4$ is a potent chemotactic agent for leukocytes, and stimulates adhesion, aggregation and enzyme release.

Much of the early drug discovery effort in the LT area was directed towards the treatment of allergy, asthma and other inflammatory conditions. Research efforts have been directed towards numerous targets in the pathway including antagonists of $LTB_4$ and the cysteinyl leukotrienes $LTC_4$, $LTD_4$ and $LTE_4$, as well as inhibitors of 5-lipoxygenase (5-LO), $LTA_4$ hydrolase and inhibitors of 5-lipoxygenase activating protein (FLAP) (R. W. Friesen and D. Riendeau, Leukotriene Biosynthesis Inhibitors, Ann. Rep. Med. Chem., 2005, 40, 199-214). Years of effort in the above areas have yielded a few marketed products for the treatment of asthma including a 5-LO inhibitor, zileuton, and LT antagonists, montelukast, pranlukast and zafirlukast.

More recent work has implicated LTs in cardiovascular disease, including myocardial infarction, stroke and atherosclerosis (G. Riccioni et al., J. Leukoc. Biol., 2008, 1374-1378). FLAP and 5-LO were among the components of the 5-LO and LT cascade found in atherosclerotic lesions, suggesting their involvement in atherogenesis (R. Spanbroek et al., Proc. Natl. Acad. Sci. U.S.A., 2003, 100, 1238-1243). Pharmacological inhibition of FLAP has been reported to decrease atherosclerotic lesion size in animal models. In one study, oral dosing of the FLAP inhibitor MK-886 to apoE/LDL-R double knockout mice fed a high-fat diet from 2 months of age to 6 months led to a 56% decrease in plaque coverage in the aorta and a 43% decrease in the aortic root (J. Jawien et al., Eur. J. Clin. Invest., 2006, 36, 141-146). This plaque effect was coupled with a decrease in plaque-macrophage content and a concomitant increase in collagen and smooth muscle content which suggests a conversion to a more stable plaque phenotype. In another study, it was reported that administration of MK-886 via infusion to ApoE$^{-/-}$x CD4dnTβRII mice (apoE KO mice expressing a dominant-negative TGF-beta receptor which effectively removes all TGF-beta from the system) resulted in about a 40% decrease in plaque area in the aortic root (M. Back et al., Circ. Res., 2007, 100, 946-949). The mice were only treated for four weeks after plaque growth was already somewhat mature (12 weeks) thus raising the possibility of therapeutically treating atherosclerosis via this mechanism. In a study examining human atherosclerotic lesions, it was found that the expression of FLAP, 5-LO and $LTA_4$ hydrolase was significantly increased compared to healthy controls (H. Qiu et al., Proc. Natl. Acad. Sci. U.S.A., 103, 21, 8161-8166). The 5-LO inhibitor, VIA-2291 (a.k.a. ABT761), was found to attenuate atherosclerosis in apoE-deficient mice (A. Hansson et al., Circ., 2007, 116, II_209, abstract 1048 and U.S. Pat. No. 7,495,024) and is currently under undergoing clinical trials for the treatment of acute coronary syndrome resulting from atherosclerosis. These and similar studies suggest that inhibition of the LT pathway, for example by inhibition of FLAP, would be useful for the treatment of atherosclerosis (for reviews, see M. Back Curr. Athero. Reports, 2008 10, 244-251 and Curr. Pharm. Des., 2009, 15, 3116-3132).

In addition to the work cited above, many other studies have been directed towards understanding the biological actions of LTs and the role of LTs in disease. These studies have implicated LTs as having a possible role in numerous diseases or conditions (for a review, see M. Peters-Golden and W. R. Henderson, Jr., M.D., N. Engl. J. Med., 2007, 357, 1841-1854). In addition to the specific diseases cited above, LTs have been implicated as having a possible role in numerous allergic, pulmonary, fibrotic, inflammatory and cardiovascular diseases, as well as cancer. Inhibition of FLAP is also reported to be useful for treating renal diseases such as diabetes-induced proteinuria (see for example J. M. Valdivieso et al., Journal of Nephrology, 2003, 16, 85-94 and A Montero et al., Journal of Nephrology, 2003, 16, 682-690).

A number of FLAP inhibitors have been reported in the scientific literature (see for example J. F. Evans et al., Trends in Pharmacological Sciences, 2008, 72-78) and in U.S. patents. Some have been evaluated in clinical trials for asthma, including MK-886, MK-591, and BAY X1005, also known as DG-031. More recently, the FLAP inhibitor AM-103 (J. H. Hutchinson et al., J. Med. Chem. 52, 5803-5815) has been evaluated in clinical trials, based on its anti-inflammatory properties (D. S. Lorrain et al., J. Pharm. Exp. Ther., 2009, DOI: 10.1124/jpet.109.158089). Subsequently, it was replaced by the back-up compound AM-803 (GSK-2190915) for the treatment of respiratory diseases. DG-031 has also been in clinical trials to evaluate its effect on biomarkers for myocardial infarction risk and showed a dose-dependent suppression of several biomarkers for the disease (H. Hakonarson et al., JAMA, 2005, 293, 2245-2256). MK-591 was shown in a clinical trial to reduce proteinuria in human glomerulonephritis (see for example A. Guash et al., Kidney International, 1999, 56, 291-267).

However, to date, no FLAP inhibitor has been approved as a marketed drug.

BRIEF SUMMARY OF THE INVENTION

The present invention provides novel compounds which inhibit 5-lipoxygenase activating protein (FLAP) and are thus useful for treating a variety of diseases and disorders that are mediated or sustained through the activity of leukotrienes, including allergic, pulmonary, fibrotic, inflammatory and cardiovascular diseases and cancer. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In its broadest embodiment, the present invention relates compounds of formula I:

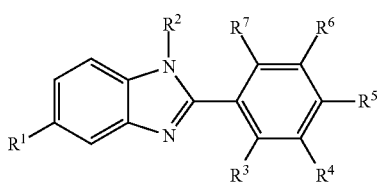

Or pharmaceutically acceptable salts thereof, wherein:
$R^1$ is selected from

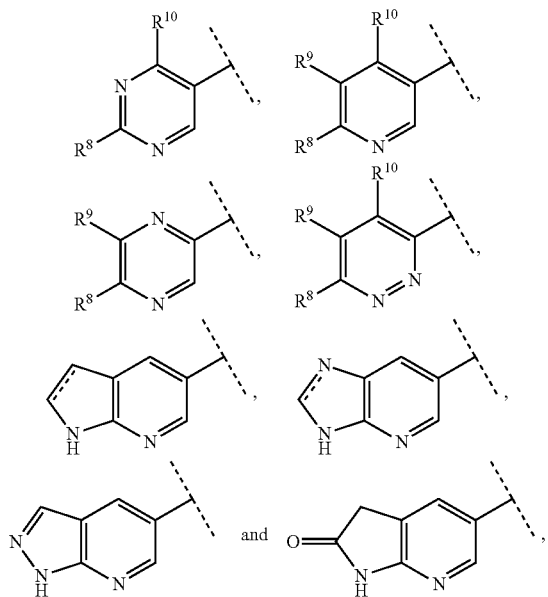

wherein --- indicates a single or double bond;
$R^2$ is —($C_1$-$C_6$)alkyl;
$R^3$, $R^4$, $R^5$, $R^6$ and $R^7$ are each independently selected from
  (a) —H,
  (b) —OH,
  (c) halogen,
  (d) —CN,
  (e) —$CF_3$,
  (f) $C_{1-6}$alkyl optionally substituted with one to three —OH, fluorine, $C_{1-6}$alkoxyl-N($R^{11}$)($R^{12}$), or —C(O)N($R^{11}$)($R^{12}$),
  (g) $C_{1-8}$alkenyl optionally substituted with —$CO_2R^{11}$,
  (h) $C_{1-6}$alkoxy optionally substituted with one to three —OH, fluorine, —$OC_{1-6}$alkyl, —$OC_{3-6}$cycloalkyl, —$CO_2H$, —$CO_2R^{11}$, $C_{3-6}$cycloalkyl, $C_{3-6}$ heterocyclyl, N($R^{11}$)($R^{12}$), or —C(O)N($R^{11}$)($R^{12}$),
  (i) —S(O)$_n$$C_{1-6}$alkyl,
  (j) —$SCF_3$,
  (k) —$CO_2R^{11}$,
  (l) —C(O)N($R^{11}$)($R^{12}$),
  (m) —NH—S(O)$_2$—$C_{1-6}$alkyl,
  (n) —S(O)$_2$N($R^{11}$)($R^{12}$),
  (o) —$OCF_3$,
  (p) —$OCHF_2$,
  (q) a 5-membered heteroaryl group optionally substituted with one to three groups selected from $C_{1-6}$alkyl, $C_{3-6}$cycloalkyl, halogen, —$CF_3$, —OH, —($CH_2$)$_n$$CO_2R^{11}$, —$SCF_3$, —C(O)N($R^{11}$)($R^{12}$), N($R^{11}$)($R^{12}$), —NH—$SO_2Cl_{1-6}$alkyl, $C_{1-6}$alkoxyl, $C_{1-6}$alkyl-O—$C_{1-3}$ alkyl, $C_{1-6}$alkylhydroxyl, $C_{1-3}$alkyl-CN, phenyl optionally substituted with halogen and —S(O)$_n$$C_{1-6}$alkyl, with the proviso that one of $R^3$, $R^4$, $R^6$ or $R^7$ must be (q);
$R^8$, $R^9$ and $R^{10}$ are each independently selected from —H, —OH, —$NR^{12}R^{13}$, —$NR^{12}C(O)C_{1-6}$alkyl, —$CH_2NH_2$, $CO_2C_{1-6}$alkyl, —CN, $C_{1-6}$alkyl, —$C_{1-6}$alkoxy, —$OC_{3-6}$cycloalkyl, —$SC_{1-6}$-alkyl, —S(O)$_n$alkyl and —$CH_2OH$;
$R^{11}$, $R^{12}$ and $R^{13}$ are each independently selected from —H and —($C_1$-$C_6$)alkyl, or $R^{11}$ and $R^{12}$ together with the nitrogen they are bonded to may form a azetidine, piperidine, pyrrolidine, piperazine or morpholine ring;
n is 0, 1 or 2.

In another embodiment, the present invention relates to a compound as described in the broadest embodiment above, or a pharmaceutically acceptable salt thereof, wherein $R^1$ is selected from

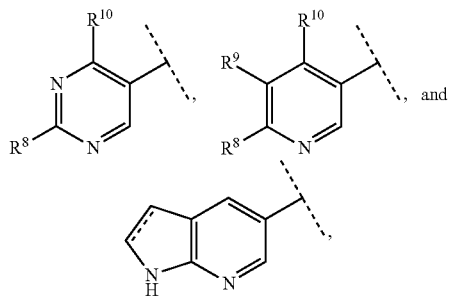

wherein --- indicates a single or double bond.

In another embodiment, the present invention relates to a compound as described in the broadest embodiment above, or a pharmaceutically acceptable salt thereof,
wherein $R^3$ is a 5-membered heteroaryl group optionally substituted with one to three groups selected from $C_{1-6}$alkyl, $C_{3-6}$cycloalkyl, halogen, —$CF_3$, —OH, —($CH_2$)$_n$$CO_2R^{11}$, —$SCF_3$, —C(O)N($R^{11}$)($R^{12}$), —N($R^{11}$)($R^{12}$), —NH—$SO_2C_{1-6}$alkyl, $C_{1-6}$alkoxyl, $C_{1-6}$alkyl-O—$C_{1-3}$ alkyl, $C_{1-6}$alkylhydroxyl, $C_{1-3}$alkyl-CN, phenyl optionally substituted with halogen and —S(O)$_n$$C_{1-6}$alkyl.

In another embodiment there is provided a compound of formula (I) as described in the broadest embodiment above, or a pharmaceutically acceptable salt thereof, wherein:
$R^1$ is selected from

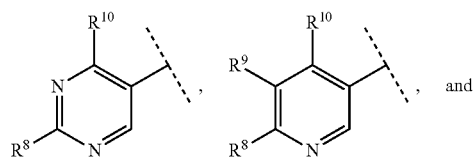

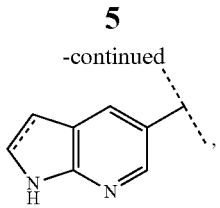

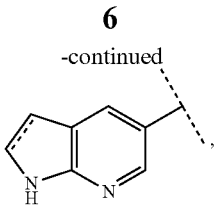

wherein --- indicates a single or double bond;
R² is —(C₁-C₆)alkyl;
R³ is a 5-membered heteroaryl group optionally substituted with one to three groups selected from $C_{1-6}$alkyl, $C_{3-6}$cycloalkyl, halogen, —CF₃, —OH, —CO₂R₁₁, —SCF₃, —C(O)NHR¹¹, —N(R¹¹)(R¹²)—NH—SO₂C₁₋₆alkyl, $C_{1-6}$alkoxyl, $C_{1-6}$alkyl-O—C₁₋₃ alkyl, $C_{1-6}$alkylhydroxyl, $C_{1-3}$alkyl-CN, phenyl optionally substituted with halogen and —S(O)ₙC₁₋₆alkyl;
R⁴, R⁵ and R⁶ are each independently selected from
 (a) —H,
 (b) —OH,
 (c) halogen,
 (d) —CN,
 (e) —CF₃,
 (f) $C_{1-6}$alkyl optionally substituted with $C_{1-6}$alkoxyl,
 (g) $C_{1-6}$alkenyl,
 (h) $C_{1-6}$alkoxy optionally substituted with —CO₂R¹¹,
 (i) —O(CH₂)₂(morpholin-4-yl),
 (j) —O(CH₂)₂OCH₃, and
 (k) —OCH₂C₃₋₆cycloalkyl;
R⁷ is H;
R⁸, R⁹ and R¹⁰ are selected from —H, —OH, —NR¹²R¹³, —NR¹²C(O)C₁₋₆alkyl, —CH₂NH₂, —CO₂C₁₋₆alkyl, —CN, $C_{1-6}$alkyl, —$C_{1-6}$alkoxy, —OC₃₋₆cycloalkyl, —SC₁₋₆alkyl, —S(O)ₙalkyl and —CH₂OH;
R¹¹, R¹² and R¹³ are each independently selected from —H and —(C₁-C₆)alkyl;
n is 0, 1 or 2.

In another embodiment there is provided a compound as described in the above embodiment above, or a pharmaceutically acceptable salt thereof, wherein R³ is a 5-membered heteroaryl group selected from imidazolyl, [1,2,4]oxadiazolyl, [[1,3,4]oxadiazolyl, pyrazolyl, tetrazolyl, thiazolyl, [1,2,4]thiadiazolyl, [1,3,4]thiadiazolyl, [1,2,4]triazolyl and [1,2,3]triazolyl, wherein said heteroaryl group is optionally substituted with one to three groups selected from $C_{1-6}$alkyl, $C_{3-6}$cycloalkyl, halogen, —CF₃, —OH, —CO₂R₁₁, —SCF₃, —C(O)N(R¹¹)(R¹²), —N(R¹¹)(R¹²), —NH—SO₂C₁₋₆alkyl, $C_{1-6}$alkoxyl, $C_{1-6}$alkyl-O—C₁₋₃ alkyl, $C_{1-3}$alkylhydroxyl, $C_{1-3}$alkyl-CN, phenyl optionally substituted with halogen and —S(O)ₙC1-6alkyl.

In another embodiment there is provided a compound of formula (I) as described in the broadest embodiment above, or a pharmaceutically acceptable salt thereof, wherein:
R¹ is selected from

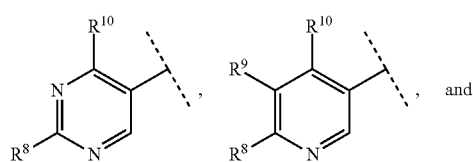

wherein --- indicates a single or double bond;
R² is —C(CH₃)₃;
R³ is a 5-membered heteroaryl group selected from imidazolyl, [1,2,4]oxadiazolyl, [[1,3,4]oxadiazolyl, pyrazolyl, tetrazolyl, thiazolyl, [1,2,4]thiadiazolyl, [1,3,4]thiadiazolyl, [1,2,4]triazolyl and [1,2,3]triazolyl, wherein said heteroaryl group is optionally substituted with one to three groups selected from $C_{1-6}$alkyl, $C_{3-6}$cycloalkyl, halogen, —CF₃, —OH, —CO₂R₁₁, —SCF₃, —C(O)NHR¹¹, —N(R¹¹)(R¹²), —NH—SO₂C₁₋₆alkyl, $C_{1-6}$alkoxyl, $C_{1-6}$alkyl-O—C₁₋₃ alkyl, $C_{1-3}$alkylhydroxyl, $C_{1-3}$alkyl-CN, phenyl substituted with chloro and —S(O)ₙC1-6alkyl;
R⁴, R⁵ and R⁶ are each independently selected from
 (a) —H,
 (b) —OH,
 (c) -halogen selected from —F, —Cl and —Br,
 (d) —CN,
 (e) —CF₃,
 (f) —CH₃ optionally substituted with $C_{1-2}$alkoxyl,
 (g) —CH₂CH=CH₂,
 (h) —OCH₃,
 (i) —O(CH₂)₂(morpholin-4-yl),
 (j) —O(CH₂)₂OCH₃, and
 (k) —OCH₂cyclopropyl;
R⁷ is H;
R⁸, R⁹ and R¹⁰ are selected from —H, —OH, —NH₂, —CH₃, and —CH₂OH; and
or a pharmaceutically acceptable salt thereof.

In another embodiment there is provided a compound as described in the embodiment above, or a pharmaceutically acceptable salt thereof, wherein R¹ is selected from

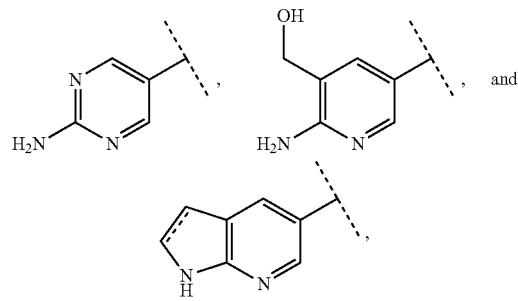

wherein --- indicates a single or double bond.

In another embodiment there is provided a compound as described in the embodiment above, or a pharmaceutically acceptable salt thereof, wherein R³ is a 5-membered heteroaryl group selected from imidazolyl, [1,2,4]oxadiazolyl, [1,3,4]oxadiazolyl, pyrazolyl, tetrazolyl, thiazolyl, [1,2,4]thiadiazolyl, [1,3,4]thiadiazolyl, [1,2,4]triazolyl and [1,2,3]triazolyl, wherein said heteroaryl group is optionally substituted with one to three groups selected from $C_{1-4}$alkyl, cyclopropyl, —CF₃, —CO₂C₁₋₂alkyl, —OCH₃, —C(O)NHR¹¹, —N(R¹¹)(R¹²) and —S(O)₂CH₃; and
R¹¹ and R¹² are selected from H and —CH₃;
or a pharmaceutically acceptable salt thereof.

The following are representative compounds of the invention which can be made by the general synthetic schemes, the examples, and known methods in the art.

TABLE 1

| Structure | Name |
|---|---|
| 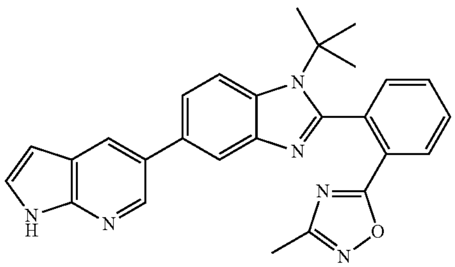 [SMILES: Cc1noc(-c2ccccc2-c2nc3cc(-c4cnc5[nH]ccc5c4)ccc3n2C(C)(C)C)n1] | 1-tert-Butyl-2-[2-(3-methyl-[1,2,4]oxadiazol-5-yl)-phenyl]-5-(1H-pyrrolo[2,3-b]pyridin-5-yl)-1H-benzimidazole |
| 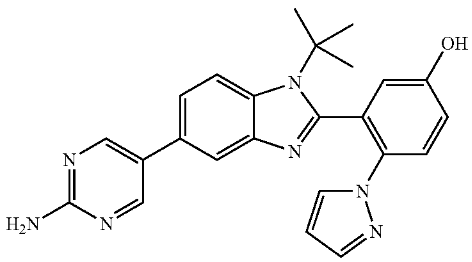 [SMILES: CC(C)(C)n1c(-c2cc(O)ccc2-n2cccn2)nc2cc(-c3cnc(N)nc3)ccc21] | 3-[5-(2-Amino-pyrimidin-5-yl)-1-tert-butyl-1H-benzimidazol-2-yl]-4-pyrazol-1-yl-phenol |
| 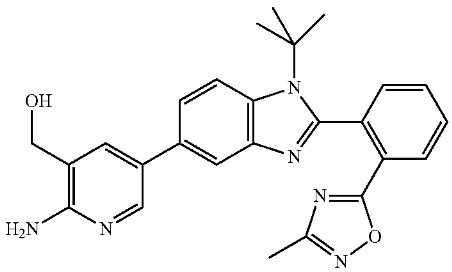 [SMILES: Cc1noc(-c2ccccc2-c2nc3cc(-c4cnc(N)c(CO)c4)ccc3n2C(C)(C)C)n1] | (2-Amino-5-{1-tert-butyl-2-[2-(3-methyl-[1,2,4]oxadiazol-5-yl)-phenyl]-1H-benzimidazol-5-yl}-pyridin-3-yl)-methanol |
| 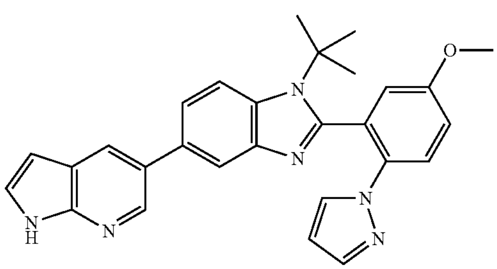 [SMILES: COc1ccc(-n2cccn2)c(-c2nc3cc(-c4cnc5[nH]ccc5c4)ccc3n2C(C)(C)C)c1] | 1-tert-Butyl-2-(5-methoxy-2-pyrazol-1-yl-phenyl)-5-(1H-pyrrolo[2,3-b]pyridin-5-yl)-1H-benzimidazole |
| 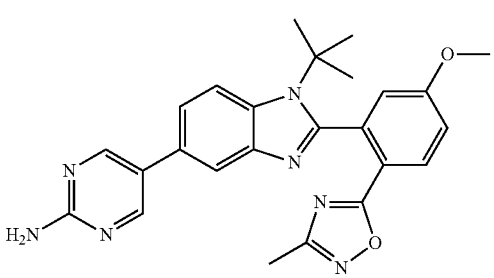 [SMILES: COc1ccc(-c2nc(C)no2)c(-c2nc3cc(-c4cnc(N)nc4)ccc3n2C(C)(C)C)c1] | 5-{1-tert-Butyl-2-[5-methoxy-2-(3-methyl-[1,2,4]oxadiazol-5-yl)-phenyl]-1H-benzimidazol-5-yl}-pyrimidin-2-ylamine |

TABLE 1-continued

| Structure | Name |
|---|---|
| 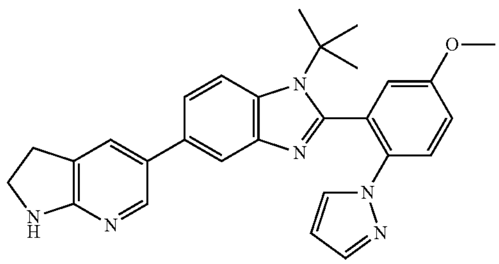 [SMILES: COc1ccc(-n2cccn2)c(-c2nc3cc(-c4cnc5c(c4)CCN5)ccc3n2C(C)(C)C)c1] | 1-tert-Butyl-5-(2,3-dihydro-1H-pyrrolo[2,3-b]pyridin-5-yl)-2-(5-methoxy-2-pyrazol-1-yl-phenyl)-1H-benzimidazole |
| 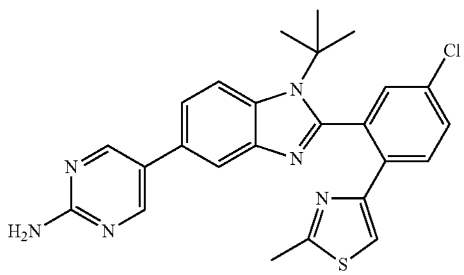 [SMILES: Cc1nc(-c2ccc(Cl)cc2-c2nc3cc(-c4cnc(N)nc4)ccc3n2C(C)(C)C)cs1] | 5-{1-tert-Butyl-2-[5-chloro-2-(2-methyl-thiazol-4-yl)-phenyl]-1H-benzimidazol-5-yl}-pyrimidin-2-ylamine |
| 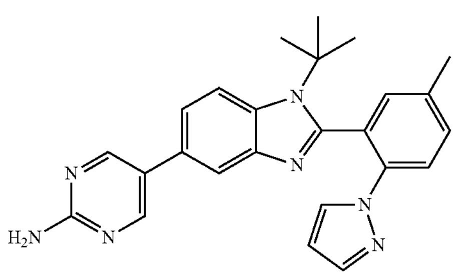 [SMILES: Cc1ccc(-n2cccn2)c(-c2nc3cc(-c4cnc(N)nc4)ccc3n2C(C)(C)C)c1] | 5-[1-tert-Butyl-2-(5-methyl-2-pyrazol-1-yl-phenyl)-1H-benzimidazol-5-yl]-pyrimidin-2-ylamine |
| 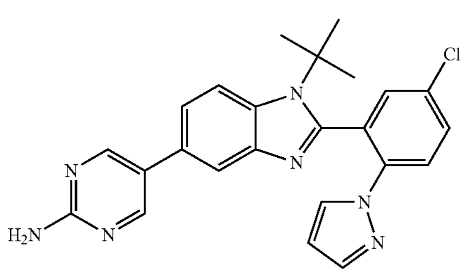 [SMILES: CC(C)(C)n1c(-c2cc(Cl)ccc2-n2cccn2)nc2cc(-c3cnc(N)nc3)ccc21] | 5-[1-tert-Butyl-2-(5-chloro-2-pyrazol-1-yl-phenyl)-1H-benzimidazol-5-yl]-pyrimidin-2-ylamine |
| 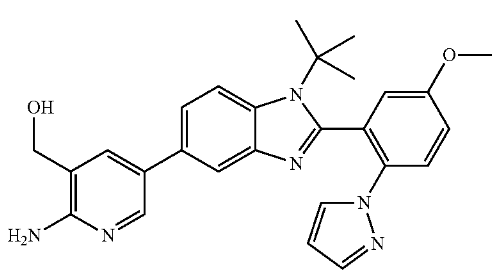 [SMILES: COc1ccc(-n2cccn2)c(-c2nc3cc(-c4cnc(N)c(CO)c4)ccc3n2C(C)(C)C)c1] | {2-Amino-5-[1-tert-butyl-2-(5-methoxy-2-pyrazol-1-yl-phenyl)-1H-benzimidazol-5-yl]-pyridin-3-yl}-methanol |

TABLE 1-continued

| Structure | Name |
| --- | --- |
| 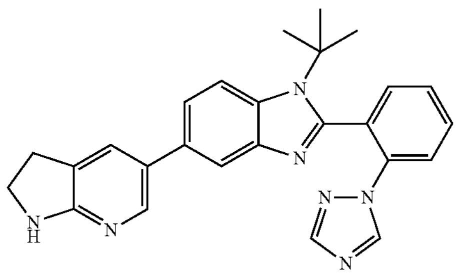 [SMILES: CC(C)(C)n1c(-c2ccccc2-n2cncn2)nc2cc(-c3cnc4c(c3)CCN4)ccc21] | 1-tert-Butyl-5-(2,3-dihydro-1H-pyrrolo[2,3-b]pyridin-5-yl)-2-(2-[1,2,4]triazol-1-yl-phenyl)-1H-benzimidazole |
| 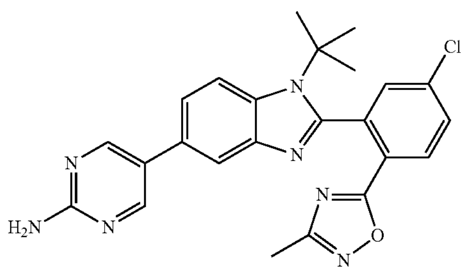 [SMILES: Cc1noc(-c2ccc(Cl)cc2-c2nc3cc(-c4cnc(N)nc4)ccc3n2C(C)(C)C)n1] | 5-{1-tert-Butyl-2-[5-chloro-2-(3-methyl-[1,2,4]oxadiazol-5-yl)phenyl]-1H-benzimidazol-5-yl}-pyrimidin-2-ylamine |
| 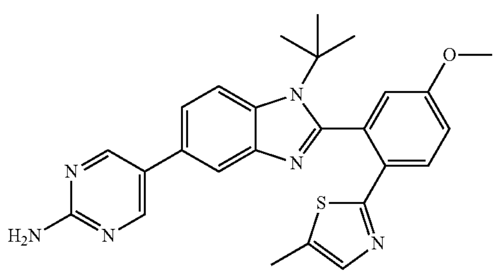 [SMILES: COc1ccc(-c2ncc(C)s2)c(-c2nc3cc(-c4cnc(N)nc4)ccc3n2C(C)(C)C)c1] | 5-{1-tert-Butyl-2-[5-methoxy-2-(5-methyl-thiazol-2-yl)-phenyl]-1H-benzimidazol-5-yl}-pyrimidin-2-ylamine |
| 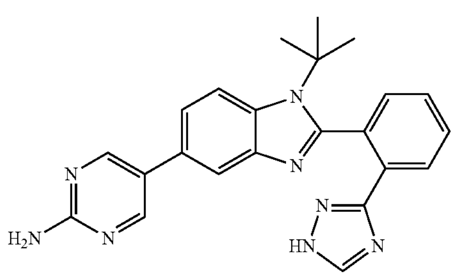 [SMILES: CC(C)(C)n1c(-c2ccccc2-c2nc[nH]n2)nc2cc(-c3cnc(N)nc3)ccc21] | 5-{1-tert-Butyl-2-[2-(1H-[1,2,4]triazol-3-yl)-phenyl]-1H-benzimidazol-5-yl}-pyrimidin-2-ylamine |
| 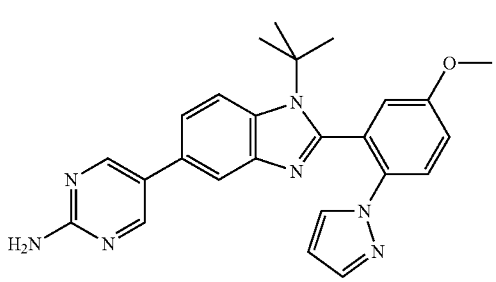 [SMILES: COc1ccc(-n2cccn2)c(-c2nc3cc(-c4cnc(N)nc4)ccc3n2C(C)(C)C)c1] | 5-[1-tert-Butyl-2-(5-methoxy-2-pyrazol-1-yl-phenyl)-1H-benzimidazol-5-yl]-pyrimidin-2-ylamine |

TABLE 1-continued

| Structure | Name |
|---|---|
| 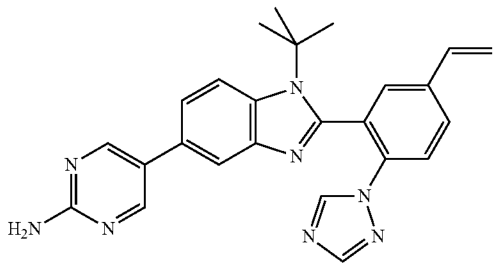 [SMILES: C=Cc1ccc(-n2cncn2)c(-c2nc3cc(-c4cnc(N)nc4)ccc3n2C(C)(C)C)c1] | 5-[1-tert-Butyl-2-(2-[1,2,4]triazol-1-yl-5-vinyl-phenyl)-1H-benzimidazol-5-yl]-pyrimidin-2-ylamine |
| 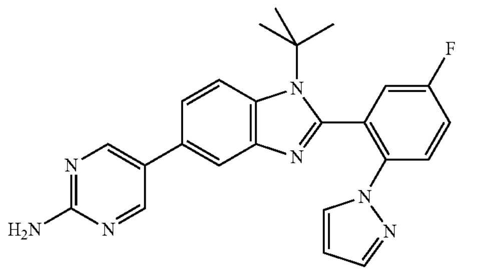 [SMILES: CC(C)(C)n1c(-c2cc(F)ccc2-n2cccn2)nc2cc(-c3cnc(N)nc3)ccc21] | 5-[1-tert-Butyl-2-(5-fluoro-2-pyrazol-1-yl-phenyl)-1H-benzimidazol-5-yl]-pyrimidin-2-ylamine |
| 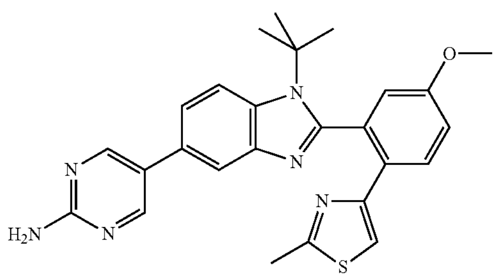 [SMILES: COc1ccc(-c2csc(C)n2)c(-c2nc3cc(-c4cnc(N)nc4)ccc3n2C(C)(C)C)c1] | 5-{1-tert-Butyl-2-[5-methoxy-2-(2-methyl-thiazol-4-yl)-phenyl]-1H-benzimidazol-5-yl}-pyrimidin-2-ylamine |
| 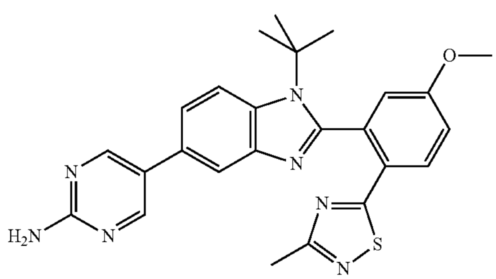 [SMILES: COc1ccc(-c2nc(C)ns2)c(-c2nc3cc(-c4cnc(N)nc4)ccc3n2C(C)(C)C)c1] | 5-{1-tert-Butyl-2-[5-methoxy-2-(3-methyl-[1,2,4]thiadiazol-5-yl)-phenyl]-1H-benzimidazol-5-yl}-pyrimidin-2-ylamine |
| 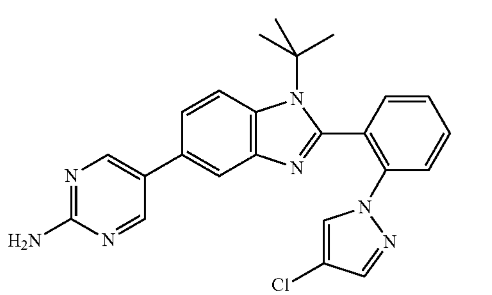 [SMILES: CC(C)(C)n1c(-c2ccccc2-n2cc(Cl)cn2)nc2cc(-c3cnc(N)nc3)ccc21] | 5-{1-tert-Butyl-2-[2-(4-chloro-pyrazol-1-yl)-phenyl]-1H-benzimidazol-5-yl}-pyrimidin-2-ylamine |

TABLE 1-continued

| Structure | Name |
|---|---|
| 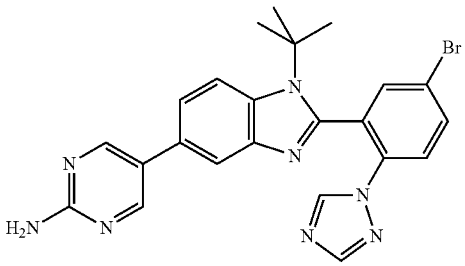 [SMILES: CC(C)(C)n1c(-c2cc(Br)ccc2-n2cncn2)nc2cc(-c3cnc(N)nc3)ccc21] | 5-[2-(5-Bromo-2-[1,2,4]triazol-1-yl-phenyl)-1-tert-butyl-1H-benzimidazol-5-yl]-pyrimidin-2-ylamine |
| 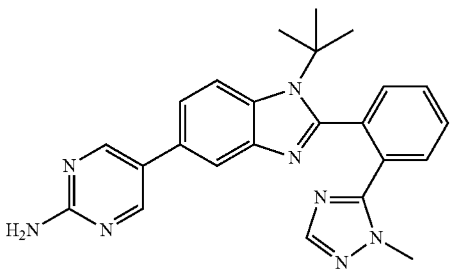 [SMILES: Cn1ncnc1-c1ccccc1-c1nc2cc(-c3cnc(N)nc3)ccc2n1C(C)(C)C] | 5-{1-tert-Butyl-2-[2-(2-methyl-2H-[1,2,4]triazol-3-yl)-phenyl]-1H-benzimidazol-5-yl}-pyrimidin-2-ylamine |
| 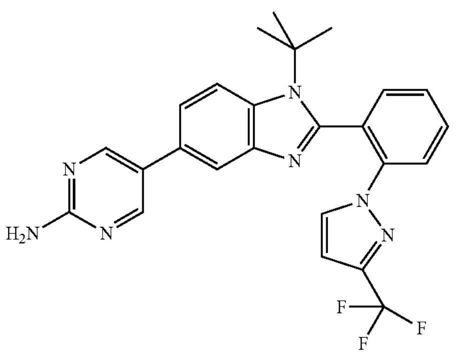 [SMILES: CC(C)(C)n1c(-c2ccccc2-n2ccc(C(F)(F)F)n2)nc2cc(-c3cnc(N)nc3)ccc21] | 5-{1-tert-Butyl-2-[2-(3-trifluoromethyl-pyrazol-1-yl)-phenyl]-1H-benzimidazol-5-yl}-pyrimidin-2-ylamine |
| 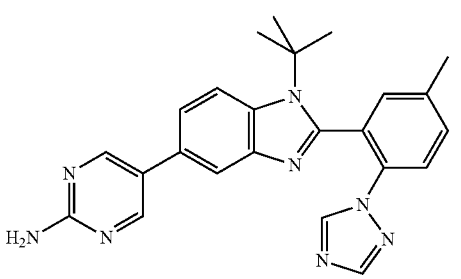 [SMILES: Cc1ccc(-n2cncn2)c(-c2nc3cc(-c4cnc(N)nc4)ccc3n2C(C)(C)C)c1] | 5-[1-tert-Butyl-2-(5-methyl-2-[1,2,4]triazol-1-yl-phenyl)-1H-benzimidazol-5-yl]-pyrimidin-2-ylamine |
| 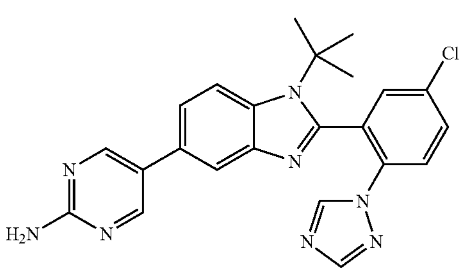 [SMILES: CC(C)(C)n1c(-c2cc(Cl)ccc2-n2cncn2)nc2cc(-c3cnc(N)nc3)ccc21] | 5-[1-tert-Butyl-2-(5-chloro-2-[1,2,4]triazol-1-yl-phenyl)-1H-benzimidazol-5-yl]-pyrimidin-2-ylamine |

TABLE 1-continued

| Structure | Name |
|---|---|
| 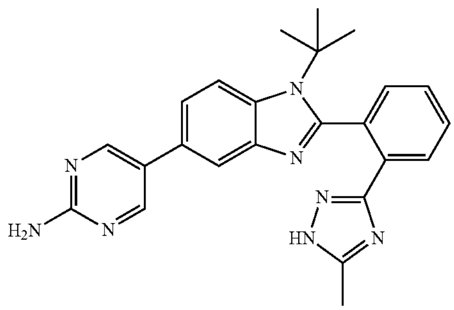 [SMILES: Cc1nc(-c2ccccc2-c2nc3cc(-c4cnc(N)nc4)ccc3n2C(C)(C)C)n[nH]1] | 5-{1-tert-Butyl-2-[2-(5-methyl-1H-[1,2,4]triazol-3-yl)-phenyl]-1H-benzimidazol-5-yl}-pyrimidin-2-ylamine |
| 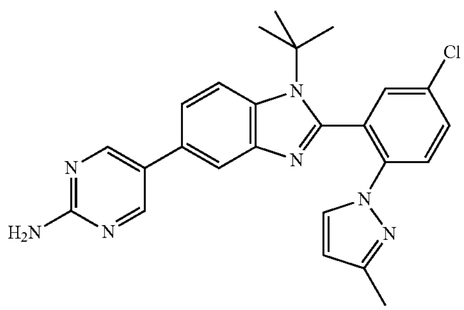 [SMILES: Cc1ccn(-c2ccc(Cl)cc2-c2nc3cc(-c4cnc(N)nc4)ccc3n2C(C)(C)C)n1] | 5-{1-tert-Butyl-2-[5-chloro-2-(3-methyl-pyrazol-1-yl)-phenyl]-1H-benzimidazol-5-yl}-pyrimidin-2-ylamine |
| 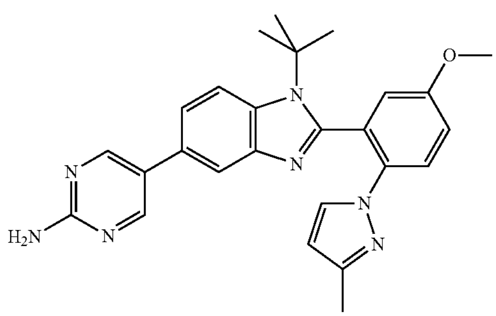 [SMILES: COc1ccc(-n2ccc(C)n2)c(-c2nc3cc(-c4cnc(N)nc4)ccc3n2C(C)(C)C)c1] | 5-{1-tert-Butyl-2-[5-methoxy-2-(3-methyl-pyrazol-1-yl)-phenyl]-1H-benzimidazol-5-yl}-pyrimidin-2-ylamine |
| 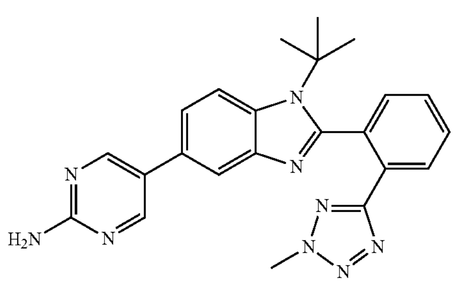 [SMILES: Cn1nnc(-c2ccccc2-c2nc3cc(-c4cnc(N)nc4)ccc3n2C(C)(C)C)n1] | 5-{1-tert-Butyl-2-[2-(2-methyl-2H-tetrazol-5-yl)-phenyl]-1H-benzimidazol-5-yl}-pyrimidin-2-ylamine |
| 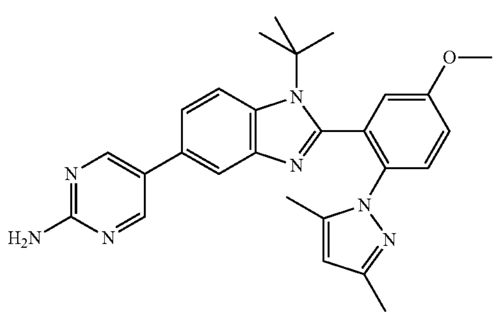 [SMILES: COc1ccc(-n2nc(C)cc2C)c(-c2nc3cc(-c4cnc(N)nc4)ccc3n2C(C)(C)C)c1] | 5-{1-tert-Butyl-2-[2-(3,5-dimethyl-pyrazol-1-yl)-5-methoxy-phenyl]-1H-benzimidazol-5-yl}-pyrimidin-2-ylamine |

TABLE 1-continued

| Structure | Name |
|---|---|
| 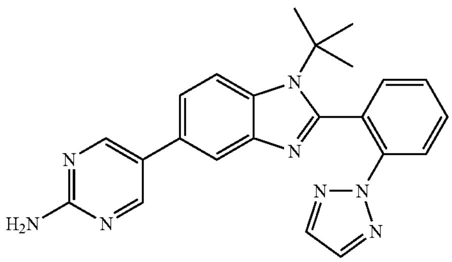 [SMILES: CC(C)(C)n1c(-c2ccccc2-n2nccn2)nc2cc(-c3cnc(N)nc3)ccc21] | 5-[1-tert-Butyl-2-(2-[1,2,3]triazol-2-yl-phenyl)-1H-benzimidazol-5-yl]-pyrimidin-2-ylamine |
| 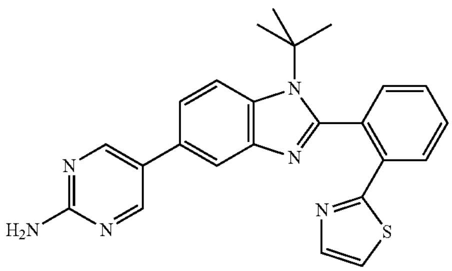 [SMILES: CC(C)(C)n1c(-c2ccccc2-c2nccs2)nc2cc(-c3cnc(N)nc3)ccc21] | 5-[1-tert-Butyl-2-(2-thiazol-2-yl-phenyl)-1H-benzimidazol-5-yl]-pyrimidin-2-ylamine |
| 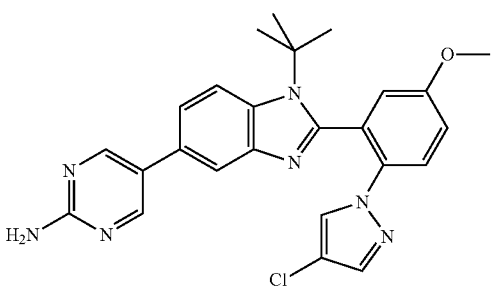 [SMILES: COc1ccc(-n2cc(Cl)cn2)c(-c2nc3cc(-c4cnc(N)nc4)ccc3n2C(C)(C)C)c1] | 5-{1-tert-Butyl-2-[2-(4-chloro-pyrazol-1-yl)-5-methoxy-phenyl]-1H-benzimidazol-5-yl}-pyrimidin-2-ylamine |
| 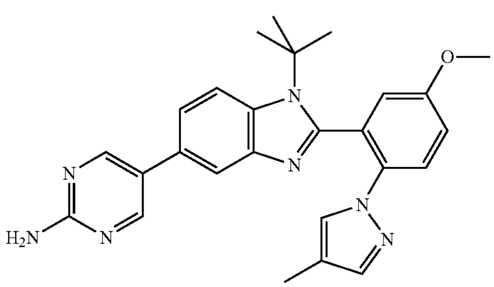 [SMILES: COc1ccc(-n2cc(C)cn2)c(-c2nc3cc(-c4cnc(N)nc4)ccc3n2C(C)(C)C)c1] | 5-{1-tert-Butyl-2-[5-methoxy-2-(4-methyl-pyrazol-1-yl)-phenyl]-1H-benzimidazol-5-yl}-pyrimidin-2-ylamine |
| 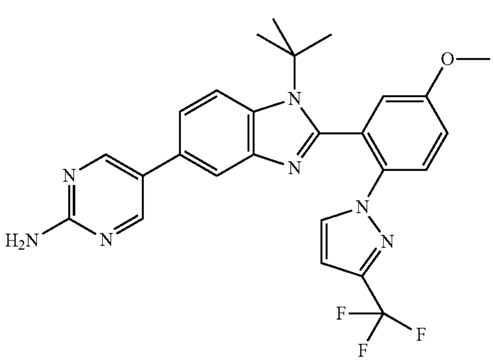 [SMILES: COc1ccc(-n2ccc(C(F)(F)F)n2)c(-c2nc3cc(-c4cnc(N)nc4)ccc3n2C(C)(C)C)c1] | 5-{1-tert-Butyl-2-[5-methoxy-2-(3-trifluoromethyl-pyrazol-1-yl)-phenyl]-1H-benzimidazol-5-yl}-pyrimidin-2-ylamine |

TABLE 1-continued

| Structure | Name |
|---|---|
| 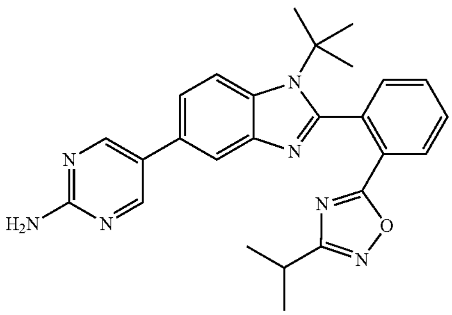 [SMILES: CC(C)c1noc(-c2ccccc2-c2nc3cc(-c4cnc(N)nc4)ccc3n2C(C)(C)C)n1] | 5-{1-tert-Butyl-2-[2-(3-isopropyl-[1,2,4]oxadiazol-5-yl)-phenyl]-1H-benzimidazol-5-yl}-pyrimidin-2-ylamine |
| 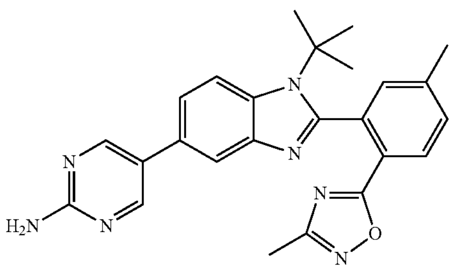 [SMILES: Cc1ccc(-c2nc(C)no2)c(-c2nc3cc(-c4cnc(N)nc4)ccc3n2C(C)(C)C)c1] | 5-{1-tert-Butyl-2-[5-methyl-2-(3-methyl-[1,2,4]oxadiazol-5-yl)-phenyl]-1H-benzimidazol-5-yl}-pyrimidin-2-ylamine |
| 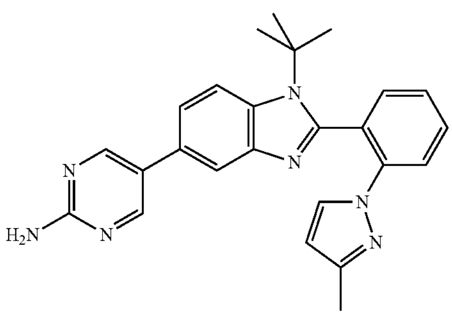 [SMILES: Cc1ccn(-c2ccccc2-c2nc3cc(-c4cnc(N)nc4)ccc3n2C(C)(C)C)n1] | 5-{1-tert-Butyl-2-[2-(3-methyl-pyrazol-1-yl)-phenyl]-1H-benzimidazol-5-yl}-pyrimidin-2-ylamine |
| 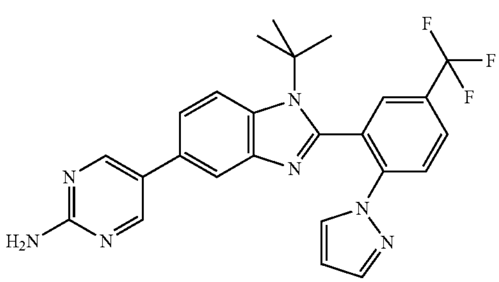 [SMILES: CC(C)(C)n1c(-c2cc(C(F)(F)F)ccc2-n2cccn2)nc2cc(-c3cnc(N)nc3)ccc21] | 5-[1-tert-Butyl-2-(2-pyrazol-1-yl-5-trifluoromethyl-phenyl)-1H-benzimidazol-5-yl]-pyrimidin-2-ylamine |
| 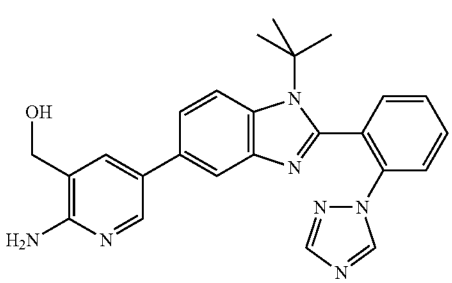 [SMILES: CC(C)(C)n1c(-c2ccccc2-n2cncn2)nc2cc(-c3cnc(N)c(CO)c3)ccc21] | {2-Amino-5-[1-tert-butyl-2-(2-[1,2,4]triazol-1-yl-phenyl)-1H-benzimidazol-5-yl]-pyridin-3-yl}-methanol |

TABLE 1-continued

| Structure | Name |
|---|---|
| 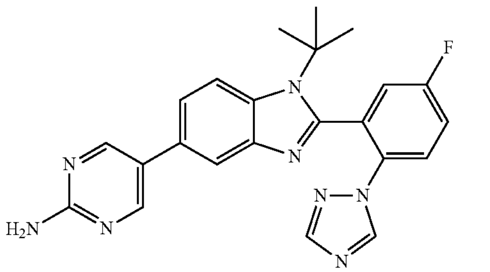 [SMILES: CC(C)(C)n1c(-c2cc(F)ccc2-n2cncn2)nc2cc(-c3cnc(N)nc3)ccc21] | 5-[1-tert-Butyl-2-(5-fluoro-2-[1,2,4]triazol-1-yl-phenyl)-1H-benzimidazol-5-yl]-pyrimidin-2-ylamine |
| 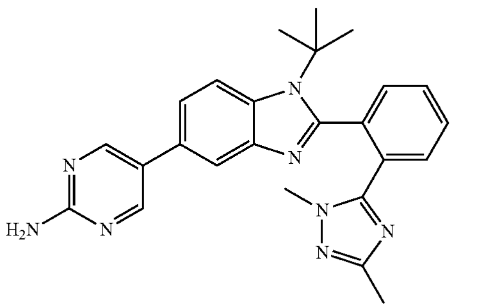 [SMILES: Cc1nc(-c2ccccc2-c2nc3cc(-c4cnc(N)nc4)ccc3n2C(C)(C)C)n(C)n1] | 5-{1-tert-Butyl-2-[2-(2,5-dimethyl-2H-1,2,4-triazol-3-yl)-phenyl]-1H-benzimidazol-5-yl}-pyrimidin-2-ylamine |
| 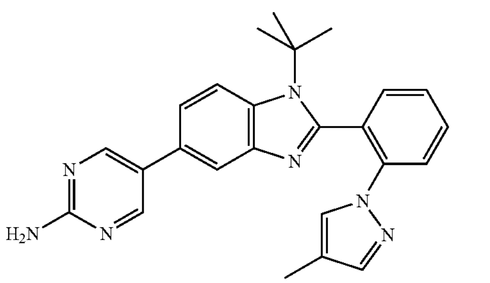 [SMILES: Cc1cnn(-c2ccccc2-c2nc3cc(-c4cnc(N)nc4)ccc3n2C(C)(C)C)c1] | 5-{1-tert-Butyl-2-[2-(4-methyl-pyrazol-1-yl)-phenyl]-1H-benzimidazol-5-yl}-pyrimidin-2-ylamine |
| 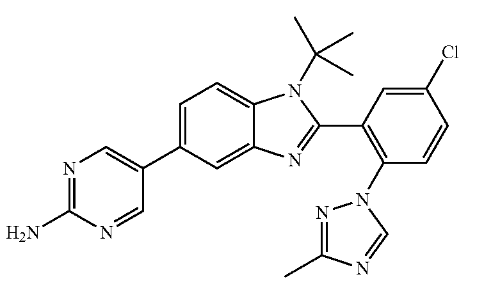 [SMILES: Cc1ncn(-c2ccc(Cl)cc2-c2nc3cc(-c4cnc(N)nc4)ccc3n2C(C)(C)C)n1] | 5-{1-tert-Butyl-2-[5-chloro-2-(3-methyl-[1,2,4]triazol-1-yl)-phenyl]-1H-benzimidazol-5-yl}-pyrimidin-2-ylamine |
| 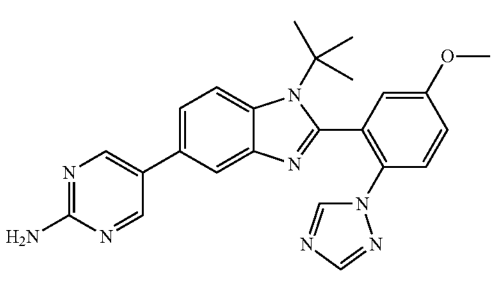 [SMILES: COc1ccc(-n2cncn2)c(-c2nc3cc(-c4cnc(N)nc4)ccc3n2C(C)(C)C)c1] | 5-[1-tert-Butyl-2-(5-methoxy-2-[1,2,4]triazol-1-yl-phenyl)-1H-benzimidazol-5-yl]-pyrimidin-2-ylamine |

TABLE 1-continued

| Structure | Name |
|---|---|
| 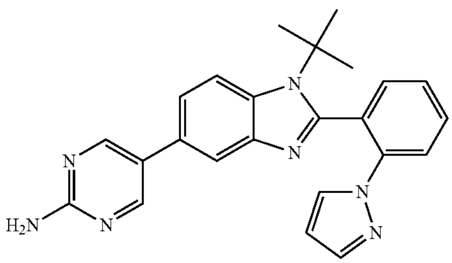 [SMILES: CC(C)(C)n1c(-c2ccccc2-n2cccn2)nc2cc(-c3cnc(N)nc3)ccc21] | 5-[1-tert-Butyl-2-(2-pyrazol-1-yl-phenyl)-1H-benzimidazol-5-yl]-pyrimidin-2-ylamine |
| 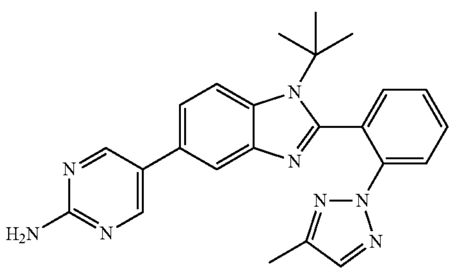 [SMILES: Cc1cnn(-c2ccccc2-c2nc3cc(-c4cnc(N)nc4)ccc3n2C(C)(C)C)n1] | 5-{1-tert-Butyl-2-[2-(3-methyl-[1,2,4]triazol-1-yl)-phenyl]-1H-benzimidazol-5-yl}-pyrimidin-2-ylamine |
| 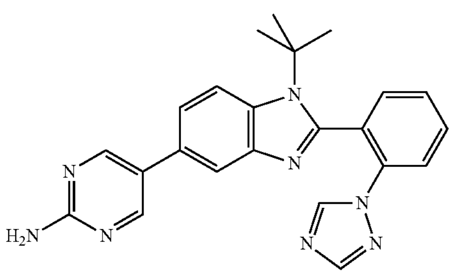 [SMILES: CC(C)(C)n1c(-c2ccccc2-n2cncn2)nc2cc(-c3cnc(N)nc3)ccc21] | 5-[1-tert-Butyl-2-(2-[1,2,4]triazol-1-yl-phenyl)-1H-benzimidazol-5-yl]-pyrimidin-2-ylamine |
| 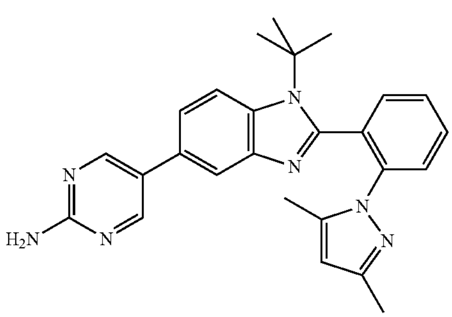 [SMILES: Cc1cc(C)n(-c2ccccc2-c2nc3cc(-c4cnc(N)nc4)ccc3n2C(C)(C)C)n1] | 5-{1-tert-Butyl-2-[2-(3,5-dimethyl-pyrazol-1-yl)-phenyl]-1H-benzimidazol-5-yl}-pyrimidin-2-ylamine |
| 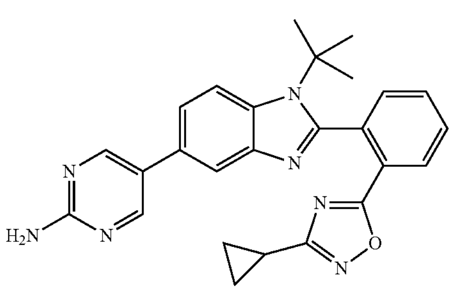 [SMILES: CC(C)(C)n1c(-c2ccccc2-c2nc(C3CC3)no2)nc2cc(-c3cnc(N)nc3)ccc21] | 5-{1-tert-Butyl-2-[2-(3-cyclopropyl-[1,2,4]oxadiazol-5-yl)-phenyl]-1H-benzimidazol-5-yl}-pyrimidin-2-ylamine |

TABLE 1-continued

| Structure | Name |
|---|---|
| 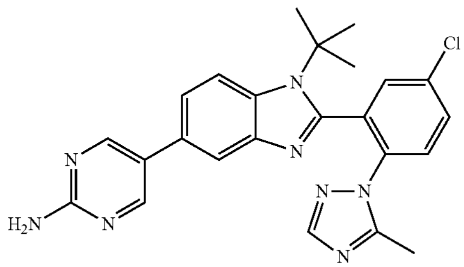 [SMILES: Cc1ncnn1-c1ccc(Cl)cc1-c1nc2cc(-c3cnc(N)nc3)ccc2n1C(C)(C)C] | 5-{1-tert-Butyl-2-[5-chloro-2-(5-methyl-[1,2,4]triazol-1-yl)-phenyl]-1H-benzimidazol-5-yl}-pyrimidin-2-ylamine |
| 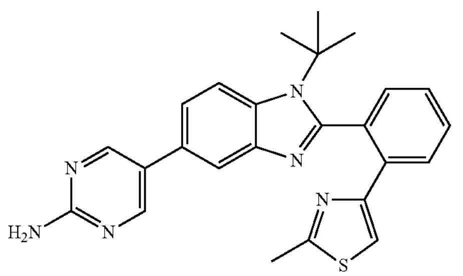 [SMILES: Cc1nc(-c2ccccc2-c2nc3cc(-c4cnc(N)nc4)ccc3n2C(C)(C)C)cs1] | 5-{1-tert-Butyl-2-[2-(2-methyl-thiazol-4-yl)-phenyl]-1H-benzimidazol-5-yl}-pyrimidin-2-ylamine |
| 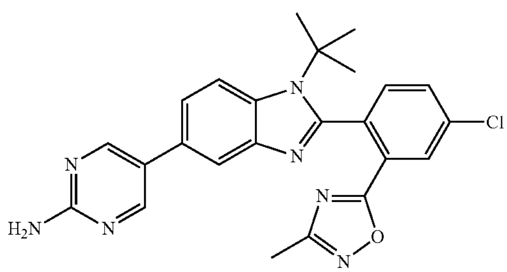 [SMILES: Cc1noc(-c2cc(Cl)ccc2-c2nc3cc(-c4cnc(N)nc4)ccc3n2C(C)(C)C)n1] | 5-{1-tert-Butyl-2-[4-chloro-2-(3-methyl-[1,2,4]oxadiazol-5-yl)-phenyl]-1H-benzimidazol-5-yl}-pyrimidin-2-ylamine |
| 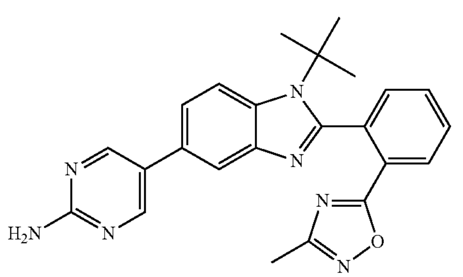 [SMILES: Cc1noc(-c2ccccc2-c2nc3cc(-c4cnc(N)nc4)ccc3n2C(C)(C)C)n1] | 5-{1-tert-Butyl-2-[2-(3-methyl-[1,2,4]oxadiazol-5-yl)-phenyl]-1H-benzimidazol-5-yl}-pyrimidin-2-ylamine |
| 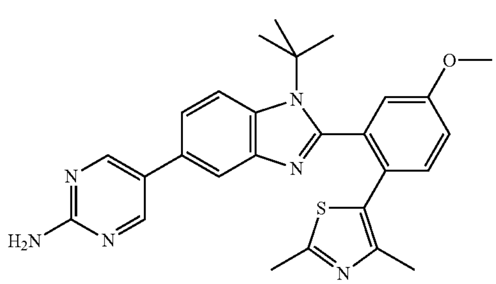 [SMILES: COc1ccc(-c2sc(C)nc2C)c(-c2nc3cc(-c4cnc(N)nc4)ccc3n2C(C)(C)C)c1] | 5-{1-tert-Butyl-2-[2-(2,4-dimethyl-thiazol-5-yl)-5-methoxy-phenyl]-1H-benzimidazol-5-yl}-pyrimidin-2-ylamine |

TABLE 1-continued

| Structure | Name |
|---|---|
| 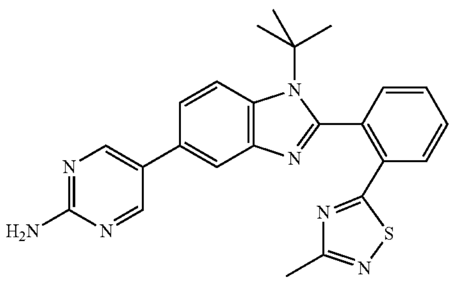 [SMILES: Cc1nsc(-c2ccccc2-c2nc3cc(-c4cnc(N)nc4)ccc3n2C(C)(C)C)n1] | 5-{1-tert-Butyl-2-[2-(3-methyl-[1,2,4]-thiadiazol-5-yl)-phenyl]-1H-benzimidazol-5-yl}-pyrimidin-2-ylamine |
| 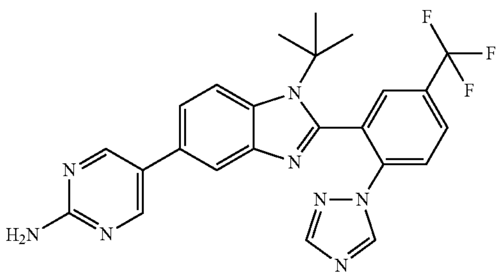 [SMILES: CC(C)(C)n1c(-c2cc(C(F)(F)F)ccc2-n2cncn2)nc2cc(-c3cnc(N)nc3)ccc21] | 5-[1-tert-Butyl-2-(2-[1,2,4]triazol-1-yl-5-trifluoromethyl-phenyl)-1H-benzimidazol-5-yl]-pyrimidin-2-ylamine |
| 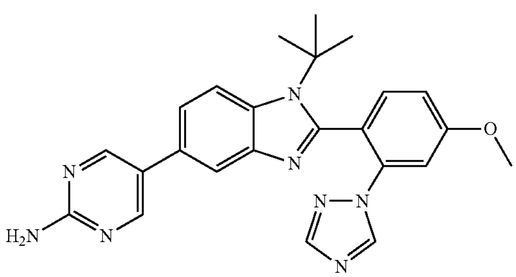 [SMILES: COc1ccc(-c2nc3cc(-c4cnc(N)nc4)ccc3n2C(C)(C)C)c(-n2cncn2)c1] | 5-[1-tert-Butyl-2-(4-methoxy-2-[1,2,4]triazol-1-yl-phenyl)-1H-benzimidazol-5-yl]-pyrimidin-2-ylamine |
| 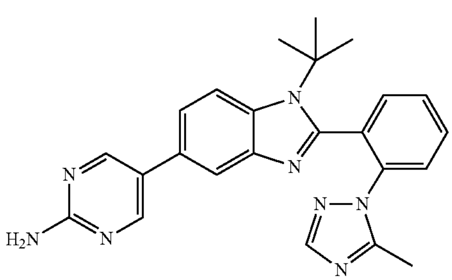 [SMILES: Cc1ncnn1-c1ccccc1-c1nc2cc(-c3cnc(N)nc3)ccc2n1C(C)(C)C] | 5-{1-tert-Butyl-2-[2-(5-methyl-[1,2,4]triazol-1-yl)-phenyl]-1H-benzimidazol-5-yl}-pyrimidin-2-ylamine |
| 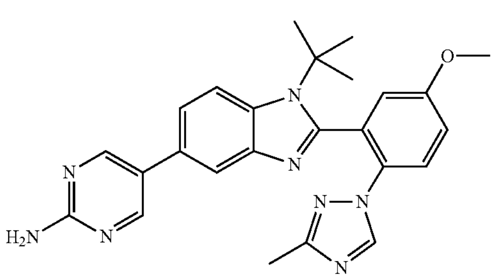 [SMILES: COc1ccc(-n2cnc(C)n2)c(-c2nc3cc(-c4cnc(N)nc4)ccc3n2C(C)(C)C)c1] | 5-{1-tert-Butyl-2-[5-methoxy-2-(3-methyl-[1,2,4]triazol-1-yl)-phenyl]-1H-benzimidazol-5-yl}-pyrimidin-2-ylamine |

TABLE 1-continued

| Structure | Name |
|---|---|
| 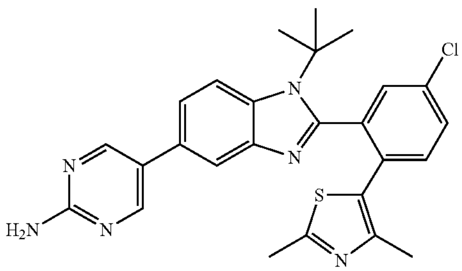 [SMILES: Cc1nc(C)c(-c2ccc(Cl)cc2-c2nc3cc(-c4cnc(N)nc4)ccc3n2C(C)(C)C)s1] | 5-{1-tert-Butyl-2-[5-chloro-2-(2,4-dimethyl-thiazol-5-yl)-phenyl]-1H-benzimidazol-5-yl}-pyrimidin-2-ylamine |
| 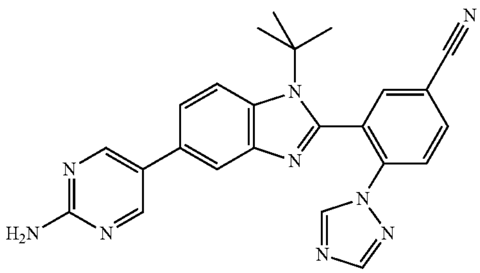 [SMILES: CC(C)(C)n1c(-c2cc(C#N)ccc2-n2cncn2)nc2cc(-c3cnc(N)nc3)ccc21] | 3-[5-(2-Amino-pyrimidin-5-yl)-1-tert-butyl-1H-benzimidazol-2-yl]-4-[1,2,4]triazol-1-yl-benzonitrile |
| 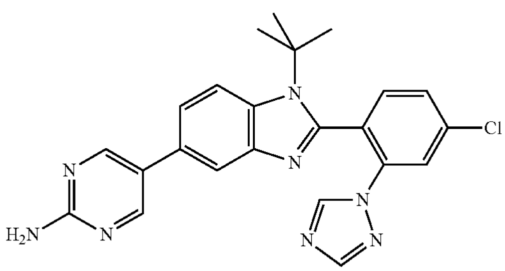 [SMILES: CC(C)(C)n1c(-c2ccc(Cl)cc2-n2cncn2)nc2cc(-c3cnc(N)nc3)ccc21] | 5-[1-tert-Butyl-2-(4-chloro-2-[1,2,4]triazol-1-yl-phenyl)-1H-benzimidazol-5-yl]-pyrimidin-2-ylamine |
| 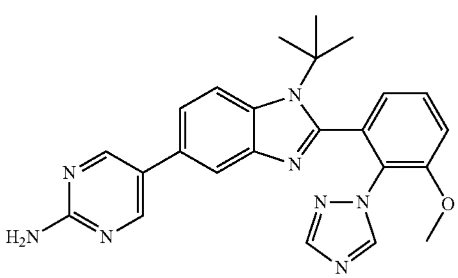 [SMILES: COc1cccc(-c2nc3cc(-c4cnc(N)nc4)ccc3n2C(C)(C)C)c1-n1cncn1] | 5-[1-tert-Butyl-2-(3-methoxy-2-[1,2,4]triazol-1-yl-phenyl)-1H-benzimidazol-5-yl]-pyrimidin-2-ylamine |
| 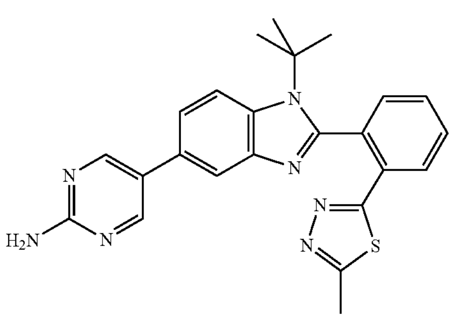 [SMILES: Cc1nnc(-c2ccccc2-c2nc3cc(-c4cnc(N)nc4)ccc3n2C(C)(C)C)s1] | 5-{1-tert-Butyl-2-[2-(5-methyl-[1,3,4]thiadiazol-2-yl)-phenyl]-1H-benzimidazol-5-yl}-pyrimidin-2-ylamine |

TABLE 1-continued

| Structure | Name |
|---|---|
| 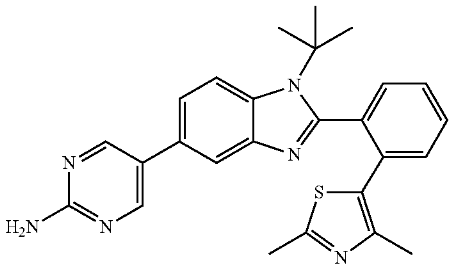 [SMILES: Cc1nc(C)c(-c2ccccc2-c2nc3cc(-c4cnc(N)nc4)ccc3n2C(C)(C)C)s1] | 5-{1-tert-Butyl-2-[2-(2,4-dimethyl-thiazol-5-yl)-phenyl]-1H-benzimidazol-5-yl}-pyrimidin-2-ylamine |
| 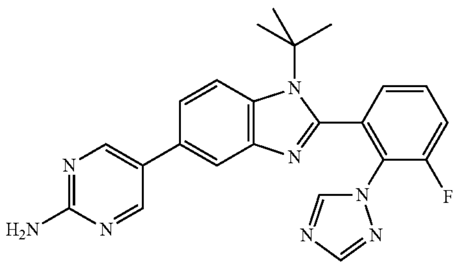 [SMILES: CC(C)(C)n1c(-c2cccc(F)c2-n2cncn2)nc2cc(-c3cnc(N)nc3)ccc21] | 5-[1-tert-Butyl-2-(3-fluoro-2-[1,2,4]triazol-1-yl-phenyl)-1H-benzimidazol-5-yl]-pyrimidin-2-ylamine |
| 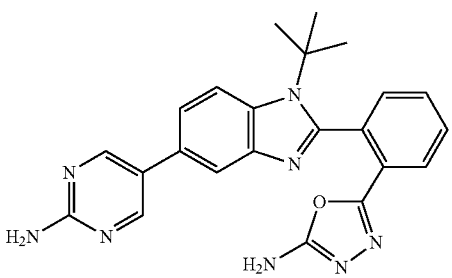 [SMILES: CC(C)(C)n1c(-c2ccccc2-c2nnc(N)o2)nc2cc(-c3cnc(N)nc3)ccc21] | 5-{2-[2-(5-Amino-[1,3,4]oxadiazol-2-yl)-phenyl]-1-tert-butyl-1H-benzimidazol-5-yl}-pyrimidin-2-ylamine |
| 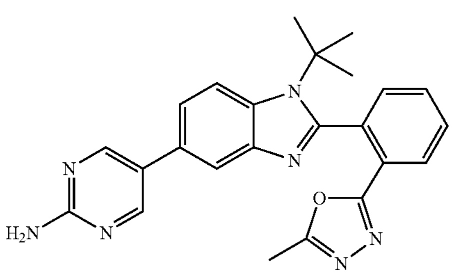 [SMILES: Cc1nnc(-c2ccccc2-c2nc3cc(-c4cnc(N)nc4)ccc3n2C(C)(C)C)o1] | 5-{1-tert-Butyl-2-[2-(5-methyl-[1,3,4]oxadiazol-2-yl)-phenyl]-1H-benzimidazol-5-yl}-pyrimidin-2-ylamine |
| 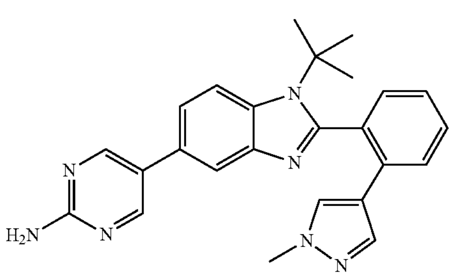 [SMILES: Cn1cc(-c2ccccc2-c2nc3cc(-c4cnc(N)nc4)ccc3n2C(C)(C)C)cn1] | 5-{1-tert-Butyl-2-[2-(1-methyl-1H-pyrazol-4-yl)-phenyl]-1H-benzimidazol-5-yl}-pyrimidin-2-ylamine |

TABLE 1-continued

| Structure | Name |
|---|---|
| 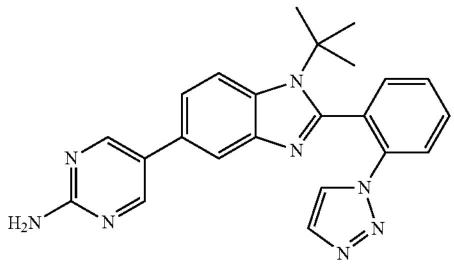 [SMILES: CC(C)(C)n1c(-c2ccccc2-n2ccnn2)nc2cc(-c3cnc(N)nc3)ccc21] | 5-[1-tert-Butyl-2-(2-[1,2,3]triazol-1-yl-phenyl)-1H-benzimidazol-5-yl]-pyrimidin-2-ylamine |
| 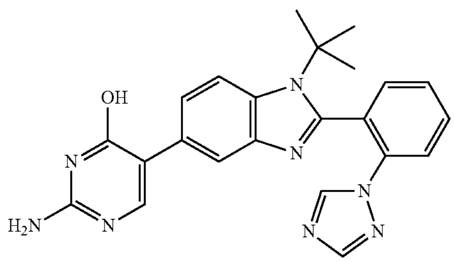 [SMILES: CC(C)(C)n1c(-c2ccccc2-n2cncn2)nc2cc(-c3cnc(N)nc3O)ccc21] | 2-Amino-5-[1-tert-butyl-2-(2-[1,2,4]triazol-1-yl-phenyl)-1H-benzimidazol-5-yl]-pyrimidin-4-ol |
| 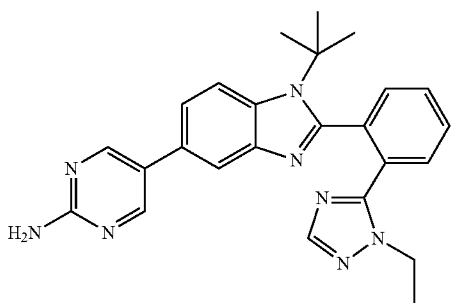 [SMILES: CCn1ncnc1-c1ccccc1-c1nc2cc(-c3cnc(N)nc3)ccc2n1C(C)(C)C] | 5-{1-tert-Butyl-2-[2-(2-ethyl-2H-1,2,4-triazol-3-yl)-phenyl]-1H-benzimidazol-5-yl}-pyrimidin-2-ylamine |
| 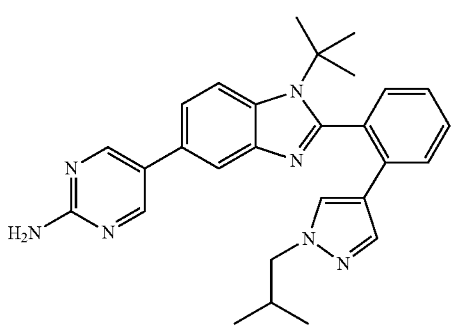 [SMILES: CC(C)Cn1cc(-c2ccccc2-c2nc3cc(-c4cnc(N)nc4)ccc3n2C(C)(C)C)cn1] | 5-{1-tert-Butyl-2-[2-(1-isobutyl-1H-pyrazol-4-yl)-phenyl]-1H-benzimidazol-5-yl}-pyrimidin-2-ylamine |
| 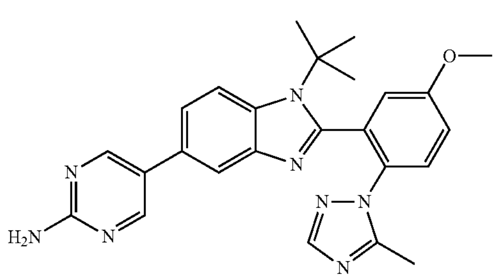 [SMILES: COc1ccc(-n2ncnc2C)c(-c2nc3cc(-c4cnc(N)nc4)ccc3n2C(C)(C)C)c1] | 5-{1-tert-Butyl-2-[5-methoxy-2-(5-methyl-[1,2,4]triazol-1-yl)-phenyl]-1H-benzimidazol-5-yl}-yrimidin-2-ylamine |

TABLE 1-continued

| Structure | Name |
| --- | --- |
| 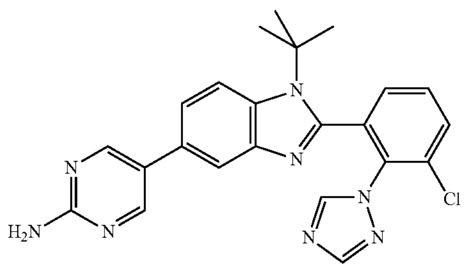 [SMILES: CC(C)(C)n1c(-c2cccc(Cl)c2-n2cncn2)nc2cc(-c3cnc(N)nc3)ccc21] | 5-[1-tert-Butyl-2-(3-chloro-2-[1,2,4]triazol-1-yl-phenyl)-1H-benzimidazol-5-yl]-pyrimidin-2-ylamine |
| 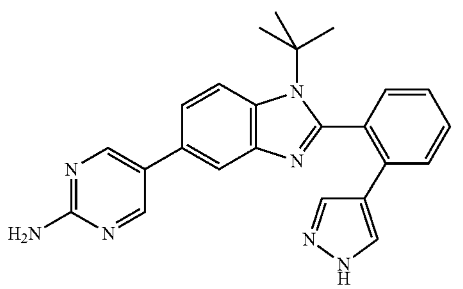 [SMILES: CC(C)(C)n1c(-c2ccccc2-c2cn[nH]c2)nc2cc(-c3cnc(N)nc3)ccc21] | 5-{1-tert-Butyl-2-[2-(1H-pyrazol-4-yl)-phenyl]-1H-benzimidazol-5-yl}-pyrimidin-2-ylamine |
| 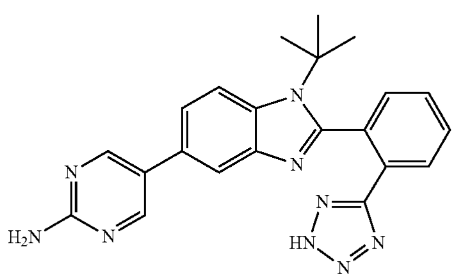 [SMILES: CC(C)(C)n1c(-c2ccccc2-c2nn[nH]n2)nc2cc(-c3cnc(N)nc3)ccc21] | 5-{1-tert-Butyl-2-[2-(2H-tetrazol-5-yl)-phenyl]-1H-benzimidazol-5-yl}-pyrimidin-2-ylamine |
| 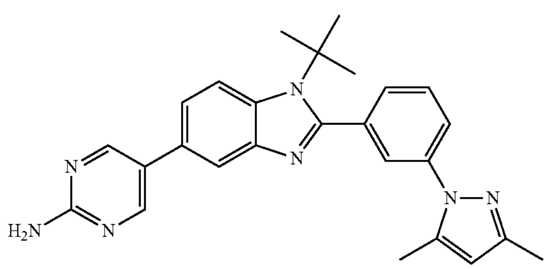 [SMILES: Cc1cc(C)n(-c2cccc(-c3nc4cc(-c5cnc(N)nc5)ccc4n3C(C)(C)C)c2)n1] | 5-{1-tert-Butyl-2-[3-(3,5-dimethyl-pyrazol-1-yl)-phenyl]-1H-benzimidazol-5-yl}-pyrimidin-2-ylamine |
| 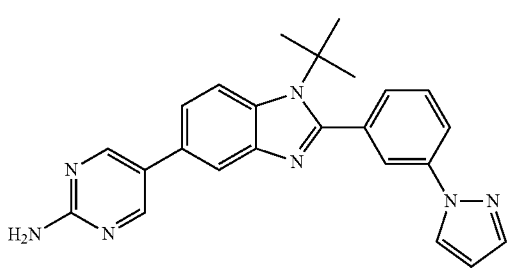 [SMILES: CC(C)(C)n1c(-c2cccc(-n3cccn3)c2)nc2cc(-c3cnc(N)nc3)ccc21] | 5-[1-tert-Butyl-2-(3-pyrazol-1-yl-phenyl)-1H-benzimidazol-5-yl]-pyrimidin-2-ylamine |
| 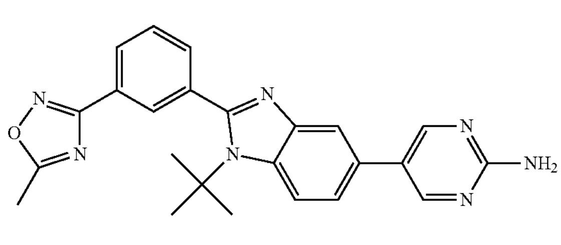 [SMILES: Cc1nc(-c2cccc(-c3nc4cc(-c5cnc(N)nc5)ccc4n3C(C)(C)C)c2)no1] | 5-{1-tert-Butyl-2-[3-(5-methyl-[1,2,4]oxadiazol-3-yl)-phenyl]-1H-benzimidazol-5-yl}-pyrimidin-2-ylamine |

TABLE 1-continued

| Structure | Name |
|---|---|
| 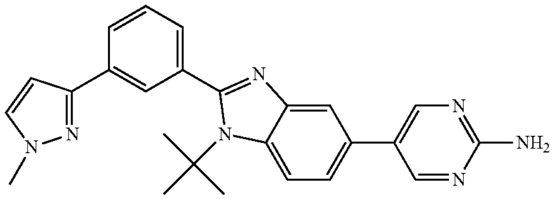 [SMILES: Cn1ccc(-c2cccc(-c3nc4cc(-c5cnc(N)nc5)ccc4n3C(C)(C)C)c2)n1] | 5-{1-tert-Butyl-2-[3-(1-methyl-1H-pyrazol-3-yl)-phenyl]-1H-benzimidazol-5-yl}-pyrimidin-2-ylamine |
| 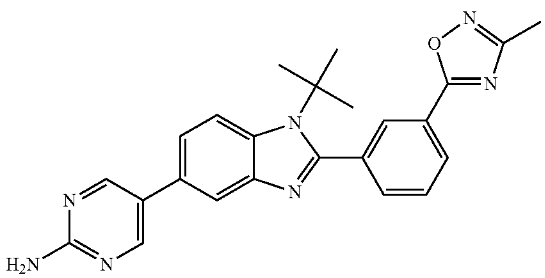 [SMILES: Cc1noc(-c2cccc(-c3nc4cc(-c5cnc(N)nc5)ccc4n3C(C)(C)C)c2)n1] | 5-{1-tert-Butyl-2-[3-(3-methyl-[1,2,4]oxadiazol-5-yl)-phenyl]-1H-benzimidazol-5-yl}-pyrimidin-2-ylamine |
| 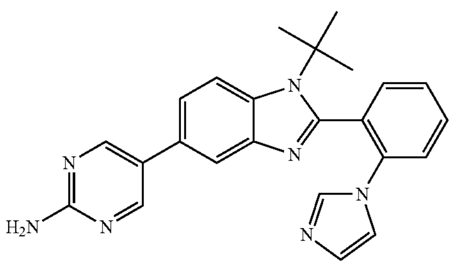 [SMILES: CC(C)(C)n1c(-c2ccccc2-n2ccnc2)nc2cc(-c3cnc(N)nc3)ccc21] | 5-[1-tert-Butyl-2-(2-imidazol-1-yl-phenyl)-1H-benzimidazol-5-yl]-pyrimidin-2-ylamine |
| 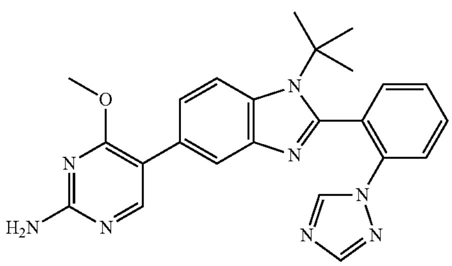 [SMILES: COc1nc(N)ncc1-c1ccc2c(c1)nc(-c1ccccc1-n1cncn1)n2C(C)(C)C] | 5-[1-tert-Butyl-2-(2-[1,2,4]triazol-1-yl-phenyl)-1H-benzimidazol-5-yl]-4-methoxy-pyrimidin-2-ylamine |
| 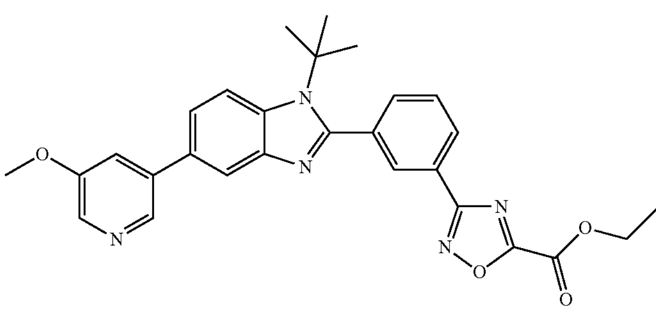 [SMILES: CCOC(=O)c1nc(-c2cccc(-c3nc4cc(-c5cncc(OC)c5)ccc4n3C(C)(C)C)c2)no1] | 3-{3-[1-tert-Butyl-5-(5-methoxy-pyridin-3-yl)-1H-benzimidazol-2-yl]-phenyl}-[1,2,4]oxadiazole-5-carboxylic acid ethyl ester |
| 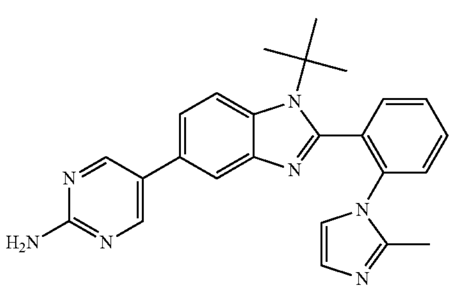 [SMILES: Cc1nccn1-c1ccccc1-c1nc2cc(-c3cnc(N)nc3)ccc2n1C(C)(C)C] | 5-{1-tert-Butyl-2-[2-(2-methyl-imidazol-1-yl)-phenyl]-1H-benzimidazol-5-yl}-pyrimidin-2-ylamine |

TABLE 1-continued

| Structure | Name |
|---|---|
| 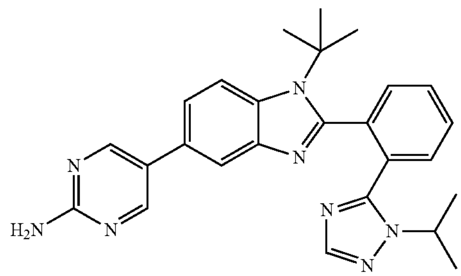 [SMILES: CC(C)n1ncnc1-c1ccccc1-c1nc2cc(-c3cnc(N)nc3)ccc2n1C(C)(C)C] | 5-{1-tert-Butyl-2-[2-(2-isopropyl-2H-1,2,4-triazol-3-yl)-phenyl]-1H-benzimidazol-5-yl}-pyrimidin-2-ylamine |
| 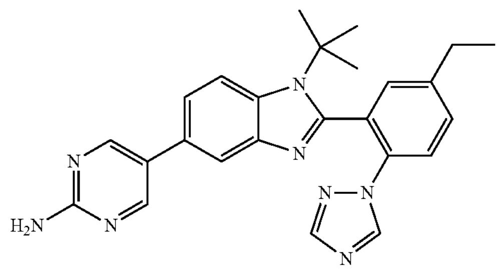 [SMILES: CCc1ccc(-n2cncn2)c(-c2nc3cc(-c4cnc(N)nc4)ccc3n2C(C)(C)C)c1] | 5-[1-tert-Butyl-2-(5-ethyl-2-1,2,4-triazol-1-yl-phenyl)-1H-benzimidazol-5-yl]-pyrimidin-2-ylamine |
| 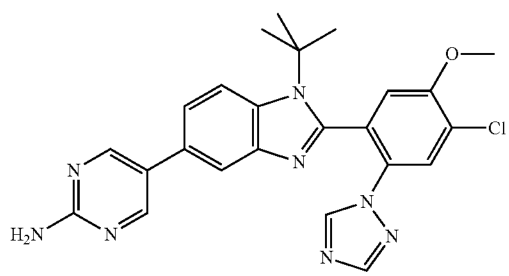 [SMILES: COc1cc(-c2nc3cc(-c4cnc(N)nc4)ccc3n2C(C)(C)C)c(-n2cncn2)cc1Cl] | 5-[1-tert-Butyl-2-(4-chloro-5-methoxy-2-1,2,4-triazol-1-yl-phenyl)-1H-benzimidazol-5-yl]-pyrimidin-2-ylamine |
| 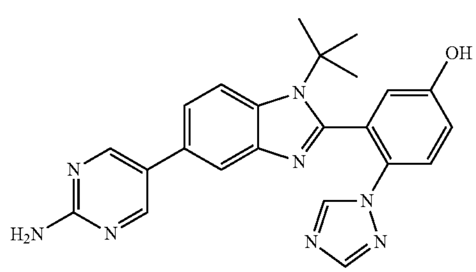 [SMILES: CC(C)(C)n1c(-c2cc(O)ccc2-n2cncn2)nc2cc(-c3cnc(N)nc3)ccc21] | 3-[5-(2-Amino-pyrimidin-5-yl)-1-tert-butyl-1H-benzimidazol-2-yl]-4-1,2,4-triazol-1-yl-phenol |
| 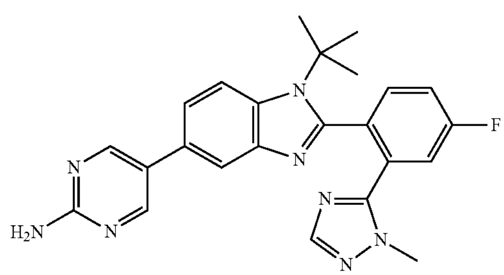 [SMILES: Cn1ncnc1-c1cc(F)ccc1-c1nc2cc(-c3cnc(N)nc3)ccc2n1C(C)(C)C] | 5-{1-tert-Butyl-2-[4-fluoro-2-(2-methyl-2H-1,2,4-triazol-3-yl)-phenyl]-1H-benzimidazol-5-yl}-pyrimidin-2-ylamine |

TABLE 1-continued

| Structure | Name |
|---|---|
| 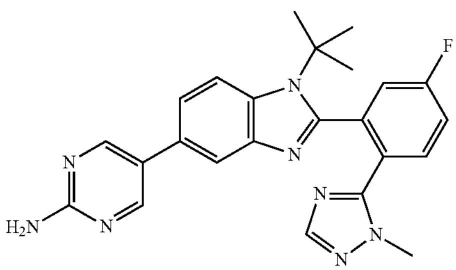 [SMILES: Cn1ncnc1-c1ccc(F)cc1-c1nc2cc(-c3cnc(N)nc3)ccc2n1C(C)(C)C] | 5-{1-tert-Butyl-2-[5-fluoro-2-(2-methyl-2H-1,2,4-triazol-3-yl)-phenyl]-1H-benzimidazol-5-yl}-pyrimidin-2-ylamine |
| 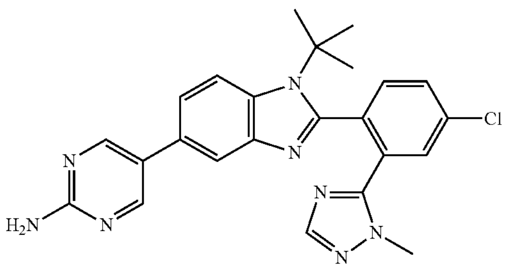 [SMILES: Cn1ncnc1-c1cc(Cl)ccc1-c1nc2cc(-c3cnc(N)nc3)ccc2n1C(C)(C)C] | 5-{1-tert-Butyl-2-[4-chloro-2-(2-methyl-2H-1,2,4-triazol-3-yl)-phenyl]-1H-benzimidazol-5-yl}-pyrimidin-2-ylamine |
| 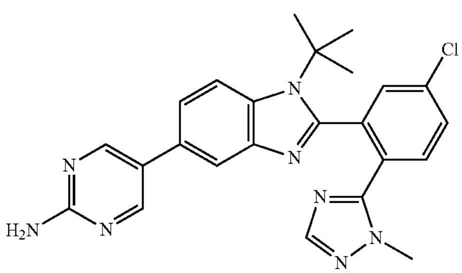 [SMILES: Cn1ncnc1-c1ccc(Cl)cc1-c1nc2cc(-c3cnc(N)nc3)ccc2n1C(C)(C)C] | 5-{1-tert-Butyl-2-[5-chloro-2-(2-methyl-2H-1,2,4-triazol-3-yl)-phenyl]-1H-benzimidazol-5-yl}-pyrimidin-2-ylamine |
| 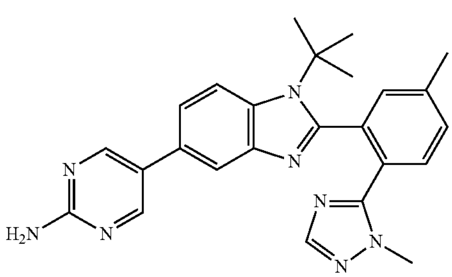 [SMILES: Cc1ccc(-c2ncnn2C)c(-c2nc3cc(-c4cnc(N)nc4)ccc3n2C(C)(C)C)c1] | 5-{1-tert-Butyl-2-[4-methyl-2-(2-methyl-2H-1,2,4-triazol-3-yl)-phenyl]-1H-benzimidazol-5-yl}-pyrimidin-2-ylamine |
| 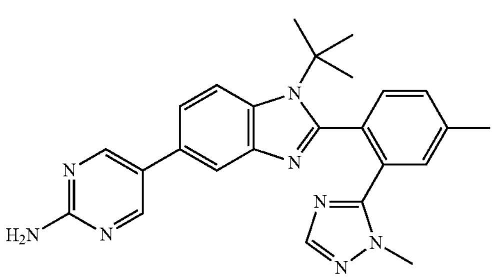 [SMILES: Cc1ccc(-c2nc3cc(-c4cnc(N)nc4)ccc3n2C(C)(C)C)c(-c2ncnn2C)c1] | 5-{1-tert-Butyl-2-[5-methyl-2-(2-methyl-2H-1,2,4-triazol-3-yl)-phenyl]-1H-benzimidazol-5-yl}-pyrimidin-2-ylamine |

TABLE 1-continued

| Structure | Name |
|---|---|
| 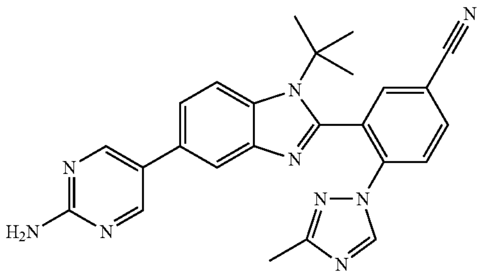 [SMILES: Cc1ncn(-c2ccc(C#N)cc2-c2nc3cc(-c4cnc(N)nc4)ccc3n2C(C)(C)C)n1] | 3-[5-(2-Amino-5-yl)-1-tert-butyl-1H-benzimidazol-2-yl]-4-(3-methyl-1,2,4-triazol-1-yl)-benzonitrile |
| 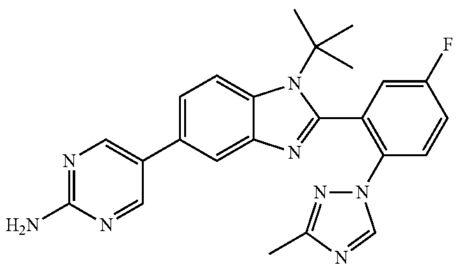 [SMILES: Cc1ncn(-c2ccc(F)cc2-c2nc3cc(-c4cnc(N)nc4)ccc3n2C(C)(C)C)n1] | 5-{1-tert-Butyl-2-[5-fluoro-2-(3-methyl-1,2,4-triazol-1-yl)-phenyl]-1H-benzimidazol-5-yl}-pyrimidin-2-ylamine |
| 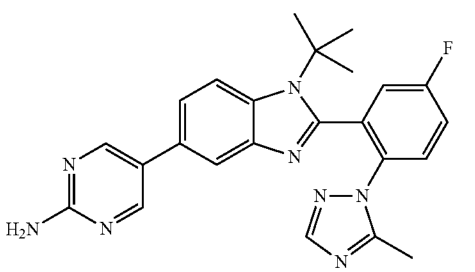 [SMILES: Cc1ncnn1-c1ccc(F)cc1-c1nc2cc(-c3cnc(N)nc3)ccc2n1C(C)(C)C] | 5-{1-tert-Butyl-2-[5-fluoro-2-(5-methyl-1,2,4-triazol-1-yl)-phenyl]-1H-benzimidazol-5-yl}-pyrimidin-2-ylamine |
| | 3-[5-(2-Amino-pyrimidin-5-yl)-1-tert-butyl-1H-benzimidazol-2-yl]-4-(5-methyl-1,2,4-triazol-1-yl)-benzonitrile |
| 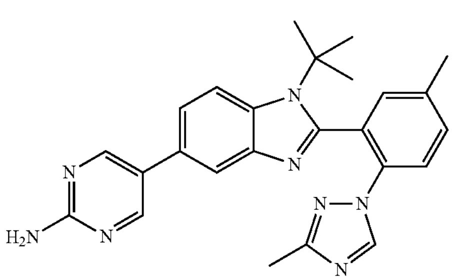 [SMILES: Cc1ccc(-n2cnc(C)n2)c(-c2nc3cc(-c4cnc(N)nc4)ccc3n2C(C)(C)C)c1] | 5-{1-tert-Butyl-2-[5-methyl-2-(3-methyl-1,2,4-triazol-1-yl)-phenyl]-1H-enzimidazol-5-yl}-pyrimidin-2-ylamine |

TABLE 1-continued

| Structure | Name |
|---|---|
| 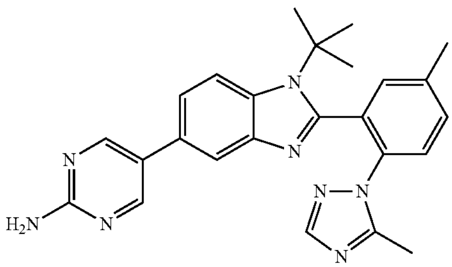 [SMILES: Cc1ccc(-n2ncnc2C)c(-c2nc3cc(-c4cnc(N)nc4)ccc3n2C(C)(C)C)c1] | 5-{1-tert-Butyl-2-[5-methyl-2-(5-methyl-1,2,4-triazol-1-yl)-phenyl]-1H-benzimidazol-5-yl}-pyrimidin-2-ylamine |
| 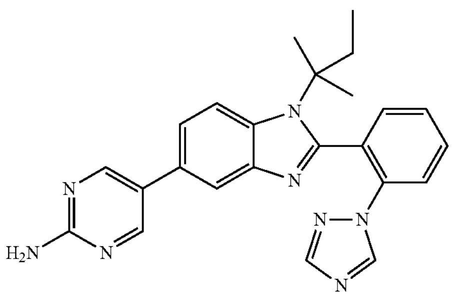 [SMILES: CCC(C)(C)n1c(-c2ccccc2-n2cncn2)nc2cc(-c3cnc(N)nc3)ccc21] | 5-[1-(1,1-Dimethyl-propyl)-2-(2-1,2,4-triazol-1-yl-phenyl)-1H-benzimidazol-5-yl]-pyrimidin-2-ylamine |
| 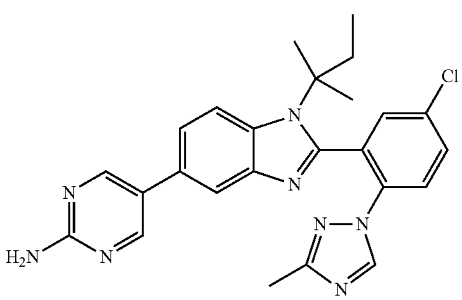 [SMILES: CCC(C)(C)n1c(-c2cc(Cl)ccc2-n2cnc(C)n2)nc2cc(-c3cnc(N)nc3)ccc21] | 5-[2-[5-Chloro-2-(3-methyl-1,2,4-triazol-1-yl)-phenyl]-1-(1,1-dimethyl-propyl)-1H-benzimidazol-5-yl]-pyrimidin-2-ylamine |
| 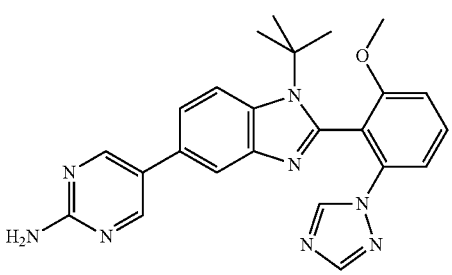 [SMILES: COc1cccc(-n2cncn2)c1-c1nc2cc(-c3cnc(N)nc3)ccc2n1C(C)(C)C] | 5-[1-tert-Butyl-2-(2-methoxy-6-1,2,4-triazol-1-yl-phenyl)-1H-benzimidazol-5-yl]-pyrimidin-2-ylamine |
| 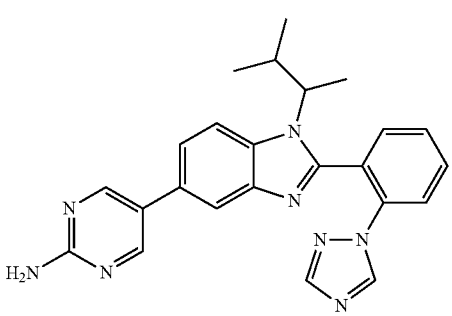 [SMILES: CC(C)C(C)n1c(-c2ccccc2-n2cncn2)nc2cc(-c3cnc(N)nc3)ccc21] | 5-[1-(1,2-Dimethyl-propyl)-2-(2-1,2,4-triazol-1-yl-phenyl)-1H-benzimidazol-5-yl]-pyrimidin-2-ylamine |

TABLE 1-continued

| Structure | Name |
|---|---|
| 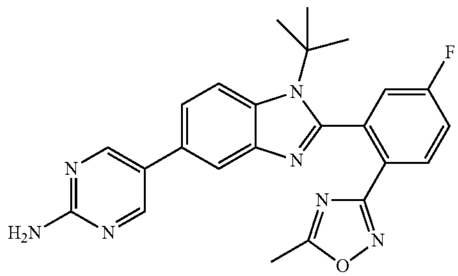 [SMILES: Cc1nc(-c2ccc(F)cc2-c2nc3cc(-c4cnc(N)nc4)ccc3n2C(C)(C)C)no1] | 5-{1-tert-Butyl-2-[5-fluoro-2-(5-methyl-[1,2,4]oxadiazol-3-yl)-phenyl]-1H-benzimidazol-5-yl}-pyrimidin-2-ylamine |
| 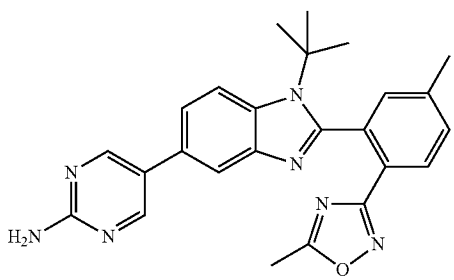 [SMILES: Cc1ccc(-c2noc(C)n2)c(-c2nc3cc(-c4cnc(N)nc4)ccc3n2C(C)(C)C)c1] | 5-{1-tert-Butyl-2-[5-methyl-2-(5-methyl-[1,2,4]oxadiazol-3-yl)-phenyl]-1H-benzimidazol-5-yl}-pyrimidin-2-ylamine |
| 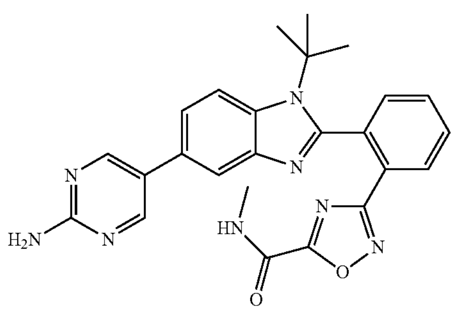 [SMILES: CNC(=O)c1nc(-c2ccccc2-c2nc3cc(-c4cnc(N)nc4)ccc3n2C(C)(C)C)no1] | 3-{2-[5-(2-Amino-pyrimidin-5-yl)-1-tert-butyl-1H-benzimidazol-2-yl]-4-methyl-phenyl}-[1,2,4]oxadiazole-5-carboxylic acid methylamide |
| 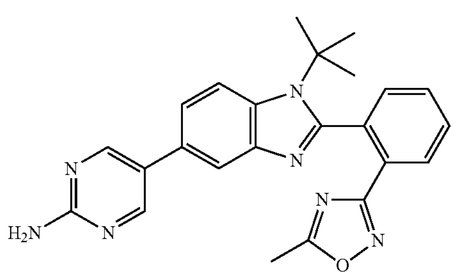 [SMILES: Cc1nc(-c2ccccc2-c2nc3cc(-c4cnc(N)nc4)ccc3n2C(C)(C)C)no1] | 5-{1-tert-Butyl-2-[2-(5-methyl-[1,2,4]oxadiazol-3-yl)-pheny]-1H-benzimidazol-5-yl}-pyrimidin-2-ylamine |
| 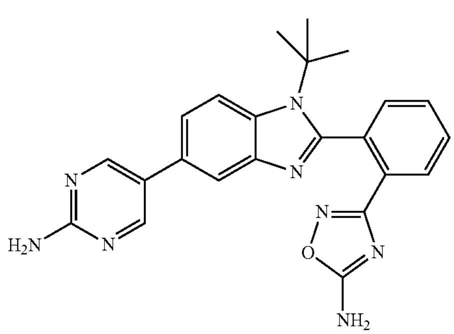 [SMILES: CC(C)(C)n1c(-c2ccccc2-c2noc(N)n2)nc2cc(-c3cnc(N)nc3)ccc21] | 5-{2-[2-(5-Amino-[1,2,4]oxadiazol-3-yl)-phenyl]-1-tert-butyl-1H-benzimidazol-5-yl}-pyrimidin-2-ylamine |

TABLE 1-continued

| Structure | Name |
|---|---|
| 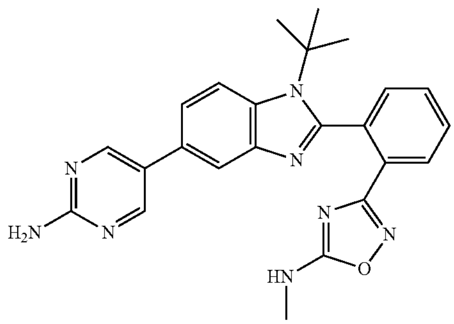 [SMILES: CNc1nc(-c2ccccc2-c2nc3cc(-c4cnc(N)nc4)ccc3n2C(C)(C)C)no1] | 5-{1-tert-Butyl-2-[2-(5-methylamino-[1,2,4]oxadiazol-3-yl)-phenyl]-1H-benzimidazol-5-yl}-pyrimidin-2-ylamine |
| 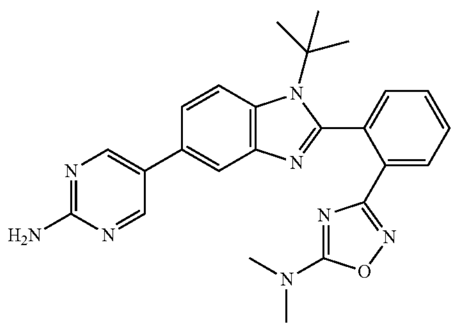 [SMILES: CN(C)c1nc(-c2ccccc2-c2nc3cc(-c4cnc(N)nc4)ccc3n2C(C)(C)C)no1] | 5-{1-tert-Butyl-2-[2-(5-dimethylamino-[1,2,4]oxadiazol-3-yl)-phenyl]-1H-benzimidazol-5-yl}-pyrimidin-2-ylamine |
| 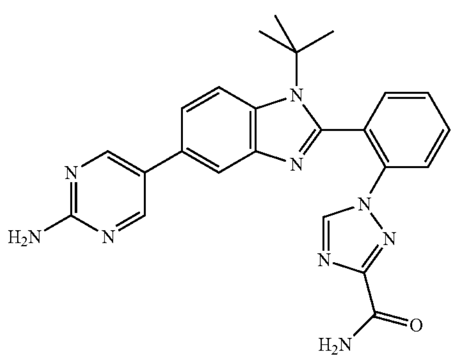 [SMILES: CC(C)(C)n1c(-c2ccccc2-n2cnc(C(N)=O)n2)nc2cc(-c3cnc(N)nc3)ccc21] | 1-{2-[5-(2-Amino-pyrimidin-5-yl)-1-tert-butyl-1H-benzimidazol-2-yl]-phenyl}-1H-1,2,4-triazole-3-carboxylic acid amide |
| 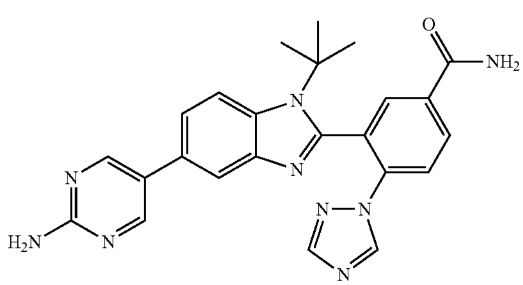 [SMILES: CC(C)(C)n1c(-c2cc(C(N)=O)ccc2-n2cncn2)nc2cc(-c3cnc(N)nc3)ccc21] | 3-[5-(2-Amino-pyrimidin-5-yl)-1-tert-butyl-1H-benzimidazol-2-yl]-4-1,2,4-triazol-1-yl-benzamide |
| 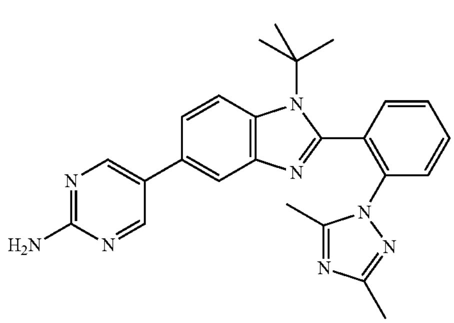 [SMILES: Cc1nc(C)n(-c2ccccc2-c2nc3cc(-c4cnc(N)nc4)ccc3n2C(C)(C)C)n1] | 5-{1-tert-Butyl-2-[2-(3,5-dimethyl-1,2,4-triazol-1-yl)-phenyl]-1H-benzimidazol-5-yl}-pyrimidin-2-ylamine |

TABLE 1-continued

| Structure | Name |
|---|---|
| 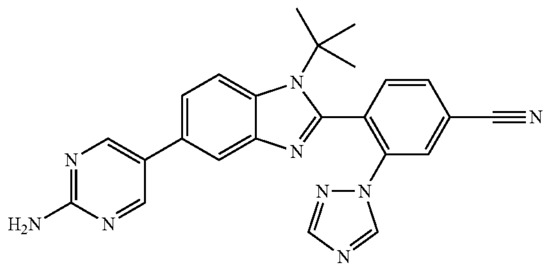 [SMILES: CC(C)(C)n1c(-c2ccc(C#N)cc2-n2cncn2)nc2cc(-c3cnc(N)nc3)ccc21] | 4-[5-(2-Amino-pyrimidin-5-yl)-1-tert-butyl-1H-benzimidazol-2-yl]-3-1,2,4-triazol-1-yl-benzonitrile |
| 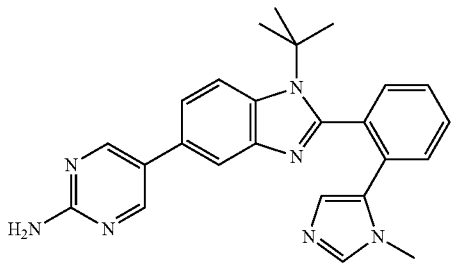 [SMILES: Cn1cncc1-c1ccccc1-c1nc2cc(-c3cnc(N)nc3)ccc2n1C(C)(C)C] | 5-{1-tert-Butyl-2-[2-(3-methyl-3H-imidazol-4-yl)-phenyl]-1H-benzimidazol-5-yl}-pyrimidin-2-ylamine |
| 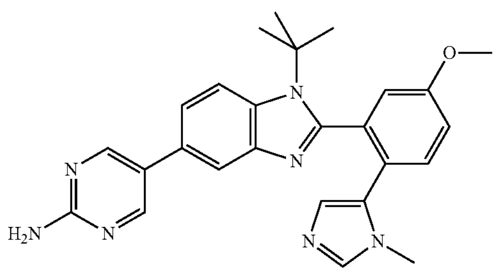 [SMILES: COc1ccc(-c2cncn2C)c(-c2nc3cc(-c4cnc(N)nc4)ccc3n2C(C)(C)C)c1] | 5-{1-tert-Butyl-2-[5-methoxy-2-(3-methyl-3H-imidazol-4-yl)-phenyl]-1H-benzimidazol-5-yl}-pyrimidin-2-ylamine |
| 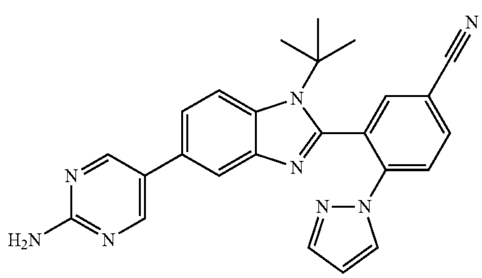 [SMILES: CC(C)(C)n1c(-c2cc(C#N)ccc2-n2cccn2)nc2cc(-c3cnc(N)nc3)ccc21] | 3-[5-(2-Amino-pyrimidin-5-yl)-1-tert-butyl-1H-benzimidazol-2-yl]-4-pyrazol-1-yl-benzonitrile |
| 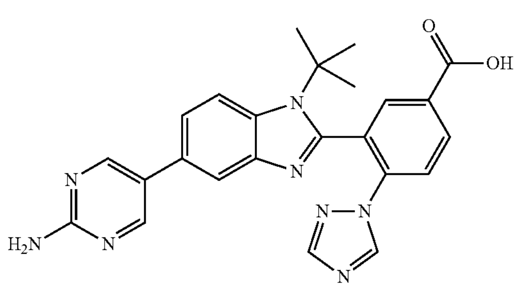 [SMILES: CC(C)(C)n1c(-c2cc(C(=O)O)ccc2-n2cncn2)nc2cc(-c3cnc(N)nc3)ccc21] | 3-[5-(2-Amino-pyrimidin-5-yl)-1-tert-butyl-1H-benzimidazol-2-yl]-4-1,2,4-triazol-1-yl-benzoic acid |

TABLE 1-continued

| Structure | Name |
|---|---|
| 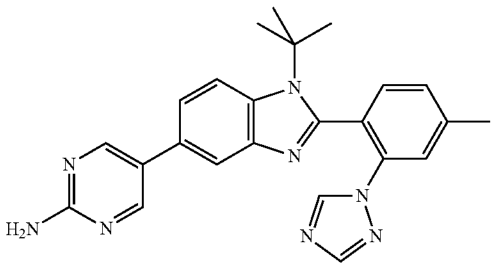 [SMILES: Cc1ccc(-c2nc3cc(-c4cnc(N)nc4)ccc3n2C(C)(C)C)c(-n2cncn2)c1] | 5-[1-tert-Butyl-2-(4-methyl-2-1,2,4-triazol-1-yl-phenyl)-1H-benzimidazol-5-yl]-pyrimidin-2-ylamine |
| 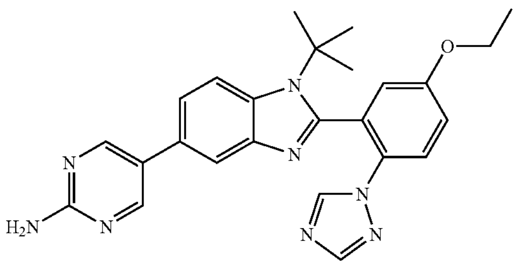 [SMILES: CCOc1ccc(-n2cncn2)c(-c2nc3cc(-c4cnc(N)nc4)ccc3n2C(C)(C)C)c1] | 5-[1-tert-Butyl-2-(5-ethoxy-2-1,2,4-triazol-1-yl-phenyl)-1H-benzimidazol-5-yl]-pyrimidin-2-ylamine |
| 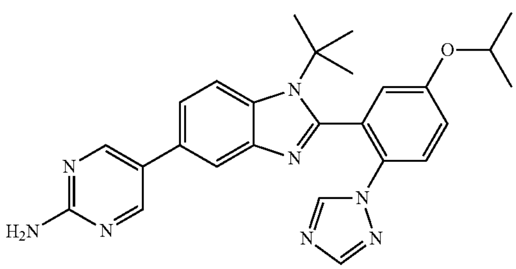 [SMILES: CC(C)Oc1ccc(-n2cncn2)c(-c2nc3cc(-c4cnc(N)nc4)ccc3n2C(C)(C)C)c1] | 5-[1-tert-Butyl-2-(5-isopropoxy-2-1,2,4-triazol-1-yl-phenyl)-1H-benzimidazol-5-yl]-pyrimidin-2-ylamine |
| 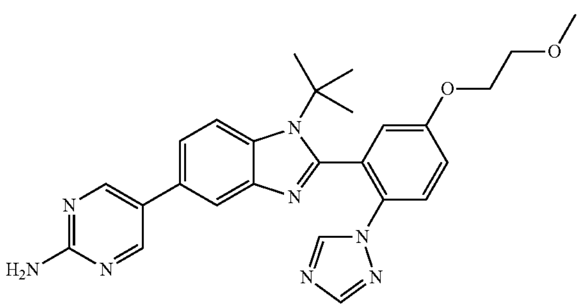 [SMILES: COCCOc1ccc(-n2cncn2)c(-c2nc3cc(-c4cnc(N)nc4)ccc3n2C(C)(C)C)c1] | 5-{1-tert-Butyl-2-[5-(2-methoxy-ethoxy)-2-1,2,4-triazol-1-yl-phenyl]-1H-benzimidazol-5-yl}-pyrimidin-2-ylamine |
| 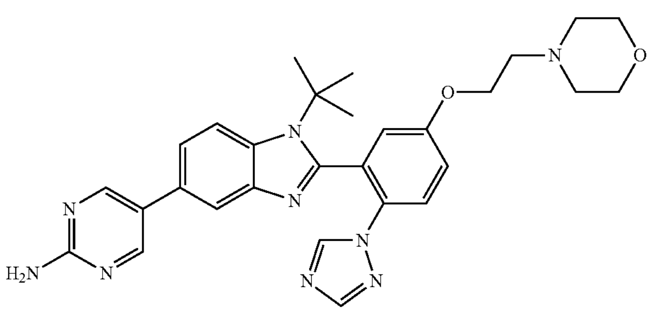 [SMILES: CC(C)(C)n1c(-c2cc(OCCN3CCOCC3)ccc2-n2cncn2)nc2cc(-c3cnc(N)nc3)ccc21] | 5-{1-tert-Butyl-2-[5-(2-morpholin-4-yl-ethoxy)-2-1,2,4-triazol-1-yl-phenyl]-1H-benzimidazol-5-yl}-pyrimidin-2-ylamine |

TABLE 1-continued

| Structure | Name |
|---|---|
| 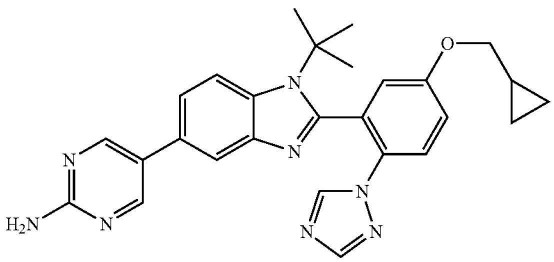 [SMILES: CC(C)(C)n1c(-c2cc(OCC3CC3)ccc2-n2cncn2)nc2cc(-c3cnc(N)nc3)ccc21] | 5-[1-tert-Butyl-2-(5-cyclopropylmethoxy-2-1,2,4-triazol-1-yl-phenyl)-1H-benzimidazol-5-yl]-pyrimidin-2-ylamine |
| 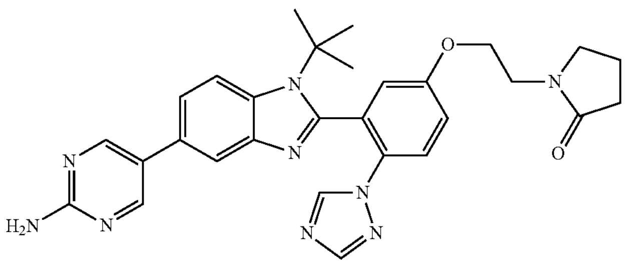 [SMILES: CC(C)(C)n1c(-c2cc(OCCN3CCCC3=O)ccc2-n2cncn2)nc2cc(-c3cnc(N)nc3)ccc21] | 1-(2-{3-[5-(2-Amino-pyrimidin-5-yl)-1-tert-butyl-1H-benzimidazol-2-yl]-4-1,2,4-triazol-1-yl-phenoxy}-ethyl)-pyrrolidin-2-one |
| 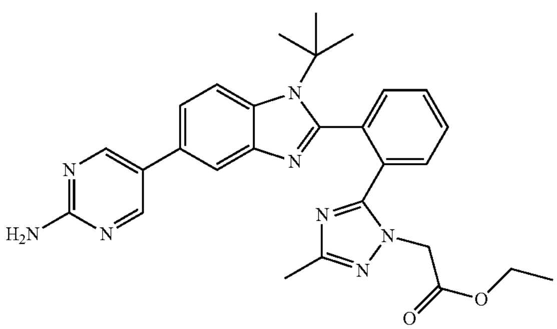 [SMILES: CCOC(=O)Cn1nc(C)nc1-c1ccccc1-c1nc2cc(-c3cnc(N)nc3)ccc2n1C(C)(C)C] | (5-{2-[5-(2-Amino-pyrimidin-5-yl)-1-tert-butyl-1H-benzimidazol-2-yl]-phenyl}-3-methyl-1,2,4-triazol-1-yl)-acetic acid ethyl ester |
| 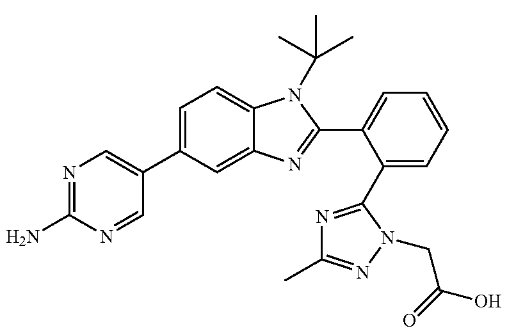 [SMILES: Cc1nc(-c2ccccc2-c2nc3cc(-c4cnc(N)nc4)ccc3n2C(C)(C)C)n(CC(=O)O)n1] | (5-{2-[5-(2-Amino-pyrimidin-5-yl)-1-tert-butyl-1H-benzimidazol-2-yl]-phenyl}-3-methyl-1,2,4-triazol-1-yl)-acetic acid |
| 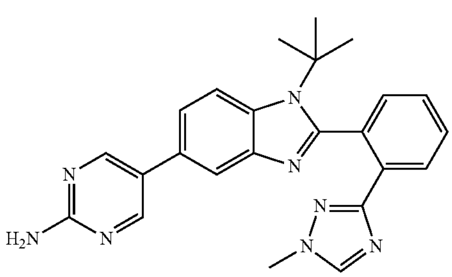 [SMILES: Cn1cnc(-c2ccccc2-c2nc3cc(-c4cnc(N)nc4)ccc3n2C(C)(C)C)n1] | 5-{1-tert-Butyl-2-[2-(1-methyl-1H-[1,2,4]triazol-3-yl)-phenyl]-1H-benzimidazol-5-yl}-pyrimidin-2-ylamine |

TABLE 1-continued

| Structure | Name |
|---|---|
| 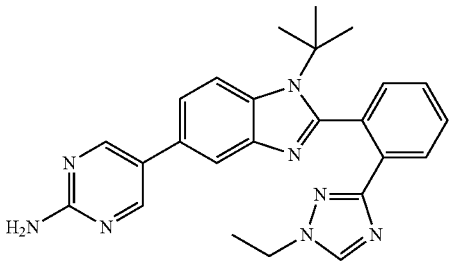 [SMILES: CCn1cnc(-c2ccccc2-c2nc3cc(-c4cnc(N)nc4)ccc3n2C(C)(C)C)n1] | 5-{1-tert-Butyl-2-[2-(1-ethyl-1H-[1,2,4]triazol-3-yl)-phenyl]-1H-benzimidazol-5-yl}-pyrimidin-2-ylamine |
| 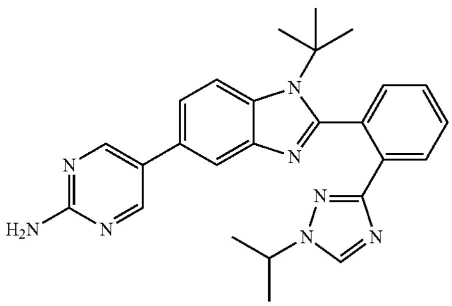 [SMILES: CC(C)n1cnc(-c2ccccc2-c2nc3cc(-c4cnc(N)nc4)ccc3n2C(C)(C)C)n1] | 5-{1-tert-Butyl-2-[2-(1-isopropyl-1H-[1,2,4]triazol-3-yl)-phenyl]-1H-benzimidazol-5-yl}-pyrimidin-2-ylamine |
| 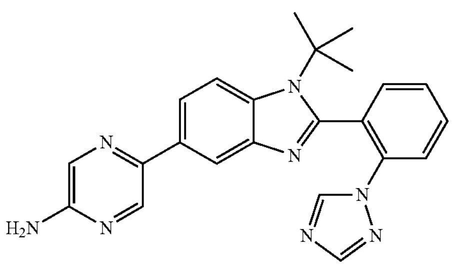 [SMILES: CC(C)(C)n1c(-c2ccccc2-n2cncn2)nc2cc(-c3cnc(N)cn3)ccc21] | 5-{1-tert-Butyl-2-[2-(1-methyl-1H-[1,2,4]triazol-3-yl)-phenyl]-1H-benzimidazol-5-yl}-pyrimidin-2-ylamine |
| 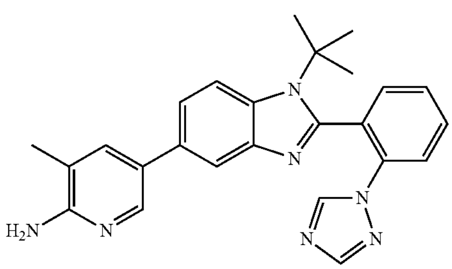 [SMILES: Cc1cc(-c2ccc3c(c2)nc(-c2ccccc2-n2cncn2)n3C(C)(C)C)cnc1N] | 5-[1-tert-Butyl-2-(2-[1,2,4]triazol-1-yl-phenyl)-1H-benzimidazol-5-yl]-3-methyl-pyridin-2-ylamine |
| 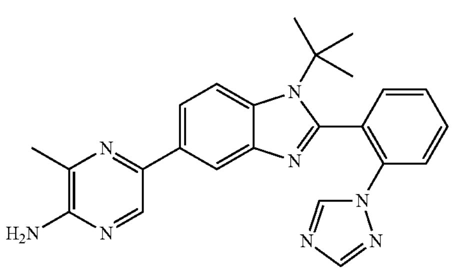 [SMILES: Cc1nc(-c2ccc3c(c2)nc(-c2ccccc2-n2cncn2)n3C(C)(C)C)cnc1N] | 5-[1-tert-Butyl-2-(2-[1,2,4]triazol-1-yl-phenyl)-1H-benzimidazol-5-yl]-3-methyl-pyrazin-2-ylamine |

TABLE 1-continued

| Structure | Name |
|---|---|
| 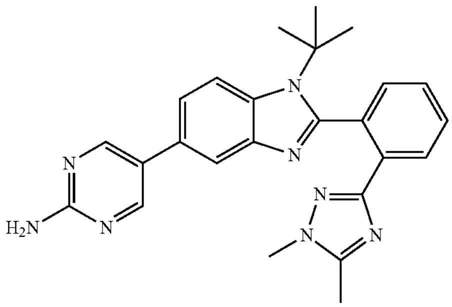 [SMILES: Cc1nc(-c2ccccc2-c2nc3cc(-c4cnc(N)nc4)ccc3n2C(C)(C)C)nn1C] | 5-{1-tert-Butyl-2-[2-(1,5-dimethyl-1H-[1,2,4]triazol-3-yl)-phenyl]-1H-benzimidazol-5-yl}-pyrimidin-2-ylamine |
| 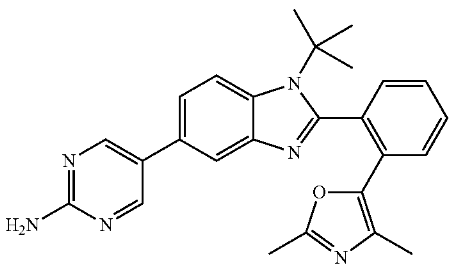 [SMILES: Cc1nc(C)c(-c2ccccc2-c2nc3cc(-c4cnc(N)nc4)ccc3n2C(C)(C)C)o1] | 5-{1-tert-Butyl-2-[2-(2,4-dimethyl-oxazol-5-yl)-phenyl]-1H-benzimidazol-5-yl}-pyrimidin-2-ylamine |
| 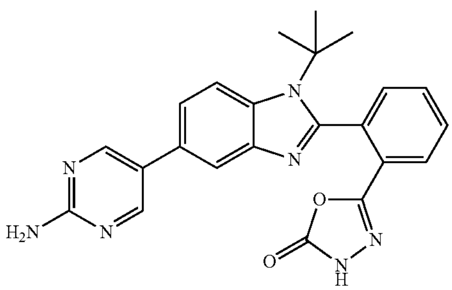 [SMILES: CC(C)(C)n1c(-c2ccccc2-c2n[nH]c(=O)o2)nc2cc(-c3cnc(N)nc3)ccc21] | 5-{2-[5-(2-Amino-pyrimidin-5-yl)-1-tert-butyl-1H-benzimidazol-2-yl]-phenyl}-3H-[1,3,4]oxadiazol-2-one |
| 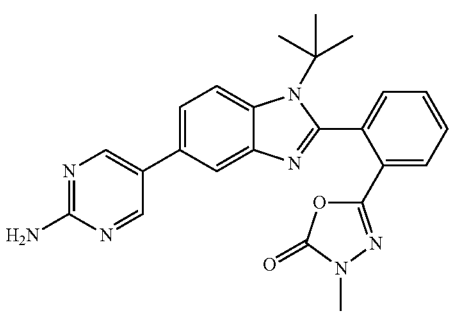 [SMILES: Cn1nc(-c2ccccc2-c2nc3cc(-c4cnc(N)nc4)ccc3n2C(C)(C)C)oc1=O] | 5-{2-[5-(2-Amino-pyrimidin-5-yl)-1-tert-butyl-1H-benzimidazol-2-yl]-phenyl}-3-methyl-3H-[1,3,4]oxadiazol-2-one |
| 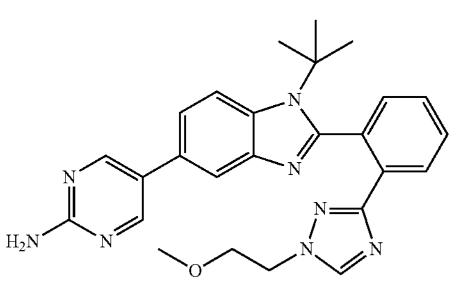 [SMILES: COCCn1cnc(-c2ccccc2-c2nc3cc(-c4cnc(N)nc4)ccc3n2C(C)(C)C)n1] | 5-(1-tert-Butyl-2-{2-[1-(2-methoxy-ethyl)-1H-[1,2,4]triazol-3-yl]-phenyl}-1H-benzoimidazol-5-yl)-pyrimidin-2-ylamine |

TABLE 1-continued

| Structure | Name |
|---|---|
| 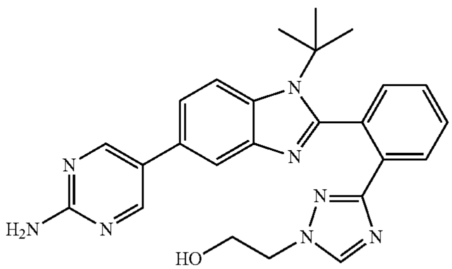 [SMILES: CC(C)(C)n1c(-c2ccccc2-c2ncn(CCO)n2)nc2cc(-c3cnc(N)nc3)ccc21] | 2-(3-{2-[5-(2-Amino-pyrimidin-5-yl)-1-tert-butyl-1H-benzoimidazol-2-yl]-phenyl}-[1,2,4]triazol-1-yl)-ethanol |
| 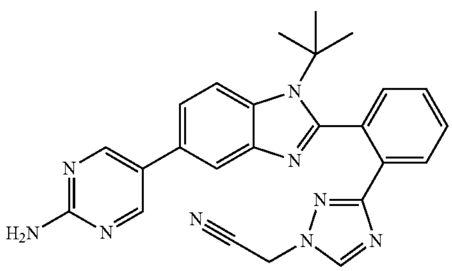 [SMILES: CC(C)(C)n1c(-c2ccccc2-c2ncn(CC#N)n2)nc2cc(-c3cnc(N)nc3)ccc21] | (3-{2-[5-(2-Amino-pyrimidin-5-yl)-1-tert-butyl-1H-benzoimidazol-2-yl]-phenyl}-[1,2,4]triazol-1-yl)-acetonitrile |
| 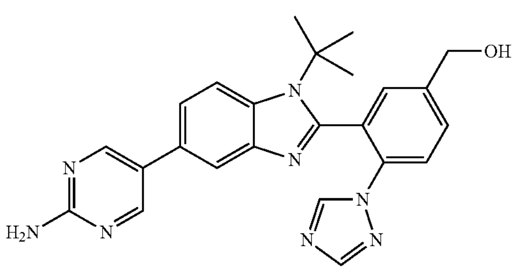 [SMILES: CC(C)(C)n1c(-c2cc(CO)ccc2-n2cncn2)nc2cc(-c3cnc(N)nc3)ccc21] | {3-[5-(2-Amino-pyrimidin-5-yl)-1-tert-butyl-1H-benzoimidazol-2-yl]-4-[1,2,4]triazol-1-yl-phenyl}-methanol |
| 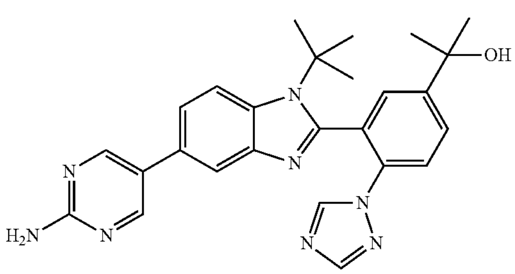 [SMILES: CC(C)(O)c1ccc(-n2cncn2)c(-c2nc3cc(-c4cnc(N)nc4)ccc3n2C(C)(C)C)c1] | 2-{3-[5-(2-Amino-pyrimidin-5-yl)-1-tert-butyl-1H-benzoimidazol-2-yl]-4-[1,2,4]triazol-1-yl-phenyl}-propan-2-ol |
| 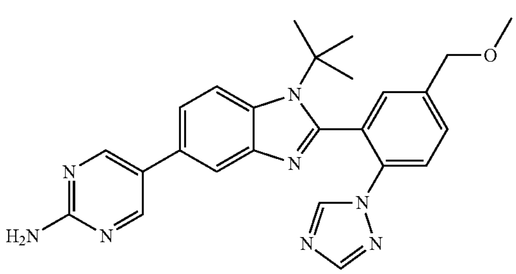 [SMILES: COCc1ccc(-n2cncn2)c(-c2nc3cc(-c4cnc(N)nc4)ccc3n2C(C)(C)C)c1] | 5-[1-tert-Butyl-2-(5-methoxymethyl-2-[1,2,4]triazol-1-yl-phenyl)-1H-benzoimidazol-5-yl]-pyrimidin-2-ylamine |

TABLE 1-continued

| Structure | Name |
|---|---|
| 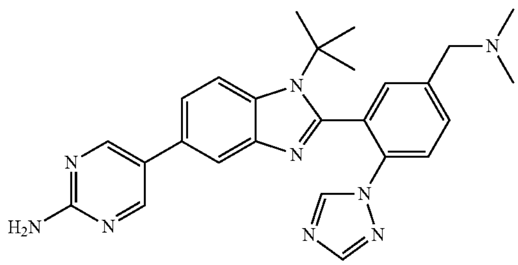 [SMILES: CN(C)Cc1ccc(-n2cncn2)c(-c2nc3cc(-c4cnc(N)nc4)ccc3n2C(C)(C)C)c1] | 5-[1-tert-Butyl-2-(5-dimethylaminomethyl-2-[1,2,4]triazol-1-yl-phenyl)-1H-benzoimidazol-5-yl]-pyrimidin-2-ylamine |
| 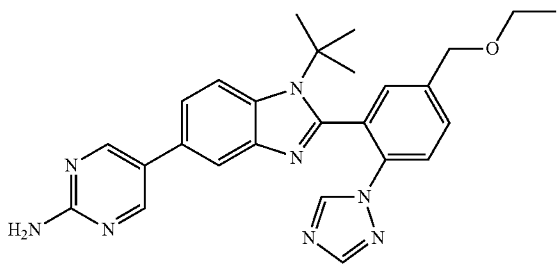 [SMILES: CCOCc1ccc(-n2cncn2)c(-c2nc3cc(-c4cnc(N)nc4)ccc3n2C(C)(C)C)c1] | 5-[1-tert-Butyl-2-(5-ethoxymethyl-2-[1,2,4]triazol-1-yl-phenyl)-1H-benzoimidazol-5-yl]-pyrimidin-2-ylamine |
| 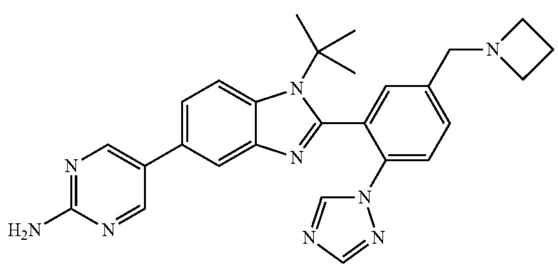 [SMILES: CC(C)(C)n1c(-c2cc(CN3CCC3)ccc2-n2cncn2)nc2cc(-c3cnc(N)nc3)ccc21] | 5-[2-(5-Azetidin-1-ylmethyl-2-[1,2,4]triazol-1-yl-phenyl)-1-tert-butyl-1H-benzoimidazol-5-yl]-pyrimidin-2-ylamine |
| 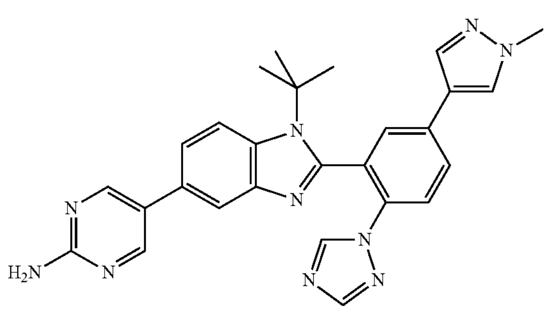 [SMILES: Cn1cc(-c2ccc(-n3cncn3)c(-c3nc4cc(-c5cnc(N)nc5)ccc4n3C(C)(C)C)c2)cn1] | 5-{1-tert-Butyl-2-[5-(1-methyl-1H-pyrazol-4-yl)-2-[1,2,4]triazol-1-yl-phenyl]-1H-benzoimidazol-5-yl}-pyrimidin-2-ylamine |
| 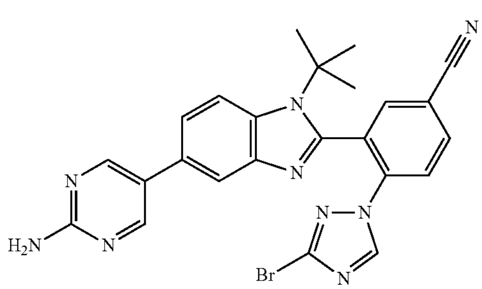 [SMILES: CC(C)(C)n1c(-c2cc(C#N)ccc2-n2cnc(Br)n2)nc2cc(-c3cnc(N)nc3)ccc21] | 3-[5-(2-Amino-pyrimidin-5-yl)-1-tert-butyl-1H-benzoimidazol-2-yl]-4-(3-bromo-[1,2,4]triazol-1-yl)-benzonitrile |

TABLE 1-continued

| Structure | Name |
|---|---|
| 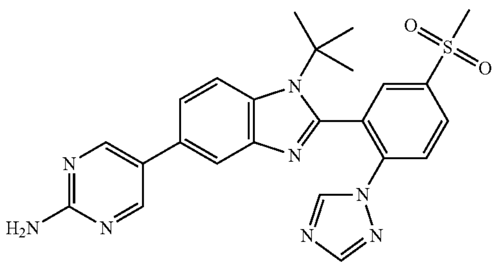 [SMILES: CC(C)(C)n1c(-c2cc(S(C)(=O)=O)ccc2-n2cncn2)nc2cc(-c3cnc(N)nc3)ccc21] | 5-[1-tert-Butyl-2-(5-methanesulfonyl-2-[1,2,4]triazol-1-yl-phenyl)-1H-benzoimidazol-5-yl]-pyrimidin-2-ylamine |
| 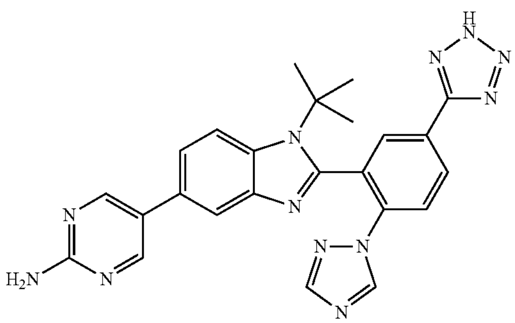 [SMILES: CC(C)(C)n1c(-c2cc(-c3nn[nH]n3)ccc2-n2cncn2)nc2cc(-c3cnc(N)nc3)ccc21] | 5-{1-tert-Butyl-2-[5-(2H-tetrazol-5-yl)-2-[1,2,4]triazol-1-yl-phenyl]-1H-benzoimidazol-5-yl}-pyrimidin-2-ylamine |
| 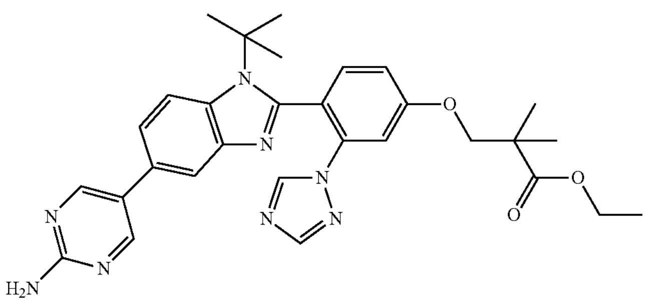 [SMILES: CCOC(=O)C(C)(C)COc1ccc(-c2nc3cc(-c4cnc(N)nc4)ccc3n2C(C)(C)C)c(-n2cncn2)c1] | 3-{4-[5-(2-Amino-pyrimidin-5-yl)-1-tert-butyl-1H-benzoimidazol-2-yl]-3-[1,2,4]triazol-1-yl-phenoxy}-2,2-dimethyl-propionic acid ethyl ester |
| 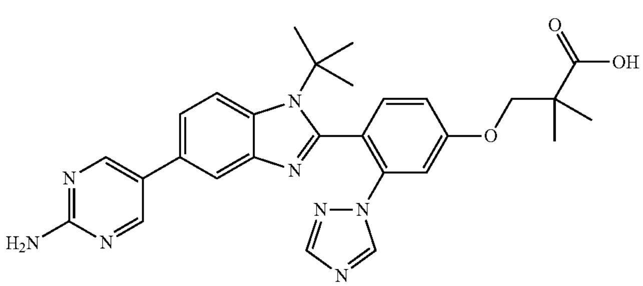 [SMILES: CC(C)(COc1ccc(-c2nc3cc(-c4cnc(N)nc4)ccc3n2C(C)(C)C)c(-n2cncn2)c1)C(=O)O] | 3-{4-[5-(2-Amino-pyrimidin-5-yl)-1-tert-butyl-1H-benzoimidazol-2-yl]-3-[1,2,4]triazol-1-yl-phenoxy}-2,2-dimethyl-propionic acid |
| 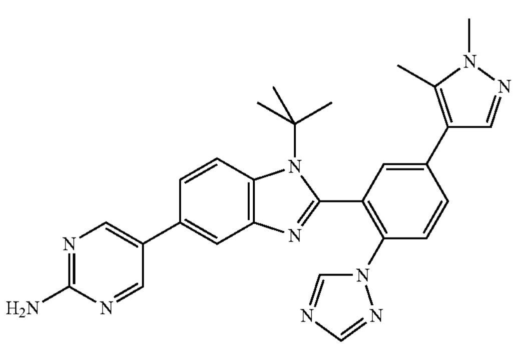 [SMILES: Cc1c(-c2ccc(-n3cncn3)c(-c3nc4cc(-c5cnc(N)nc5)ccc4n3C(C)(C)C)c2)cnn1C] | 5-{1-tert-Butyl-2-[5-(1,5-dimethyl-1H-pyrazol-4-yl)-2-[1,2,4]triazol-1-yl-phenyl]-1H-benzoimidazol-5-yl}-pyrimidin-2-ylamine |

TABLE 1-continued

| Structure | Name |
|---|---|
| 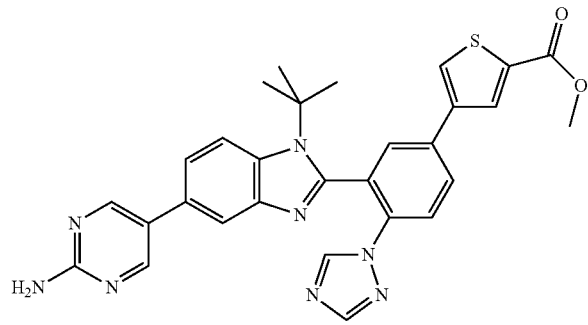 | 4-{3-[5-(2-Amino-pyrimidin-5-yl)-1-tert-butyl-1H-benzoimidazol-2-yl]-4-[1,2,4]triazol-1-yl-phenyl}-thiophene-2-carboxylic acid methyl ester |
| 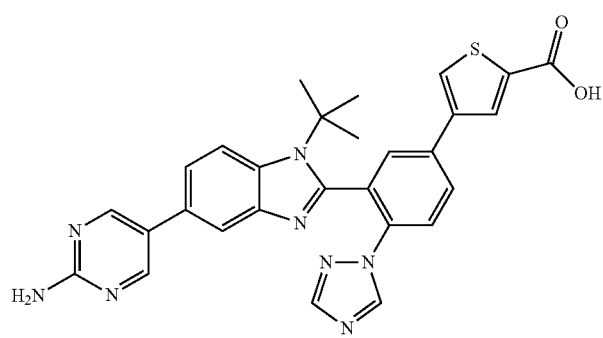 [SMILES: CC(C)(C)n1c(-c2cc(-c3csc(C(=O)O)c3)ccc2-n2cncn2)nc2cc(-c3cnc(N)nc3)ccc21] | 4-{3-[5-(2-Amino-pyrimidin-5-yl)-1-tert-butyl-1H-benzoimidazol-2-yl]-4-[1,2,4]triazol-1-yl-phenyl}-thiophene-2-carboxylic acid |
| 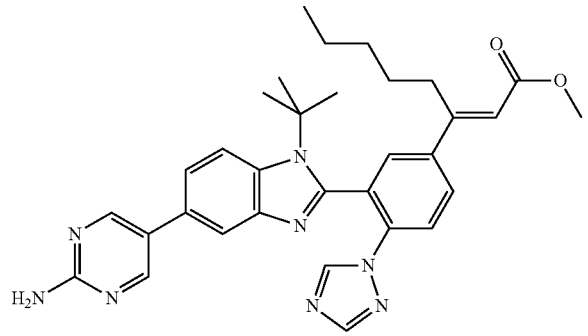 [SMILES: CCCCC/C(=C\C(=O)OC)c1ccc(-n2cncn2)c(-c2nc3cc(-c4cnc(N)nc4)ccc3n2C(C)(C)C)c1] | (E)-3-{3-[5-(2-Amino-pyrimidin-5-yl)-1-tert-butyl-1H-benzoimidazol-2-yl]-4-[1,2,4]triazol-1-yl-phenyl}-oct-2-enoic acid methyl ester |
| 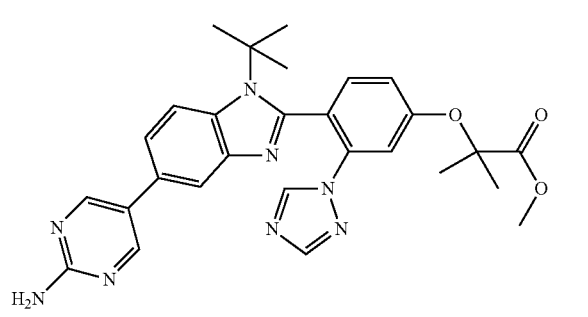 [SMILES: COC(=O)C(C)(C)Oc1ccc(-c2nc3cc(-c4cnc(N)nc4)ccc3n2C(C)(C)C)c(-n2cncn2)c1] | 2-{4-[5-(2-Amino-pyrimidin-5-yl)-1-tert-butyl-1H-benzoimidazol-2-yl]-3-[1,2,4]triazol-1-yl-phenoxy}-2-methyl-propionic acid methyl ester |
| 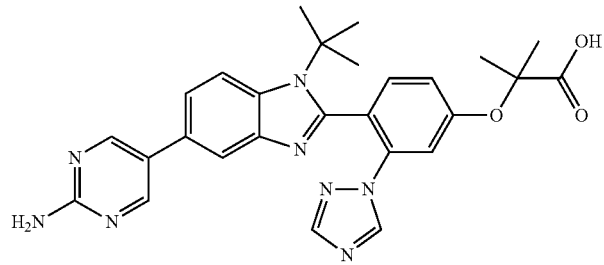 [SMILES: CC(C)(Oc1ccc(-c2nc3cc(-c4cnc(N)nc4)ccc3n2C(C)(C)C)c(-n2cncn2)c1)C(=O)O] | 2-{4-[5-(2-Amino-pyrimidin-5-yl)-1-tert-butyl-1H-benzoimidazol-2-yl]-3-[1,2,4]triazol-1-yl-phenoxy}-2-methyl-propionic acid |

TABLE 1-continued

| Structure | Name |
|---|---|
| 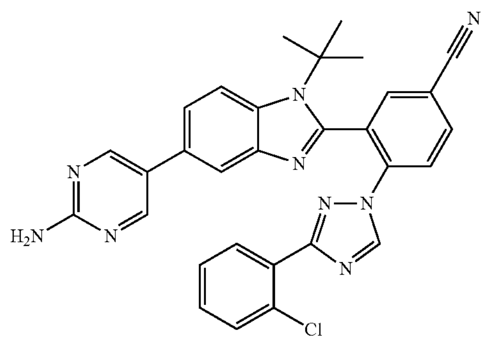 [SMILES: CC(C)(C)n1c(-c2cc(C#N)ccc2-n2cnc(-c3ccccc3Cl)n2)nc2cc(-c3cnc(N)nc3)ccc21] | 3-[5-(2-Amino-pyrimidin-5-yl)-1-tert-butyl-1H-benzoimidazol-2-yl]-4-[3-(2-chloro-phenyl)-[1,2,4]triazol-1-yl]-benzonitrile |
| 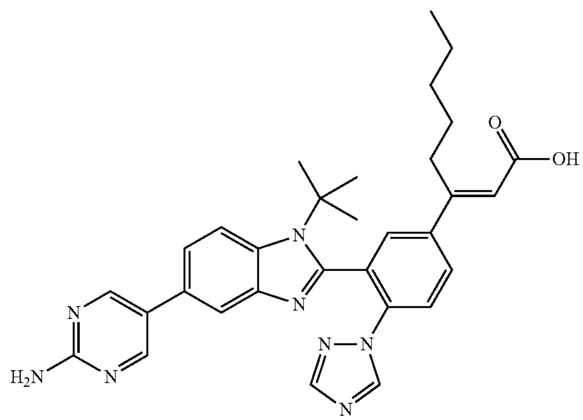 [SMILES: CCCCC/C(=C\C(=O)O)c1ccc(-n2cncn2)c(-c2nc3cc(-c4cnc(N)nc4)ccc3n2C(C)(C)C)c1] | (E)-3-{3-[5-(2-Amino-pyrimidin-5-yl)-1-tert-butyl-1H-benzoimidazol-2-yl]-4-[1,2,4]triazol-1-yl-phenyl}-oct-2-enoic acid |
| 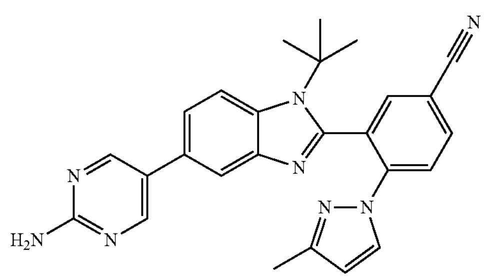 [SMILES: Cc1ccn(-c2ccc(C#N)cc2-c2nc3cc(-c4cnc(N)nc4)ccc3n2C(C)(C)C)n1] | 3-[5-(2-Amino-pyrimidin-5-yl)-1-tert-butyl-1H-benzoimidazol-2-yl]-4-(3-methyl-pyrazol-1-yl)-benzonitrile |
| 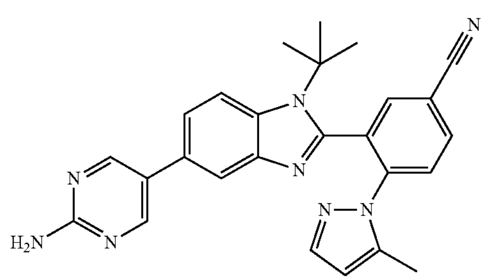 [SMILES: Cc1ccnn1-c1ccc(C#N)cc1-c1nc2cc(-c3cnc(N)nc3)ccc2n1C(C)(C)C] | 3-[5-(2-Amino-pyrimidin-5-yl)-1-tert-butyl-1H-benzoimidazol-2-yl]-4-(5-methyl-pyrazol-1-yl)-benzonitrile |
| 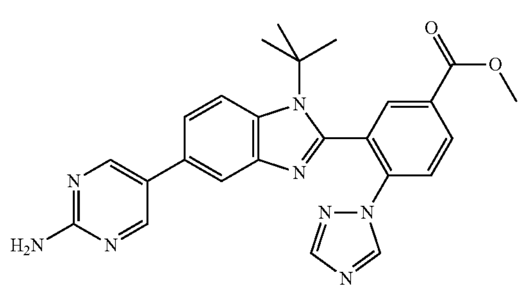 [SMILES: COC(=O)c1ccc(-n2cncn2)c(-c2nc3cc(-c4cnc(N)nc4)ccc3n2C(C)(C)C)c1] | 3-[5-(2-Amino-pyrimidin-5-yl)-1-tert-butyl-1H-benzoimidazol-2-yl]-4-[1,2,4]triazol-1-yl-benzoic acid methyl ester |

TABLE 1-continued

| Structure | Name |
|---|---|
| 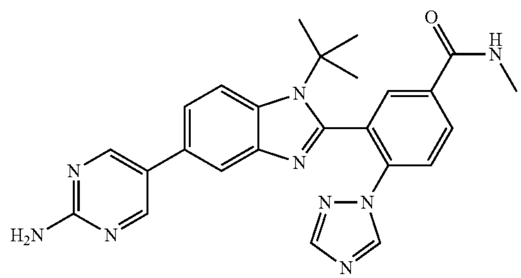 [SMILES: CNC(=O)c1ccc(-n2cncn2)c(-c2nc3cc(-c4cnc(N)nc4)ccc3n2C(C)(C)C)c1] | 3-[5-(2-Amino-pyrimidin-5-yl)-1-tert-butyl-1H-benzoimidazol-2-yl]-N-methyl-4-[1,2,4]triazol-1-yl-benzamide |
| 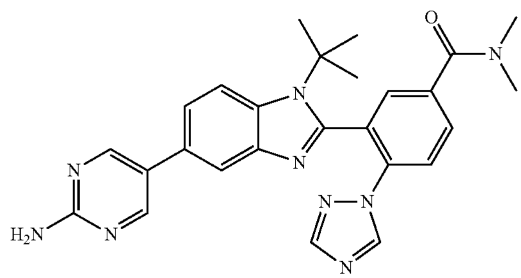 [SMILES: CN(C)C(=O)c1ccc(-n2cncn2)c(-c2nc3cc(-c4cnc(N)nc4)ccc3n2C(C)(C)C)c1] | 3-[5-(2-Amino-pyrimidin-5-yl)-1-tert-butyl-1H-benzoimidazol-2-yl]-N,N-dimethyl-4-[1,2,4]triazol-1-yl-benzamide |
| 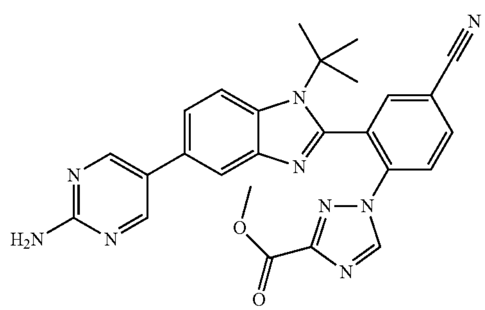 [SMILES: COC(=O)c1ncn(-c2ccc(C#N)cc2-c2nc3cc(-c4cnc(N)nc4)ccc3n2C(C)(C)C)n1] | 1-{2-[5-(2-Amino-pyrimidin-5-yl)-1-tert-butyl-1H-benzoimidazol-2-yl]-4-cyano-phenyl}-1H-[1,2,4]triazole-3-carboxylic acid methyl ester |
| 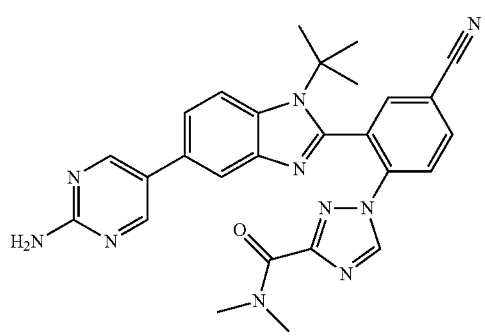 [SMILES: CN(C)C(=O)c1ncn(-c2ccc(C#N)cc2-c2nc3cc(-c4cnc(N)nc4)ccc3n2C(C)(C)C)n1] | 1-{2-[5-(2-Amino-pyrimidin-5-yl)-1-tert-butyl-1H-benzoimidazol-2-yl]-4-cyano-phenyl}-1H-[1,2,4]triazole-3-carboxylic acid dimethylamide |
| 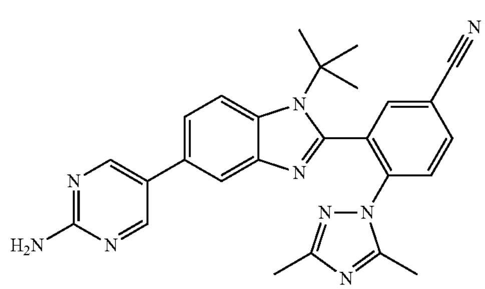 [SMILES: Cc1nc(C)n(-c2ccc(C#N)cc2-c2nc3cc(-c4cnc(N)nc4)ccc3n2C(C)(C)C)n1] | 3-[5-(2-Amino-pyrimidin-5-yl)-1-tert-butyl-1H-benzoimidazol-2-yl]-4-(3,5-dimethyl-[1,2,4]triazol-1-yl)-benzonitrile |

TABLE 1-continued

| Structure | Name |
|---|---|
| 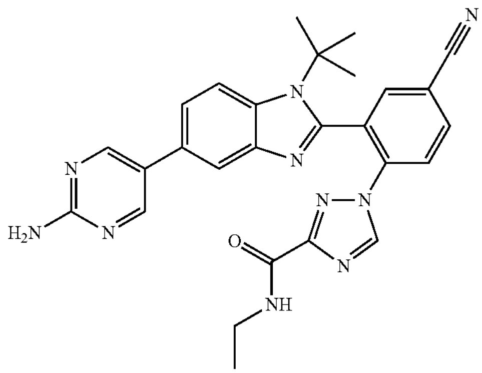 [SMILES: CCNC(=O)c1ncn(-c2ccc(C#N)cc2-c2nc3cc(-c4cnc(N)nc4)ccc3n2C(C)(C)C)n1] | 1-{2-[5-(2-Amino-pyrimidin-5-yl)-1-tert-butyl-1H-benzoimidazol-2-yl]-4-cyano-phenyl}-1H-[1,2,4]triazole-3-carboxylic acid ethylamide |
| 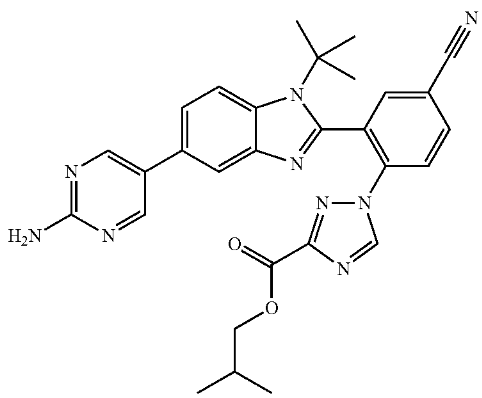 [SMILES: CC(C)COC(=O)c1ncn(-c2ccc(C#N)cc2-c2nc3cc(-c4cnc(N)nc4)ccc3n2C(C)(C)C)n1] | 1-{2-[5-(2-Amino-pyrimidin-5-yl)-1-tert-butyl-1H-benzoimidazol-2-yl]-4-cyano-phenyl}-1H-[1,2,4]triazole-3-carboxylic acid isobutyl ester |
| 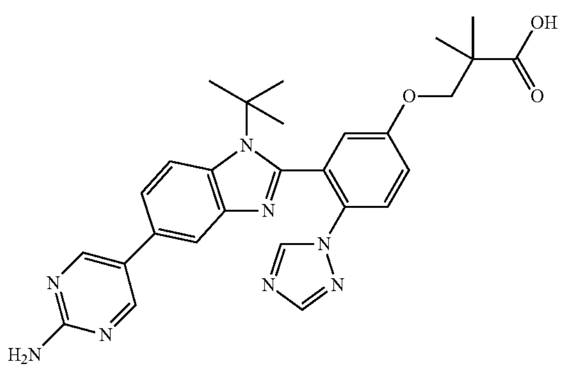 [SMILES: CC(C)(COc1ccc(-n2cncn2)c(-c2nc3cc(-c4cnc(N)nc4)ccc3n2C(C)(C)C)c1)C(=O)O] | 3-{3-[5-(2-Amino-pyrimidin-5-yl)-1-tert-butyl-1H-benzimidazol-2-yl]-4-1,2,4-triazol-1-yl-phenoxy}-2,2-dimethyl-propionic acid |
| 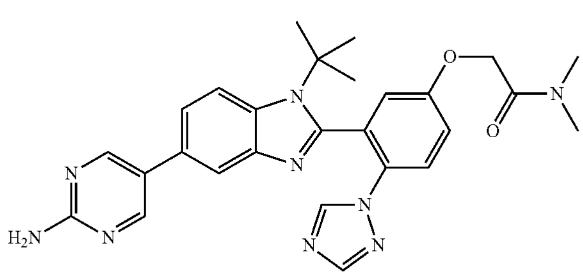 [SMILES: CN(C)C(=O)COc1ccc(-n2cncn2)c(-c2nc3cc(-c4cnc(N)nc4)ccc3n2C(C)(C)C)c1] | 2-{3-[5-(2-Amino-pyrimidin-5-yl)-1-tert-butyl-1H-benzimidazol-2-yl]-4-1,2,4-triazol-1-yl-phenoxy}-N,N-dimethyl-acetamide |

TABLE 1-continued

| Structure | Name |
|---|---|
| 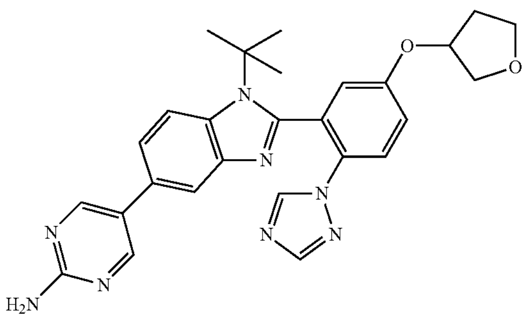 [SMILES: CC(C)(C)n1c(-c2cc(OC3CCOC3)ccc2-n2cncn2)nc2cc(-c3cnc(N)nc3)ccc21] | 5-{1-tert-Butyl-2-[5-(tetrahydro-furan-3-yloxy)-2-1,2,4-triazol-1-yl-phenyl]-1H-benzimidazol-5-yl}-pyrimidin-2-ylamine |
| 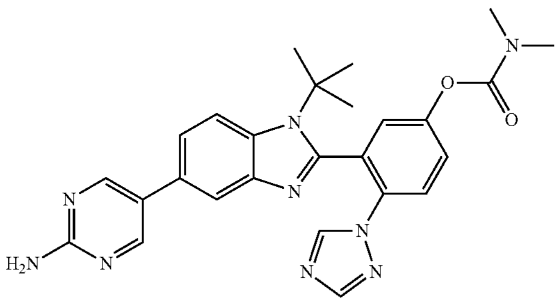 [SMILES: CN(C)C(=O)Oc1ccc(-n2cncn2)c(-c2nc3cc(-c4cnc(N)nc4)ccc3n2C(C)(C)C)c1] | Dimethyl-carbamic acid 3-[5-(2-amino-pyrimidin-5-yl)-1-tert-butyl-1H-benzimidazol-2-yl]-4-1,2,4-triazol-1-yl-phenyl ester |
| 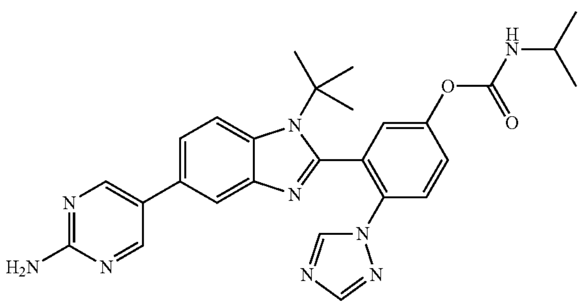 [SMILES: CC(C)NC(=O)Oc1ccc(-n2cncn2)c(-c2nc3cc(-c4cnc(N)nc4)ccc3n2C(C)(C)C)c1] | Isopropyl-carbamic acid 3-[5-(2-amino-pyrimidin-5-yl)-1-tert-butyl-1H-benzimidazol-2-yl]-4-1,2,4-triazol-1-yl-phenyl ester |
| 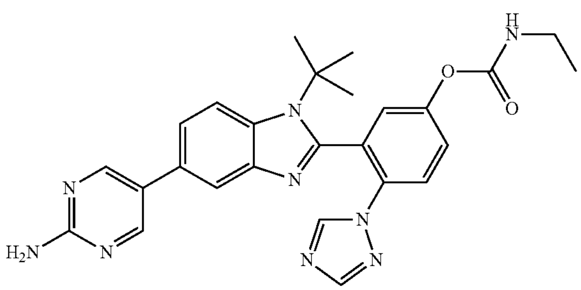 [SMILES: CCNC(=O)Oc1ccc(-n2cncn2)c(-c2nc3cc(-c4cnc(N)nc4)ccc3n2C(C)(C)C)c1] | Ethyl-carbamic acid 3-[5-(2-amino-pyrimidin-5-yl)-1-tert-butyl-1H-benzimidazol-2-yl]-4-1,2,4-triazol-1-yl-phenyl ester |
| 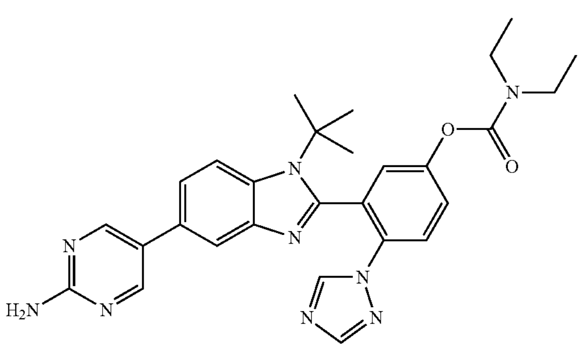 [SMILES: CCN(CC)C(=O)Oc1ccc(-n2cncn2)c(-c2nc3cc(-c4cnc(N)nc4)ccc3n2C(C)(C)C)c1] | Diethyl-carbamic acid 3-[5-(2-amino-pyrimidin-5-yl)-1-tert-butyl-1H-benzimidazol-2-yl]-4-1,2,4-triazol-1-yl-phenyl ester |

TABLE 1-continued

| Structure | Name |
|---|---|
| 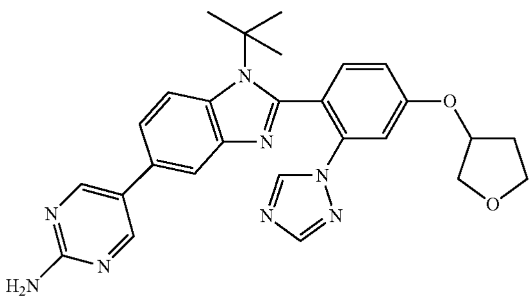 [SMILES: CC(C)(C)n1c(-c2ccc(OC3CCOC3)cc2-n2cncn2)nc2cc(-c3cnc(N)nc3)ccc21] | 5-{1-tert-Butyl-2-[4-(tetrahydro-furan-3-yloxy)-2-1,2,4-triazol-1-yl-phenyl]-1H-benzimidazol-5-yl}-pyrimidin-2-ylamine |
| 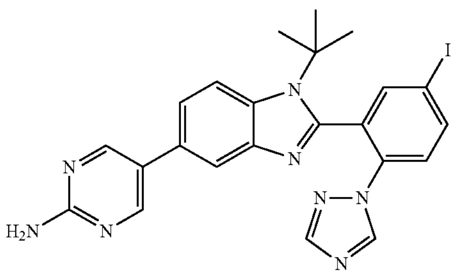 [SMILES: CC(C)(C)n1c(-c2cc(I)ccc2-n2cncn2)nc2cc(-c3cnc(N)nc3)ccc21] | 5-[1-tert-Butyl-2-(5-iodo-2-1,2,4-triazol-1-yl-phenyl)-1H-benzimidazol-5-yl]-pyrimidin-2-ylamine |
| 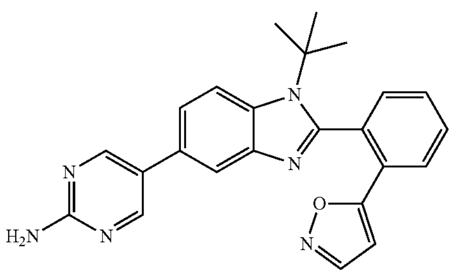 [SMILES: CC(C)(C)n1c(-c2ccccc2-c2ccno2)nc2cc(-c3cnc(N)nc3)ccc21] | 5-[1-tert-butyl-2-(2-isoxazol-5-yl-phenyl)-1H-benzoimidazol-5-yl]-pyrimidin-2-ylamine |

In one embodiment, the invention relates to any of the compounds depicted in Table 1 above and the pharmaceutically acceptable salts thereof.

In another embodiment, the invention relates to any of the compounds in the group consisting of:

1-tert-Butyl-2-[2-(3-methyl-[1,2,4]oxadiazol-5-yl)-phenyl]-5-(1H-pyrrolo[2,3-b]pyridin-5-yl)-1H-benzimidazole;

1-tert-Butyl-2-(5-methoxy-2-pyrazol-1-yl-phenyl)-5-(1H-pyrrolo[2,3-b]pyridin-5-yl)-1H-benzimidazole;

1-tert-Butyl-5-(2,3-dihydro-1H-pyrrolo[2,3-b]pyridin-5-yl)-2-(5-methoxy-2-pyrazol-1-yl-phenyl)-1H-benzimidazole;

5-{1-tert-Butyl-2-[5-chloro-2-(2-methyl-thiazol-4-yl)-phenyl]-1H-benzimidazol-5-yl}-pyrimidin-2-ylamine;

5-[1-tert-Butyl-2-(5-methyl-2-pyrazol-1-yl-phenyl)-1H-benzimidazol-5-yl]-pyrimidin-2-ylamine;

5-[1-tert-Butyl-2-(5-chloro-2-pyrazol-1-yl-phenyl)-1H-benzimidazol-5-yl]-pyrimidin-2-ylamine;

1-tert-Butyl-5-(2,3-dihydro-1H-pyrrolo[2,3-b]pyridin-5-yl)-2-(2-[1,2,4]triazol-1-yl-phenyl)-1H-benzimidazole;

5-{1-tert-Butyl-2-[5-methoxy-2-(5-methyl-thiazol-2-yl)-phenyl]-1H-benzimidazol-5-yl}-pyrimidin-2-ylamine;

5-[1-tert-Butyl-2-(5-methoxy-2-pyrazol-1-yl-phenyl)-1H-benzimidazol-5-yl]-pyrimidin-2-ylamine;

5-[1-tert-Butyl-2-(5-fluoro-2-pyrazol-1-yl-phenyl)-1H-benzimidazol-5-yl]-pyrimidin-2-ylamine;

5-{1-tert-Butyl-2-[5-methoxy-2-(2-methyl-thiazol-4-yl)-phenyl]-1H-benzimidazol-5-yl}-pyrimidin-2-ylamine;

5-{1-tert-Butyl-2-[5-methoxy-2-(3-methyl-[1,2,4]thiadiazol-5-yl)-phenyl]-1H-benzimidazol-5-yl}-pyrimidin-2-ylamine;

5-{1-tert-Butyl-2-[2-(4-chloro-pyrazol-1-yl)-phenyl]-1H-benzimidazol-5-yl}-pyrimidin-2-ylamine;

5-[2-(5-Bromo-2-[1,2,4]triazol-1-yl-phenyl)-1-tert-butyl-1H-benzimidazol-5-yl]-pyrimidin-2-ylamine;

5-{1-tert-Butyl-2-[2-(2-methyl-2H-[1,2,4]triazol-3-yl)-phenyl]-1H-benzimidazol-5-yl}-pyrimidin-2-ylamine;

5-{1-tert-Butyl-2-[2-(3-trifluoromethyl-pyrazol-1-yl)-phenyl]-1H-benzimidazol-5-yl}-pyrimidin-2-ylamine;

5-[1-tert-Butyl-2-(5-methyl-2-[1,2,4]triazol-1-yl-phenyl)-1H-benzimidazol-5-yl]-pyrimidin-2-ylamine;

5-[1-tert-Butyl-2-(5-chloro-2-[1,2,4]triazol-1-yl-phenyl)-1H-benzimidazol-5-yl]-pyrimidin-2-ylamine;

5-{1-tert-Butyl-2-[5-chloro-2-(3-methyl-pyrazol-1-yl)-phenyl]-1H-benzimidazol-5-yl}-pyrimidin-2-ylamine;

5-{1-tert-Butyl-2-[5-methoxy-2-(3-methyl-pyrazol-1-yl)-phenyl]-1H-benzimidazol-5-yl}-pyrimidin-2-ylamine;

5-[1-tert-Butyl-2-(2-[1,2,3]triazol-2-yl-phenyl)-1H-benzimidazol-5-yl]-pyrimidin-2-ylamine;

5-[1-tert-Butyl-2-(2-thiazol-2-yl-phenyl)-1H-benzimidazol-5-yl]-pyrimidin-2-ylamine;

5-{1-tert-Butyl-2-[2-(4-chloro-pyrazol-1-yl)-5-methoxy-phenyl]-1H-benzimidazol-5-yl}-pyrimidin-2-ylamine;

5-{1-tert-Butyl-2-[5-methoxy-2-(4-methyl-pyrazol-1-yl)-phenyl]-1H-benzimidazol-5-yl}-pyrimidin-2-ylamine;

5-{1-tert-Butyl-2-[5-methoxy-2-(3-trifluoromethyl-pyrazol-1-yl)-phenyl]-1H-benzimidazol-5-yl}-pyrimidin-2-ylamine;
5-{1-tert-Butyl-2-[5-methyl-2-(3-methyl-[1,2,4]oxadiazol-5-yl)-phenyl]-1H-benzimidazol-5-yl}-pyrimidin-2-ylamine;
5-{1-tert-Butyl-2-[2-(3-methyl-pyrazol-1-yl)-phenyl]-1H-benzimidazol-5-yl}-pyrimidin-2-ylamine;
5-[1-tert-Butyl-2-(2-pyrazol-1-yl-5-trifluoromethyl-phenyl)-1H-benzimidazol-5-yl]-pyrimidin-2-ylamine;
5-[1-tert-Butyl-2-(5-fluoro-2-[1,2,4]triazol-1-yl-phenyl)-1H-benzimidazol-5-yl]-pyrimidin-2-ylamine;
5-{1-tert-Butyl-2-[2-(4-methyl-pyrazol-1-yl)-phenyl]-1H-benzimidazol-5-yl}-pyrimidin-2-ylamine;
5-[1-tert-Butyl-2-(5-methoxy-2-[1,2,4]triazol-1-yl-phenyl)-1H-benzimidazol-5-yl]-pyrimidin-2-ylamine;
5-[1-tert-Butyl-2-(2-pyrazol-1-yl-phenyl)-1H-benzimidazol-5-yl]-pyrimidin-2-ylamine;
5-{1-tert-Butyl-2-[2-(3-methyl-[1,2,4]triazol-1-yl)-phenyl]-1H-benzimidazol-5-yl}-pyrimidin-2-ylamine;
5-[1-tert-Butyl-2-(2-[1,2,4]triazol-1-yl-phenyl)-1H-benzimidazol-5-yl]-pyrimidin-2-ylamine;
5-{1-tert-Butyl-2-[2-(3-cyclopropyl-[1,2,4]oxadiazol-5-yl)-phenyl]-1H-benzimidazol-5-yl}-pyrimidin-2-ylamine;
5-{1-tert-Butyl-2-[2-(2-methyl-thiazol-4-yl)-phenyl]-1H-benzimidazol-5-yl}-pyrimidin-2-ylamine;
5-{1-tert-Butyl-2-[2-(3-methyl-[1,2,4]oxadiazol-5-yl)-phenyl]-1H-benzimidazol-5-yl}-pyrimidin-2-ylamine;
5-{1-tert-Butyl-2-[2-(2,4-dimethyl-thiazol-5-yl)-5-methoxy-phenyl]-1H-benzimidazol-5-yl}-pyrimidin-2-ylamine;
5-{1-tert-Butyl-2-[2-(3-methyl-[1,2,4]thiadiazol-5-yl)-phenyl]-1H-benzimidazol-5-yl}-pyrimidin-2-ylamine;
5-[1-tert-Butyl-2-(2-[1,2,4]triazol-1-yl-5-trifluoromethyl-phenyl)-1H-benzimidazol-5-yl]-pyrimidin-2-ylamine;
5-[1-tert-Butyl-2-(4-methoxy-2-[1,2,4]triazol-1-yl-phenyl)-1H-benzimidazol-5-yl]-pyrimidin-2-ylamine;
5-{1-tert-Butyl-2-[2-(5-methyl-[1,2,4]triazol-1-yl)-phenyl]-1H-benzimidazol-5-yl}-pyrimidin-2-ylamine;
5-{1-tert-Butyl-2-[5-methoxy-2-(3-methyl-[1,2,4]triazol-1-yl)-phenyl]-1H-benzimidazol-5-yl}-pyrimidin-2-ylamine;
5-{1-tert-Butyl-2-[5-chloro-2-(2,4-dimethyl-thiazol-5-yl)-phenyl]-1H-benzimidazol-5-yl}-pyrimidin-2-ylamine;
5-[1-tert-Butyl-2-(3-methoxy-2-[1,2,4]triazol-1-yl-phenyl)-1H-benzimidazol-5-yl]-pyrimidin-2-ylamine;
5-{1-tert-Butyl-2-[2-(2,4-dimethyl-thiazol-5-yl)-phenyl]-1H-benzimidazol-5-yl}-pyrimidin-2-ylamine;
5-[1-tert-Butyl-2-(2-[1,2,3]triazol-1-yl-phenyl)-1H-benzimidazol-5-yl]-pyrimidin-2-ylamine; and
5-{1-tert-Butyl-2-[5-methoxy-2-(5-methyl-[1,2,4]triazol-1-yl)-phenyl]-1H-benzimidazol-5-yl}-pyrimidin-2-ylamine;
5-{1-tert-Butyl-2-[5-methoxy-2-(3-methyl-[1,2,4]oxadiazol-5-yl)-phenyl]-1H-benzimidazol-5-yl}-pyrimidin-2-ylamine;
5-{1-tert-Butyl-2-[5-chloro-2-(3-methyl-[1,2,4]oxadiazol-5-yl)-phenyl]-1H-benzimidazol-5-yl}-pyrimidin-2-ylamine;
5-[1-tert-Butyl-2-(2-[1,2,4]triazol-1-yl-5-vinyl-phenyl)-1H-benzimidazol-5-yl]-pyrimidin-2-ylamine;
5-{1-tert-Butyl-2-[2-(2-methyl-2H-tetrazol-5-yl)-phenyl]-1H-benzimidazol-5-yl}-pyrimidin-2-ylamine;
5-{1-tert-Butyl-2-[2-(1,5-dimethyl-1H-[1,2,4]triazol-3-yl)-phenyl]-1H-benzimidazol-5-yl}-pyrimidin-2-ylamine;
5-{1-tert-Butyl-2-[5-chloro-2-(3-methyl-[1,2,4]triazol-1-yl)-phenyl]-1H-benzimidazol-5-yl}-pyrimidin-2-ylamine;
5-{1-tert-Butyl-2-[5-chloro-2-(5-methyl-[1,2,4]triazol-1-yl)-phenyl]-1H-benzimidazol-5-yl}-pyrimidin-2-ylamine;
5-{1-tert-Butyl-2-[4-chloro-2-(3-methyl-[1,2,4]oxadiazol-5-yl)-phenyl]-1H-benzimidazol-5-yl}-pyrimidin-2-ylamine;
3-[5-(2-Amino-pyrimidin-5-yl)-1-tert-butyl-1H-benzimidazol-2-yl]-4-[1,2,4]triazol-1-yl-benzonitrile;
5-[1-tert-Butyl-2-(4-chloro-2-[1,2,4]triazol-1-yl-phenyl)-1H-benzimidazol-5-yl]-pyrimidin-2-ylamine;
5-[1-tert-Butyl-2-(3-fluoro-2-[1,2,4]triazol-1-yl-phenyl)-1H-benzimidazol-5-yl]-pyrimidin-2-ylamine;
5-{1-tert-Butyl-2-[2-(1-ethyl-1H-[1,2,4]triazol-3-yl)-phenyl]-1H-benzimidazol-5-yl}-pyrimidin-2-ylamine;
5-[1-tert-Butyl-2-(3-chloro-2-[1,2,4]triazol-1-yl-phenyl)-1H-benzimidazol-5-yl]-pyrimidin-2-ylamine;
5-[1-tert-Butyl-2-(5-ethyl-2-1,2,4-triazol-1-yl-phenyl)-1H-benzimidazol-5-yl]-pyrimidin-2-ylamine;
5-(1-tert-Butyl-2-{2-[1-(2-methoxy-ethyl)-1H-[1,2,4]triazol-3-yl]-phenyl}-1H-benzoimidazol-5-yl)-pyrimidin-2-ylamine;
2-(3-{2-[5-(2-Amino-pyrimidin-5-yl)-1-tert-butyl-1H-benzoimidazol-2-yl]-phenyl}-[1,2,4]triazol-1-yl)-ethanol;
(3-{2-[5-(2-Amino-pyrimidin-5-yl)-1-tert-butyl-1H-benzoimidazol-2-yl]-phenyl}-[1,2,4]triazol-1-yl)-acetonitrile;
{3-[5-(2-Amino-pyrimidin-5-yl)-1-tert-butyl-1H-benzoimidazol-2-yl]-4-[1,2,4]triazol-1-yl-phenyl}-methanol;
2-{3-[5-(2-Amino-pyrimidin-5-yl)-1-tert-butyl-1H-benzoimidazol-2-yl]-4-[1,2,4]triazol-1-yl-phenyl}-propan-2-ol;
5-[1-tert-Butyl-2-(5-methoxymethyl-2-[1,2,4]triazol-1-yl-phenyl)-1H-benzoimidazol-5-yl]-pyrimidin-2-ylamine;
5-[1-tert-Butyl-2-(5-dimethylaminomethyl-2-[1,2,4]triazol-1-yl-phenyl)-1H-benzoimidazol-5-yl]-pyrimidin-2-ylamine;
5-[1-tert-Butyl-2-(5-ethoxymethyl-2-[1,2,4]triazol-1-yl-phenyl)-1H-benzoimidazol-5-yl]-pyrimidin-2-ylamine;
5-[2-(5-Azetidin-1-ylmethyl-2-[1,2,4]triazol-1-yl-phenyl)-1-tert-butyl-1H-benzoimidazol-5-yl]-pyrimidin-2-ylamine;
5-{1-tert-Butyl-2-[5-(1-methyl-1H-pyrazol-4-yl)-2-[1,2,4]triazol-1-yl-phenyl]-1H-benzoimidazol-5-yl}-pyrimidin-2-ylamine;
3-[5-(2-Amino-pyrimidin-5-yl)-1-tert-butyl-1H-benzoimidazol-2-yl]-4-(3-bromo-[1,2,4]triazol-1-yl)-benzonitrile;
5-[1-tert-Butyl-2-(5-methanesulfonyl-2-[1,2,4]triazol-1-yl-phenyl)-1H-benzoimidazol-5-yl]-pyrimidin-2-ylamine;
5-{1-tert-Butyl-2-[5-(2H-tetrazol-5-yl)-2-[1,2,4]triazol-1-yl-phenyl]-1H-benzoimidazol-5-yl}-pyrimidin-2-ylamine;
3-{4-[5-(2-Amino-pyrimidin-5-yl)-1-tert-butyl-1H-benzoimidazol-2-yl]-3-[1,2,4]triazol-1-yl-phenoxy}-2,2-dimethyl-propionic acid ethyl ester;
3-{4-[5-(2-Amino-pyrimidin-5-yl)-1-tert-butyl-1H-benzoimidazol-2-yl]-3-[1,2,4]triazol-1-yl-phenoxy}-2,2-dimethyl-propionic acid;
5-{1-tert-Butyl-2-[5-(1,5-dimethyl-1H-pyrazol-4-yl)-2-[1,2,4]triazol-1-yl-phenyl]-1H-benzoimidazol-5-yl}-pyrimidin-2-ylamine;
4-{3-[5-(2-Amino-pyrimidin-5-yl)-1-tert-butyl-1H-benzoimidazol-2-yl]-4-[1,2,4]triazol-1-yl-phenyl}-thiophene-2-carboxylic acid methyl ester;

4-{3-[5-(2-Amino-pyrimidin-5-yl)-1-tert-butyl-1H-benzoimidazol-2-yl]-4-[1,2,4]triazol-1-yl-phenyl}-thiophene-2-carboxylic acid;

(E)-3-{3-[5-(2-Amino-pyrimidin-5-yl)-1-tert-butyl-1H-benzoimidazol-2-yl]-4-[1,2,4]triazol-1-yl-phenyl}-oct-2-enoic acid methyl ester;

2-{4-[5-(2-Amino-pyrimidin-5-yl)-1-tert-butyl-1H-benzoimidazol-2-yl]-3-[1,2,4]triazol-1-yl-phenoxy}-2-methyl-propionic acid methyl ester;

2-{4-[5-(2-Amino-pyrimidin-5-yl)-1-tert-butyl-1H-benzoimidazol-2-yl]-3-[1,2,4]triazol-1-yl-phenoxy}-2-methyl-propionic acid;

3-[5-(2-Amino-pyrimidin-5-yl)-1-tert-butyl-1H-benzoimidazol-2-yl]-4-[3-(2-chloro-phenyl)-[1,2,4]triazol-1-yl]-benzonitrile;

(E)-3-{3-[5-(2-Amino-pyrimidin-5-yl)-1-tert-butyl-1H-benzoimidazol-2-yl]-4-[1,2,4]triazol-1-yl-phenyl}-oct-2-enoic acid;

3-[5-(2-Amino-pyrimidin-5-yl)-1-tert-butyl-1H-benzoimidazol-2-yl]-4-(3-methyl-pyrazol-1-yl)-benzonitrile;

3-[5-(2-Amino-pyrimidin-5-yl)-1-tert-butyl-1H-benzoimidazol-2-yl]-4-(5-methyl-pyrazol-1-yl)-benzonitrile;

3-[5-(2-Amino-pyrimidin-5-yl)-1-tert-butyl-1H-benzoimidazol-2-yl]-4-[1,2,4]triazol-1-yl-benzoic acid methyl ester;

3-[5-(2-Amino-pyrimidin-5-yl)-1-tert-butyl-1H-benzoimidazol-2-yl]-N-methyl-4-[1,2,4]triazol-1-yl-benzamide;

3-[5-(2-Amino-pyrimidin-5-yl)-1-tert-butyl-1H-benzoimidazol-2-yl]-N,N-dimethyl-4-[1,2,4]triazol-1-yl-benzamide;

1-{2-[5-(2-Amino-pyrimidin-5-yl)-1-tert-butyl-1H-benzoimidazol-2-yl]-4-cyano-phenyl}-1H-[1,2,4]triazole-3-carboxylic acid methyl ester;

1-{2-[5-(2-Amino-pyrimidin-5-yl)-1-tert-butyl-1H-benzoimidazol-2-yl]-4-cyano-phenyl}-1H-[1,2,4]triazole-3-carboxylic acid dimethylamide;

3-[5-(2-Amino-pyrimidin-5-yl)-1-tert-butyl-1H-benzoimidazol-2-yl]-4-(3,5-dimethyl-[1,2,4]triazol-1-yl)-benzonitrile;

1-{2-[5-(2-Amino-pyrimidin-5-yl)-1-tert-butyl-1H-benzoimidazol-2-yl]-4-cyano-phenyl}-1H-[1,2,4]triazole-3-carboxylic acid ethylamide;

1-{2-[5-(2-Amino-pyrimidin-5-yl)-1-tert-butyl-1H-benzoimidazol-2-yl]-4-cyano-phenyl}-1H-[1,2,4]triazole-3-carboxylic acid isobutyl ester;

3-{3-[5-(2-Amino-pyrimidin-5-yl)-1-tert-butyl-1H-benzimidazol-2-yl]-4-1,2,4-triazol-1-yl-phenoxy}-2,2-dimethyl-propionic acid;

2-{3-[5-(2-Amino-pyrimidin-5-yl)-1-tert-butyl-1H-benzimidazol-2-yl]-4-1,2,4-triazol-1-yl-phenoxy}-N,N-dimethyl-acetamide;

5-{1-tert-Butyl-2-[5-(tetrahydro-furan-3-yloxy)-2-1,2,4-triazol-1-yl-phenyl]-1H-benzimidazol-5-yl}-pyrimidin-2-ylamine;

Dimethyl-carbamic acid 3-[5-(2-amino-pyrimidin-5-yl)-1-tert-butyl-1H-benzimidazol-2-yl]-4-1,2,4-triazol-1-yl-phenyl ester;

Isopropyl-carbamic acid 3-[5-(2-amino-pyrimidin-5-yl)-1-tert-butyl-1H-benzimidazol-2-yl]-4-1,2,4-triazol-1-yl-phenyl ester;

Ethyl-carbamic acid 3-[5-(2-amino-pyrimidin-5-yl)-1-tert-butyl-1H-benzimidazol-2-yl]-4-1,2,4-triazol-1-yl-phenyl ester;

Diethyl-carbamic acid 3-[5-(2-amino-pyrimidin-5-yl)-1-tert-butyl-1H-benzimidazol-2-yl]-4-1,2,4-triazol-1-yl-phenyl ester;

5-{1-tert-Butyl-2-[4-(tetrahydro-furan-3-yloxy)-2-1,2,4-triazol-1-yl-phenyl]-1H-benzimidazol-5-yl}-pyrimidin-2-ylamine;

5-[1-tert-Butyl-2-(5-iodo-2-1,2,4-triazol-1-yl-phenyl)-1H-benzimidazol-5-yl]-pyrimidin-2-ylamine;

5-[1-tert-butyl-2-(2-isoxazol-5-yl-phenyl)-1H-benzoimidazol-5-yl]-pyrimidin-2-ylamine;

or the pharmaceutically acceptable salts thereof.

For all compounds disclosed hereinabove in this application, in the event the nomenclature is in conflict with the structure, it shall be understood that the compound is defined by the structure.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g. $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-6}$ alkoxy" is a $C_{1-6}$ alkyl with a terminal oxygen, such as methoxy, ethoxy, propoxy, butoxy. All alkyl, alkenyl, and alkynyl groups shall be understood as being branched or unbranched where structurally possible and unless otherwise specified. Other more specific definitions are as follows:

The term "alkyl" refers to both branched and unbranched alkyl groups. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C═O).

In all alkyl groups or carbon chains, one or more carbon atoms can be optionally replaced by heteroatoms such as O, S or N. It shall be understood that if N is not substituted then it is NH. It shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo. As used herein, "nitrogen" and "sulfur" include any oxidized form of nitrogen and sulfur and the quaternized form of any basic nitrogen. For example, for a —S—$C_{1-6}$ alkyl radical, unless otherwise specified, shall be understood to include —S(O)—$C_{1-6}$ alkyl and —S(O)$_2$—$C_{1-6}$ alkyl.

The term "$C_{3-10}$ carbocycle" refers to a nonaromatic 3 to 10-membered (but preferably, 3 to 6-membered) monocyclic carbocyclic radical or a nonaromatic 6 to 10-membered fused bicyclic, bridged bicyclic, or spirocyclic carbocyclic radical. The $C_{3-10}$ carbocycle may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[3.3.0]octane, bicyclo[4.3.0]nonane, and bicyclo[4.4.0]decanyl (decahydronaphthalenyl). Non-limiting examples of 6 to 10-membered bridged bicyclic carbocyclic radicals include bicyclo[2.2.2]heptanyl, bicyclo[2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro[4,4]heptanyl.

The term "$C_{6-10}$ aryl" refers to aromatic hydrocarbon rings containing from six to ten carbon ring atoms. The term $C_{6-10}$ aryl includes monocyclic rings and bicyclic rings where at least one of the rings is aromatic. Non-limiting examples of $C_{6-10}$ aryls include phenyl, indanyl, indenyl, benzocyclobutanyl, dihydronaphthyl, tetrahydronaphthyl, naphthyl, benzocycloheptanyl and benzocycloheptenyl.

The term "5 to 11-membered heterocycle" refers to a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl.

The term "5 to 11-membered heteroaryl" shall be understood to mean an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S, Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl, benzodioxolyl, benzoxazolyl and benzothiazolyl.

It will be understood that one to three carbon ring moieties in the each of the $C_{3-10}$ carbocyclic rings, the 5 to 11-membered heterocyclic rings, the nonaromatic portion of the bicyclic aryl rings, and the nonaromatic portion of the bicyclic heteroaryl rings can independently be replaced with a carbonyl, thiocarbonyl, or iminyl moiety, i.e., —C(=O)—, —C(=S)— and —C(=NR$^8$)—, respectively, where R$^8$ is as defined above. The term "heteroatom" as used herein shall be understood to mean atoms other than carbon such as O, N, and S.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, a non-limiting example would be —CH$_2$CHF$_2$, —CF$_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$-$C_4$ alkyl)$_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The compounds of the invention may be prepared by the methods described below. In each of the schemes below, the groups $R^1$ to $R^7$ are as defined above for general formula I unless noted. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Typically, reaction progress may be monitored by thin layer chromatography (TLC) or HPLC-MS if desired. Intermediates and products may be purified by chromatography on silica gel, recrystallization, HPLC and/or reverse phase HPLC.

Starting materials and reagents are either commercially available or may be prepared by one skilled in the art using methods described in the chemical literature and in the Synthetic Examples section below.

Compounds of formula I may be prepared as shown in Scheme 1.

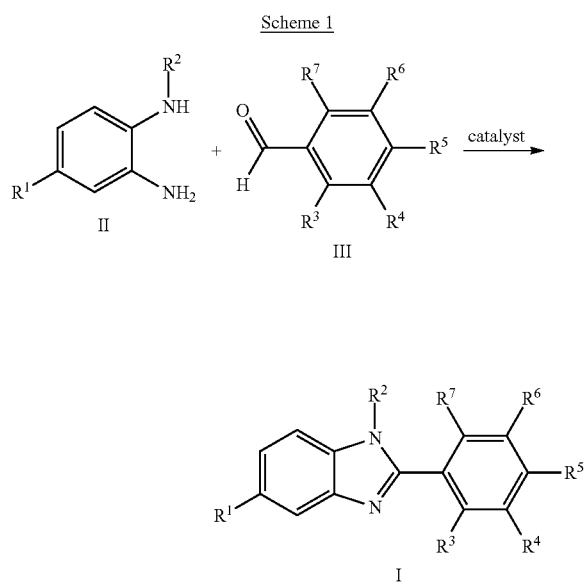

As illustrated in Scheme 1, a 1,2-diaminobenzene derivative substituted with $R^1$ and $R^2$ may be reacted with a benzaldehyde derivative substituted with $R^3$-$R^7$ to provide the desired compound of formula I. The reaction may be run in acetic acid or in aqueous DMF in the presence of oxone or alternatively, in a suitable solvent such as methanol, in the presence of a suitable catalyst such as proline or p-toluenesulfonic acid.

Intermediates III having $R^3$ being a nitrogen containing heteroaryl connected to the phenyl ring by the nitrogen may be prepared as illustrated in Schemes 2 and 3.

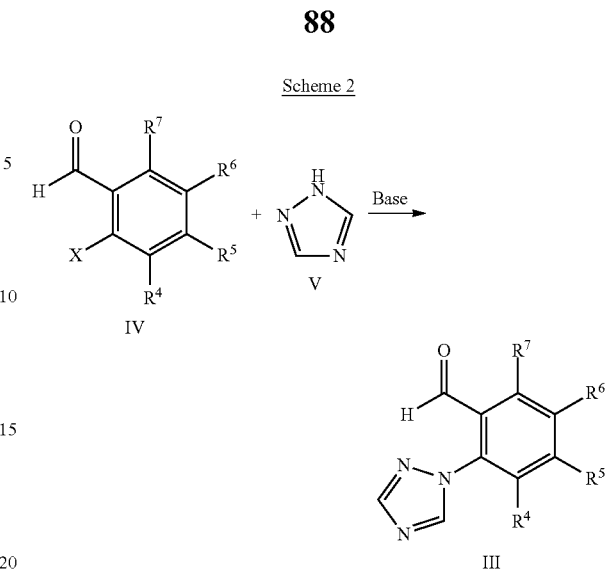

In Scheme 2 a substituted benzaldehyde bearing a halogen X in the 2-position, preferably a fluorine, is reacted with a heteroaryl group having a NH in the ring, for example triazole V, in the presence of a suitable base such as potassium carbonate in a suitable solvent such as DMSO to provide the desired intermediate of formula III ($R^3$=triazole).

An alternate procedure is illustrated in Scheme 3, below. Using this method, a substituted benzaldehyde bearing a boronic acid group in the 2-position is reacted with a heteroaryl having a NH in the ring, for example pyrazole VI, in the presence of a suitable catalyst such as $Cu(OAc)_2$, and a suitable base such as pyridine in a solvent such as DMF to provide the desired intermediate of formula III ($R^3$=pyrazole).

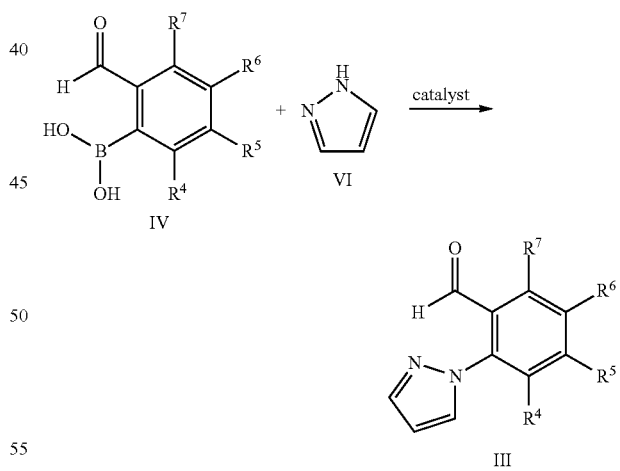

Compounds of formula I having a heteroaryl group at $R^3$ that is connected by a carbon atom may be prepared as illustrated in Scheme 4. Intermediate VII is prepared as shown for the preparation of I in Scheme 1 using intermediate III having $R^3$=Br. Reaction of VII with a heteroaryl, such as the 1-methylpyrazole VIII shown, bearing a boronic acid ester such as the pinacol ester shown in VIII, in the presence of a palladium catalyst, preferably $Pd(Ph_3)_4$ and a suitable base such as potassium carbonate in a solvent such as DMF provides the desired compound of formula I.

Scheme 4

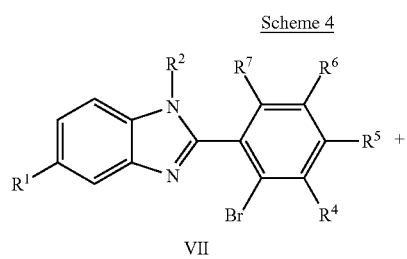

Scheme 5 illustrates an alternate method that may be used to prepare compounds of formula I. Using this method, intermediate IX is prepared from the 4-bromo-1,2-diaminobenzene intermediate IX and intermediate III using the method described in Scheme 1. Intermediate IX is then reacted with an R¹ bearing a boronic acid ester such as the pinacol ester shown in X using conditions described in Scheme 4 to provide the desired compound of formula I.

Scheme 5

-continued

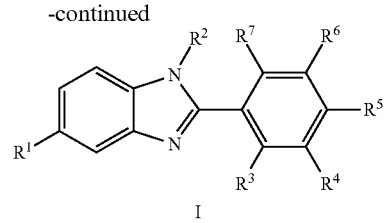

Compounds of formula I as well as intermediates prepared by the above methods may be further converted to additional intermediates or compounds of formula I by methods known in the art and exemplified in the Synthetic Examples section below.

SYNTHETIC EXAMPLES

Synthesis of Intermediates

Intermediate 1

4-(2-Amino-pyrimidin-5-yl)-N1-tert-butyl-benzene-1,2-diamine

To a solution of 4-bromo-1-fluoro-2-nitrobenzen (25 g, 0.1 mol) in THF (100 mL) is added t-butylamine (18 mL, 0.17 mol). The solution is heated at 60° C. for 16 hours. The solvent is removed in vacuum. The residue is suspended in methanol (20 mL). The precipitate is collected by filtration and washed with methanol to give (4-bromo-2-nitro-phenyl)-tert-butyl-amine as an orange solid (30 g, 97%).

To a solution of (4-bromo-2-nitro-phenyl)-tert-butyl-amine (7.2 g, 0.026 mol) in DMF (100 mL) and H$_2$O (10 mL) are added 5-(4,4,5,5-tetramethyl-1,3,2-dioxaborolan-2-yl)-pyrimidin-2-ylamine (8.7 g, 0.04 mol), Pd(PPh$_3$)$_4$ (3 g, 0.003 mol) and K$_2$CO$_3$ (7.3 g, 0.053 mol) at room temperature. The solution is heated to 100° C. for 2 hours. The solution is cooled down, washed with H$_2$O (100 mL) and extracted with EtOAc (3×50 mL). The combined organic layer is dried with MgSO$_4$ and filtered. The filtrate is concentrated and the residue is re-crystallized in CH$_2$Cl$_2$ (10 mL) to afford 5-(4-tert-butylamino-3-nitro-phenyl)-pyrimidin-2-ylamine as a scarlet solid (6.3 g, 83%).

To a round bottom flask are added 5-(4-tert-butylamino-3-nitro-phenyl)-pyrimidin-2-ylamine (6.3 g, 0.02 mol) and ammonium formate (6.9 g, 0.1 mol) in EtOH, (100 mL), followed by the addition of zinc dust (4.3 g, 0.066 mol). The reaction mixture is stirred at 50° C. for 2 hours. The reaction mixture is filtered through a short pad of diatomaceous earth. The filter pad is rinsed with MeOH (50 mL) and the combined filtrate is concentrated. The residue is extracted with H$_2$O (50 mL) and EtOAc (3×50 mL). The combined organic layer is washed with saturated NaHCO$_3$ solution (30 mL), dried (MgSO$_4$) and filtered. The filtrate is concentrated to afford 4-(2-amino-pyrimidin-5-yl)-N1-tert-butyl-benzene-1,2-diamine as a dark purple solid (4.5 g, 80%). LCMS (ESMS): m/z 258.20 (M$^+$+1)

Intermediate 2

N$^1$-tert-Butyl-4-(2,3-dihydro-1H-pyrrolo[2,3-b]pyridin-5-yl)-benzene-1,2-diamine

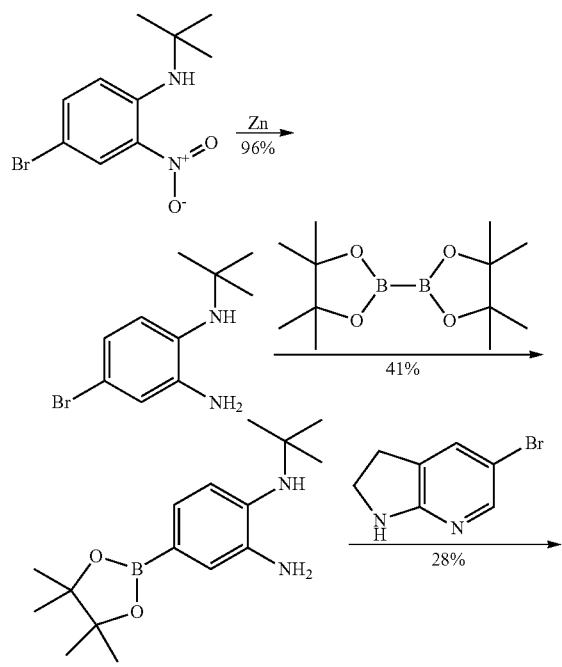

To a round bottom flask is added (4-bromo-2-nitro-phenyl)-tert-butyl-amine (refer to intermediate 1, step 1) (5 g, 18.3 mmol) in MeOH (120 mL). The suspension is heated at 70° C., followed by the addition of ammonium formate (11.5 g, 180 mmol) in water (50 mL). Zinc dust (3.6 g, 55 mmol) is added in portions. The reaction mixture is stirred at 70° C. for 2 hours and then concentrated. The residue is diluted with EtOAc (50 mL) and washed with saturated NaHCO$_3$ solution (20 mL). The organic layer is dried (Na$_2$SO$_4$), filtered and concentrated to afford a dark solid product (4.3 g, 96%). The crude product is used in the next step of the synthesis without further purification.

In a round bottom flask are added crude 4-bromo-N$^1$-tert-butyl-benzene-1,2-diamine (600 mg, 2.5 mmol), bis(pinacolato)diboron (940 mg, 3.7 mmol) and KOAc (727 mg, 7.4 mmol) in 1,4-dioxane (20 mL). The solution is degassed using nitrogen for 10 minutes and then 1,1-bis(diphenylphosphino)(ferrocenedichloropalladium (II))CH$_2$Cl$_2$ (201 mg, 0.25 mmol) is added. The reaction mixture is stirred at 100° C. for 24 hours. The mixture is cooled to room temperature and is poured into H$_2$O (20 mL) and extracted with EtOAc (3×25 mL). The combined organic layer is dried (MgSO$_4$) and filtered. The filtrate is concentrated and the residue purified using silica gel flash column chromatography with 5% MeOH in CH$_2$Cl$_2$ as the eluent to give N$^1$-tert-Butyl-4-(4,4,5,5-tetramethyl-1,3,2-dioxaborolan-2-yl)-benzene-1,2-diamine. (290 mg, 41%)

In a microwave vial are added N$^1$-tert-Butyl-4-(4,4,5,5-tetramethyl-1,3,2-dioxaborolan-2-yl)-benzene-1,2-diamine (100 mg, 0.5 mmol) and 5-bromo-2,3-dihydro-1H-pyrrolo[2,3-b]pyridine (180 mg, 0.62 mmol), tetrakis(triphenylphosphine)palladium(0) (58 mg, 0.05 mmol) and K$_2$CO$_3$ (139 mg, 1 mmol) in DMF (4 mL) and H$_2$O (0.2 mL). The reaction mixture is heated at 110° C. in a microwave reactor for 1 hour. The reaction is cooled down to room temperature, poured into H$_2$O (10 mL) and extracted with EtOAc (3×10 mL). The combined organic layer is dried (MgSO$_4$), filtered and concentrated. The residue is purified by silica gel flash column chromatography eluting with 10% MeOH in CH$_2$Cl$_2$ to afford the title intermediate (40 mg, 28%). LCMS (ESMS): m/z 283.20 (M$^+$+1)

The following intermediates are synthesized using similar procedures.

Intermediate 3

N$^1$-tert-Butyl-4-(1H-pyrrolo[2,3-b]pyridin-5-yl)-benzene-1,2-diamine. LCMS (ESMS): m/z 281.20 (M$^+$+1)

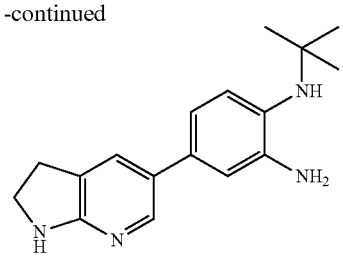

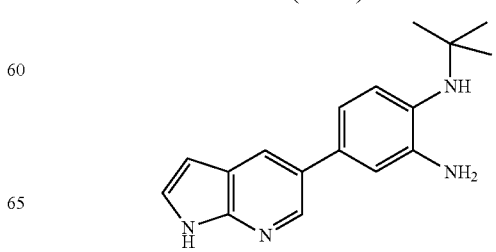

Intermediate 4

[2-Amino-5-(3-amino-4-tert-butylamino-phenyl)-pyridin-3-yl]-methanol. LCMS (ESMS): m/z 287.20 (M$^+$+1)

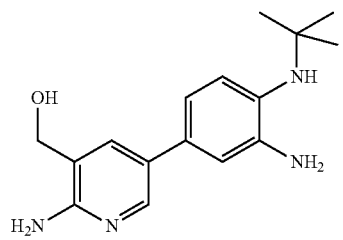 [SMILES: CC(C)(C)Nc1ccc(-c2cnc(N)c(CO)c2)cc1N]

EXAMPLES

Example 1

5-[1-tert-Butyl-2-(2-1,2,4-triazol-1-yl-phenyl)-1H-benzimidazol-5-yl]-pyrimidin-2-ylamine

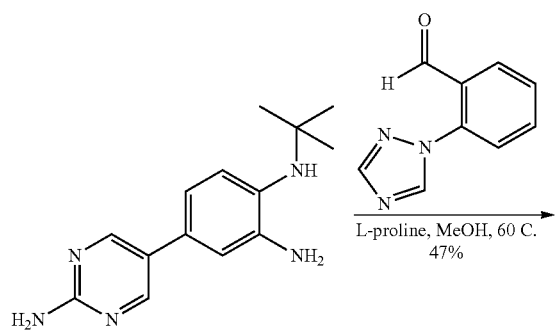

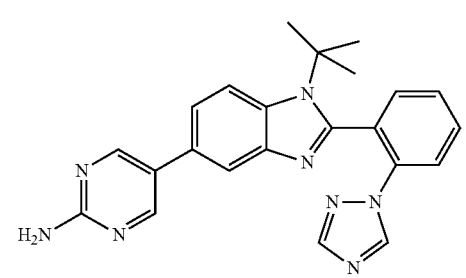

To a solution of 4-(2-Amino-pyrimidin-5-yl)-N-1-tert-butyl-benzene-1,2-diamine (40 mg, 0.16 mmol) in MeOH (5 mL) are added 2-[1,2,4]-triazol-1-yl-benzaldehyde (40 mg, 0.23 mmol) and catalytic amount of L-proline (3.6 mg, 0.031 mmol) at room temperature. The solution is heated to 60° C. for 12 hours. The solution is cooled down and is concentrated under reduced pressure. The residue is purified by silica gel flash column chromatography with 10% MeOH in CH$_2$Cl$_2$ as the eluent to afford the title compound as a pale brown oil. Acetonitrile (3 mL) is added to the oil and the solution is sonicated for 10 seconds. The solution is led to stand at room temperature and the solid that crystallizes out from the solution is collected by filtration (30 mg, 47%). LCMS (ESMS): m/z 411.68 (M$^+$+1)

Example 2

5-[1-tert-Butyl-2-(5-methoxy-2-pyrazol-1-yl-phenyl)-1H-benzimidazol-5-yl]-pyrimidin-2-ylamine

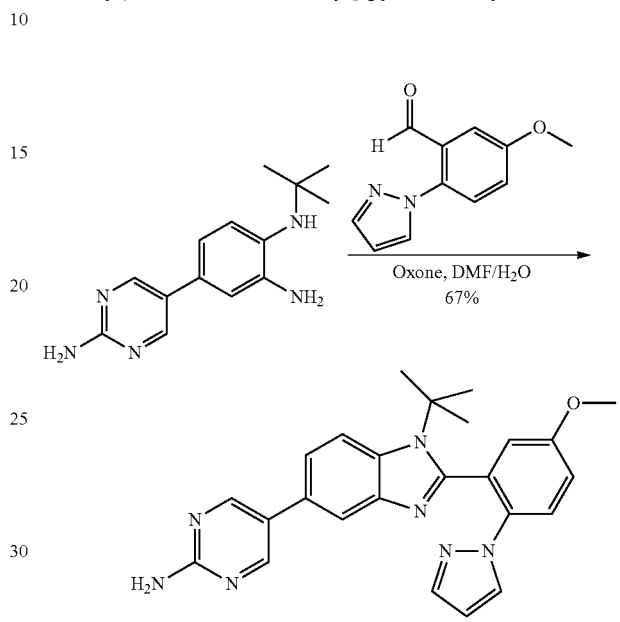

To a solution of 4-(2-amino-pyrimidin-5-yl)-N1-tert-butyl-benzene-1,2-diamine (50 mg, 0.19 mmol) in DMF (10 mL) is added 5-methoxy-2-(1H-pyrazol-1-yl)benzaldehyde (59 mg, 0.29 mmol) at room temperature. Oxone (119 mg, 0.19 mmol) in H$_2$O (2 mL) is added and the solution is stirred for 1 hour. Saturated sodium thiosulfate solution (5 mL) is added and the mixture is extracted with EtOAc (3×10 mL) and H$_2$O (5 mL). The combined organic layer is dried with MgSO$_4$, filtered and concentrated. The residue is purified by silica gel flash column chromatography eluting with 10% MeOH in CH$_2$Cl$_2$ to afford the title compound (56 mg, 67%) as a white solid. LCMS (ESMS): m/z 440.20 (M$^+$+1)

The following compounds are made using the procedure described in this Example:

5-[1-tert-Butyl-2-(5-methyl-2-pyrazol-1-yl-phenyl)-1H-benzimidazol-5-yl]-pyrimidin-2-ylamine. LCMS (ESMS): m/z 424.20 (M$^+$+1)

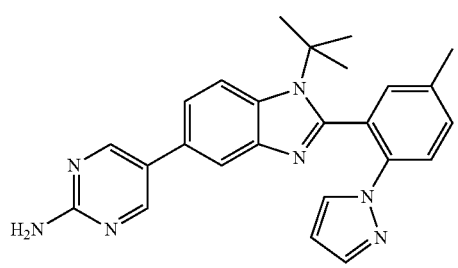 [SMILES: Cc1ccc(-n2cccn2)c(-c2nc3cc(-c4cnc(N)nc4)ccc3n2C(C)(C)C)c1]

95

5-[1-tert-Butyl-2-(2-pyrazol-1-yl-phenyl)-1H-benz-
imidazol-5-yl]-pyrimidin-2-ylamine. LCMS
(ESMS): m/z 410.00 (M⁺+1)

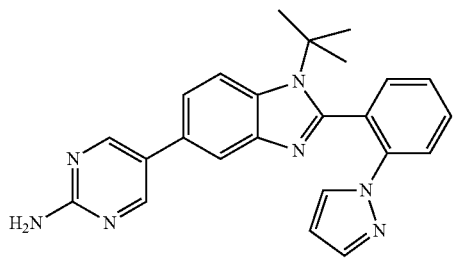 [SMILES: CC(C)(C)n1c(-c2ccccc2-n2cccn2)nc2cc(-c3cnc(N)nc3)ccc21]

5-{1-tert-Butyl-2-[3-(3,5-dimethyl-pyrazol-1-yl)-
phenyl]-1H-benzimidazol-5-yl}-pyrimidin-2-
ylamine. LCMS (ESMS): m/z 438.10 (M⁺+1)

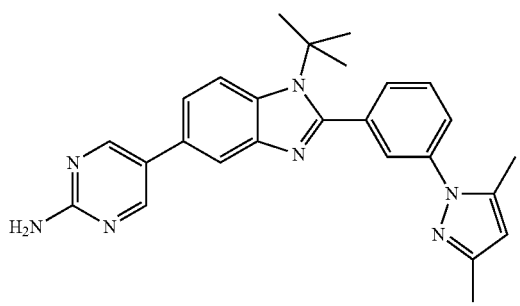 [SMILES: Cc1cc(C)n(-c2cccc(-c3nc4cc(-c5cnc(N)nc5)ccc4n3C(C)(C)C)c2)n1]

5-[1-tert-Butyl-2-(3-pyrazol-1-yl-phenyl)-1H-benz-
imidazol-5-yl]-pyrimidin-2-ylamine. LCMS
(ESMS): m/z 410.10 (M⁺+1)

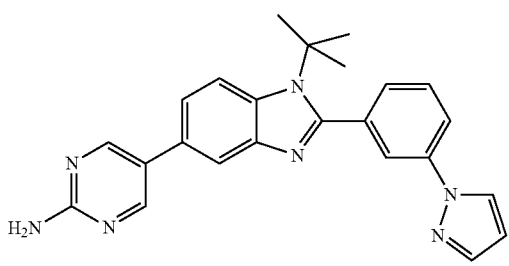 [SMILES: CC(C)(C)n1c(-c2cccc(-n3cccn3)c2)nc2cc(-c3cnc(N)nc3)ccc21]

5-{1-tert-Butyl-2-[3-(5-methyl-[1,2,4]oxadiazol-3-
yl)-phenyl]-1H-benzimidazol-5-yl}-pyrimidin-2-
ylamine. LCMS (ESMS): m/z 426.00 (M⁺+1)

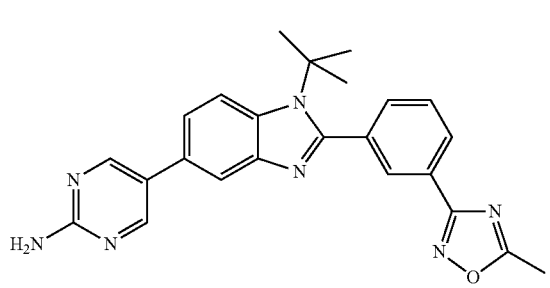 [SMILES: Cc1nc(-c2cccc(-c3nc4cc(-c5cnc(N)nc5)ccc4n3C(C)(C)C)c2)no1]

96

5-{1-tert-Butyl-2-[3-(1-methyl-1H-pyrazol-3-yl)-
phenyl]-1H-benzimidazol-5-yl}-pyrimidin-2-
ylamine. LCMS (ESMS): m/z 424.10 (M⁺+1)

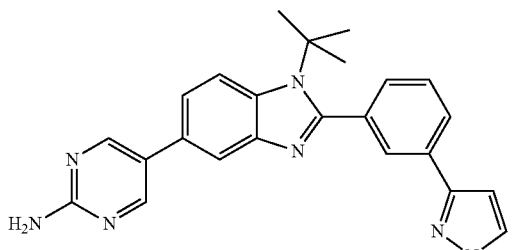

5-{1-tert-Butyl-2-[2-(3-methyl-[1,2,4]oxadiazol-5-
yl)-phenyl]-1H-benzimidazol-5-yl}-pyrimidin-2-
ylamine. LCMS (ESMS): m/z 426.10 (M⁺+1)

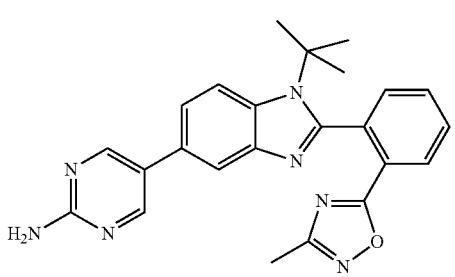 [SMILES: Cc1noc(-c2ccccc2-c2nc3cc(-c4cnc(N)nc4)ccc3n2C(C)(C)C)n1]

5-{1-tert-Butyl-2-[3-(3-methyl-[1,2,4]oxadiazol-5-
yl)-phenyl]-1H-benzimidazol-5-yl}-pyrimidin-2-
ylamine. LCMS (ESMS): m/z 426.10 (M⁺+1)

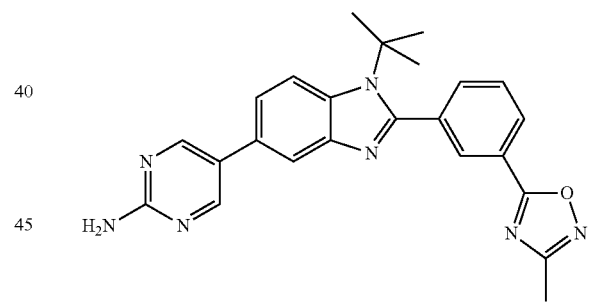

5-[1-tert-Butyl-2-(2-imidazol-1-yl-phenyl)-1H-benz-
imidazol-5-yl]-pyrimidin-2-ylamine. LCMS
(ESMS): m/z 410.10 (M⁺+1)

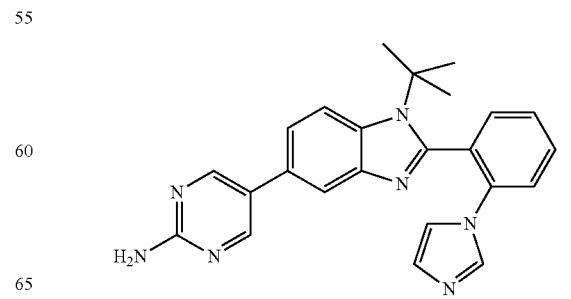

5-{1-tert-Butyl-2-[2-(2-methyl-imidazol-1-yl)-phenyl]-1H-benzimidazol-5-yl}-pyrimidin-2-ylamine. LCMS (ESMS): m/z 424.10 (M$^+$+1)

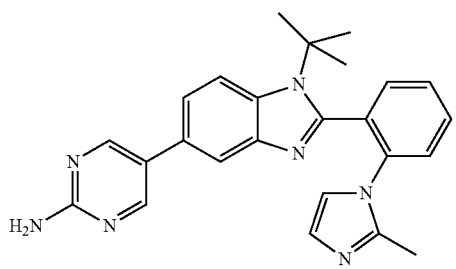 [SMILES: Cc1nccn1-c1ccccc1-c1nc2cc(-c3cnc(N)nc3)ccc2n1C(C)(C)C]

Example 3

5-[1-tert-Butyl-2-(5-methoxy-2-1,2,4-triazol-1-yl-phenyl)-1H-benzimidazol-5-yl]-pyrimidin-2-ylamine

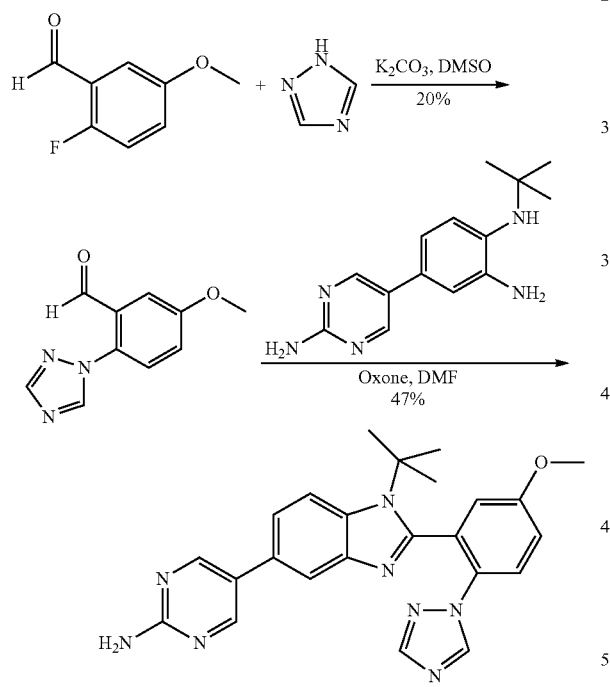

To a solution of 2-fluoro-5-methoxybenzaldehyde (200 mg, 1.29 mmol) in DMSO (10 mL) are added 1,2,4-triazole (134 mg, 1.95 mmol) and K$_2$CO$_3$ (359 mg, 2.60 mmol) at room temperature. The solution is heated to 100° C. for 2 hours. The solution is cooled and is extracted with H$_2$O (30 mL) and EtOAc (3×15 mL). The combined organic layer is dried with MgSO$_4$ and is filtered. The filtrate is concentrated and the residue is purified by silica gel flash column chromatography with 50% EtOAc in heptane as the eluent to afford 5-methoxy-2-1,2,4-triazol-1-yl-benzaldehyde (53 mg, 20%) as a white foam.

To a solution of 4-(2-amino-pyrimidin-5-yl)-N$^1$-tert-butyl-benzene-1,2-diamine (50 mg, 0.194 mmol) in DMF (10 mL) is added 5-methoxy-2-1,2,4-triazol-1-yl-benzaldehyde (47 mg, 0.233 mmol) at room temperature. Oxone (119 mg, 0.194 mmol) in H$_2$O (2 mL) is added and the solution is stirred for 1 hour. Saturated sodium thiosulfate solution (5 mL) is added and the mixture is extracted with EtOAc (3×10 mL) and H$_2$O (10 mL). The combined organic layer is dried with MgSO$_4$, filtered and concentrated. The residue is purified by silica gel flash column chromatography eluting with 10% MeOH in CH$_2$Cl$_2$ to afford the title compound (41 mg, 47%) as a pale brown solid. LCMS (ESMS): m/z 441.20 (M$^+$+1).

The following compounds are made using the procedure described in this Example:

5-[1-tert-Butyl-2-(3-methoxy-2-1,2,4-triazol-1-yl-phenyl)-1H-benzimidazol-5-yl]-pyrimidin-2-ylamine. LCMS (ESMS): m/z 441.20 (M$^+$+1)

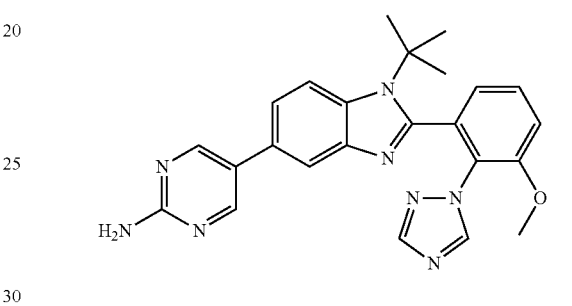

5-[1-tert-Butyl-2-(4-methoxy-2-1,2,4-triazol-1-yl-phenyl)-1H-benzimidazol-5-yl]-pyrimidin-2-ylamine. LCMS (ESMS): m/z 441.20 (M$^+$+1)

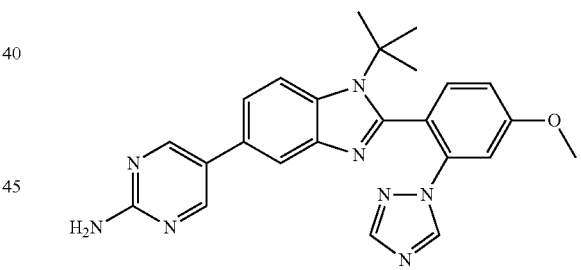

Example 4

5-[1-tert-Butyl-2-(2-1,2,4-triazol-1-yl-5-vinyl-phenyl)-1H-benzimidazol-5-yl]-pyrimidin-2-ylamine

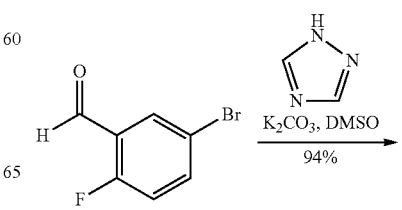

-continued

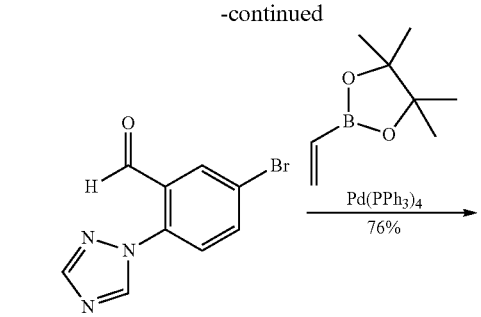

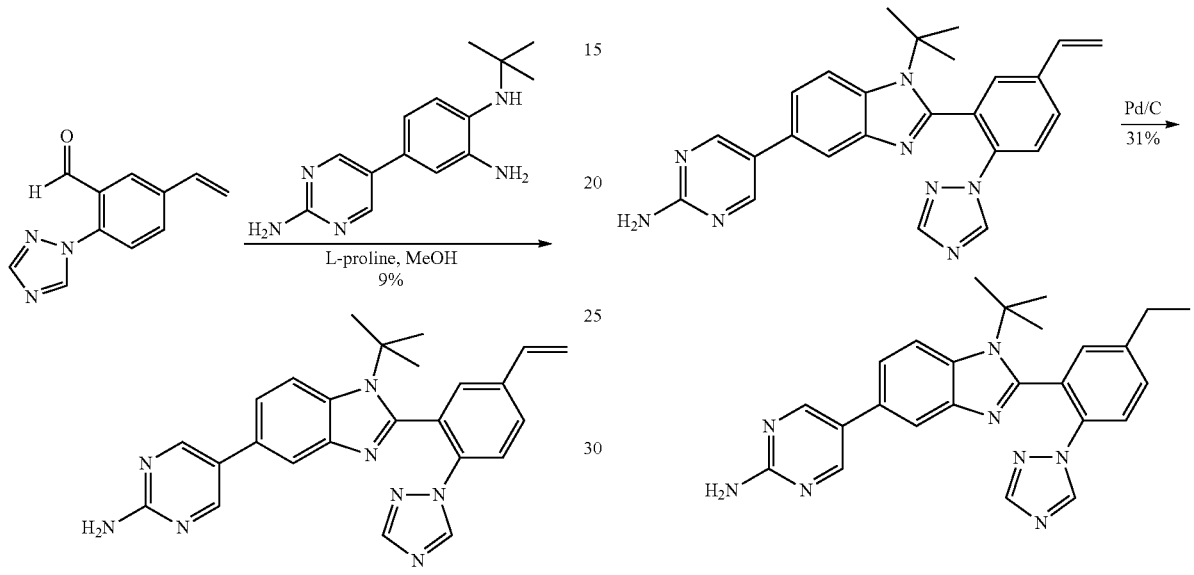

To a solution of 5-bromo-2-fluorobenzaldehyde (0.18 mL, 1.5 mmol) in DMSO (10 mL) are added 1,2,4-triazole (153 mg, 2.2 mmol) and $K_2CO_3$ (408 mg, 2.9 mmol) at room temperature. The solution is heated to 80° C. for 5 minutes in a microwave reactor, then cooled and washed with $H_2O$ (20 mL). The solution is then extracted with EtOAc (3×15 mL). The combined organic layer is dried ($MgSO_4$), filtered and concentrated The residue (350 mg, 94%) is used in the next step without further purification.

To a solution of crude 5-bromo-2-1,2,4-triazol-1-yl-benzaldehyde (100 mg, 0.39 mmol) in DMF (10 mL) and $H_2O$ (2 mL) are added 4,4,5,5-tetramethyl-2-vinyl-1,3,2-dioxaborolane (0.08 mL, 0.48 mmol), $Pd(PPh_3)_4$ (46 mg, 0.04 mmol) and $K_2CO_3$ (110 mg, 0.79 mmol) at room temperature. The solution is heated to 120° C. for 1 hour in a microwave reactor. The reaction mixture is cooled down and 3-mercaptopropyl-functionalized silica gel (500 mg) is added. The solution is stirred for 15 minutes and is filtered. The filtrate is washed with $H_2O$ (10 mL) and extracted with EtOAc (3×15 mL). The combined organic layer is dried ($MgSO_4$), filtered and concentrated and the residue (60 mg, 78%) is used in the next step without further purification.

To a solution of 4-(2-amino-pyrimidin-5-yl)-N1-tert-butyl-benzene-1,2-diamine (100 mg, 0.39 mmol) in MeOH (5 mL) are added crude 2-1,2,4-triazol-1-yl-5-vinyl-benzaldehyde (93 mg, 0.47 mmol) and L-proline (4 mg, 0.04 mmol) at room temperature. The solution is heated to 60° C. for 12 hours, then cooled down and is concentrated under reduced pressure. The residue is purified by silica gel flash column chromatography eluting with 10% MeOH in $CH_2Cl_2$ to afford the title compound (15 mg, 9%) as a white solid. LCMS (ESMS): m/z 437.72 ($M^+$+1)

Example 5

5-[1-tert-Butyl-2-(5-ethyl-2-1,2,4-triazol-1-yl-phenyl)-1H-benzimidazol-5-yl]-pyrimidin-2-ylamine To a solution of 5-[1-tert-butyl-2-(2-1,2,4-triazol-1-yl-5-vinyl-phenyl)-1H-benzimidazol-5-yl]-pyrimidin-2-ylamine (100 mg, 0.23 mmol) in EtOH (5 mL) is added 10% Pd/C (10 mg) at room temperature. The reaction vessel is de-gased and is filled with $H_2$ using a balloon. The mixture is stirred at the same temperature for 12 hours. The mixture is filtered and the filtrate is concentrated. The residue is purified by silica gel flash column chromatography eluting with 10% MeOH in $CH_2Cl_2$ to afford the title compound (31 mg, 31%) as a pale brown foam. LCMS (ESMS): m/z 439.73 ($M^+$+1)

Example 6

5-[2-(5-Bromo-2-1,2,4-triazol-1-yl-phenyl)-1-tert-butyl-1H-benzimidazol-5-yl]-pyrimidin-2-ylamine

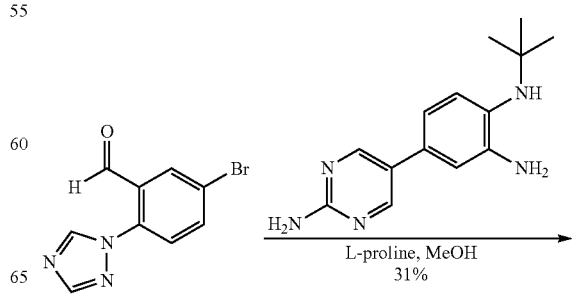

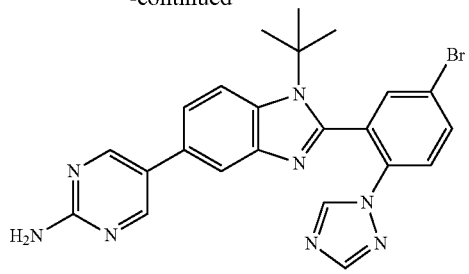

To a solution of 4-(2-amino-pyrimidin-5-yl)-N1-tert-butyl-benzene-1,2-diamine (100 mg, 0.39 mmol) in MeOH (5 mL) are added 5-bromo-2-1,2,4-triazol-1-yl-benzaldehyde (refer to example 4 step 1) (147 mg, 0.58 mmol) and L-proline (4 mg, 0.04 mmol) at room temperature. The solution is heated to 60° C. for 24 hours and then cooled down and is concentrated under reduced pressure. The residue is purified by silica gel flash column chromatography eluting with 10% MeOH in CH$_2$Cl$_2$ to afford the title compound (59 mg, 31%) as a white foam. LCMS (ESMS): m/z 489.20 (M$^+$)

Example 7

3-[5-(2-Amino-pyrimidin-5-yl)-1-tert-butyl-1H-benzimidazol-2-yl]-4-1,2,4-triazol-1-yl-benzonitrile

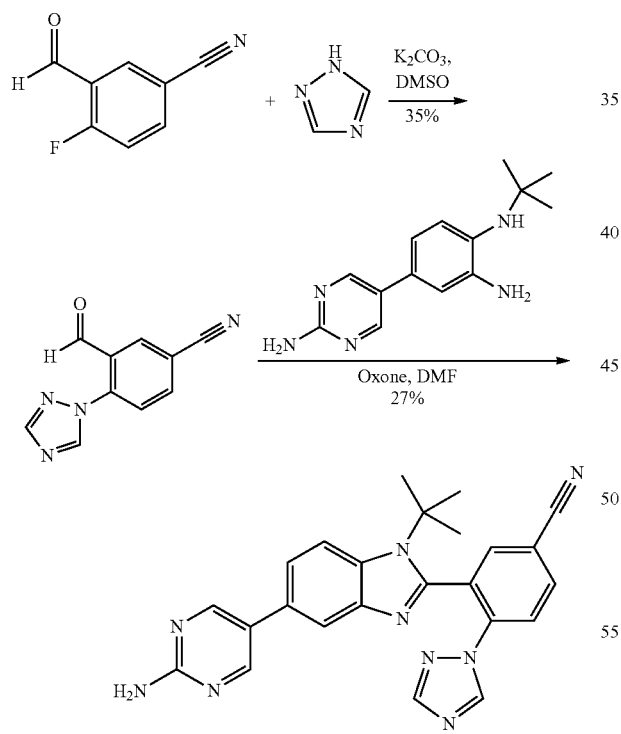

To a solution of 5-cyano-2-fluorobenzaldehyde (200 mg, 1.34 mmol) in DMSO (8 mL) are added 1,2,4-triazole (139 mg, 2.01 mmol) and K$_2$CO$_3$ (370 mg, 2.7 mmol) at room temperature. The solution is heated to 80° C. for 5 minutes in a microwave reactor and then cooled down and washed with H$_2$O (20 mL). The solution is extracted with EtOAc (3×15 mL). The combined organic layer is dried (MgSO$_4$), filtered and concentrated. The residue (120 mg, 45%) is used in the next step of the synthesis without further purification.

To a solution of 4-(2-amino-pyrimidin-5-yl)-N1-tert-butyl-benzene-1,2-diamine (100 mg, 0.39 mmol) in DMF (5 mL) is added 3-formyl-4-1,2,4-triazol-1-yl-benzonitrile (115 mg, 0.58 mmol) at room temperature. Oxone (239 mg, 0.39 mmol) in H$_2$O (1 mL) is added and the solution is stirred for 3 hours. Saturated sodium thiosulfate solution (5 mL) is added and the mixture is extracted with EtOAc (3×15 mL) and H$_2$O (10 mL). The combined organic layer is dried (MgSO$_4$), filtered and concentrated. The residue is purified by silica gel flash column chromatography eluting with 10% MeOH in CH$_2$Cl$_2$ eluent to afford the title compound (46 mg, 27%) as a white foam. LCMS (ESMS): m/z 436.72 (M$^+$+1)

The following compounds are made using the procedure described in this Example:

5-[1-tert-Butyl-2-(4-chloro-5-methoxy-2-1,2,4-triazol-1-yl-phenyl)-1H-benzimidazol-5-yl]-pyrimidin-2-ylamine. LCMS (ESMS): m/z 475.67 (M$^+$+1)

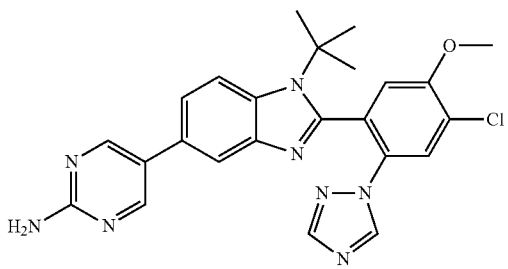 [SMILES: COc1cc(-c2nc3cc(-c4cnc(N)nc4)ccc3n2C(C)(C)C)c(-n2cncn2)cc1Cl]

5-[1-tert-Butyl-2-(5-chloro-2-1,2,4-triazol-1-yl-phenyl)-1H-benzimidazol-5-yl]-pyrimidin-2-ylamine. LCMS (ESMS): m/z 445.20 (M$^+$+1)

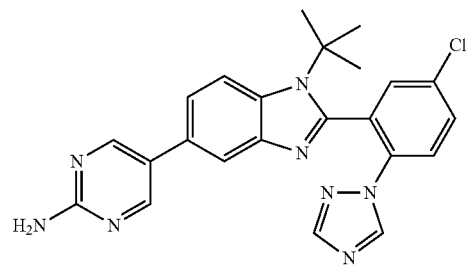 [SMILES: CC(C)(C)n1c(-c2cc(Cl)ccc2-n2cncn2)nc2cc(-c3cnc(N)nc3)ccc21]

Example 8

5-{1-tert-Butyl-2-[2-(1-methyl-1H-pyrazol-4-yl)-phenyl]-1H-benzimidazol-5-yl}-pyrimidin-2-ylamine

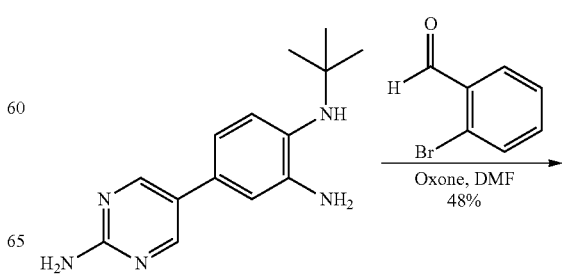

-continued

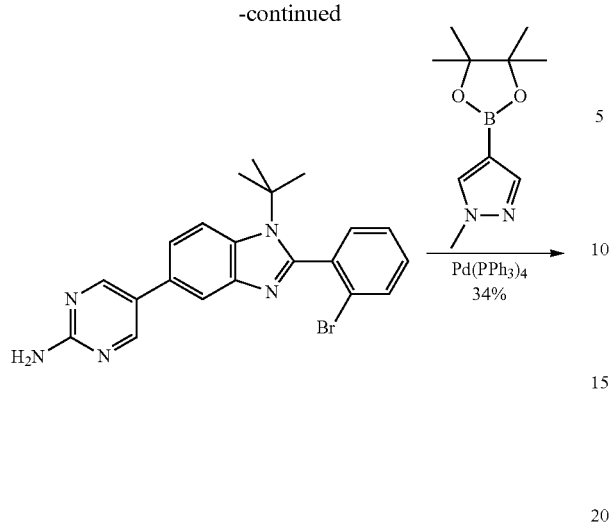

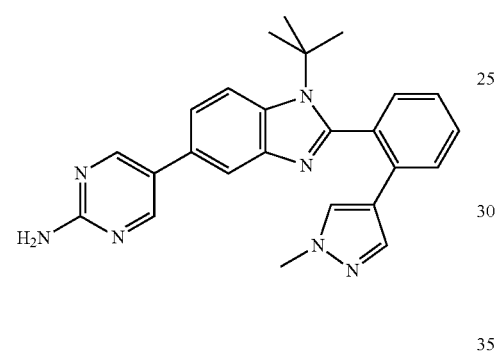

To a solution of 4-(2-amino-pyrimidin-5-yl)-N1-tert-butyl-benzene-1,2-diamine (1 g, 3.89 mmol) in DMF (30 mL) is added 2-bromobenzaldehyde (0.7 mL, 5.83 mmol) at room temperature. Oxone (2.4 g, 3.89 mmol) in H₂O (5 mL) is added and the solution is stirred for 1 hour. Saturated sodium thiosulfate solution (10 mL) is added and the mixture is extracted with EtOAc (3×15 mL) and H₂O (20 mL). The combined organic layer is dried (MgSO₄), filtered and concentrated. The residue is purified by silica gel flash column chromatography eluting with 10% MeOH in CH₂Cl₂ to afford 5-[2-(2-bromo-phenyl)-1-tert-butyl-1H-benzimidazol-5-yl]-pyrimidin-2-ylamine (800 mg, 48%) as a white solid.

To a solution of 5-[2-(2-bromo-phenyl)-1-tert-butyl-1H-benzimidazol-5-yl]-pyrimidin-2-ylamine (70 mg, 0.17 mmol) in DMF (5 mL) and H₂O (1 mL) are added 1-methylpyrazole-4-boronic acid pinacol ester (52 mg, 0.25 mmol), Pd(PPh₃)₄ (19 mg, 0.017 mmol) and K₂CO₃ (23 mg, 0.17 mmol) at room temperature. The solution is heated to 120° C. for 1 hour in a microwave reactor. The solution is cooled down and 3-mercaptopropyl-functionalized silica gel (500 mg) is added. The solution is stirred for 15 minutes and then filtered. The filtrate is washed with H₂O (10 mL) and is extracted with EtOAc (3×15 mL). The combined organic layer is dried (MgSO₄), filtered and concentrated. The residue is purified by silica gel flash chromatography eluting with 10% MeOH in CH₂Cl₂ to afford the title compound (24 mg, 34%) as a white solid. LCMS (ESMS): m/z 424.20 (M⁺+1)

The following compound is made using the procedure described in this Example:

5-{1-tert-Butyl-2-[2-(1-isobutyl-1H-pyrazol-4-yl)-phenyl]-1H-benzimidazol-5-yl}-pyrimidin-2-ylamine. LCMS (ESMS): m/z 466.20 (M⁺+1)

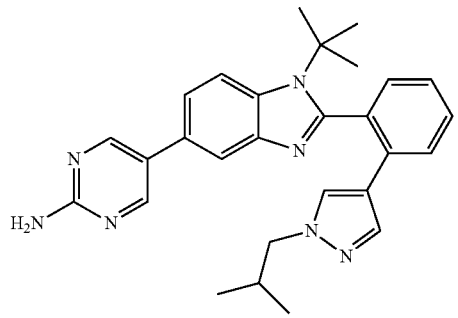 [SMILES: CC(C)Cn1cc(-c2ccccc2-c2nc3cc(-c4cnc(N)nc4)ccc3n2C(C)(C)C)cn1]

Example 9

1-tert-Butyl-2-[2-(3-methyl-1,2,4-oxadiazol-5-yl)-phenyl]-5-(1H-pyrrolo[2,3-b]pyridin-5-yl)-1H-benzimidazole

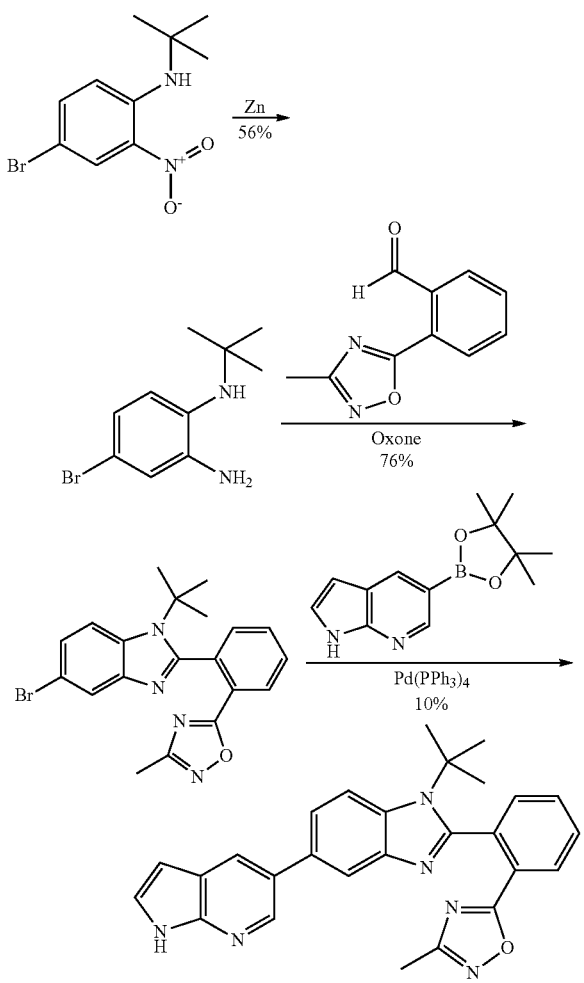

To a round bottom flask are added (4-bromo-2-nitro-phenyl)-tert-butyl-amine (refer to intermediate 1, step 1) (5 g, 18.3 mmol) and ammonium formate (5.8 g, 91.5 mmol) in EtOH (80 mL), followed by the addition of zinc dust (2.4 g, 36.6 mmol). The reaction mixture is stirred at 50° C. for 2 hours and then filtered through a short pad of diatomaceous earth (5 g), rinsing with MeOH (50 mL). The combined filtrate is concentrated and the residue is extracted with $CH_2Cl_2$ (3×30 mL) and $H_2O$ (50 mL). The combined organic layer is dried ($Na_2SO_4$), filtered and concentrated. The residue (2.5 g, 56%) is used in the next step of the synthesis without further purification.

To a solution of 4-bromo-$N^1$-tert-butyl-benzene-1,2-diamine (700 mg, 2.8 mmol) in DMF (15 mL) is added 2-(3-methyl-1,2,4-oxadiazol-5-yl)benzaldehyde (813 mg, 4.3 mmol) at room temperature. Oxone (1.7 g, 2.8 mmol) in $H_2O$ (4 mL) is added and the solution is stirred for 1 hour. Saturated sodium thiosulfate solution (10 mL) is added and the mixture is extracted with EtOAc (3×10 mL) and $H_2O$ (10 mL). The combined organic layer is dried, ($MgSO_4$), filtered and concentrated. The residue is purified by silica gel flash column chromatography eluting with 10% MeOH in $CH_2Cl_2$ to afford the 5-bromo-1-tert-butyl-2-[2-(3-methyl-1,2,4-oxadiazol-5-yl)-phenyl]-1H-benzimidazole (900 mg, 76%) as a pale brown solid.

To a solution of 5-bromo-1-tert-butyl-2-[2-(3-methyl-1,2,4-oxadiazol-5-yl)-phenyl]-1H-benzimidazole (100 mg, 0.24 mmol) in DMF (5 mL) and $H_2O$ (1 mL) are added 7-azaindole-5-boronic acid pinacol ester (89 mg, 0.37 mmol), Pd(PPh$_3$)$_4$ (28 mg, 0.024 mmol) and $K_2CO_3$ (34 mg, 0.24 mmol) at room temperature. The solution is heated to 120° C. for 1 hour in a microwave reactor. The solution is cooled down and 3-mercaptopropyl-functionalized silica gel (500 mg) is added. The mixture is stirred for 15 minutes and is filtered. The filtrate is washed with $H_2O$ (10 mL) and is extracted with EtOAc (3×15 mL). The combined organic layer is ($MgSO_4$), filtered and concentrated and the residue is purified by preparative HPLC to afford the title compound (11 mg, 10%) as a white foam. LCMS (ESMS): m/z 449.77 (M$^+$+1)

Example 10

5-{1-tert-Butyl-2-[2-(2-methyl-thiazol-4-yl)-phenyl]-1H-benzimidazol-5-yl}-pyrimidin-2-ylamine

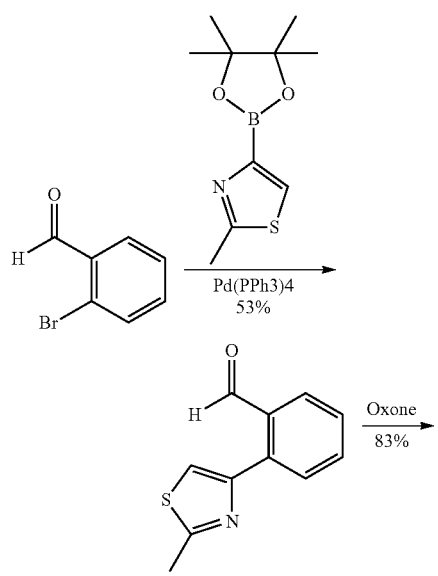

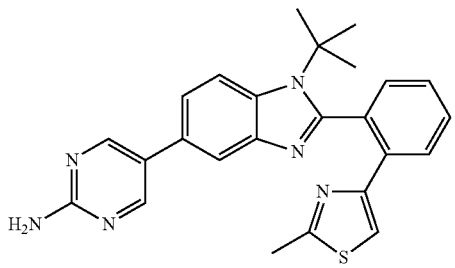

To a solution of 2-bromobenzaldehyde (0.063 mL, 0.54 mmol) in DMF (5 mL) and $H_2O$ (1 mL) are added 2-methylthiazole-4-boronic acid pinacol ester (122 mg, 0.54 mmol), Pd(PPh$_3$)$_4$ (63 mg, 0.054 mmol) and $K_2CO_3$ (112 mg, 0.81 mmol) at room temperature. The solution is heated to 120° C. for 1 hour in a microwave reactor. The reaction is cooled down and 3-mercaptopropyl-functionalized silica gel (500 mg) is added. The solution is stirred for 15 minutes and is filtered. The filtrate is washed with $H_2O$ (10 mL) and is extracted with EtOAc (3×15 mL). The combined organic layer is dried ($MgSO_4$), filtered and concentrated. The residue is purified by silica gel flash chromatography eluting with 50% EtOAc in heptane to afford 2-(2-methyl-thiazol-4-yl)-benzaldehyde (58 mg, 53%) as a white foam.

To a solution of 4-(2-amino-pyrimidin-5-yl)-N1-tert-butyl-benzene-1,2-diamine (50 mg, 0.19 mmol) in DMF (5 mL) is added 2-(2-methyl-thiazol-4-yl)-benzaldehyde (59 mg, 0.29 mmol) at room temperature. Oxone (119 mg, 0.19 mmol) in $H_2O$ (1 mL) is added and the solution is stirred for 1 hour. Saturated sodium thiosulfate solution (5 mL) is added and the mixture is extracted with EtOAc (3×10 mL) and $H_2O$ (10 mL). The combined organic layer is dried ($MgSO_4$), filtered and concentrated and the residue is purified by silica gel flash column chromatography eluting with 10% MeOH in $CH_2Cl_2$ to afford the title compound (71 mg, 83%) as a pale brown solid. LCMS (ESMS): m/z 441.20 (M$^+$+1)

The following compounds are made using the procedure described in this Example:

5-{1-tert-Butyl-2-[2-(2,4-dimethyl-thiazol-5-yl)-phenyl]-1H-benzimidazol-5-yl}-pyrimidin-2-ylamine. LCMS (ESMS): m/z 455.20 (M$^+$+1)

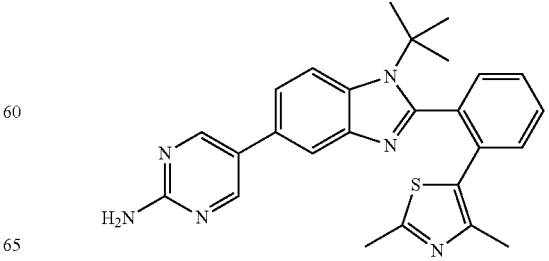

5-{1-tert-Butyl-2-[5-chloro-2-(2-methyl-thiazol-4-yl)-phenyl]-1H-benzimidazol-5-yl}-pyrimidin-2-ylamine. LCMS (ESMS): m/z 477.20 (M⁺+1)

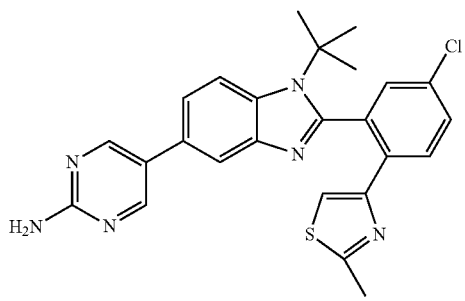 [SMILES: Cc1nc(-c2ccc(Cl)cc2-c2nc3cc(-c4cnc(N)nc4)ccc3n2C(C)(C)C)cs1]

Example 11

3-[5-(2-Amino-pyrimidin-5-yl)-1-tert-butyl-1H-benzimidazol-2-yl]-4-pyrazol-1-yl-phenol

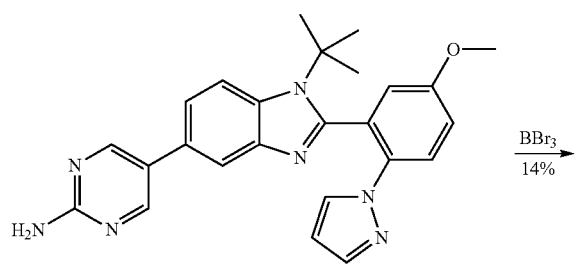

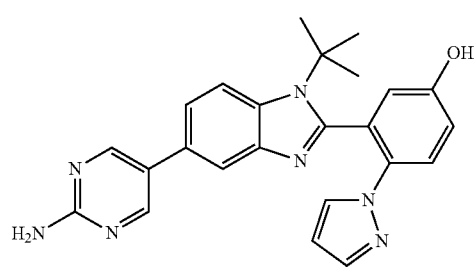

To a solution of 5-[1-tert-butyl-2-(5-methoxy-2-pyrazol-1-yl-phenyl)-1H-benzimidazol-5-yl]-pyrimidin-2-ylamine (Example 2) (75 mg, 0.17 mmol) in CH₂Cl₂ (10 mL) is added BBr₃ (1M in THF) (0.5 mL, 0.51 mmol) at 0° C. under nitrogen atmosphere. The solution is warmed to room temperature and stirred for 48 hours. The solution is cooled down to 4° C. and saturated NaHCO₃ solution (5 mL) is added. The mixture is extracted with EtOAc (3×10 mL) and the combined organic layer is dried (MgSO₄), filtered and concentrated and the residue is purified by silica gel flash chromatography eluting with 10% MeOH in CH₂Cl₂ to afford the title compound (10 mg, 14%) as a white foam. LCMS (ESMS): m/z 426.20 (M⁺+1)

Example 12

5-[1-tert-Butyl-2-(5-chloro-2-pyrazol-1-yl-phenyl)-1H-benzimidazol-5-yl]-pyrimidin-2-ylamine

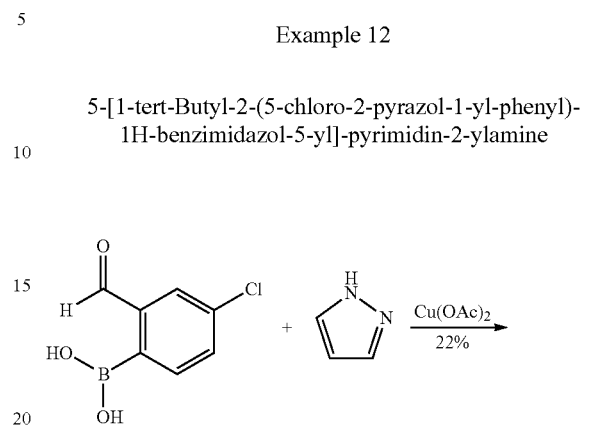

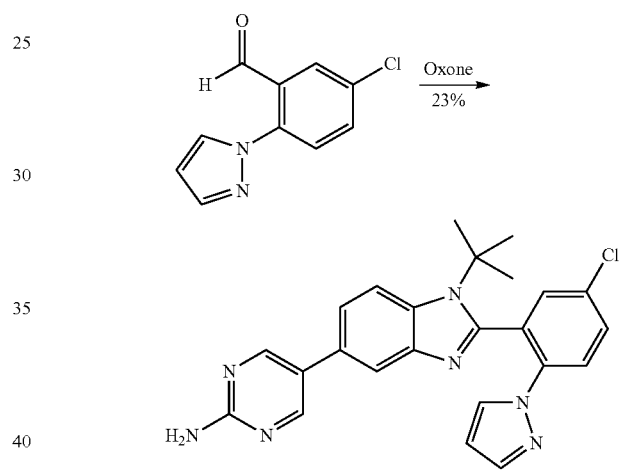

To a solution of 4-chloro-2-formylphenylboronic acid (200 mg, 1.09 mmol) in DMF (10 mL) are added pyrazole (88 mg, 1.3 mmol), Cu(OAc)₂ (295 mg, 1.6 mmol), pyridine (171 mg, 2.2 mmol) and molecular sieve (200 mg) at room temperature. The mixture is stirred for 48 hours with open cap. The mixture is filtered through a short pad of diatomaceous earth (2 g) rinsing with MeOH (10 mL). The combined filtrate is extracted with H₂O (15 mL) and EtOAc (3×10 mL). The combined organic layer is dried with MgSO₄ and filtered. The filtrate is concentrated and the residue is purified by silica gel flash column chromatography eluting with 10% EtOAc in heptane to afford 5-chloro-2-pyrazol-1-yl-benzaldehyde (50 mg, 22%) as a white solid.

To a solution of 4-(2-amino-pyrimidin-5-yl)-N¹-tert-butyl-benzene-1,2-diamine (50 mg, 0.19 mmol) in DMF (5 mL) is added 5-chloro-2-pyrazol-1-yl-benzaldehyde (60 mg, 0.29 mmol) at room temperature. Oxone (119 mg, 0.19 mmol) in H₂O (1 mL) is added and the solution is stirred for 1 hour. Saturated sodium thiosulfate solution (5 mL) is added and the mixture is extracted with EtOAc (3×10 mL) and H₂O (10 mL). The combined organic layer is dried with MgSO₄ and is filtered. The filtrate is concentrated and the residue is purified by silica gel flash column chromatography eluting with 10%

MeOH in CH$_2$Cl$_2$ to afford the title compound (20 mg, 23%) as a pale brown solid. LCMS (ESMS): m/z 444.69 (M$^+$+1)

Example 13

5-{1-tert-Butyl-2-[2-(2,4-dimethyl-thiazol-5-yl)-5-methoxy-phenyl]-1H-benzimidazol-5-yl}-pyrimidin-2-ylamine

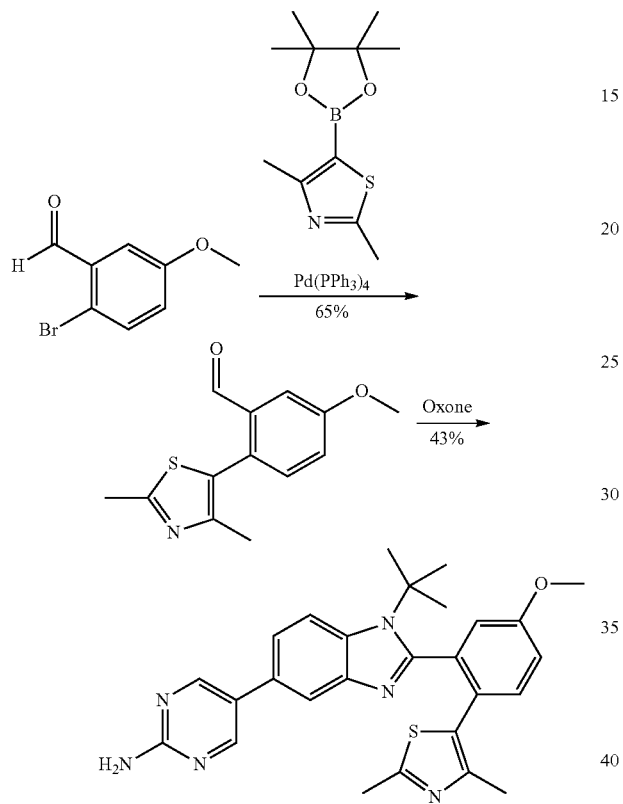

To a solution of 2-bromo-5-methoxybenzaldehyde (200 mg, 0.93 mmol) in DMF (10 mL) and H$_2$O (2 mL) are added 2,4-dimethyl-5-(4,4,5,5-tetramethyl-1,3,2-dioxaborolan-2-yl)-1,3-thiazole (333 mg, 1.4 mmol), Pd(PPh$_3$)$_4$ (107 mg, 0.09 mmol) and K$_2$CO$_3$ (257 mg, 1.9 mmol) at room temperature. The solution is heated to 120° C. for 1 hour in a microwave reactor. The solution is cooled down and 3-mercaptopropyl-functionalized silica gel (500 mg) is added. The solution is stirred for 15 minutes and is filtered. The filtrate is washed with H$_2$O (10 mL) and is extracted with EtOAc (3×10 mL). The combined organic layer is dried, (MgSO$_4$), filtered and is concentrated and the residue is purified by silica gel flash chromatography eluting with 50% EtOAc in heptane to afford 2-(2,4-Dimethyl-thiazol-5-yl)-5-methoxy-benzaldehyde (150 mg, 65%) as a white foam.

To a solution of 4-(2-amino-pyrimidin-5-yl)-N$^1$-tert-butyl-benzene-1,2-diamine (100 mg, 0.39 mmol) in DMF (5 mL) is added 2-(2,4-dimethyl-thiazol-5-yl)-5-methoxy-benzaldehyde (144 mg, 0.58 mmol) at room temperature. Oxone (239 mg, 0.39 mmol) in H$_2$O (1 mL) is added and the solution is stirred for 4 hours. Saturated sodium thiosulfate solution (5 mL) is added and the mixture is extracted with EtOAc (3×10 mL) and H$_2$O (10 mL). The combined organic layer is dried with MgSO$_4$ and is filtered. The filtrate is concentrated and the residue is purified by silica gel flash column chromatography eluting with 10% MeOH in CH$_2$Cl$_2$ to afford the title compound (81 mg, 43%) as a pale brown foam. LCMS (ESMS): m/z 485.72 (M$^+$+1)

The following compounds are made using the procedure described in this Example:

5-{1-tert-Butyl-2-[5-methoxy-2-(2-methyl-thiazol-4-yl)-phenyl]-1H-benzimidazol-5-yl}-pyrimidin-2-ylamine. LCMS (ESMS): m/z 471.20 (M$^+$+1)

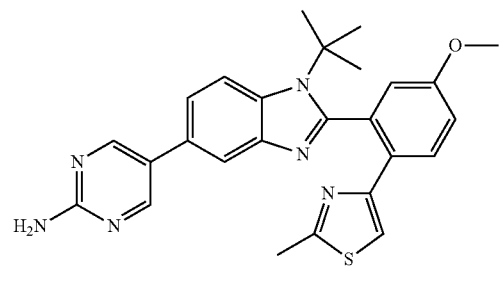 [SMILES: COc1ccc(-c2csc(C)n2)c(-c2nc3cc(-c4cnc(N)nc4)ccc3n2C(C)(C)C)c1]

5-{1-tert-Butyl-2-[5-chloro-2-(2,4-dimethyl-thiazol-5-yl)-phenyl]-1H-benzimidazol-5-yl}-pyrimidin-2-ylamine. LCMS (ESMS): m/z 489.20 (M$^+$)

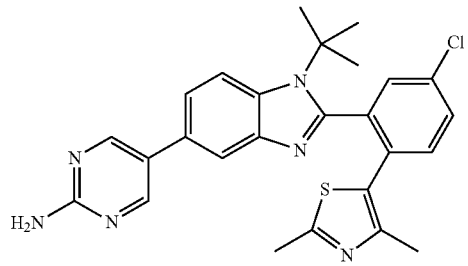

Example 14

5-[1-tert-Butyl-2-(2-1,2,3-triazol-2-yl-phenyl)-1H-benzimidazol-5-yl]-pyrimidin-2-ylamine and

Example 15

5-[1-tert-Butyl-2-(2-1,2,3-triazol-1-yl-phenyl)-1H-benzimidazol-5-yl]-pyrimidin-2-ylamine

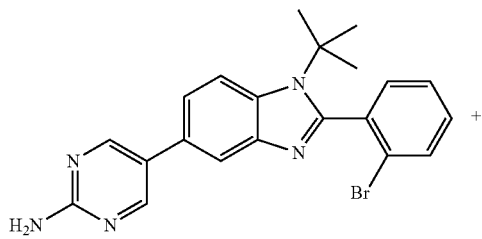

dazol-5-yl]-pyrimidin-2-ylamine (Example 15) (7 mg, 13%) LCMS (ESMS): m/z 411.68 (M⁺+1) as the minor product.

Example 16

5-{1-tert-Butyl-2-[2-(5-methyl-1,3,4-oxadiazol-2-yl)-phenyl]-1H-benzimidazol-5-yl}-pyrimidin-2-ylamine

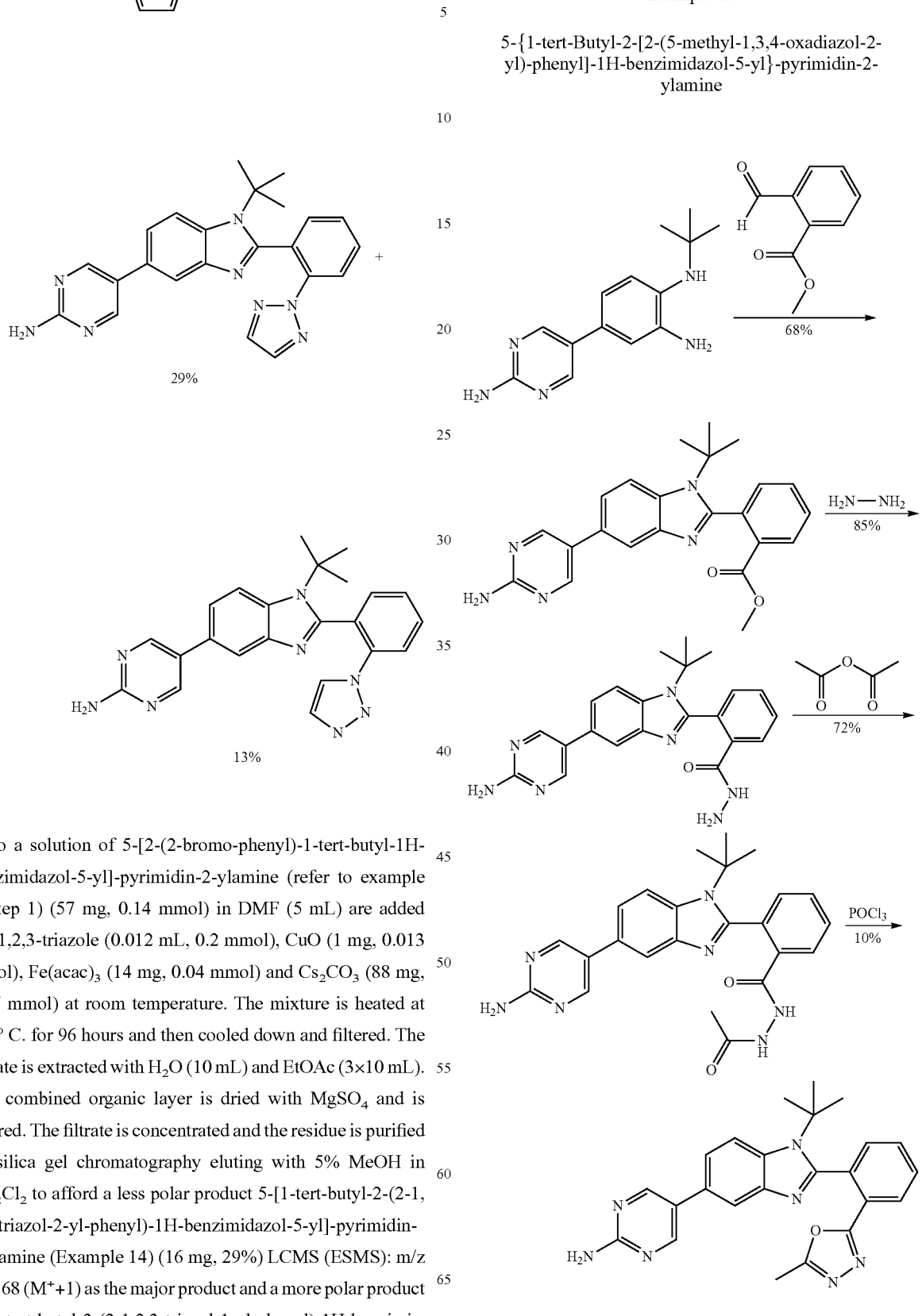

To a solution of 5-[2-(2-bromo-phenyl)-1-tert-butyl-1H-benzimidazol-5-yl]-pyrimidin-2-ylamine (refer to example 8, step 1) (57 mg, 0.14 mmol) in DMF (5 mL) are added 1H-1,2,3-triazole (0.012 mL, 0.2 mmol), CuO (1 mg, 0.013 mmol), Fe(acac)₃ (14 mg, 0.04 mmol) and Cs₂CO₃ (88 mg, 0.27 mmol) at room temperature. The mixture is heated at 120° C. for 96 hours and then cooled down and filtered. The filtrate is extracted with H₂O (10 mL) and EtOAc (3×10 mL). The combined organic layer is dried with MgSO₄ and is filtered. The filtrate is concentrated and the residue is purified by silica gel chromatography eluting with 5% MeOH in CH₂Cl₂ to afford a less polar product 5-[1-tert-butyl-2-(2-1,2,3-triazol-2-yl-phenyl)-1H-benzimidazol-5-yl]-pyrimidin-2-ylamine (Example 14) (16 mg, 29%) LCMS (ESMS): m/z 411.68 (M⁺+1) as the major product and a more polar product 5-[1-tert-butyl-2-(2-1,2,3-triazol-1-yl-phenyl)-1H-benzimi- To a solution of 4-(2-amino-pyrimidin-5-yl)-N$^1$-tert-butyl-benzene-1,2-diamine (300 mg, 1.17 mmol) in DMF (10 mL) is added methyl-2-formybenzoate (287 mg, 1.75 mmol) at room temperature. Oxone (717 mg, 1.17 mmol) in H$_2$O (2 mL) is added and the solution is stirred for 1 hour. Saturated sodium thiosulfate solution (5 mL) is added and the mixture is extracted with EtOAc (3×10 mL) and H$_2$O (10 mL). The combined organic layer is dried with MgSO$_4$ and is filtered. The filtrate is concentrated and the residue is purified by silica gel flash column chromatography with 10% MeOH in CH$_2$Cl$_2$ as the eluent to afford 2-[5-(2-amino-pyrimidin-5-yl)-1-tert-butyl-1H-benzimidazol-2-yl]-benzoic acid methyl ester (320 mg, 68%) as a pale brown solid.

To a solution of 2-[5-(2-amino-pyrimidin-5-yl)-1-tert-butyl-1H-benzimidazol-2-yl]-benzoic acid methyl ester (100 mg, 0.25 mmol) in EtOH (10 mL) is added hydrazine (0.11 mL, 1.2 mmol) at room temperature. The solution is heated under reflux for 48 hours. The solution is cooled down and water (5 mL) is added. The solution is extracted with EtOAc (3×10 mL) and the combined organic layer is dried with MgSO$_4$ and is filtered. The filtrate is concentrated and the residue (85 mg, 85%) is used in the next step of the synthesis without further purification.

To a solution of crude 2-[5-(2-amino-pyrimidin-5-yl)-1-tert-butyl-1H-benzimidazol-2-yl]-benzoic acid hydrazide (85 mg, 0.21 mmol) in DMF (10 mL) are added acetic anhydride (0.03 mL, 0.31 mmol) and iPr$_2$NEt (0.08 mL, 0.42 mmol) at room temperature. The solution is stirred for 2 hours. The solution is extracted with saturated NaHCO$_3$ solution (10 mL) and EtOAc (3×10 mL). The combined organic layer is dried with Na$_2$SO$_4$ and is filtered. The filtrate is concentrated and the residue (67 mg, 72%) is used in the next step without further purification.

2-[5-(2-amino-pyrimidin-5-yl)-1-tert-butyl-1H-benzimidazol-2-yl]-benzoic acid N-acetyl-hydrazide (67 mg, 0.15 mmol) is dissolved in POCl$_3$ (3 mL) at room temperature. The solution is heated to 100° C. for 1 hour. The solution is cooled down and is placed in an ice-bath. The pH of the solution is adjusted to 7 with 2M NaOH solution. The solution is extracted with EtOAc (3×10 mL). The combined organic layer is dried with Na$_2$SO$_4$ and is filtered. The filtrate is concentrated and the residue is purified by silica gel flash column chromatography eluting with 10% MeOH in CH$_2$Cl$_2$ to afford the title compound (6.4 mg, 10%) as a white foam. LCMS (ESMS): m/z 426.20 (M$^+$+1)

Example 17

5-{1-tert-Butyl-2-[5-methoxy-2-(5-methyl-thiazol-2-yl)-phenyl]-1H-benzimidazol-5-yl}-pyrimidin-2-ylamine

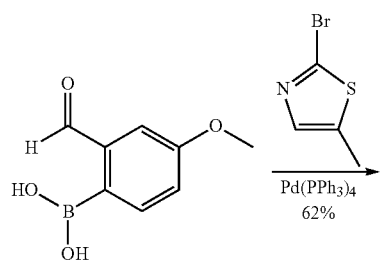

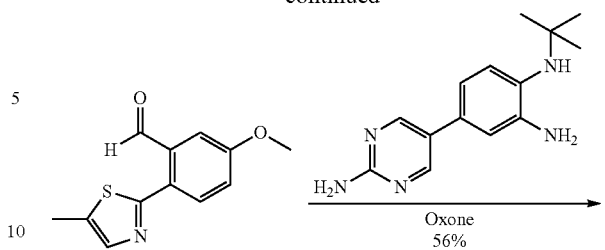

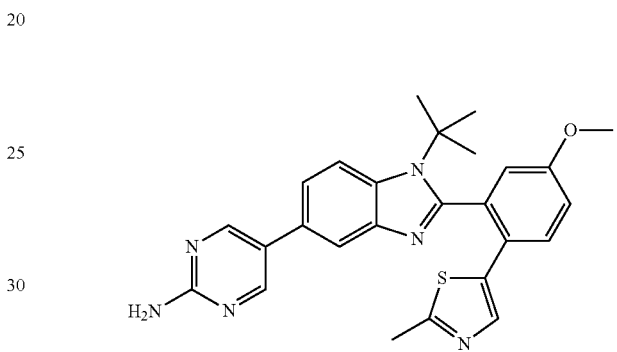

To a solution of 2-formyl-4-methoxyphenylboronic acid (200 mg, 1.11 mmol) in DMF (10 mL) and H$_2$O (2 mL) are added 2-bromo-5-methylthiazole (217 mg, 1.22 mmol), Pd(PPh$_3$)$_4$ (128 mg, 0.11 mmol) and K$_2$CO$_3$ (230 mg, 1.67 mmol) at room temperature. The solution is heated to 120° C. for 1 hour in a microwave reactor. The solution is cooled down and 3-mercaptopropyl-functionalized silica gel (500 mg) is added. The solution is stirred for 15 minutes and filtered. The filtrate is washed with H$_2$O (15 mL) and is extracted with EtOAc (3×15 mL). The combined organic layer is dried with MgSO$_4$ and is filtered. The filtrate is concentrated and the residue is purified by silica gel flash chromatography eluting with 50% EtOAc in heptane to afford 5-methoxy-2-(5-methyl-thiazol-2-yl)-benzaldehyde (160 mg, 63%) as a white foam.

To a solution of 4(2-amino-pyrimidin-5-yl)-N1-tert-butyl-benzene-1,2-diamine (100 mg, 0.39 mmol) in DMF (10 mL) is added 5-methoxy-2-(5-methyl-thiazol-2-yl)-benzaldehyde (99 mg, 0.43 mmol) at room temperature. Oxone (239 mg, 0.39 mmol) in H$_2$O (2 mL) is added and the solution is stirred for 1 hour. Saturated sodium thiosulfate solution (5 mL) is added and the mixture is extracted with EtOAc (3×10 mL) and H$_2$O (10 mL). The combined organic layer is dried with MgSO$_4$ and filtered. The filtrate is concentrated and the residue is purified by silica gel flash column chromatography eluting with 10% MeOH in $CH_2Cl_2$ to afford the title compound (103 mg, 56%) as a white solid. LCMS (ESMS): m/z 471.20 ($M^+$+1)

Example 18

5-{1-tert-Butyl-2-[2-(3-methyl-1,2,4-triazol-1-yl)-phenyl]-1H-benzimidazol-5-yl}-pyrimidin-2-ylamine

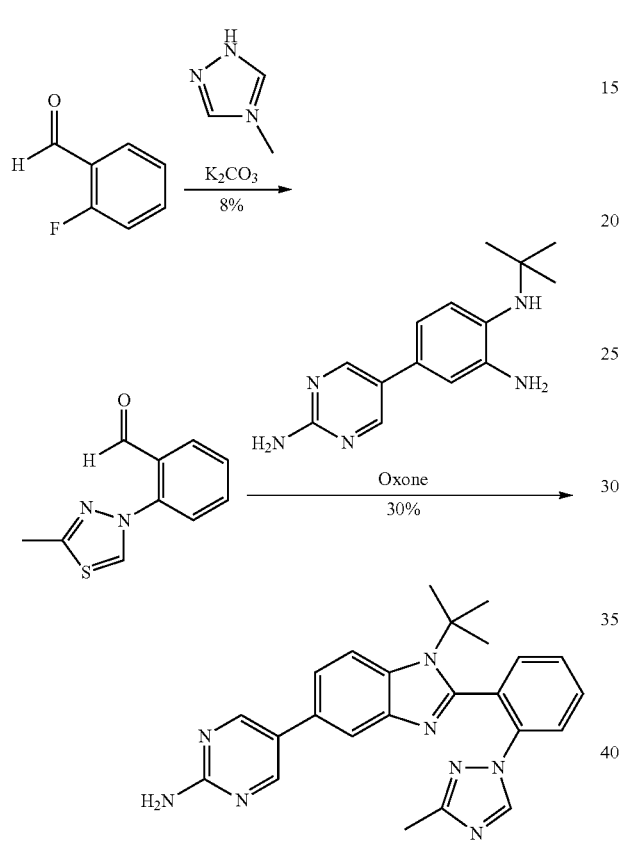

To a solution of 2-fluorobenzaldehyde (400 mg, 3.22 mmol) in DMSO (10 mL) are added 3-methyl-1H-1,2,4-triazole (321 mg, 3.87 mmol) and $K_2CO_3$ (890 mg, 6.45 mmol) at room temperature. The solution is heated to 100° C. for 2 hours. The solution is cooled down and extracted with $H_2O$ (10 mL) and EtOAc (3×10 mL). The combined organic layer is dried ($MgSO_4$), filtered and concentrated. The residue is purified by silica gel chromatography eluting with 50% EtOAc in heptane as the eluent to afford 2-(3-methyl-1,2,4-triazol-1-yl)-benzaldehyde (55 mg, 8%) as a white solid.

To a solution of 4-(2-amino-pyrimidin-5-yl)-N1-tert-butyl-benzene-1,2-diamine (50 mg, 0.19 mmol) in DMF (5 mL) is added 2-(3-methyl-1,2,4-triazol-1-yl)-benzaldehyde (44 mg, 0.23 mmol) at room temperature. Oxone (119 mg, 0.19 mmol) in $H_2O$ (1 mL) is added and the solution stirred for 1 hour. Saturated sodium thiosulfate solution (5 mL) is added and the mixture is extracted with EtOAc (3×10 mL) and $H_2O$ (10 mL). The combined organic layer is dried with ($MgSO_4$), filtered and concentrated. The residue is purified by silica gel flash column chromatography eluting with 10% MeOH in $CH_2Cl_2$ to afford the title compound (25 mg, 30%) as a white solid. LCMS (ESMS): m/z 425.20 ($M^+$+1)

The following compound is made using the procedure described in this Example:

5-{1-tert-Butyl-2-[2-(5-methyl-1,2,4-triazol-1-yl)-phenyl]-1H-benzimidazol-5-yl}-pyrimidin-2-ylamine. LCMS (ESMS): m/z 425.20 ($M^+$+1)

Example 19

{2-Amino-5-[1-tert-butyl-2-(2-1,2,4-triazol-1-yl-phenyl)-1H-benzimidazol-5-yl]-pyridin-3-yl}-methanol

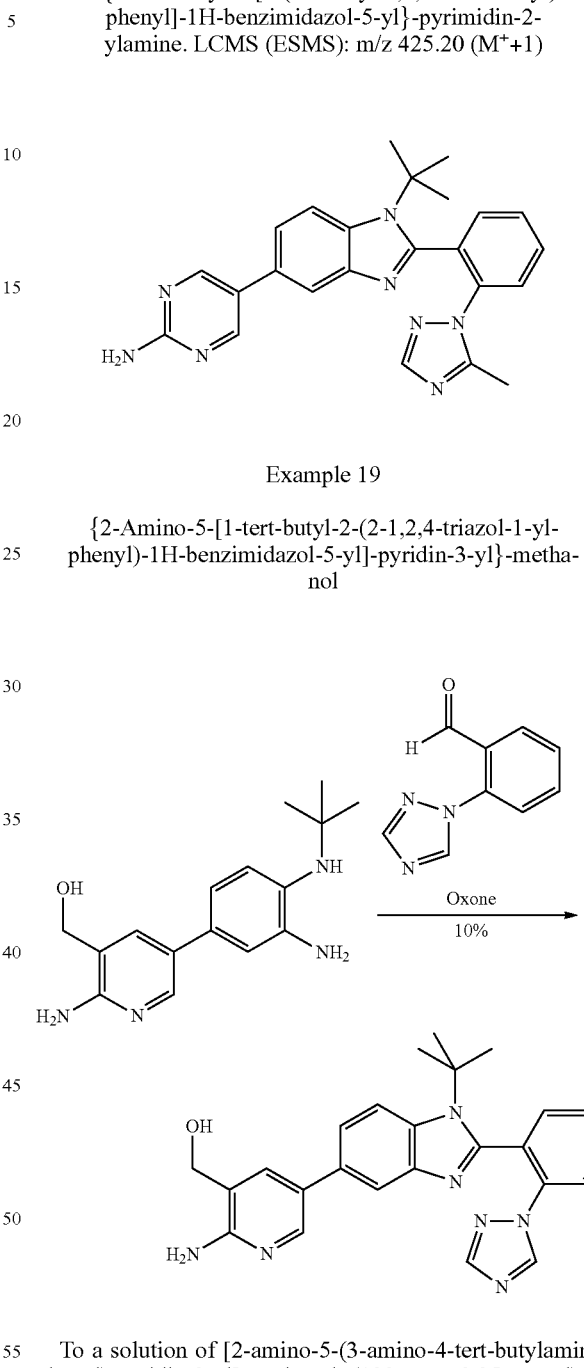

To a solution of [2-amino-5-(3-amino-4-tert-butylamino-phenyl)-pyridin-3-yl]-methanol (100 mg, 0.35 mmol) in DMF (5 mL) is added 2-[1,2,4]-triazol-1-yl-benzaldehyde (73 mg, 0.42 mmol) at room temperature. Oxone (215 mg, 0.35 mmol) in $H_2O$ (1 mL) is added and the solution is stirred for 4 hours. Saturated sodium thiosulfate solution (5 mL) is added and the mixture is extracted with EtOAc (3×10 mL) and $H_2O$ (10 mL). The combined organic layer is dried with $MgSO_4$ and is filtered. The filtrate is concentrated and the residue is purified by silica gel flash column chromatography eluting with 10% MeOH in $CH_2Cl_2$ to afford the title compound (16 mg, 10%) as a pale brown foam. LCMS (ESMS): m/z 440.20 ($M^+$+1)

The following compounds are made using the procedure described in this Example:

(2-Amino-5-{1-tert-butyl-2-[2-(3-methyl-1,2,4-oxadiazol-5-yl)-phenyl]-1H-benzimidazol-5-yl}-pyridin-3-yl)-methanol. LCMS (ESMS): m/z 455.20 (M++1)

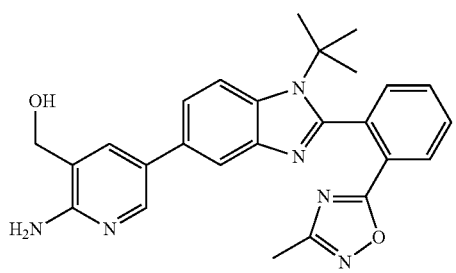 [SMILES: Cc1noc(-c2ccccc2-c2nc3cc(-c4cnc(N)c(CO)c4)ccc3n2C(C)(C)C)n1]

1-tert-Butyl-5-(2,3-dihydro-1H-pyrrolo[2,3-b]pyridin-5-yl)-2-(2-1,2,4-triazol-1-yl-phenyl)-1H-benzimidazole. LCMS (ESMS): m/z 436.20 (M++1)

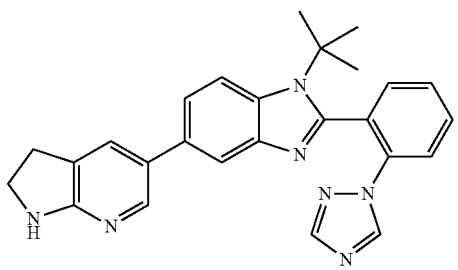 [SMILES: CC(C)(C)n1c(-c2ccccc2-n2cncn2)nc2cc(-c3cnc4c(c3)CCN4)ccc21]

Example 20

5-{1-tert-Butyl-2-[2-(5-methyl-1,3,4-thiadiazol-2-yl)-phenyl]-1H-benzimidazol-5-yl}-pyrimidin-2-ylamine

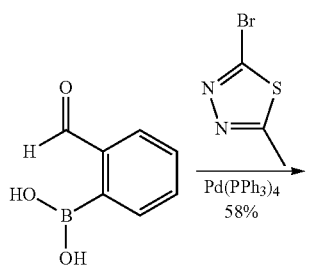

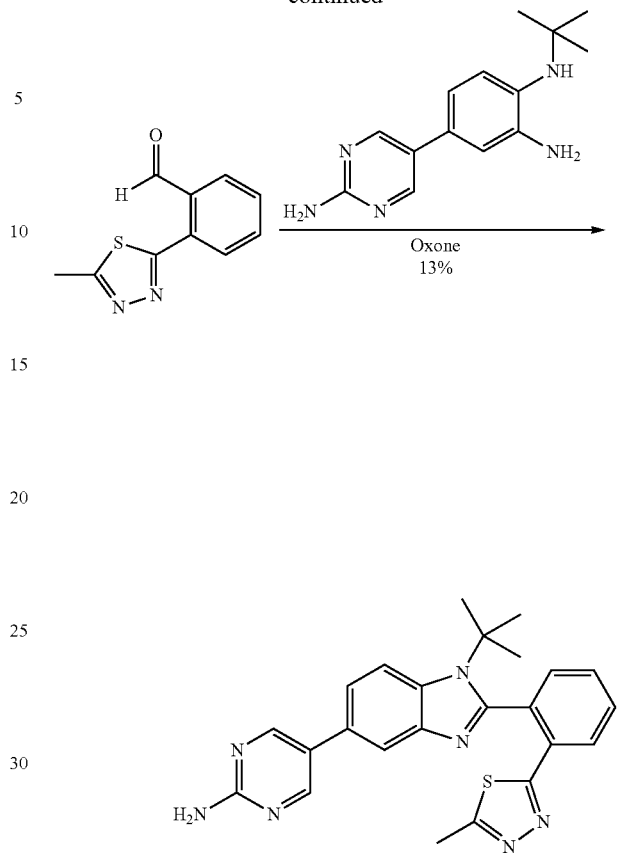

To a solution of 2-bromo-5-methyl-1,3,4-thiadiazole (150 mg, 0.84 mmol) in 1,2-dimethoxyethane (5 mL) are added 2-formylphenylboronic acid (190 mg, 1.26 mmol), Pd(PPh$_3$)$_4$ (97 mg, 0.08 mmol) and Na$_2$CO$_3$ (sat., 0.10 mL) at room temperature. The solution is heated to 100° C. for 18 hours then cooled and poured into water and EtOAc. Layers are separated and the aqueous phase extracted with EtOAc (1×10 mL). The combined organics are dried (MgSO$_4$), filtered and concentrated to give the crude product which is purified via flash chromatography (12 g silica gel, 5-60% EtOAc/hexanes). The product-containing fractions are combined and concentrated to give 2-(5-methyl-1,3,4-thiadiazol-2-yl)-benzaldehyde (100 mg, 58%) which is used without further purification.

To a solution of 4-(2-amino-pyrimidin-5-yl)-N1-tert-butyl-benzene-1,2-diamine (100 mg, 0.39 mmol) in DMF (3 mL) is added 2-(5-methyl-1,3,4-thiadiazol-2-yl)-benzaldehyde (100 mg, 0.49 mmol) at room temperature. Oxone (240 mg, 0.39 mmol) in H$_2$O (1 mL) is added and the solution is stirred at the same temperature for 3 hours. The reaction is poured into water (75 mL) and sodium thiosulfate (sat., 15 mL). The product is extracted into EtOAc (3×) and the combined organics are then dried (MgSO$_4$), filtered, and concentrated. Purification via flash chromatography (12 g silica gel, 0-10% MeOH/CH$_2$Cl$_2$) gives impure product which is re-purified via preparative TLC (0.5 mm silica gel, 5% MeOH/

CH$_2$Cl$_2$). The product band is isolated to give the title compound (23 mg, 13%). LCMS (ESMS): m/z 442.20 (M$^+$+1)

Example 21

5-{1-tert-Butyl-2-[2-(1H-pyrazol-4-yl)-phenyl]-1H-benzimidazol-5-yl}-pyrimidin-2-ylamine

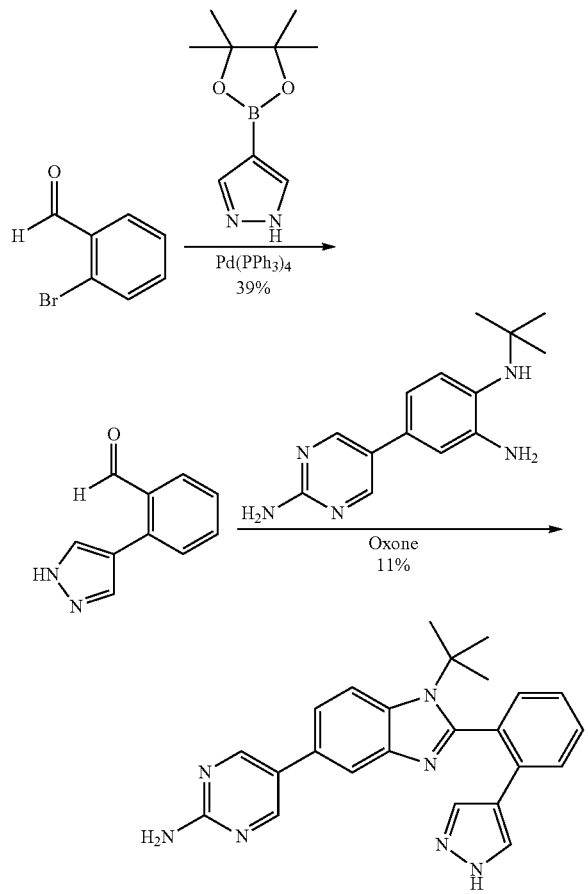

To a solution of 2-bromobenzaldehyde (300 mg, 1.62 mmol) in DMF (10 mL) are added 4-(4,4,5,5-tetramethyl-1,3,2-dioxaborolan-2-yl)-1H-pyrazole (470 mg, 2.43 mmol), Pd(PPh$_3$)$_4$ (190 mg, 0.16 mmol) and 2M Na$_2$CO$_3$ (0.50 mL) at room temperature. The solution is heated to 100° C. for 1 hour in a microwave reactor, cooled and poured into water and EtOAc. Layers are separated and the aqueous phase extracted with EtOAc (1×10 mL). The combined organics are dried (MgSO$_4$), filtered and are concentrated to give the crude product which is purified via flash chromatography (12 g silica gel, 0-10% MeOH/CH$_2$Cl$_2$). The product-containing fractions are combined and concentrated to give 2-(1H-pyrazol-4-yl)-benzaldehyde (110 mg, 39%) which is used without further purification.

To a solution of 4-(2-amino-pyrimidin-5-yl)-N1-tert-butyl-benzene-1,2-diamine (150 mg, 0.58 mmol) in DMF (5 mL) is added 2-(1H-pyrazol-4-yl)-benzaldehyde (100 mg, 0.58 mmol) at room temperature. Oxone (360 mg, 0.58 mmol) in H$_2$O (1 mL) is added and the reaction is stirred at the same temperature for 3 hours. The reaction is poured into water (75 mL) and sodium thiosulfate (sat., 15 mL). The product is extracted into EtOAc (3×) and the combined organics are then dried (MgSO$_4$), filtered, and concentrated. Purification via flash chromatography (12 g silica gel, 0-10% MeOH/CH$_2$Cl$_2$) gives the title compound (25 mg, 10%). LCMS (ESMS): m/z 410.20 (M$^+$+1)

Example 22

{2-Amino-5-[1-tert-butyl-2-(5-methoxy-2-pyrazol-1-yl-phenyl)-1H-benzimidazol-5-yl]-pyridin-3-yl}-methanol

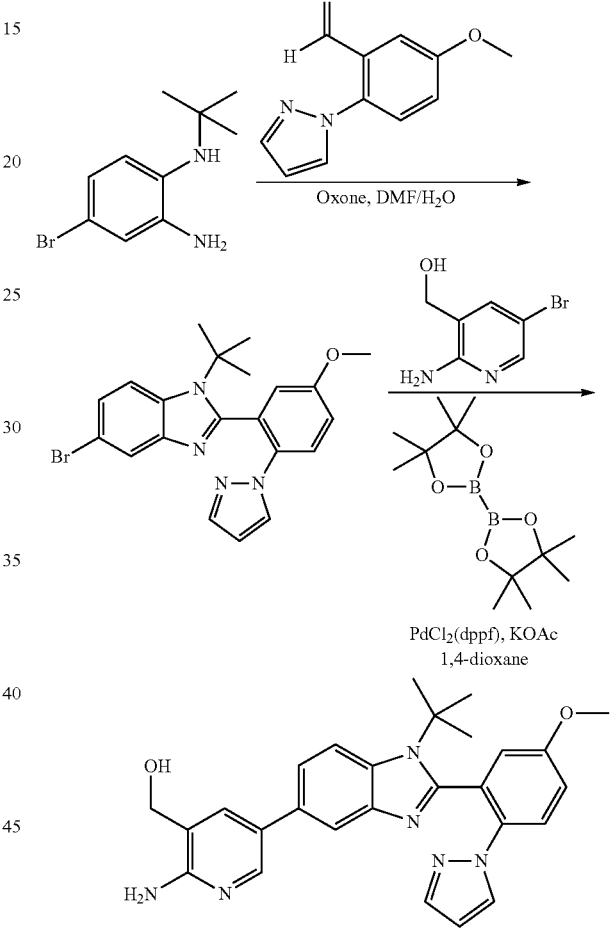

To a solution of 4-bromo-N$^1$-tert-butyl-benzene-1,2-diamine (500 mg, 2.06 mmol) in DMF (10 mL) is added 5-methoxy-2-(1H-pyrazol-1-yl)benzaldehyde (620 mg, 3.08 mmol) at room temperature. Oxone (1.26 g, 2.06 mmol) in H$_2$O (3 mL) is added and the solution is stirred at the same temperature for 3 hours. The reaction is poured into water (75 mL) and sodium thiosulfate (sat., 10 mL) and the resulting solid is collected via filtration. The crude solid product is used without further purification.

To a high pressure vessel are added 2-amino-3-hyroxymethyl-5-bromopyridine (90 mg, 0.44 mmol), bis(pinacolato) diboron (135 mg, 0.53 mmol) and KOAc (131 mg, 1.33 mmol) in 10 mL of 1,4-dioxane. The solution is degassed with nitrogen for 10 minutes, followed by the addition of PdCl$_2$ (dppf) (36 mg, 0.04 mmol). The reaction mixture is warmed to 80° C. and stirred for 1 hour. After this time a solution of 5-bromo-1-tert-butyl-2-(5-methoxy-2-pyrazol-1-yl-phenyl)-

1H-benzimidazole (226 mg, 0.53 mmol) and additional PdCl$_2$(dppf) (16 mg, 0.02 mmol) in DMF (1 mL) and 2M Na$_2$CO$_3$ (0.1 mL) are added. The reaction is heated at 80° C. for 12 hours, then cooled to room temperature and poured into water. The mixture is extracted with EtOAc (3×) and the combined organics are dried (MgSO$_4$), filtered and concentrated. Purification via flash chromatography (12 g silica gel, 0-8% MeOH/CH$_2$Cl$_2$) and preparative TLC (0.5 mm silica gel, 8% MeOH/CH$_2$Cl$_2$) gives the title compound (15 mg, 7%). LCMS (ESMS): m/z 469.20 (M$^+$+1)

Example 23

5-{1-tert-Butyl-2-[2-(3,5-dimethyl-pyrazol-1-yl)-phenyl]-1H-benzimidazol-5-yl}-pyrimidin-2-ylamine

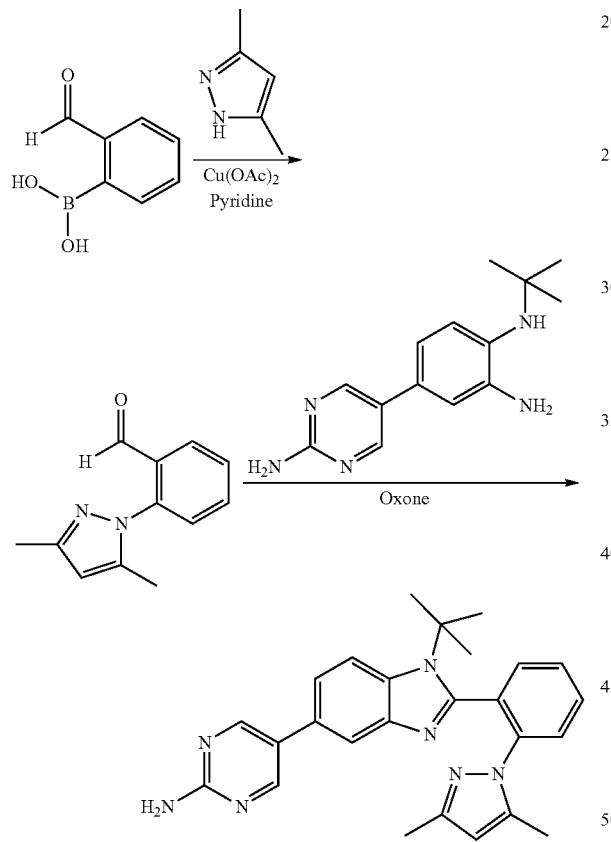

To a solution of 2-formylphenylboronic acid (500 mg, 3.33 mmol) in CH$_2$Cl$_2$ (30 mL) are added 3,5-dimethyl-1H-pyrazole (160 mg, 1.67 mmol), Cu(OAc)$_2$ (909 mg, 5.0 mmol), pyridine (528 mg, 6.67 mmol) and molecular sieves (1.0 g) at room temperature. The mixture is stirred at the same temperature for 4 days with loose cap. The mixture is filtered through a short pad of diatomaceous earth and the solids are washed with CH$_2$Cl$_2$. The combined filtrates are concentrated and purified via flash chromatography (12 g silica gel, CH$_2$Cl$_2$ then 20% EtOAc/heptane) to afford 2-(3,5-dimethyl-pyrazol-1-yl)-benzaldehyde (50 mg, 8%).

To a solution of 4-(2-amino-pyrimidin-5-yl)-N1-tert-butyl-benzene-1,2-diamine (64 mg, 0.25 mmol) in DMF (3 mL) is added 2-(3,5-dimethyl-pyrazol-1-yl)-benzaldehyde (50 mg, 0.25 mmol) at room temperature. Oxone (150 mg, 0.25 mmol) in H$_2$O (1 mL) is added and the solution is stirred at the same temperature for 3 hours. The reaction is poured into water (25 mL) and sodium thiosulfate (sat., 50 mL). The product is extracted into EtOAc (2×) and the combined organics are then dried (MgSO$_4$), filtered, and concentrated. Purification via flash chromatography (4 g silica gel, 0-6% MeOH/CH$_2$Cl$_2$) affords the title compound (50 mg, 46%). LCMS (ESMS): m/z 438.20 (M$^+$+1)

The following compound is made using the procedure described in this Example:

5-{1-tert-Butyl-2-[2-(3-methyl-pyrazol-1-yl)-phenyl]-1H-benzimidazol-5-yl}-pyrimidin-2-ylamine. LCMS (ESMS): m/z 424.20 (M$^+$+1)

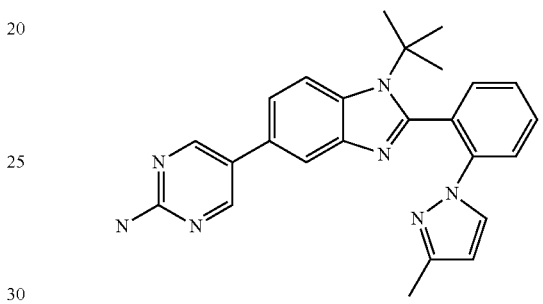

Example 24

1-tert-Butyl-5-(2,3-dihydro-1H-pyrrolo[2,3-b]pyridin-5-yl)-2-(5-methoxy-2-pyrazol-1-yl-phenyl)-1H-benzimidazole

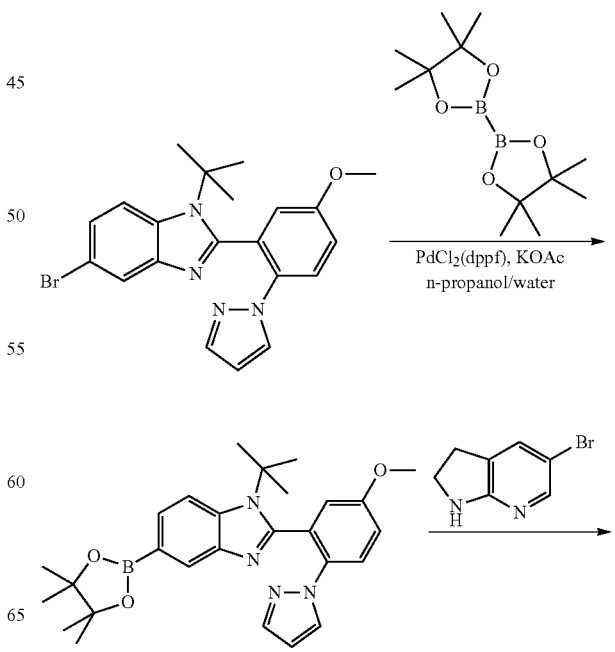

123
-continued

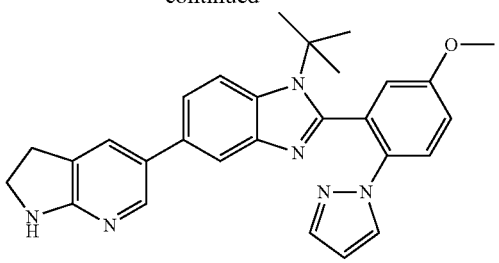

In a round bottom flask are combined 5-bromo-1-tert-butyl-2-(5-methoxy-2-pyrazol-1-yl-phenyl)-1H-benzimidazole (1.40 g, 3.29 mmol), bis(pinacolato)diboron (1.25 g, 4.94 mmol), and KOAc (0.97 g, 9.87 mmol) in 60 mL of propanol (45 mL)/water (15 mL). The solution is degassed with argon for 10 minutes. After this time, PdCl$_2$(dppf) (269 mg, 0.33 mmol) catalyst is added. The reaction mixture is stirred at 90° C. for 48 hours and cooled to room temperature. The reaction mixture is poured into water and extracted with EtOAc (2×). The combined organics are dried (MgSO$_4$), filtered, and concentrated. The residue is purified via flash chromatography (120 g silica gel, 30-80% EtOAc/heptane). Product-containing fractions are combined and concentrated to give 1-tert-butyl-2-(5-methoxy-2-pyrazol-1-yl-phenyl)-5-(4,4,5,5-tetramethyl-1,3,2-dioxaborolan-2-yl)-1H-benzimidazole (0.70 g, 45%) which is used without further purification.

In a microwave vial are combined 1-tert-butyl-2-(5-methoxy-2-pyrazol-1-yl-phenyl)-5-(4,4,5,5-tetramethyl-1,3,2-dioxaborolan-2-yl)-1H-benzimidazole (285 mg, 0.60 mmol), 5-bromo-2,3-dihydro-1H-pyrrolo[2,3-b]pyridine (100 mg, 0.50 mmol), potassium carbonate (140 mg, 1.0 mmol), and bis(di-tert-butyl(4-dimethylaminophenyl)phosphine)dichloropalladium(II) (53 mg, 0.08 mmol) in toluene (3.0 mL) and water (0.30 mL). The reaction vial is sealed and stirred at 100° C. for 4 hours in an oil bath. After this time the reaction is cooled and poured into water. The product is extracted into EtOAc (2×). The combined organics are dried (MgSO$_4$), filtered and concentrated. Purification via flash chromatography (12 g silica gel, 0-5% MeOH/CH$_2$Cl$_2$) affords the title compound (40 mg, 17%). LCMS (ESMS): m/z 465.20 (M$^+$+1)

The following compound is made using the procedure described in this Example:

1-tert-Butyl-2-(5-methoxy-2-pyrazol-1-yl-phenyl)-5-(1H-pyrrolo[2,3-b]pyridin-5-yl)-1H-benzimidazole. LCMS (ESMS): m/z 463.20 (M$^+$+1)

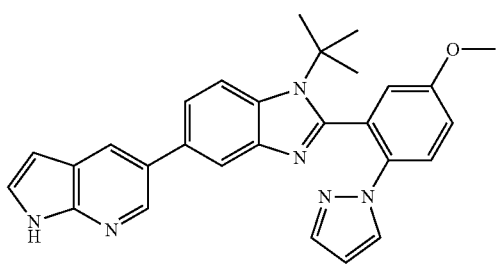 [SMILES: COc1ccc(-n2cccn2)c(-c2nc3cc(-c4cnc5[nH]ccc5c4)ccc3n2C(C)(C)C)c1]

Example 25

5-{1-tert-Butyl-2-[5-methoxy-2-(3-methyl-pyrazol-1-yl)-phenyl]-1H-benzimidazol-5-yl}-pyrimidin-2-ylamine

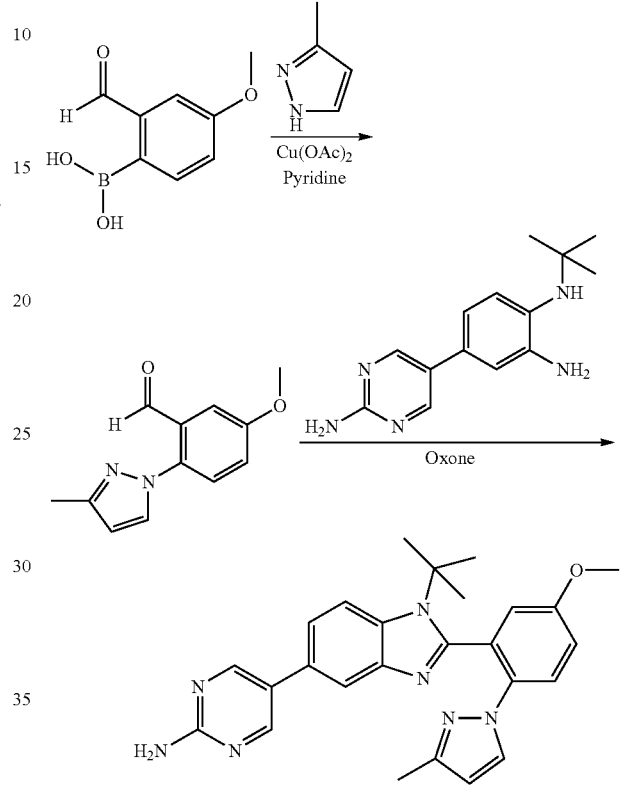

To a solution of 2-formyl-4-methoxyphenylboronic acid (2.5 g, 13.89 mmol) in CH$_2$Cl$_2$ (30 mL) and DMF (15 mL) are added 3-methyl-1H-pyrazole (0.80 g, 9.72 mmol), Cu(OAc)$_2$ (3.78 g, 20.84 mmol), pyridine (2.27 mL, 27.78 mmol) and molecular sieves (2.5 g) at room temperature. The mixture is stirred at the same temperature for 5 days with loose cap. The mixture is filtered through a short pad of diatomaceous earth and the solids are washed with CH$_2$Cl$_2$. The combined filtrates are concentrated and the remaining residue is diluted with water and ethyl acetate. The layers are separated and the aqueous phase extracted with EtOAc (3×). The combined organics are dried (MgSO$_4$), filtered, and concentrated. The remaining residue is purified via flash chromatography (silica gel, 0-15% EtOAc/heptane) to afford 5-methoxy-2-(3-methyl-pyrazol-1-yl)-benzaldehyde (90 mg, 3%).

To a solution of 4-(2-amino-pyrimidin-5-yl)-N$^1$-tert-butylbenzene-1,2-diamine (100 mg, 0.38 mmol) in DMF (3 mL) is added 5-methoxy-2-(3-methyl-pyrazol-1-yl)-benzaldehyde (90 mg, 0.42 mmol) at room temperature. Oxone (230 mg, 0.38 mmol) in H$_2$O (1 mL) is added and the solution is stirred at the same temperature for 12 hours. The reaction is poured into water (25 mL) and sodium thiosulfate (sat., 20 mL). The product is extracted into EtOAc (3×) and the combined organics are then dried (MgSO$_4$), filtered, and concentrated. Purification via flash chromatography (silica gel, 0-8% MeOH/CH$_2$Cl$_2$) affords the title compound (65 mg, 38%). LCMS (ESMS): m/z 454.20 (M$^+$+1)

The following compound is made using the procedure described in this Example:

5-{1-tert-Butyl-2-[2-(3,5-dimethyl-pyrazol-1-yl)-5-methoxy-phenyl]-1H-benzimidazol-5-yl}-pyrimidin-2-ylamine. LCMS (ESMS): m/z 468.20 (M⁺+1)

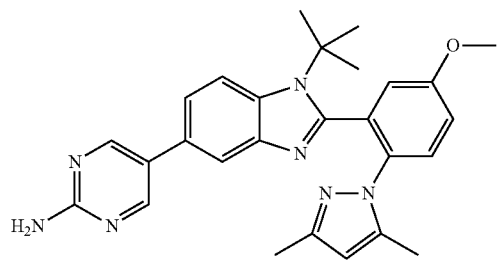 [SMILES: COc1ccc(-n2nc(C)cc2C)c(-c2nc3cc(-c4cnc(N)nc4)ccc3n2C(C)(C)C)c1]

Example 26

5-[1-tert-Butyl-2-(2-thiazol-2-yl-phenyl)-1H-benzimidazol-5-yl]-pyrimidin-2-ylamine

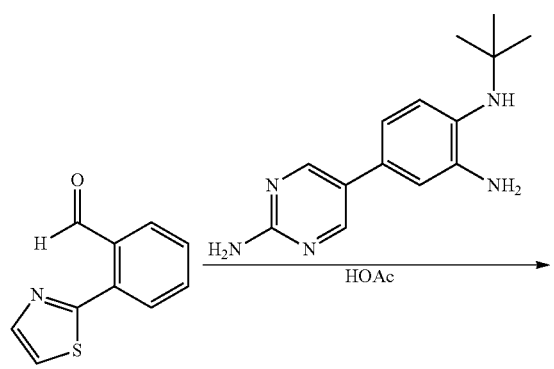

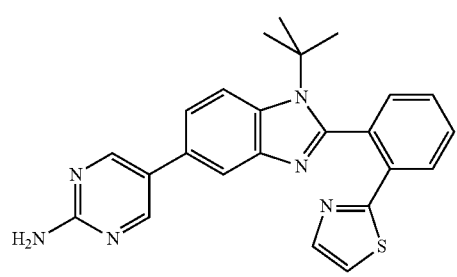

A solution of 2-thiazol-2-yl-benzaldehyde (100 mg, 0.53 mmol) and 4-(2-amino-pyrimidin-5-yl)-N1-tert-butyl-benzene-1,2-diamine (120 mg, 0.45 mmol) in acetic acid (5 mL) is warmed to 50° C. for 12 hours and then at 80° C. for 60 hours. After this time the reaction is cooled to room temperature and pour into water and NaHCO₃ (sat.). The product is extracted into EtOAc (3×) and the combined organics are dried (MgSO₄), filtered and concentrated. Purification via flash chromatography (12 g silica gel, 0-5% MeOH/CH₂Cl₂) affords the title compound (30 mg, 16%). LCMS (ESMS): m/z 427.20 (M⁺+1)

Example 27

5-{1-tert-Butyl-2-[5-methoxy-2-(3-methyl-1,2,4-thiadiazol-5-yl)-phenyl]-1H-benzimidazol-5-yl}-pyrimidin-2-ylamine

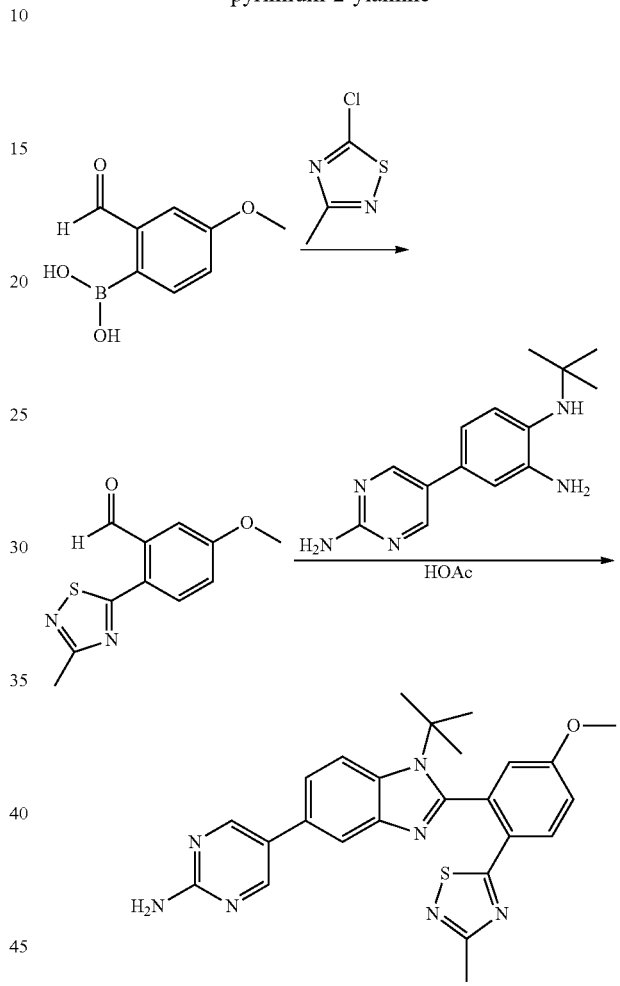

In a microwave vial are combined 2-formyl-4-methoxyphenylboronic acid (432 mg, 2.40 mmol), 5-chloro-3-methyl-1,2,4-thiadiazole (270 mg, 2.00 mmol), potassium acetate (390 mg, 4.00 mmol), and bis(di-tert-butyl(4-dimethylaminophenyl)phosphine)-dichloropalladium(II) (283 mg, 0.40 mmol) in 1,4-dioxane (6 mL) and water (0.50 mL). The reaction vial is sealed and stirred at 100° C. for 20 hours. The reaction mixture is cooled to ambient temperature and poured into water and extracted with EtOAc (3×). The combined organics are dried (MgSO₄), filtered and concentrated. Purification via flash chromatography (12 g silica gel, 5-40% EtOAc/heptane) affords 5-methoxy-2-(3-methyl-1,2,4-thiadiazol-5-yl)-benzaldehyde which is used without further purification.

A solution of 4-(2-amino-pyrimidin-5-yl)-N¹-tert-butyl-benzene-1,2-diamine (110 mg, 0.43 mmol) and 5-methoxy-2-(3-methyl-1,2,4-thiadiazol-5-yl)-benzaldehyde (100 mg, 0.43 mmol) in acetic acid (5 mL) is warmed to 50° C. for 12 hours then at 80° C. for 60 hours. The reaction mixture is cooled to room temperature and poured into water and NaHCO$_3$ (sat.). The product is extracted into EtOAc (3×) and the combined organics are dried (MgSO$_4$), filtered and concentrated. Purification via flash chromatography (12 g silica gel, 0-5% MeOH/CH$_2$Cl$_2$) affords the title compound (40 mg, 20%). LCMS (ESMS): m/z 472.20 (M$^+$+1)

The following compound is made using the procedure described in this Example:

5-{1-tert-Butyl-2-[2-(3-methyl-1,2,4-thiadiazol-5-yl)-phenyl]-1H-benzimidazol-5-yl}-pyrimidin-2-ylamine. LCMS (ESMS): m/z 442.20 (M$^+$+1)

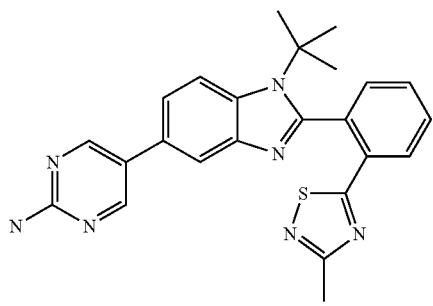 [SMILES: Cc1nsc(-c2ccccc2-c2nc3cc(-c4cnc(N)nc4)ccc3n2C(C)(C)C)n1]

Example 28

5-{1-tert-Butyl-2-[2-(4-methyl-pyrazol-1-yl)-phenyl]-1H-benzimidazol-5-yl}-pyrimidin-2-ylamine

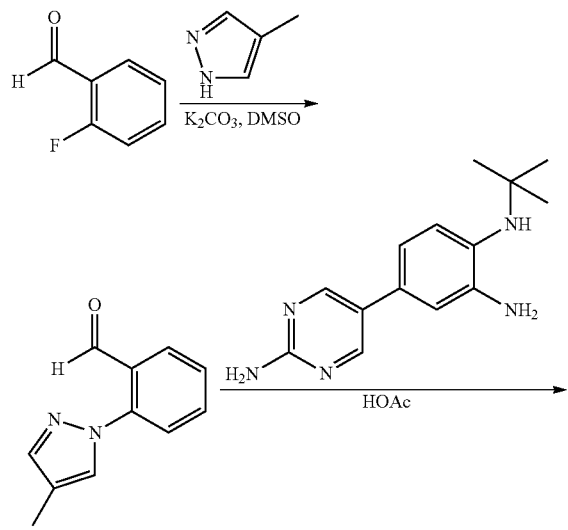

2-Fluorobenzaldehyde (250 mg, 2.01 mmol), 4-methyl-1H-pyrazole (260 mg, 3.17 mmol) and potassium carbonate (820 mg, 5.93 mmol) are combined in DMSO (15 mL) and warmed to 100° C. for 18 hours. The reaction mixture is cooled to room temperature and the potassium carbonate is removed via filtration. The solids are washed with EtOAc and the combined filtrates are poured into water. Separate the layers and extract the aqueous phase with EtOAc (1×). The combined organics are washed with water and brine and dried (MgSO$_4$), filtered, and concentrated. Purification via flash chromatography (12 g silica gel, 0-15% EtOAc/heptane) gives 2-(4-methyl-pyrazol-1-yl)-benzaldehyde.

A solution of 4-(2-amino-pyrimidin-5-yl)-N1-tert-butyl-benzene-1,2-diamine (180 mg, 0.70 mmol) and 2-(4-methyl-pyrazol-1-yl)-benzaldehyde (130 mg, 0.70 mmol) in acetic acid (5 mL) is warmed to 100° C. for 16 hours then cooled to room temperature and neutralized with NaHCO$_3$ (sat.). The product is extracted into EtOAc (3×) and the combined organics are dried (MgSO$_4$), filtered and concentrated. Purification via flash chromatography (12 g silica gel, 0-5% MeOH/CH$_2$Cl$_2$) affords the title compound (105 mg, 35%). LCMS (ESMS): m/z 424.20 (M$^+$+1)

The following compounds are made using the procedure described in this Example:

5-{1-tert-Butyl-2-[2-(4-chloro-pyrazol-1-yl)-phenyl]-1H-benzimidazol-5-yl}-pyrimidin-2-ylamine. LCMS (ESMS): m/z 444.20 (M$^+$+1)

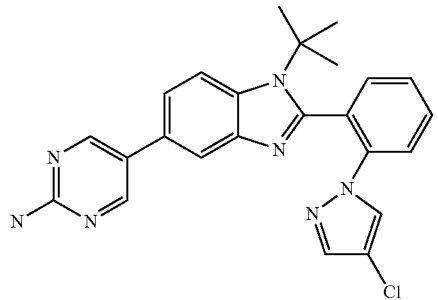 [SMILES: CC(C)(C)n1c(-c2ccccc2-n2cc(Cl)cn2)nc2cc(-c3cnc(N)nc3)ccc21]

5-{1-tert-Butyl-2-[2-(3-trifluoromethyl-pyrazol-1-yl)-phenyl]-1H-benzimidazol-5-yl}-pyrimidin-2-ylamine. LCMS (ESMS): m/z 478.20 (M$^+$+1)

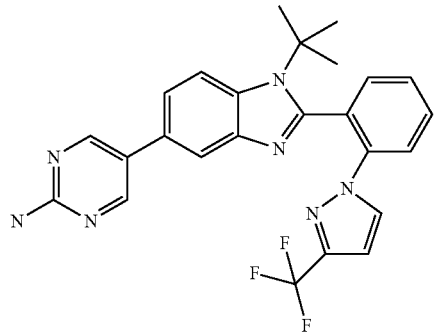 [SMILES: CC(C)(C)n1c(-c2ccccc2-n2ccc(C(F)(F)F)n2)nc2cc(-c3cnc(N)nc3)ccc21]

Example 29

5-{1-tert-Butyl-2-[2-(4-chloro-pyrazol-1-yl)-5-methoxy-phenyl]-1H-benzimidazol-5-yl}-pyrimidin-2-ylamine

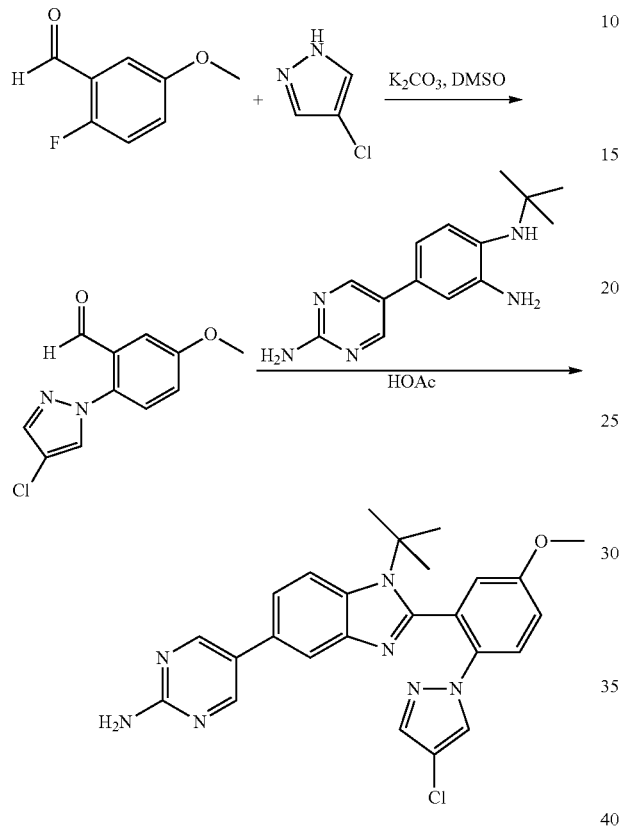

To a solution of 2-fluoro-5-methoxybenzaldehyde (450 mg, 2.92 mmol) in DMSO (13 mL) are added 4-chloro-1H-pyrazole (450 mg, 4.39 mmol) and $K_2CO_3$ (810 mg, 5.84 mmol) at room temperature. The solution is heated to 100° C. for 1.5 hours. The solution is cooled down and is diluted with $H_2O$ (150 mL) and extracted with EtOAc (3×). The combined organic layers are dried with $MgSO_4$ and filtered. The filtrate is concentrated and the residue is purified by silica gel flash column chromatography with 5-25% EtOAc in heptane as the eluent to afford 2-(4-chloro-pyrazol-1-yl)-5-methoxy-benzaldehyde which is used without further purification A solution of 4-(2-amino-pyrimidin-5-yl)-N1-tert-butyl-benzene-1,2-diamine (180 mg, 0.70 mmol) and 2-(4-chloro-pyrazol-1-yl)-5-methoxy-benzaldehyde (270 mg, 1.14 mmol) in acetic acid (5 mL) is warmed to 100° C. for 16 hours, then cooled to room temperature and neutralized with $NaHCO_3$ (sat.). The product is extracted into EtOAc (3×) and the combined organics are dried ($MgSO_4$), filtered and concentrated. Purification via flash chromatography (12 g silica gel, 0-5% MeOH/$CH_2Cl_2$) follows by reverse phase HPLC (20-100% $CH_3CN/H_2O$, each solvent containing 0.1% TFA) affords the title compound (90 mg, 27%). LCMS (ESMS): m/z 474.20 ($M^++1$)

The following compounds are made using the procedure described in this Example:

5-{1-tert-Butyl-2-[5-methoxy-2-(4-methyl-pyrazol-1-yl)-phenyl]-1H-benzimidazol-5-yl}-pyrimidin-2-ylamine. LCMS (ESMS): m/z 454.20 ($M^++1$)

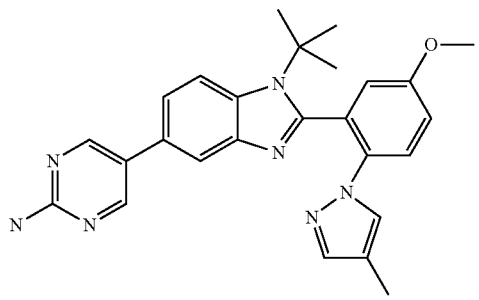 [SMILES: COc1ccc(-n2cc(C)cn2)c(-c2nc3cc(-c4cnc(N)nc4)ccc3n2C(C)(C)C)c1]

5-{1-tert-Butyl-2-[5-methoxy-2-(3-trifluoromethyl-pyrazol-1-yl)-phenyl]-1H-benzimidazol-5-yl}-pyrimidin-2-ylamine. LCMS (ESMS): m/z 508.20 ($M^++1$)

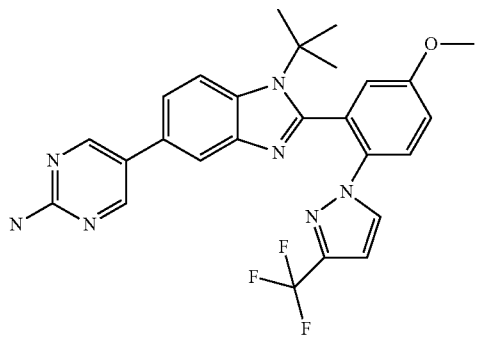 [SMILES: COc1ccc(-n2ccc(C(F)(F)F)n2)c(-c2nc3cc(-c4cnc(N)nc4)ccc3n2C(C)(C)C)c1]

Example 30

5-{1-tert-Butyl-2-[5-chloro-2-(3-methyl-pyrazol-1-yl)-phenyl]-1H-benzimidazol-5-yl}-pyrimidin-2-ylamine

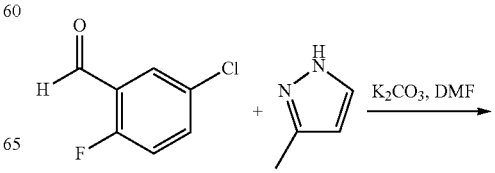

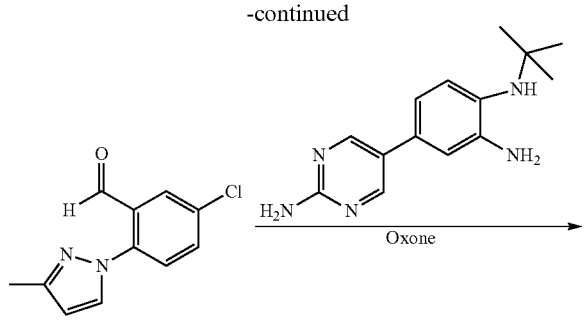

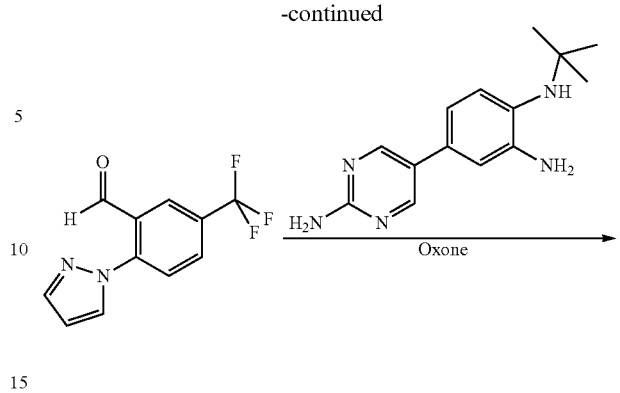

5-Chloro-2-fluoro-benzaldehyde (1.0 g, 6.31 mmol), 3-methyl-1H-pyrazole (0.78 g, 9.46 mmol) and potassium carbonate (1.74 g, 12.61 mmol) are combined in DMF (30 mL) and warmed to 50° C. for 7 hours then warmed to 70° C. and stirred for 12 hours. After this time, the reaction is warmed to 110° C. and stir for 18 hours, then cooled to room temperature and used without purification, approximately 50% product by LC-MS.

A 10 mL aliquot of 5-chloro-2-(3-methyl-pyrazol-1-yl)-benzaldehyde from the above reaction is filtered (in DMF, 50% pure by LC-MS, calculated mass based on purity is 235 mg, 1.10 mmol). The crude aldehyde is treated with 4-(2-amino-pyrimidin-5-yl)-N1-tert-butyl-benzene-1,2-diamine (200 mg, 0.78 mmol). Oxone (478 mg, 0.78 mmol) is added as a water solution (2 mL). The resulting mixture is warmed to 60° C. for 2 hours and cooled to room temperature. The reaction mixture is poured into water and extracted with EtOAc (3×). The combined organics are dried (MgSO$_4$), filtered, and concentrated. Purification via flash chromatography (12 g silica gel, 0-6% MeOH/CH$_2$Cl$_2$) followed by mass triggered HPLC(CH$_3$CN/H$_2$O) affords the title compound (45 mg, 13%). LCMS (ESMS): m/z 458.20 (M$^+$+1)

Example 31

5-[1-tert-Butyl-2-(2-pyrazol-1-yl-5-trifluoromethyl-phenyl)-1H-benzimidazol-5-yl]-pyrimidin-2-ylamine

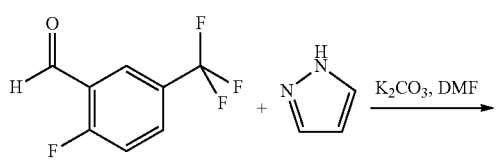

The 2-fluoro-5-trifluoromethyl-benzaldehyde (470 mg, 2.45 mmol), 1H-pyrazole (250 mg, 3.67 mmol) and potassium carbonate (680 mg, 4.89 mmol) are combined in DMF (18 mL) and warmed to 50° C. for 7 hours then warmed to 70° C. and stirred for 12 hours. The reaction is cooled to room temperature and is used without purification, approximately 50% product by LC-MS.

A 6 mL aliquot of 2-pyrazol-1-yl-5-trifluoromethyl-benzaldehyde from the above reaction is filtered (in DMF, 50% pure by LC-MS, calculated mass based on purity is 98 mg, 0.41 mmol). The crude aldehyde is treated with 4-(2-amino-pyrimidin-5-yl)-N$^1$-tert-butyl-benzene-1,2-diamine (100 mg, 0.39 mmol). Oxone (239 mg, 0.39 mmol) is added as a water solution (1 mL). The resulting mixture is warmed to 60° C. for 2 hours and cooled to room temperature, poured into water and extracted with EtOAc (3×). The combined organics are dried (MgSO$_4$), filtered, and concentrated. Purification via flash chromatography (12 g silica gel, 0-6% MeOH/CH$_2$Cl$_2$) follows by mass triggered HPLC (CH$_3$CN/H$_2$O) affords the title compound (40 mg, 22%). LCMS (ESMS): m/z 478.20 (M$^+$+1)

Example 32

5-[1-tert-Butyl-2-(4-chloro-2-1,2,4-triazol-1-yl-phenyl)-1H-benzimidazol-5-yl]-pyrimidin-2-ylamine

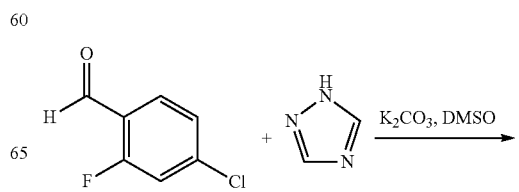

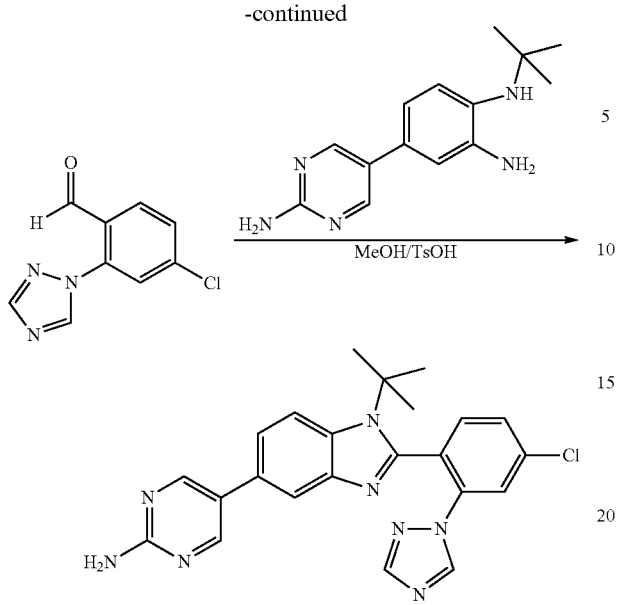

In a microwave reaction vessel are combined 4-chloro-2-fluoro-benzaldehyde (200 mg. 1.26 mmol), 1H-1,2,4-triazole (113 mg, 1.64 mmol) and potassium carbonate (350 mg, 2.52 mmol) in DMSO (5 mL) and warmed to 80° C. for 5 minutes in a microwave. The reaction mixture is cooled to room temperature and poured into water and extracted with EtOAc (3×). The combined organics are dried (MgSO$_4$), filtered and concentrated. Purification via flash chromatography (12 g silica gel, 0-3% MeOH/CH$_2$Cl$_2$) affords 4-chloro-2-1,2,4-triazol-1-yl-benzaldehyde which is used without further purification.

The 4-(2-amino-pyrimidin-5-yl)-N1-tert-butyl-benzene-1,2-diamine (185 mg, 0.72 mmol) and 4-chloro-2-1,2,4-triazol-1-yl-benzaldehyde (150 mg, 0.72 mmol) are combined in methanol (5 mL) and warmed to 65° C. After 18 hours, catalytic TsOH is added and heating is continued at 65° C. for 48 hours. The reaction mixture is cooled to room temperature and concentrated. The residue is purified via flash chromatography (12 g silica gel, 0-10% MeOH/CH$_2$Cl$_2$). Product-containing fractions are combined and concentrated. The residue is diluted with acetonitrile and the resulting solid product is collected via filtration (55 mg, 17%). LCMS (ESMS): m/z 445.20 (M$^+$+1)

The following compounds are made using the procedure described in this Example:

5-[1-tert-Butyl-2-(3-chloro-2-1,2,4-triazol-1-yl-phenyl)-1H-benzimidazol-5-yl]-pyrimidin-2-ylamine. LCMS (ESMS): m/z 445.20 (M$^+$+1)

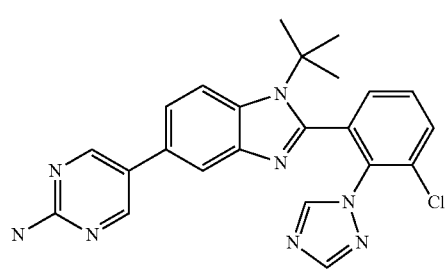 [SMILES: CC(C)(C)n1c(-c2cccc(Cl)c2-n2cncn2)nc2cc(-c3cnc(N)nc3)ccc21]

5-[1-tert-Butyl-2-(3-fluoro-2-1,2,4-triazol-1-yl-phenyl)-1H-benzimidazol-5-yl]-pyrimidin-2-ylamine. LCMS (ESMS): m/z 429.20 (M$^+$+1)

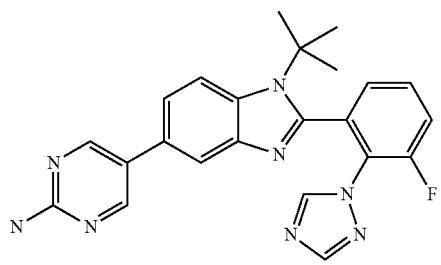 [SMILES: CC(C)(C)n1c(-c2cccc(F)c2-n2cncn2)nc2cc(-c3cnc(N)nc3)ccc21]

Example 33

5-{1-tert-Butyl-2-[2-(3-isopropyl-1,2,4-oxadiazol-5-yl)-phenyl]-1H-benzimidazol-5-yl}-pyrimidin-2-ylamine

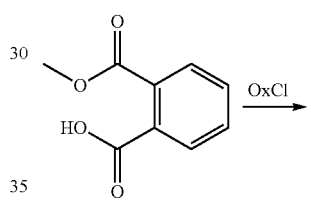

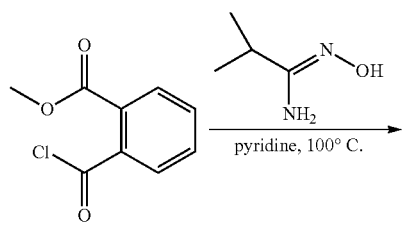

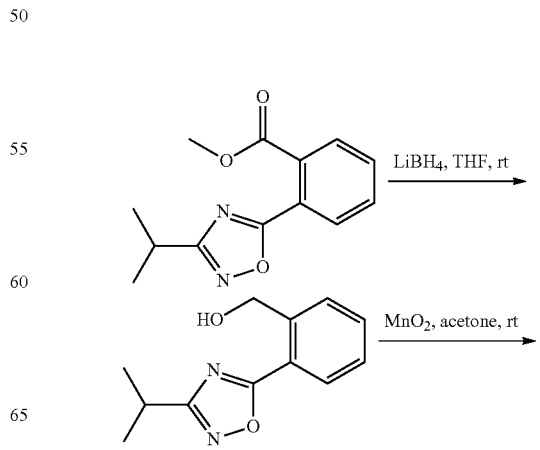

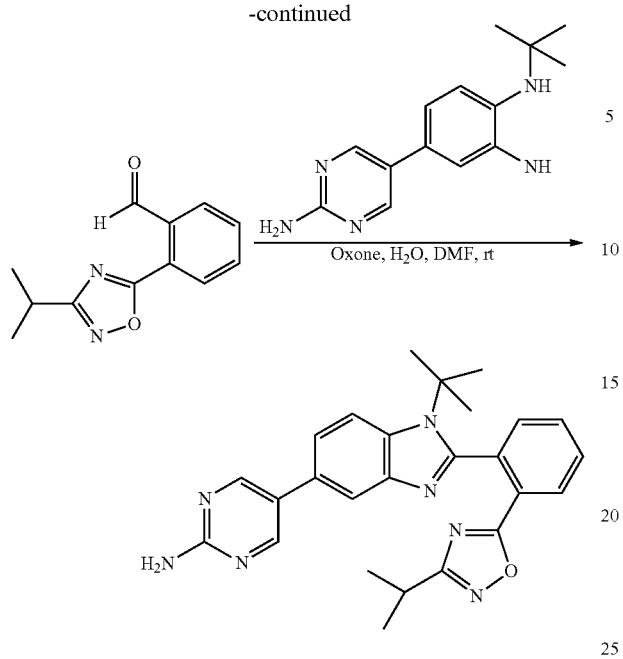

To phthalic acid monomethyl ester (1.0 g, 5.55 mmol) is added oxalyl chloride (5.0 mL). The reaction mixture is stirred at room temperature for 1 hour. The reaction mixture is concentrated under reduced pressure and the residue (1.10 g, 100%) is used in the next step of the synthesis without further purification.

To a solution of 2-chlorocarbonyl-benzoic acid methyl ester (1.10 g, 5.55 mol) in pyridine (5.0 mL) is added N-hydroxy-isobutyramidine (570 mg, 5.58 mmol). The reaction mixture is heated at 100° C. for 16 hours. The reaction mixture is allowed to cool to room temperature, diluted with EtOAc (100 mL), and is washed with $H_2O$ (75 mL×2). The organic layer is dried with $Na_2SO_4$ and is filtered. The filtrate is concentrated under reduced pressure and the residue is purified by silica gel flash column chromatography with 35% EtOAc in heptanes as the eluent to afford 2-(3-methyl-1,2,4-oxadiazol-5-yl)-benzoic acid isopropyl ester (1.03 g, 75%).

To a solution of 2-(3-methyl-1,2,4-oxadiazol-5-yl)-benzoic acid isopropyl ester (1.0 g, 4.06 mmol) in THF (25.0 mL) is added a solution of 2M $LiBH_4$ in THF (2.5 mL, 5.0 mmol). The reaction mixture is stirred at room temperature for 16 hours followed by further addition of 2M in $LiBH_4$ in THF (2.5 mL, 5.0 mmol). The reaction mixture is stirred at room temperature for a further 16 hours and then quenched with 1M HCl aq (50 mL). The quenched reaction mixture is extracted with EtOAc (50 mL×2) and the combined organic layers are dried with $Na_2SO_4$ and filtered. The filtrate is concentrated under reduced pressure and the residue is purified by silica gel flash column chromatography with 35% EtOAc in heptanes as the eluent to afford [2-(3-isopropyl-1,2,4-oxadiazol-5-yl)-phenyl]-methanol (373 mg, 42%).

To a solution of [2-(3-isopropyl-1,2,4-oxadiazol-5-yl)-phenyl]methanol (373 mg, 1.71 mmol) in $CH_2Cl_2$ (5.0 mL) is added $MnO_2$ (300 mg, 3.45 mmol). The reaction mixture is stirred at room temperature for 48 hours and is filtered through diatomaceous earth. The filtrate is concentrated under reduced pressure and the residue is purified by silica gel flash column chromatography with 30% EtOAc in heptanes as the eluent to afford 2-(3-isopropyl-1,2,4-oxadiazol-5-yl)-benzaldehyde (139 mg, 37%).

To a mixture of 4-(2-amino-pyrimidin-5-yl)-N1-tert-butyl-benzene-1,2-diamine (135 mg, 0.53 mmol) and 2-(3-isopropyl-1,2,4-oxadiazol-5-yl)-benzaldehyde (139 mg, 0.64 mmol) in DMF (5.0 mL) is added Oxone (325 mg, 0.53 mmol) in $H_2O$ (2.0 mL). The reaction mixture is stirred at room temperature for 1 hour and then quenched with saturated sodium thiosulfate aq. (25 mL). The quenched reaction mixture is extracted with EtOAc (25 mL×2) and the combined organic layers are washed with $H_2O$ (50 mL×2) and dried with $Na_2SO_4$. The filtrate is concentrated under reduced pressure and the residue is purified by silica gel flash column chromatography with 3.5% MeOH in $CH_2Cl_2$ as the eluent to afford the title compound (105 mg, 44%) as a white solid. LCMS (ESMS): m/z 454.20 ($M^++1$)

The following compound is made using the procedure described in this Example:

5-{1-tert-Butyl-2-[2-(3-cyclopropyl-1,2,4-oxadiazol-5-yl)-phenyl]-1H-benzimidazol-5-yl}-pyrimidin-2-ylamine. LCMS (ESMS): m/z 452.20 ($M^++1$)

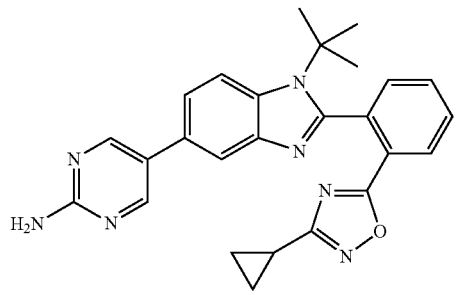 [SMILES: CC(C)(C)n1c(-c2ccccc2-c2nc(C3CC3)no2)nc2cc(-c3cnc(N)nc3)ccc21]

Example 34

5-{1-tert-Butyl-2-[5-chloro-2-(3-methyl-1,2,4-oxadiazol-5-yl)-phenyl]-1H-benzimidazol-5-yl}-pyrimidin-2-ylamine

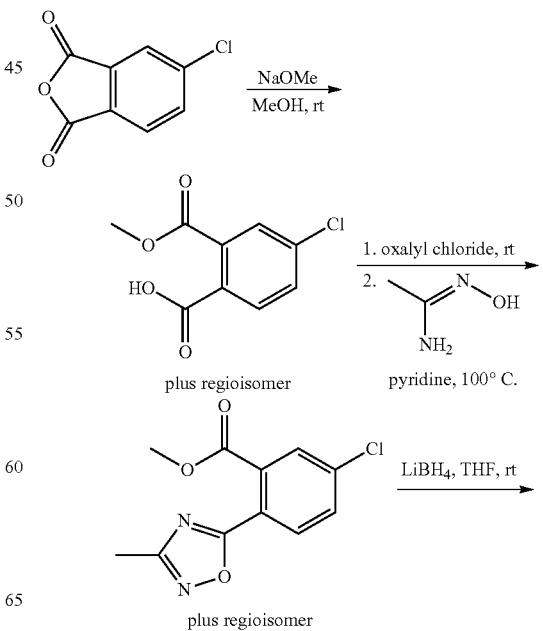

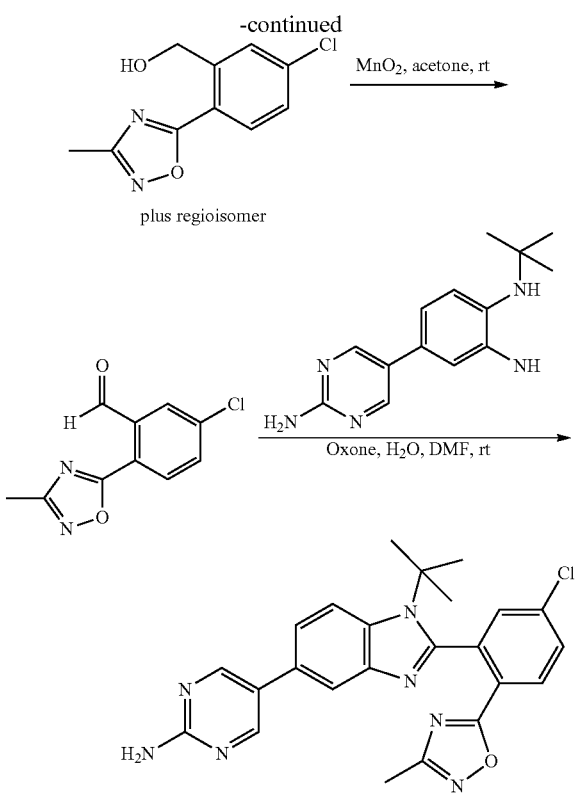

plus regioisomer

Sodium (1.3 g, 56.5 mmol) slowly over a period of 15 min to MeOH (35 mL). The reaction mixture is stirred for 30 min. To the formed solution of NaOMe in MeOH is added 5-chloro-isobenzofuran-1,3-dione (5.0 g, 27.39 mmol). The reaction mixture is stirred at room temperature for 72 hours. The reaction mixture is concentrated under reduced pressure and the resulting residue subsequently quenched with 1M HCl aq (100 mL). The quenched reaction mixture is extracted with EtOAc (75 mL×3) and the combined organic layers are dried with Na$_2$SO$_4$ and filtered. The filtrate is concentrated under reduced pressure and the residue is purified by silica gel flash column chromatography with 7.5% MeOH in CH$_2$Cl$_2$ as the eluent to afford an impure mixture of 4-chloro-phthalic acid 2-methyl ester plus regioisomer (4.5 g).

To a mixture of impure 4-chloro-phthalic acid 2-methyl ester (2.0 g) in CH$_2$Cl$_2$ (20 mL) is added oxalyl chloride (5.0 mL) and DMF (1 drop). The reaction mixture is stirred at room temperature for 1 hour, and concentrated under reduced pressure. To the freshly formed 5-chloro-2-chlorocarbonyl-benzoic acid methyl ester in pyridine (5.0 mL) is added N-hydroxy-acetamidine (700 mg, 9.45 mmol). The reaction mixture is heated at 100° C. for 16 hours. The reaction mixture is allowed to cool to room temperature, diluted with EtOAc (100 mL), and washed with H$_2$O (75 mL×2). The organic layer is dried with Na$_2$SO$_4$ and filtered. The filtrate is concentrated under reduced pressure and the residue is purified by silica gel flash column chromatography with 35% EtOAc in heptanes as the eluent to afford an impure mixture of 5-chloro-2-(3-methyl-1,2,4-oxadiazol-5-yl)-benzoic acid methyl ester plus regioisomer (900 mg).

To a mixture of impure 5-chloro-2-(3-methyl-1,2,4-oxadiazol-5-yl)-benzoic acid methyl ester (900 mg) in THF (10.0 mL) is added a solution of 2M LiBH$_4$ in THF (3.6 mL, 7.2 mmol). The reaction mixture is stirred at room temperature for 16 hours and then quenched with 1M HCl aq (50 mL). The quenched reaction mixture is extracted with EtOAc (50 mL×2) and the combined organic layers are dried with Na$_2$SO$_4$ and filtered. The filtrate is concentrated under reduced pressure and the residue is purified by silica gel flash column chromatography with 35% EtOAc in heptanes as the eluent to afford [5-chloro-2-(3-methyl-1,2,4-oxadiazol-5-yl)-phenyl]-methanol (78 mg) and the regiosiomer [4-chloro-2-(3-methyl-1,2,4-oxadiazol-5-yl)-phenyl]-methanol (60 mg).

To a solution of [5-chloro-2-(3-methyl-1,2,4-oxadiazol-5-yl)-phenyl]-methanol (78 mg, 0.35 mmol) in CH$_2$Cl$_2$ (5.0 mL) is added MnO$_2$ (125 mg, 1.22 mmol). The reaction mixture is stirred at room temperature for 16 hours and is filtered through diatomaceous earth. The filtrate is concentrated under reduced pressure and the residue is purified by silica gel flash column chromatography with 40% EtOAc in heptanes as the eluent to afford 5-chloro-2-(3-methyl-1,2,4-oxadiazol-5-yl)-benzaldehyde (27 mg, 35%).

To a mixture of 4-(2-amino-pyrimidin-5-yl)-N1-tert-butyl-benzene-1,2-diamine (25 mg, 0.10 mmol) and 5-chloro-2-(3-methyl-1,2,4-oxadiazol-5-yl)-benzaldehyde (27 mg, 0.12 mmol) in DMF (5.0 mL) is added oxone (60 mg, 0.10 mmol) in H$_2$O (2.0 mL). The reaction mixture is stirred at room temperature for 1.5 hours and then quenched with saturated sodium thiosulfate aq. (25 mL). The quenched reaction mixture is extracted with EtOAc (25 mL×2) and the combined organic layers are washed with H$_2$O (50 mL×2) and dried with Na$_2$SO$_4$. The filtrate is concentrated under reduced pressure and the residue is purified by silica gel flash column chromatography with 5% MeOH in CH$_2$Cl$_2$ as the eluent to afford the title compound (30 mg, 45%) as a white solid. LCMS (ESMS): m/z 460.20 (M$^+$+1)

Example 35

5-{1-tert-Butyl-2-[4-chloro-2-(3-methyl-1,2,4-oxadiazol-5-yl)-phenyl]-1H-benzimidazol-5-yl}-pyrimidin-2-ylamine

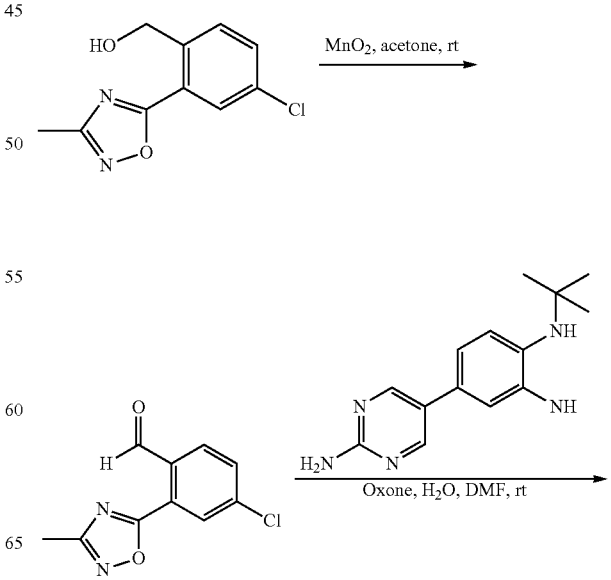

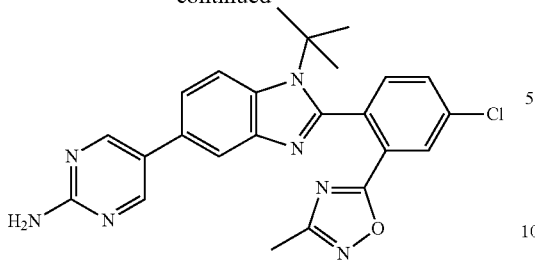

To a solution of [4-chloro-2-(3-methyl-1,2,4-oxadiazol-5-yl)-phenyl]methanol (60 mg, 0.27 mmol) (see example 34), in CH$_2$Cl$_2$ (5.0 mL) is added MnO$_2$ (100 mg, 0.98 mmol). The reaction mixture is stirred at room temperature for 16 hours and is filtered through diatomaceous earth. The filtrate is concentrated under reduced pressure and the residue is purified by silica gel flash column chromatography with 40% EtOAc in heptanes as the eluent to afford 4-chloro-2-(3-methyl-1,2,4-oxadiazol-5-yl)-benzaldehyde (10 mg, 17%).

To a mixture of 4-(2-amino-pyrimidin-5-yl)-N1-tert-butyl-benzene-1,2-diamine (11 mg, 0.043 mmol) and 4-chloro-2-(3-methyl-1,2,4-oxadiazol-5-yl)-benzaldehyde (10 mg, 0.045 mmol) in DMF (5.0 mL) is added Oxone (27 mg, 0.044 mmol) in H$_2$O (2.0 mL). The reaction mixture is stirred at room temperature for 1.5 hours and then quenched with saturated sodium thiosulfate aq. (25 mL). The quenched reaction mixture is extracted with EtOAc (25 mL×2) and the combined organic layers are washed with H$_2$O (50 mL×2), dried with Na$_2$SO$_4$ and filtered. The filtrate is concentrated under reduced pressure and the residue is purified by silica gel flash column chromatography with 10% MeOH in CH$_2$Cl$_2$ as the eluent to afford the title compound (10 mg, 50%) as a white solid. LCMS (ESMS): m/z 460.20 (M$^+$+1)

Example 36

5-{1-tert-Butyl-2-[5-methoxy-2-(3-methyl-1,2,4-oxadiazol-5-yl)-phenyl]-1H-benzimidazol-5-yl}-pyrimidin-2-ylamine

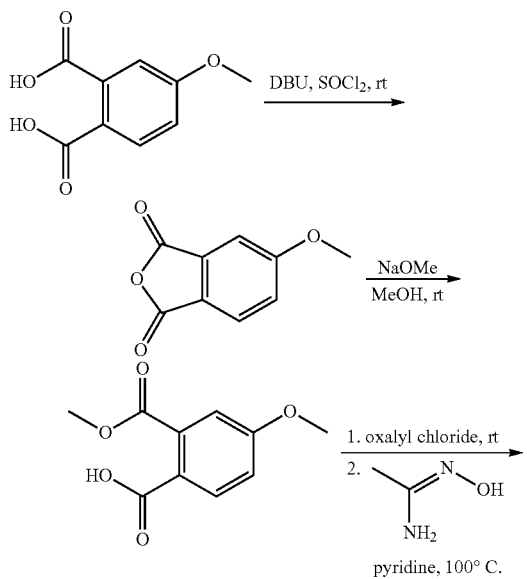

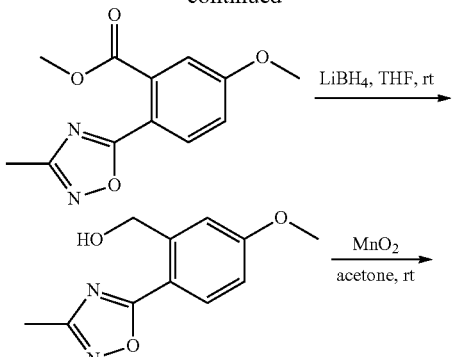

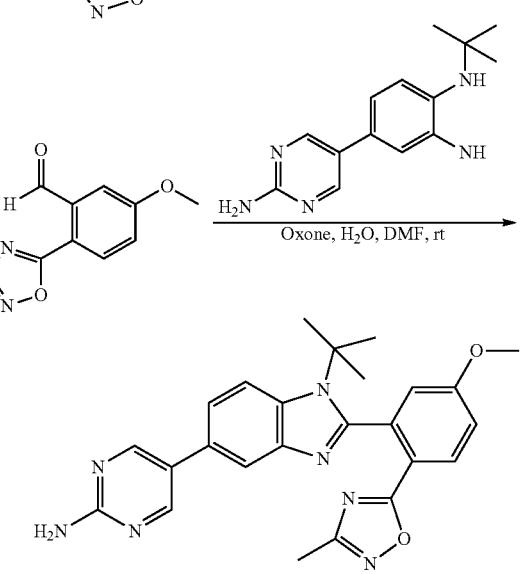

To a mixture of 4-methoxy-phthalic acid (1.8 g, 9.18 mmol), thionyl chloride (1.4 mL, 19.79 mmol) in CH$_2$Cl$_2$ (15 mL) is added DABCO (1.1 g, 9.81 mmol). The reaction mixture is stirred at room temperature for 2 hours. The reaction mixture is diluted with CH$_2$Cl$_2$ (100 mL), washed with H$_2$O (75 mL×2), dried with Na$_2$SO$_4$ and filtered. The filtrate is concentrated under reduced pressure to afford 5-methoxy-isobenzofuran-1,3-dione (950 mg, 58%).

To a mixture of 5-methoxy-isobenzofuran-1,3-dione (950 mg, 5.33 mmol) is added 0.5 M NaOMe in MeOH (16 mL, 18 mmol). The reaction mixture is stirred at room temperature for 16 hours. The reaction mixture is concentrated under reduced pressure and the resulting residue subsequently quenched with 1M HCl aq (100 mL). The quenched reaction mixture is extracted with EtOAc (100 mL×2) and the combined organic layers are dried with Na$_2$SO$_4$ and filtered. The filtrate is concentrated under reduced to afford crude 4-methoxy-phthalic acid 2-methyl ester (850 mg).

To a mixture of crude 4-methoxy-phthalic acid 2-methyl ester (850 mg) in CH$_2$Cl$_2$ (25 mL) is added oxalyl chloride (3.0 mL) and DMF (1 drop). The reaction mixture is stirred at room temperature for 1 hour, and is concentrated under reduced pressure. To the freshly formed 5-chloro-2-chlorocarbonyl-benzoic acid methyl ester in pyridine (5.0 mL) is added N-hydroxy-acetamidine (350 mg, 4.72 mmol). The reaction mixture is heated at 100° C. for 16 hours. The reaction mixture is allowed to cool to room temperature, diluted with EtOAc (100 mL), and washed with H$_2$O (75 mL×2). The organic layer is dried with Na$_2$SO$_4$ and is filtered. The filtrate is concentrated under reduced pressure and the residue is purified by silica gel flash column chromatography with 35% EtOAc in heptanes as the eluent to afford 5-methoxy-2-(3-methyl-1,2,4-oxadiazol-5-yl)-benzoic acid methyl ester (600 mg, 60%).

To a solution of 5-methoxy-2-(3-methyl-1,2,4-oxadiazol-5-yl)-benzoic acid methyl ester in THF (10.0 mL) is added a solution of 2M LiBH$_4$ in THF (2.5 mL, 5.0 mmol). The reaction mixture is stirred at room temperature for 16 hours and then quenched with 1M HCl aq (50 mL). The quenched reaction mixture is extracted with EtOAc (50 mL×2) and the combined organic layers are dried with Na$_2$SO$_4$ and filtered. The filtrate is concentrated under reduced pressure and the residue is purified by silica gel flash column chromatography with 40% EtOAc in heptanes as the eluent to afford 5-methoxy-2-(3-methyl-1,2,4-oxadiazol-5-yl)-phenyl]-methanol (173 mg, 33%).

To a solution of 5-methoxy-2-(3-methyl-1,2,4-oxadiazol-5-yl)-phenyl]methanol (173 mg, 0.79 mmol) in CH$_2$Cl$_2$ (10.0 mL) is added MnO$_2$ (250 mg, 2.44 mmol). The reaction mixture is stirred at room temperature for 48 hours and is filtered through diatomaceous earth. The filtrate is concentrated under reduced pressure and the residue is purified by silica gel flash column chromatography with 40% EtOAc in heptanes as the eluent to afford 5-methoxy-2-(3-methyl-1,2,4-oxadiazol-5-yl)-benzaldehyde (155 mg, 90%).

To a mixture of 4-(2-amino-pyrimidin-5-yl)-N1-tert-butyl-benzene-1,2-diamine (155 mg, 0.60 mmol) and 5-methoxy-2-(3-methyl-1,2,4-oxadiazol-5-yl)-benzaldehyde (155 mg, 0.60 mmol) in DMF (10.0 mL) is added Oxone (155 mg, 0.71 mmol) in H$_2$O (2.0 mL). The reaction mixture is stirred at room temperature for 1.5 hours and then quenched with saturated sodium thiosulfate aq. (25 mL). The quenched reaction mixture is extracted with EtOAc (25 mL×2) and the combined organic layers are washed with H$_2$O (50 mL×2), dried with Na$_2$SO$_4$ and filtered. The filtrate is concentrated under reduced pressure and the residue is purified by silica gel flash column chromatography with 5% MeOH in CH$_2$Cl$_2$ as the eluent to afford the title compound (25 mg, 9%) as a white solid. LCMS (ESMS): m/z 456.20 (M$^+$+1)

The following compound is made using the procedure described in this Example:

5-{1-tert-Butyl-2-[5-methyl-2-(3-methyl-1,2,4-oxadiazol-5-yl)-phenyl]-1H-benzimidazol-5-yl}-pyrimidin-2-ylamine. LCMS (ESMS): m/z 440.20 (M$^+$+1)

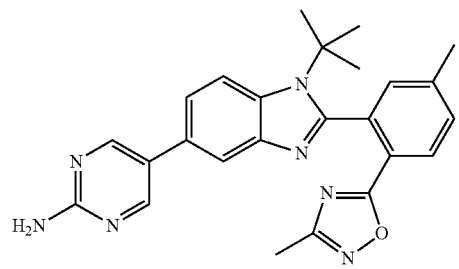 [SMILES: Cc1ccc(-c2nc(C)no2)c(-c2nc3cc(-c4cnc(N)nc4)ccc3n2C(C)(C)C)c1]

Example 37

5-{1-tert-Butyl-2-[5-chloro-2-(3-methyl-1,2,4-triazol-1-yl)-phenyl]-1H-benzimidazol-5-yl}-pyrimidin-2-ylamine and

Example 38

5-{1-tert-butyl-2-[5-chloro-2-(5-methyl-1,2,4-triazol-1-yl)-phenyl]-1H-benzimidazol-5-yl}-pyrimidin-2-ylamine

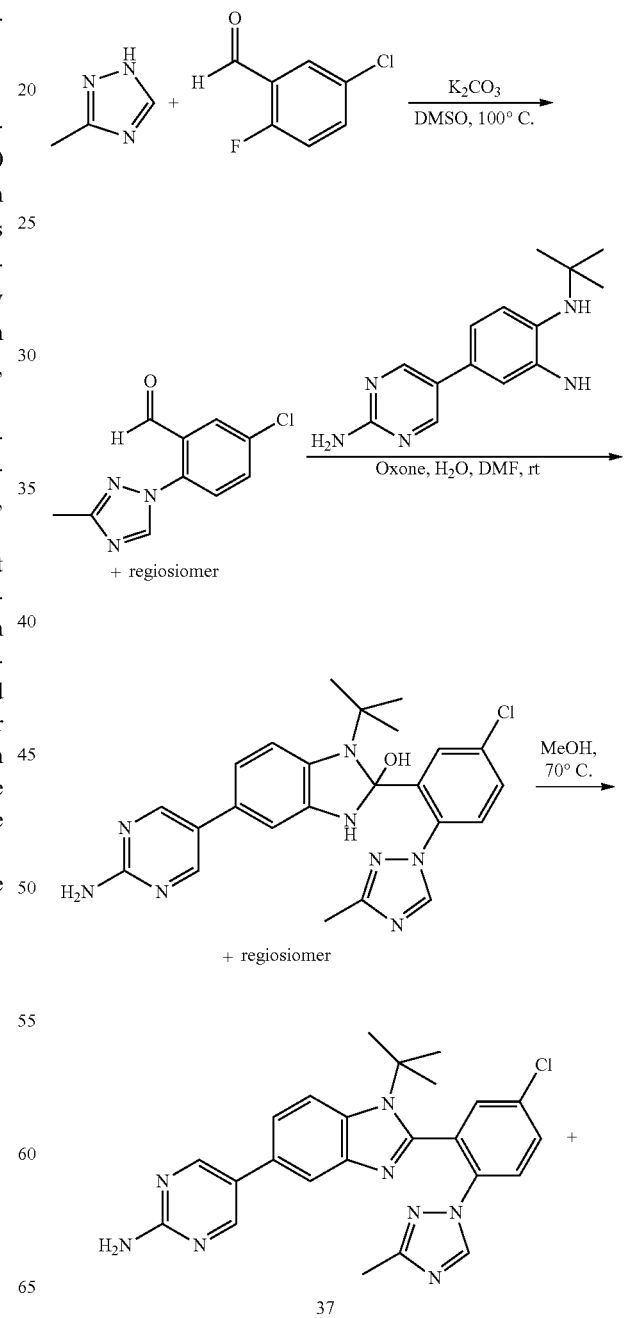

143

-continued

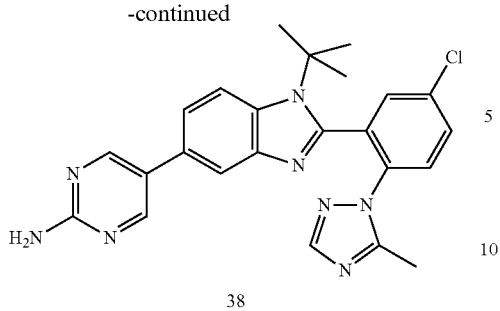

38

To a mixture of 3-methyl-1H-1,2,4-triazole (330 mg, 3.97 mmol), 5-chloro-2-fluoro-benzaldehyde (425 mg, 2.68 mmol) in DMSO (5.0 mL) is added $K_2CO_3$ (725 mg, 5.25 mmol). The reaction mixture is stirred at 100° C. for 2 hours. The reaction mixture is allowed to cool to room temperature, diluted with $CH_2Cl_2$ (100 mL), and washed with $H_2O$ (75 mL×2). The organic layer is dried with $Na_2SO_4$ and filtered. The filtrate is concentrated under reduced pressure and the residue is purified by silica gel flash column chromatography with 5% MeOH in EtOAc as the eluent to afford an impure mixture of 5-chloro-2-(3-methyl-1,2,4-triazol-1-yl)-benzaldehyde plus regiosiomer (270 mg).

To a mixture of 4-(2-amino-pyrimidin-5-yl)-N1-tert-butyl-benzene-1,2-diamine (270 mg, 1.05 mmol) and impure mixture of 5-chloro-2-(3-methyl-1,2,4-triazol-1-yl)-benzaldehyde plus regiosiomer (270 mg) in DMF (15.0 mL) is added Oxone (650 mg, 1.06 mmol) in $H_2O$ (5.0 mL). The reaction mixture is stirred at room temperature for 1.5 hours and then quenched with saturated sodium thiosulfate aq. (25 mL). The quenched reaction mixture is extracted with EtOAc (25 mL×2) and the combined organic layers are washed with $H_2O$ (50 mL×2), dried with $Na_2SO_4$ and filtered. The filtrate is concentrated under reduced pressure and the residue is purified by silica gel flash column chromatography with 5% MeOH in $CH_2Cl_2$ as the eluent to afford an impure mixture of 5-(2-amino-pyrimidin-5-yl)-1-tert-butyl-2-[5-chloro-2-(3-methyl-1,2,4-triazol-1-yl)-phenyl]-2,3-dihydro-1H-benzimidazol-2-ol plus regiosiomer (25 mg).

A mixture of 5-(2-amino-pyrimidin-5-yl)-1-tert-butyl-2-[5-chloro-2-(3-methyl-1,2,4-triazol-1-yl)-phenyl]-2,3-dihydro-1H-benzimidazol-2-ol plus regiosiomer (25 mg) in MeOH (25 mL) is heated at 70° C. for 16 hours. The reaction mixture is allowed to cool to room temperature and is concentrated under reduced pressure. The residue is purified by silica gel flash column chromatography with 5% MeOH in $CH_2Cl_2$ as the eluent followed by further purification using a HPLC C-18 column with $CH_3CN$ (0.1% TFA) in $H_2O$ (0.1% TFA) as the eluent to afford 5-{1-tert-butyl-2-[5-chloro-2-(3-methyl-1,2,4-triazol-1-yl)-phenyl]-1H-benzimidazol-5-yl}-pyrimidin-2-ylamine (Example 37) (9 mg, 37%) as a white solid LCMS (ESMS): m/z 459.20 ($M^+$+1) and 5-{1-tert-butyl-2-[5-chloro-2-(5-methyl-1,2,4-triazol-1-yl)-phenyl]-1H-benzimidazol-5-yl}-pyrimidin-2-ylamine (Example 38) (6 mg, 25%) as a white solid. LCMS (ESMS): m/z 459.20 ($M^+$+1)

144

The following compounds are made using the procedure described in this Example:

5-{1-tert-Butyl-2-[5-methoxy-2-(5-methyl-1,2,4-triazol-1-yl)-phenyl]-1H-benzimidazol-5-yl}-pyrimidin-2-ylamine. LCMS (ESMS): m/z 455.20 ($M^+$+1)

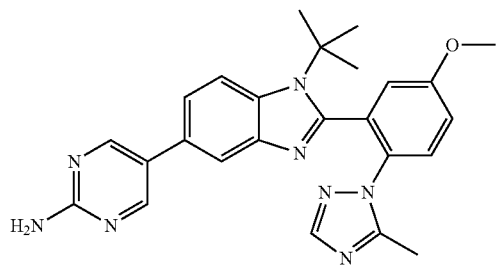 [SMILES: COc1ccc(-n2ncnc2C)c(-c2nc3cc(-c4cnc(N)nc4)ccc3n2C(C)(C)C)c1]

5-{1-tert-Butyl-2-[5-methoxy-2-(3-methyl-1,2,4-triazol-1-yl)-phenyl]-1H-benzimidazol-5-yl}-pyrimidin-2-ylamine. LCMS (ESMS): m/z 455.20 ($M^+$+1)

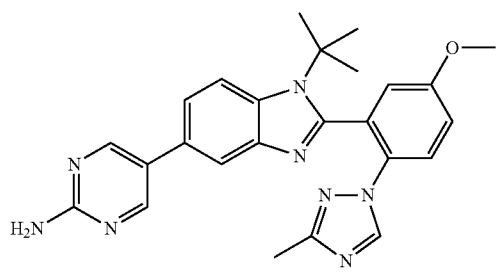 [SMILES: COc1ccc(-n2cnc(C)n2)c(-c2nc3cc(-c4cnc(N)nc4)ccc3n2C(C)(C)C)c1]

Example 39

5-{1-tert-Butyl-2-[2-(1H-1,2,4-triazol-3-yl)-phenyl]-1H-benzimidazol-5-yl}-pyrimidin-2-ylamine

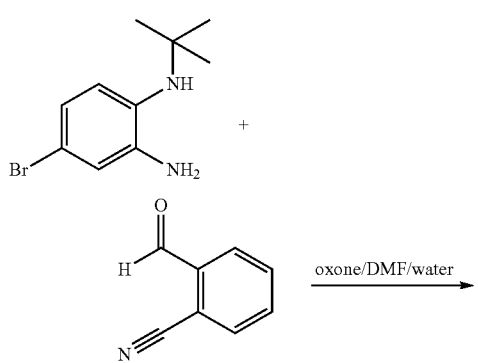

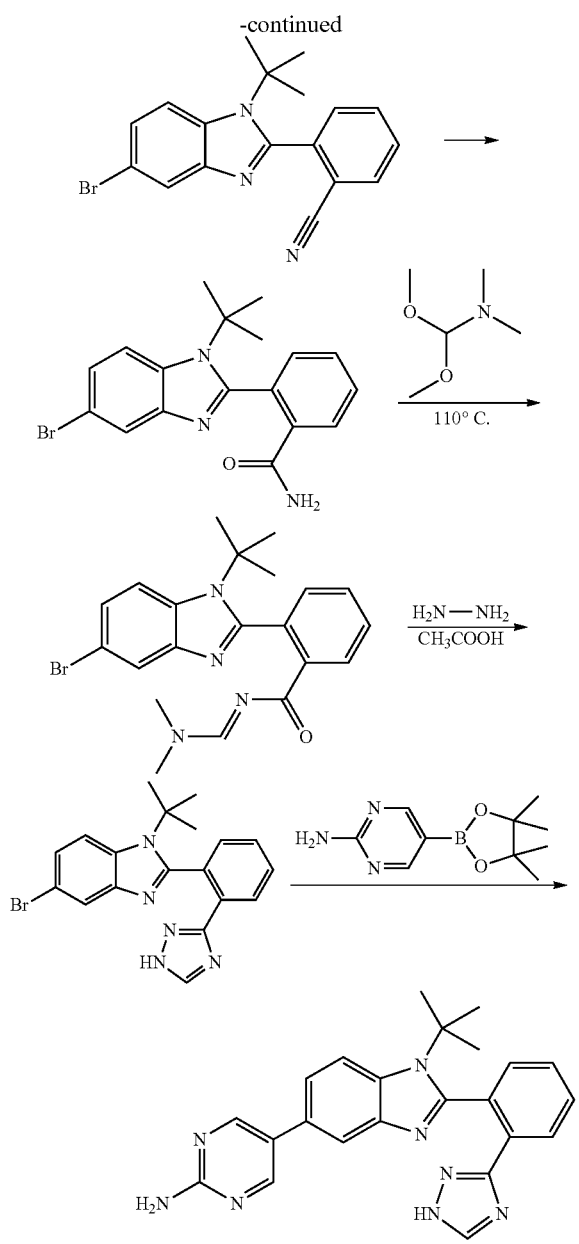

To a round bottom flask is added 4-bromo-N-1-tert-butyl-benzene-1,2-diamine (2 g, 8.23 mmol) in DMF (20 mL) and water (7 mL), followed by the addition of 2-cyanobenzladehyde (1.186 g, 9.044 mmol) and Oxone (5.06 g, 8.23 mmol). The reaction mixture is stirred at room temperature for 2 hours. Sat. sodium thiosulfate is added to the reaction mixture. The reaction mixture is diluted with EtOAc. The organic layer is separated, washed with water, brine, dried under Na$_2$SO$_4$, filtered and concentrated. The residue is loaded onto a silica gel column. The column is eluted with 0-50% EtOAc/hexane. The product fractions are collected and concentrated to afford 2-(5-bromo-1-tert-butyl-1H-benzimidazol-2-yl)-benzonitrile (2281 mg, 78%) as a light brown solid. LCMS (ESMS): m/z 354.44, 356.30 (M$^+$+1)

To a round bottom flask is added 2-(5-bromo-1-tert-butyl-1H-benzimidazol-2-yl)-benzonitrile (1800 mg, 5.08 mmol) in MeOH (40 mL), followed by the addition of ammonium hydroxide (20 mL) and hydrogen peroxide (10 mL) (30% in water). The reaction mixture is stirred at room temperature for 3 hours. The reaction mixture is concentrated in vacuo. The residue is diluted with EtOAc, washed with water then brine, dried under Na$_2$SO$_4$, filtered and concentrated. The residue is loaded onto a silica gel column. The column is eluted with 0-4% MeOH/CH$_2$Cl$_2$. The product fractions are collected and concentrated to afford 2-(5-bromo-1-tert-butyl-1H-benzimidazol-2-yl)-benzamide (1590 mg, 84%) as a light brown solid. LCMS (ESMS): m/z 372.46, 374.35 (M$^+$+1)

To a round bottom flask is added 2-(5-bromo-1-tert-butyl-1H-benzimidazol-2-yl)-benzamide (400 mg, 1.075 mmol) in N,N-dimethylformamide dimethyl acetal (8 mL). The reaction mixture is stirred at 110° C. for 3 hours. The reaction mixture is concentrated to remove all volatile material to afford 2-(5-bromo-1-tert-butyl-1H-benzimidazol-2-yl)-N-[1-dimethylamino-meth-(E)-ylidene]-benzamide (460 mg, 100%) ready for the next step. LCMS (ESMS): m/z 427.68, 429.64 (M$^+$+1)

To a round bottom flask is added 2-(5-bromo-1-tert-butyl-1H-benzimidazol-2-yl)-N-[1-dimethylamino-meth-(E)-ylidene]-benzamide (230 mg, 0.538 mmol) in glacial acetic acid (3 mL), followed by the addition of hydrazine (35% wt solution in water) (2 mL). The reaction mixture is stirred at room temperature for 2 hours. The reaction mixture is diluted with EtOAc, washed with sat. NaHCO$_3$ and brine, dried under Na$_2$SO$_4$, filtered and concentrated. The residue is loaded onto a silica gel column. The column is eluted with 0-4% 2M NH$_3$ in MeOH/CH$_2$Cl$_2$. The product fractions are collected and concentrated to afford 5-bromo-1-tert-butyl-2-[2-(1H-1,2,4-triazol-3-yl)-phenyl]-1H-benzimidazole (180 mg, 84%) as an off-white solid. LCMS (ESMS): m/z 396.68, 398.64 (M$^+$+1)

To a sealed vial is added 5-bromo-1-tert-butyl-2-[2-(1H-1,2,4-triazol-3-yl)-phenyl]-1H-benzimidazole (80 mg, 0.2 mmol) in DMF (3.5 mL), follow by the addition of 2-aminopyrimidine-5-boronic acid pinacol ester (49 mg, 0.22 mmol), bis(di-tert-butyl(4-dimethylaminophenyl)phosphine)dichloropalladium(II) (20 mg, 0.028 mmol) and 2M aq. Na$_2$CO$_3$ (0.4 mL, 0.8 mmol). The reaction mixture is heated under Argon at 100° C. for 10 hours. The residue is diluted with EtOAc, washed with brine, dried under Na$_2$SO$_4$, filtered and concentrated. The residue is loaded onto a silica gel column. The column is eluted with 0-8% 7M NH$_3$ in MeOH/CH$_2$Cl$_2$. The product fractions are collected and concentrated to afford the title compound (28 mg, 34%) as a pale-white solid. LCMS (ESMS): m/z 411.80 (M$^+$+1)

The following compounds are made using the procedure described in this Example:

5-{1-tert-Butyl-2-[2-(2-methyl-2H-1,2,4-triazol-3-yl)-phenyl]-1H-benzimidazol-5-yl}-pyrimidin-2-ylamine. LCMS (ESMS): m/z 425.79 (M$^+$+1)

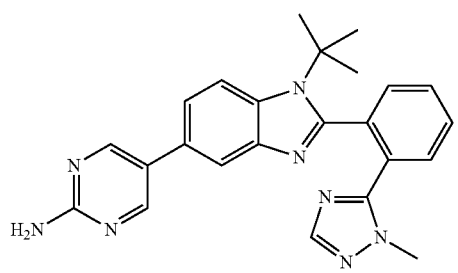 [SMILES: Cn1ncnc1-c1ccccc1-c1nc2cc(-c3cnc(N)nc3)ccc2n1C(C)(C)C]

5-{1-tert-Butyl-2-[2-(2-ethyl-2H-1,2,4-triazol-3-yl)-phenyl]-1H-benzimidazol-5-yl}-pyrimidin-2-ylamine. LCMS (ESMS): m/z 439.74 (M⁺+1)

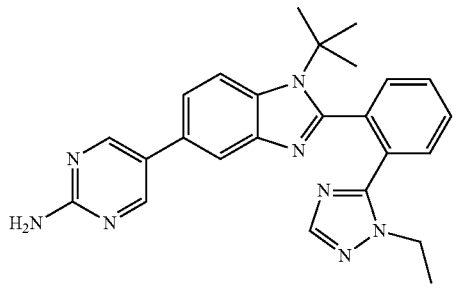 [SMILES: CCn1ncnc1-c1ccccc1-c1nc2cc(-c3cnc(N)nc3)ccc2n1C(C)(C)C]

5-{1-tert-Butyl-2-[2-(2-isopropyl-2H-1,2,4-triazol-3-yl)-phenyl]-1H-benzimidazol-5-yl}-pyrimidin-2-ylamine. LCMS (ESMS): m/z 453.77 (M⁺+1)

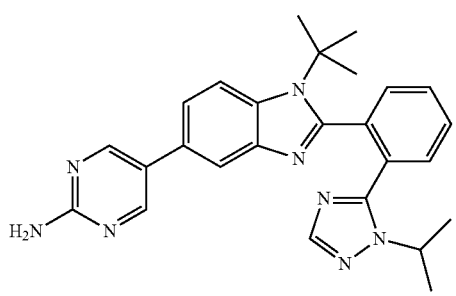 [SMILES: CC(C)n1ncnc1-c1ccccc1-c1nc2cc(-c3cnc(N)nc3)ccc2n1C(C)(C)C]

Example 40

5-{1-tert-Butyl-2-[2-(5-methyl-1H-1,2,4-triazol-3-yl)-phenyl]-1H-benzimidazol-5-yl}-pyrimidin-2-ylamine

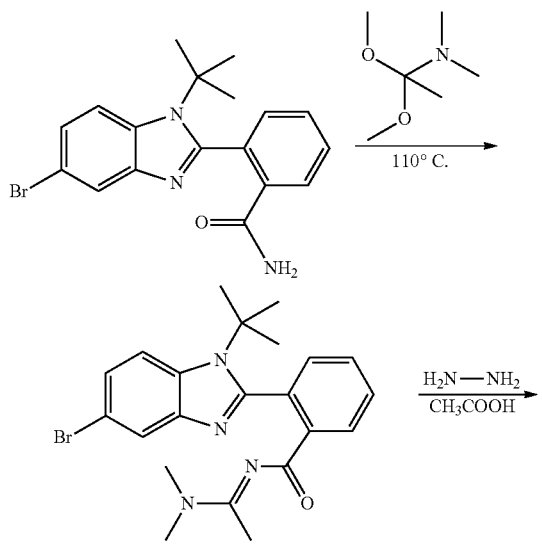

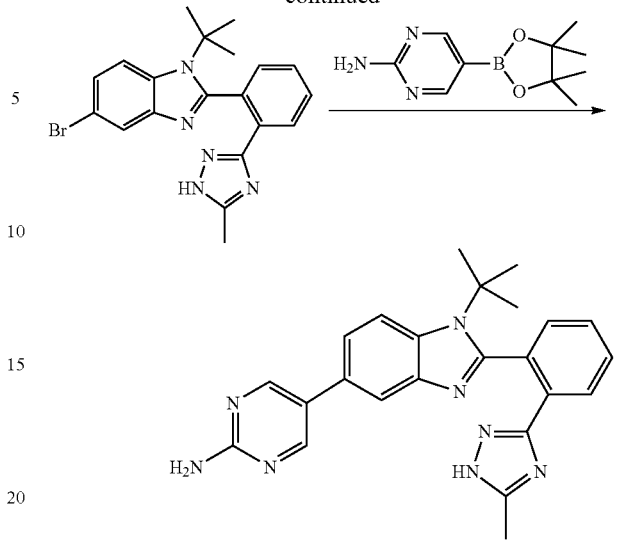

To a round bottom flask is added 2-(5-bromo-1-tert-butyl-1H-benzimidazol-2-yl)-benzamide (400 mg, 1.075 mmol) in N,N-dimethylformamide dimethyl acetal (5 mL). The reaction mixture is stirred at 110° C. for 5 hours. The reaction mixture is concentrated to remove all volatile material to afford 2-(5-bromo-1-tert-butyl-1H-benzimidazol-2-yl)-N-[1-dimethylamino-eth-(E)-ylidene]-benzamide (474 mg, 100%) ready for next step. LCMS (ESMS): m/z 441.71, 443.71 (M⁺+1)

To a round bottom flask is added 2-(5-bromo-1-tert-butyl-1H-benzimidazol-2-yl)-N-[1-dimethylamino-eth-(E)-ylidene]-benzamide (237 mg, 0.537 mmol) in glacial acetic acid (3 mL), followed by the addition of hydrazine (35% wt solution in water) (2 mL). The reaction mixture is stirred at room temperature for 2 hours. The reaction mixture is diluted with EtOAc, is washed with sat. NaHCO₃, brine, dried under anhy. Na₂SO₄, filtered and concentrated. The residue is loaded to a silica gel column. The column is eluted with 0-3% 2M NH₃ in MeOH/CH₂Cl₂. The product fractions are collected and concentrated to afford 5-bromo-1-tert-butyl-2-[2-(5-methyl-1H-1,2,4-triazol-3-yl)-phenyl]-1H-benzimidazole (78 mg, 35%) as a light brown solid. LCMS (ESMS): m/z 410.68, 412.71 (M⁺+1)

To a sealed vial is added 5-bromo-1-tert-butyl-2-[2-(5-methyl-1H-1,2,4-triazol-3-yl)-phenyl]-1H-benzimidazole (78 mg, 0.19 mmol) in DMF (3 mL), followed by the addition of 2-aminopyrimidine-5-boronic acid pinacol ester (50 mg, 0.226 mmol), bis(di-tert-butyl(4-dimethylaminophenyl)phosphine)dichloropalladium(II) (20 mg, 0.028 mmol) and 2M aq. Na₂CO₃ (0.4 mL, 0.8 mmol). The reaction mixture is heated under Argon at 100° C. for 10 hours. The residue is diluted with EtOAc, washed with brine, dried under Na₂SO₄, is filtered and is concentrated. The residue is loaded to a silica gel column. The column is eluted with 0-8% 7M NH₃ in MeOH/CH₂Cl₂. The product fractions are collected and concentrated to afford the title compound (20 mg, 25%) as a off-white solid. LCMS (ESMS): m/z 425.79 (M⁺+1)

The following compound is made using the procedure described in this Example:

5-{1-tert-Butyl-2-[2-(2,5-dimethyl-2H-1,2,4-triazol-3-yl)-phenyl]-1H-benzimidazol-5-yl}-pyrimidin-2-ylamine. LCMS (ESMS): m/z 439.79 (M⁺+1); and (5-{2-[5-(2-Amino-pyrimidin-5-yl)-1-tert-butyl-1H-benzimidazol-2-yl]-phenyl}-3-methyl-1,2,4-triazol-1-yl)-acetic acid ethyl ester

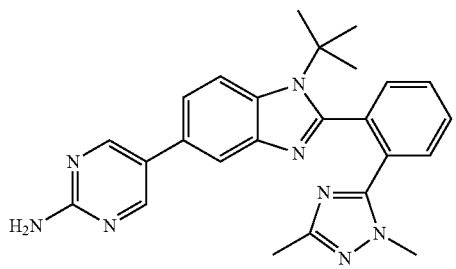 [SMILES: Cc1nc(-c2ccccc2-c2nc3cc(-c4cnc(N)nc4)ccc3n2C(C)(C)C)n(C)n1]

Example 41

5-{1-tert-Butyl-2-[2-(2H-tetrazol-5-yl)-phenyl]-1H-benzimidazol-5-yl}-pyrimidin-2-ylamine

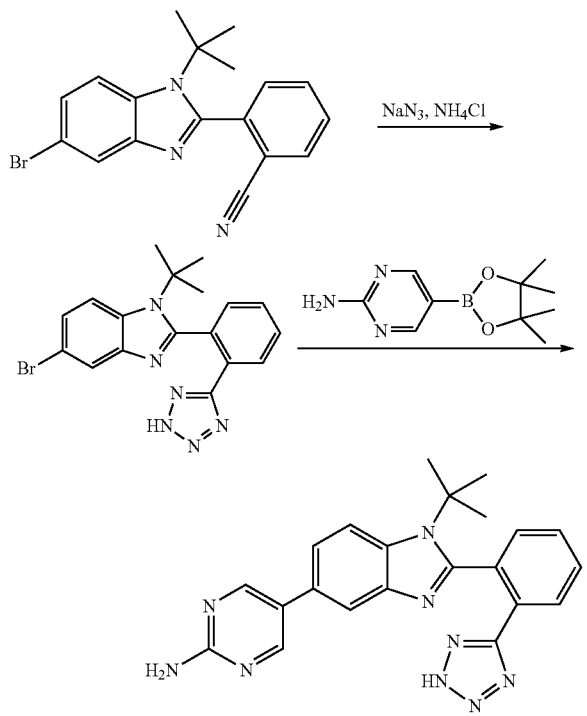

To a round bottom flask is added 2-(5-bromo-1-tert-butyl-1H-benzimidazol-2-yl)-benzonitrile (200 mg, 0.565 mmol) in DMF (3 mL), follow by the addition of NaN₃ (48 mmol, 0.738 mmol) and NH₄Cl (39 mg, 0.729 mmol). The reaction mixture is stirred at 110° C. for 48 hours. The reaction mixture is diluted with EtOAc/water. The organic layer is separated, washed with water then brine, dried with Na₂SO₄, filtered and concentrated to afford 5-bromo-1-tert-butyl-2-[2-(2H-tetrazol-5-yl)-phenyl]-1H-benzimidazole (190 mg, 85%) as a solid product. LCMS (ESMS): m/z 397.49, 399.40 (M⁺+1)

To a sealed vial is added 5-bromo-1-tert-butyl-2-[2-(2H-tetrazol-5-yl)-phenyl]-1H-benzimidazole (190 mg, 0.478 mmol) in DMF (5 mL), followed by the addition of 2-aminopyrimidine-5-boronic acid pinacol ester (126 mg, 0.57 mmol), tetrakis(triphenylphosphine)palladium(0) (55 mg, 0.048 mmol) and 2M aq. Na₂CO₃ (1 mL, 2 mmol). The reaction mixture is heated under Argon at 110° C. for 3 hours. The residue is diluted with EtOAc, washed with brine, dried with Na₂SO₄, filtered and concentrated. The residue is loaded onto a silica gel column. The column is eluted with 0-20% 7M NH₃ in MeOH/CH₂Cl₂. The product fractions are collected and concentrated to afford the title compound (16 mg, 8%) as a light yellow solid. LCMS (ESMS): m/z 412.67 (M⁺+1)

Example 42

5-{1-tert-Butyl-2-[2-(2-methyl-2H-tetrazol-5-yl)-phenyl]-1H-benzimidazol-5-yl}-pyrimidin-2-ylamine

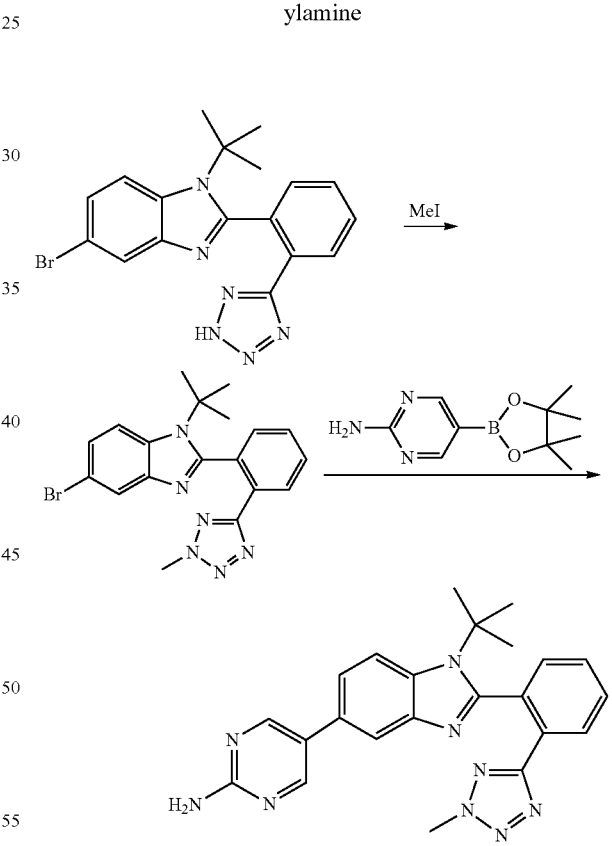

To a vial is added 5-bromo-1-tert-butyl-2-[2-(2H-tetrazol-5-yl)-phenyl]-1H-benzimidazole (158 mg, 0.4 mmol) in DMF (5 mL), followed by the addition of iodomethane (114 mg, 0.8 mmol) and K₂CO₃ (110 mg, 0.8 mmol). The reaction mixture is stirred at room temperature for 0.5 hour. The reaction mixture is diluted with EtOAc, washed with water then, brine, dried with Na₂SO₄, filtered and concentrated. The residue is loaded to a silica gel column. The column is eluted with 0-3% MeOH/CH₂Cl₂. The product fractions are collected and is concentrated to afford 5-bromo-1-tert-butyl-2-[2-(2-methyl-2H-tetrazol-5-yl)-phenyl]-1H-benzimidazole (62 mg, 38%). LCMS (ESMS): m/z 411.59, 413.47 (M$^+$+1)

To a sealed vial is added 5-bromo-1-tert-butyl-2-[2-(2-methyl-2H-tetrazol-5-yl)-phenyl]-1H-benzimidazole (55 mg, 0.134 mmol) in DMF (3 mL), followed by the addition of 2-aminopyrimidine-5-boronic acid pinacol ester (35 mg, 0.158 mmol), tetrakis(triphenylphosphine)palladium(0) (15 mg, 0.013 mmol) and 2M aq. Na$_2$CO$_3$ (0.3 mL, 0.6 mmol). The reaction mixture is heated under Argon at 110° C. for 6 hours. The residue is diluted with EtOAc, washed with brine, dried under Na$_2$SO$_4$, filtered and concentrated. The residue is loaded onto a silica gel column. The column is eluted with 0-5% 7M NH$_3$ in MeOH/CH$_2$Cl$_2$. The product fractions are collected and concentrated to afford the title compound (36 mg, 63%) as a off-white solid. LCMS (ESMS): m/z 426.70 (M$^+$+1)

Example 43

5-{2-[2-(5-Amino-1,3,4-oxadiazol-2-yl)-phenyl]-1-tert-butyl-1H-benzimidazol-5-yl}-pyrimidin-2-ylamine

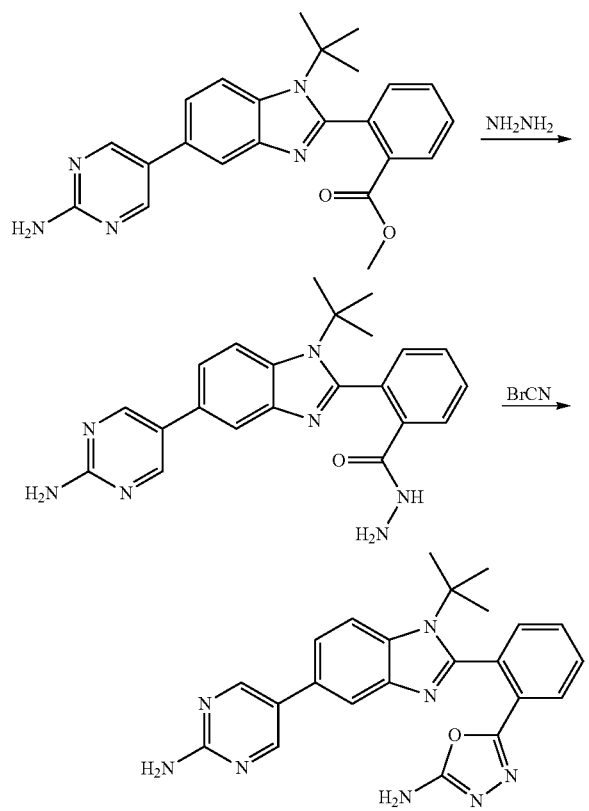

To a vial is added 2-[5-(2-amino-pyrimidin-5-yl)-1-tert-butyl-1H-benzimidazol-2-yl]-benzoic acid methyl ester (example 16) (85 mg, 0.212 mmol) in EtOH (5 mL), follow by the addition of hydrazine (35 wt % solution in water) (1 mL). The reaction mixture is stirred at 80° C. for 5 days. The reaction mixture is concentrated in vacuo. The residue is loaded to a silica gel column. The column is eluted with 0-10% 2M NH$_3$ in MeOH/CH$_2$Cl$_2$. The product fractions are collected and is concentrated to afford 2-[5-(2-amino-pyrimidin-5-yl)-1-tert-butyl-1H-benzimidazol-2-yl]-benzoic acid hydrazide (43 mg, 51%) as a off-white solid. LCMS (ESMS): m/z 402.57 (M$^+$+1)

To a vial is added 2-[5-(2-amino-pyrimidin-5-yl)-1-tert-butyl-1H-benzimidazol-2-yl]-benzoic acid hydrazide (43 mg, 0.107 mmol) in 1,4-dioxane (2 mL), followed by the addition of NaHCO$_3$ (13 mg, 0.155 mmol) in water (0.5 mL), then cyanogen bromide (13 mg, 0.123 mmol). The reaction mixture is stirred at room temperature for 18 hours. The reaction mixture is concentrated in vacuo. The residue is loaded to a silica gel column. The column is eluted with 0-8% 2M NH$_3$ in MeOH/CH$_2$Cl$_2$. The product fractions are collected and concentrated to afford the title compound (30 mg, 66%) as an off-white solid. LCMS (ESMS): m/z 427.76 (M$^+$+1)

Example 44

5-[1-tert-Butyl-2-(2-1,2,4-triazol-1-yl-phenyl)-1H-benzimidazol-5-yl]-4-methoxy-pyrimidin-2-ylamine

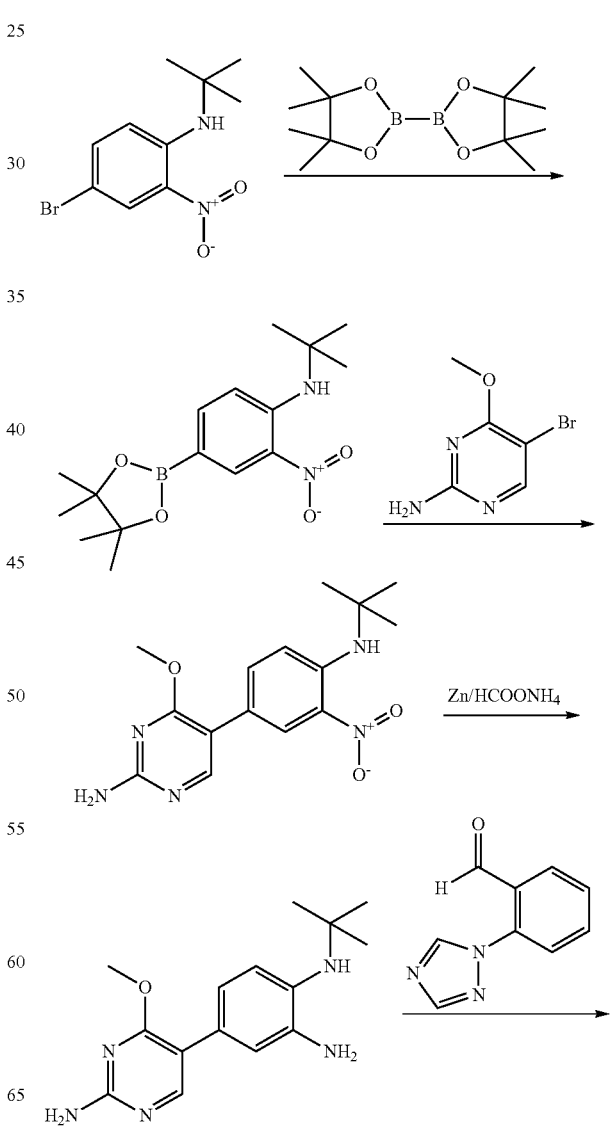

-continued

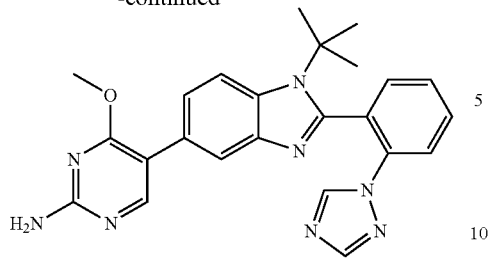

To a high pressure vessel is added (4-bromo-2-nitro-phenyl)-tert-butyl-amine (500 mg, 1.83 mmol), bis(pinacolato) diboron (558 mg, 2.2 mmol) and KOAc (720 mg, 7.34 mmol) in 1,4-dioxane (15 mL). The solution is bubbled with Argon gas for 5 minutes, followed by the addition of 1,1'-bis(diphenylphosphino)ferrocenedichlopalladium(II) CH$_2$Cl$_2$ (150 mg, 0.18 mmol). The reaction mixture is stirred at 110° C. for 4 hours. The reaction mixture is filtered through diatomaceous earth. The filtrate is concentrated in vacuo. The residue is loaded to a silica gel column. The column is eluted with 0-10% EtOAc/hexane. The product fractions are collected and concentrated to afford tert-butyl-[2-nitro-4-(4,4,5,5-tetramethyl-1,3,2-dioxaborolan-2-yl)-phenyl]-amine (300 mg, 51%) as a yellow solid. LCMS (ESMS): m/z 321.75 (M$^+$+1)

To a vial is added tert-butyl-[2-nitro-4-(4,4,5,5-tetramethyl-1,3,2-dioxaborolan-2-yl)-phenyl]-amine (300 mg, 0.937 mmol), 2-amino-5-bromo-4-methoxypyrimidine (215 mg, 1.054 mmol) and 2M Na$_2$CO$_3$ (2 mL, 4 mmol) in DMF (10 mL), followed by the addition of tetrakis(triphenylphosphine)palladium(0) (108 mg, 0.093 mmol). The vial is sealed under Argon gas. The reaction mixture is stirred at 110° C. for 18 hours. The reaction mixture is diluted with EtOAc and washed with water. The organic layer is separated, washed with brine, dried under Na$_2$SO$_4$, filtered and concentrated. The residue is loaded onto a silica gel column. The column is eluted with 0-5% MeOH/CH$_2$Cl$_2$. The product fractions are collected and concentrated to afford 5-(4-tert-butylamino-3-nitro-phenyl)-4-methoxy-pyrimidin-2-ylamine (256 mg, 86%) as a red solid. LCMS (ESMS): m/z 318.72 (M$^+$+1)

To a round bottom flask is added 5-(4-tert-Butylamino-3-nitro-phenyl)-4-methoxy-pyrimidin-2-ylamine (150 mg, 0.473 mmol) in MeOH (5 mL), followed by the addition of ammonium formate (268 mg, 4.25 mmol) and of zinc dust (154 mg, 2.37 mmol). The reaction mixture is stirred at 50° C. for 1 hour. The reaction mixture is filtered through diatomaceous earth, washing with MeOH. The filtrate is concentrated in vacuo. The residue is diluted with EtOAc, washed with water, dried with Na$_2$SO$_4$, filtered and concentrated to afford 4-(2-amino-4-methoxy-pyrimidin-5-yl)-N$^1$-tert-butyl-benzene-1,2-diamine (118 mg, 87%) as a light brown solid. LCMS (ESMS): m/z 288.48 (M$^+$+1)

To a round bottom flask is added 4-(2-amino-4-methoxy-pyrimidin-5-yl)-N$^1$-tert-butyl-benzene-1,2-diamine (118 mg, 0.411 mmol) in DMF (4 mL) and water (1 mL), followed by the addition of 2-1,2,4-triazol-1-yl-benzaldehyde (78 mg, 0.45 mmol) and oxone (51 mg, 0.443 mmol). The reaction mixture is stirred at room temperature for 4 hours. Sat. sodium thiosulfate (10 mL) is added. The reaction mixture is diluted with EtOAc. The organic layer is separated, washed with water then brine, dried with Na$_2$SO$_4$, filtered and concentrated. The residue is loaded into a silica gel column. The column is eluted with 0-4% 7M NH$_3$ in MeOH/CH$_2$Cl$_2$. The product fractions are collected and concentrated to afford the title compound (67 mg, 37%) as a light brown solid. LCMS (ESMS): m/z 441.73 (M$^+$+1)

Example 45

2-Amino-5-[1-tert-butyl-2-(2-1,2,4-triazol-1-yl-phenyl)-1H-benzimidazol-5-yl]-3H-pyrimidin-4-one

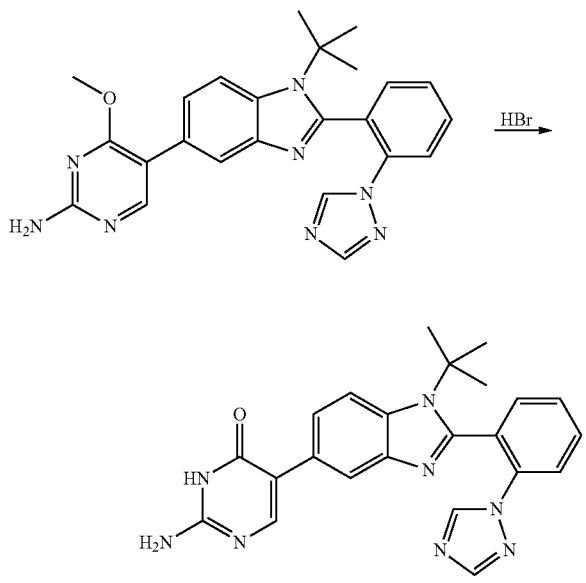

To a vial are added 5-[1-tert-butyl-2-(2-1,2,4-triazol-1-yl-phenyl)-1H-benzimidazol-5-yl]-4-methoxy-pyrimidin-2-ylamine (Example 44) (47 mg, 0.107 mmol) in THF (2 mL) and HBr (1 mL). The reaction mixture is stirred at 70° C. for 12 hours. The solvent is concentrated. The residue is purified by prep HPLC, with 5-95% acetonitrile/water as gradient to afford the title compound (31 mg, 68%) as a white-gray glass solid. LCMS (ESMS): m/z 427.72 (M$^+$+1)

Example 46

3-{3-[1-tert-Butyl-5-(5-methoxy-pyridin-3-yl)-1H-benzimidazol-2-yl]-phenyl}-[1,2,4]oxadiazole-5-carboxylic acid ethyl ester

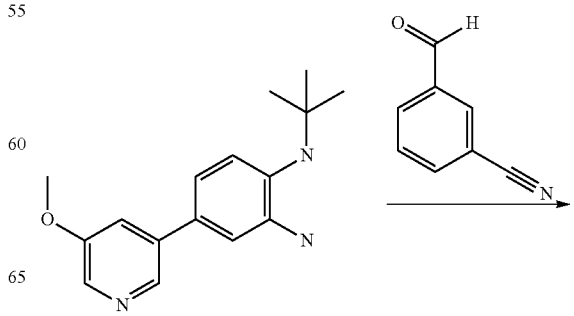

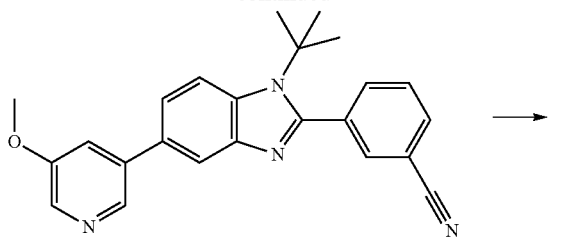

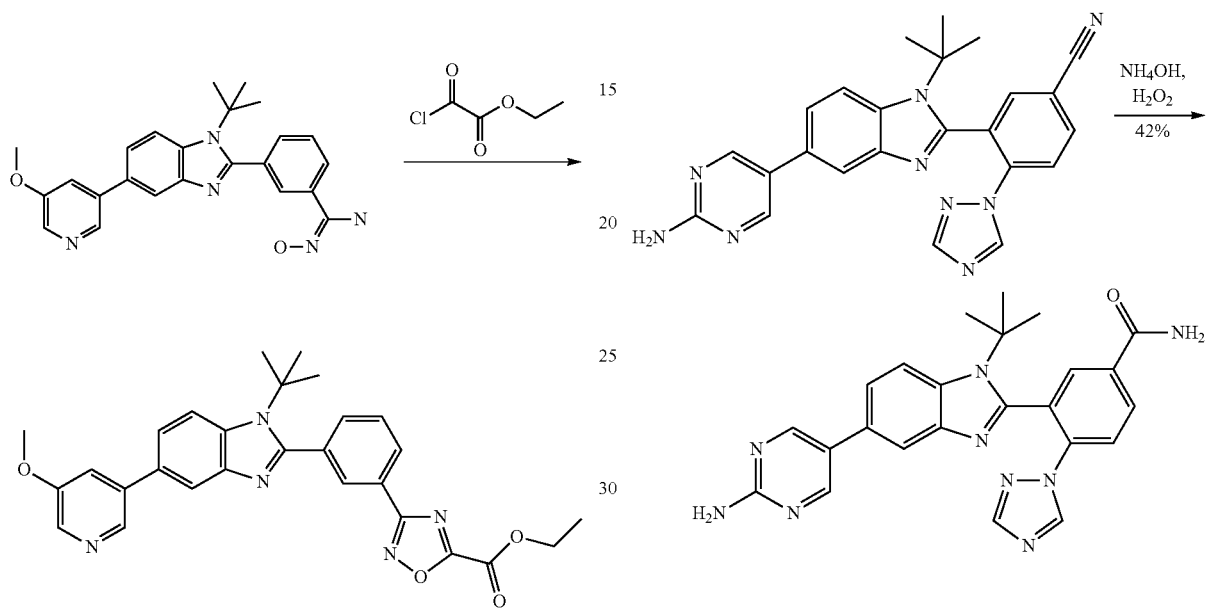

N¹-tert-Butyl-4-(5-methoxy-pyridin-3-yl)-benzene-1,2-diamine (0.630 g, 2.32 mmol) is dissolved in DMF (5 mL) and water (1 mL). To this solution is added 3-formyl-benzonitrile (0.315 g, 2.40 mmol), followed by Oxone (1.54 g, 2.50 mmol). This reaction mixture is sonicated at room temperature for 1 hour. The solvent is removed in vacuum. The residue is partitioned between EtOAc (3×10 mL) and saturated sodium bicarbonate solution (10 mL). The organic layer is washed with brine, dried over sodium sulfate and is filtered. The filtrate is concentrated and the residue is purified by flash chromatography (40 g silica gel, eluted with 0-100% EtOAc in hexane) to give 3-[1-tert-butyl-5-(5-methoxy-pyridin-3-yl)-1H-benzimidazol-2-yl]-benzonitrile (0.575 g, 65%) as a white solid.

3-[1-tert-Butyl-5-(5-methoxy-pyridin-3-yl)-1H-benzimidazol-2-yl]-benzonitrile (0.480 g, 1.255 mmol) is dissolved in ethanol (5 mL). Hydroxylamine (1.0 mL, 50% in water) is added. The reaction mixture is heated under reflux for 6 hours. The solvent is removed in vacuum to give 3-[1-tert-butyl-5-(5-methoxy-pyridin-3-yl)-1H-benzimidazol-2-yl]-N-hydroxy-benzamidine (0.531 g, 100%) as a yellow solid.

3-[1-tert-Butyl-5-(5-methoxy-pyridin-3-yl)-1H-benzimidazol-2-yl]-N-hydroxy-benzamidine (0.500 g, 1.20 mmol) is dissolved in DMF (5 mL). Chloro-oxo-acetic acid ethyl ester (0.177 g, 1.30 mmol) is added followed by diisopropyl-ethylamine (1.5 mL). The reaction mixture is stirred at room temperature for 2 hours then heated at 110° C. for 16 hours. The solvent is removed in vacuum. The residue is purified by flash chromatography (silica gel 40 g, eluted with 0-100% ethyl acetate in hexane) to give the title compound (0.454 g, 76%). LCMS (ESMS): m/z 498.61 (M⁺+1).

Example 47

3-[5-(2-Amino-pyrimidin-5-yl)-1-tert-butyl-1H-benzimidazol-2-yl]-4-1,2,4-triazol-1-yl-benzamide To a round bottom flask is added 3-[5-(2-amino-pyrimidin-5-yl)-1-tert-butyl-1H-benzimidazol-2-yl]-4-1,2,4-triazol-1-yl-benzonitrile (Example 7) (200 mg, 0.46 mmol) in MeOH (5 mL), followed by the addition of NH₄OH (2 mL) and H₂O₂ (1 mL) (30% in water). The reaction mixture is stirred at room temperature for 3 hours. The reaction mixture is diluted with EtOAc (20 mL), washed with water (10 mL), brine (5 mL), dried under anhydrous Na₂SO₄ (500 mg), filtered and concentrated. The residue is purified by silica gel flash column chromatography with 10% MeOH in CH₂Cl₂ as the eluent to afford the title compound (89 mg, 42%) as a white solid. LCMS (ESMS): m/z 454.73 (M⁺+1)

Example 48

3-[5-(2-Amino-pyrimidin-5-yl)-1-tert-butyl-1H-benzimidazol-2-yl]-4-1,2,4-triazol-1-yl-benzoic acid

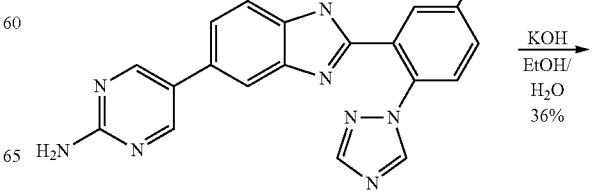

-continued

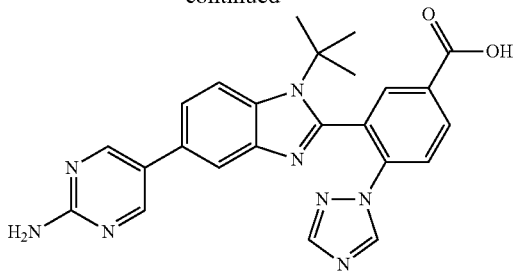

To a mixture of 3-[5-(2-amino-pyrimidin-5-yl)-1-tert-butyl-1H-benzimidazol-2-yl]-4-1,2,4-triazol-1-yl-benzonitrile (Example 7) (400 mg, 0.92 mmol) in EtOH (10 mL) is added KOH (103 mg, 1.8 mmol) in H$_2$O (1 mL) at room temperature. The mixture is heated to 80° C. for 48 hours. The solution is cooled down and is concentrated under vacuum. The residue is dissolved in H$_2$O (10 mL) and the pH of the solution is adjusted to 6 with 2M HCl solution. The white solid that precipitates out from the solution is collected by filtration. The white solid is dried under vacuum providing the title compound. LCMS (ESMS): m/z 455.20 (M$^+$+1)

Example 49

(5-{2-[5-(2-Amino-pyrimidin-5-yl)-1-tert-butyl-1H-benzimidazol-2-yl]-phenyl}-3-methyl-1,2,4-triazol-1-yl)-acetic acid

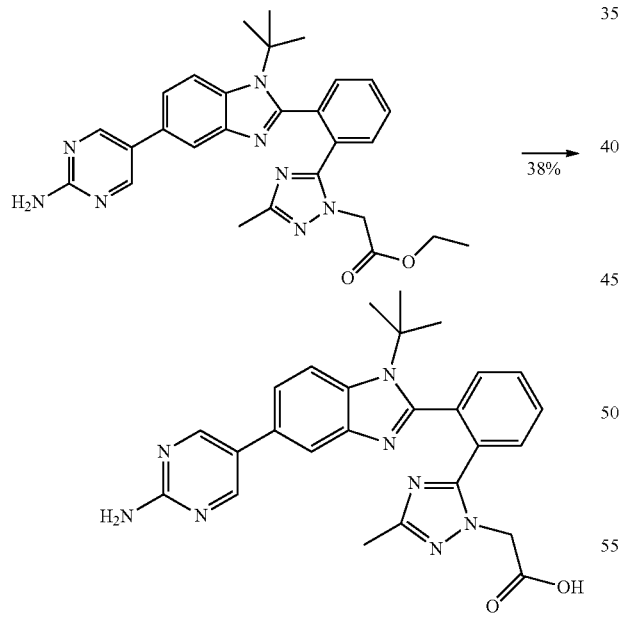

(5-{2-[5-(2-Amino-pyrimidin-5-yl)-1-tert-butyl-1H-benzimidazol-2-yl]-phenyl}-3-methyl-1,2,4-triazol-1-yl)-acetic acid ethyl ester (40 mg, 0.078 mmol) and Amberlyst A26 (OH$^-$ form) (450 mg, 0.6 mmol) are combined in acetonitrile (5 mL) and the mixture is agitated for 3 hours, filtered, and the isolate is washed with acetonitrile (2×5 mL). The product is purified by silica gel flash column chromatography eluting with 20% formic acid in acetonitrile (1 mL). The eluent is concentrated to afford the title compound (37 mg, 38%) LCMS (ESMS): m/z 483.2 (M$^+$+1)

Example 50

5-[1-tert-Butyl-2-(5-ethoxy-2-1,2,4-triazol-1-yl-phenyl)-1H-benzimidazol-5-yl]-pyrimidin-2-ylamine

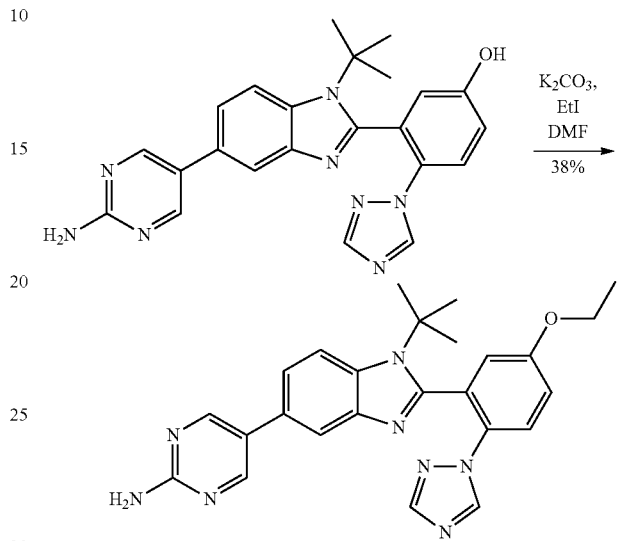

To a stirred solution of 3-[5-(2-amino-pyrimidin-5-yl)-1-tert-butyl-1H-benzimidazol-2-yl]-4-1,2,4-triazol-1-yl-phenol (50 mg, 0.12 mmol) in DMF (3 mL) is added potassium carbonate (24 mg, 0.18 mmol) followed by iodoethane (9.4 ul, 0.12 mmol). The resulting mixture is stirred at room temperature for 3 hours and then is warmed to 65° C. for 4 hours. The reaction is cooled to room temperature, poured into water and the product extracted into EtOAc (2×). The combined organics are dried (MgSO$_4$), filtered, and concentrated. The remaining residue is purified by silica gel flash column chromatography (12 g silica gel, 2-8% MeOH/DCM). Product-containing fractions are combined and concentrated to give a solid which is diluted with acetonitrile. The white solid is collected via filtration and washed with acetonitrile to afford the title compound (20 mg, 38%). LCMS (ESMS): m/z 455.74 (M$^+$+1)

The following compounds are made using the procedure described in this Example:

5-[1-tert-Butyl-2-(5-isopropoxy-2-1,2,4-triazol-1-yl-phenyl)-1H-benzimidazol-5-yl]-pyrimidin-2-ylamine. LCMS (ESMS): m/z 469.20 (M$^+$+1)

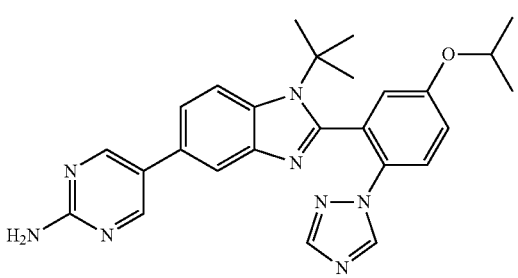 [SMILES: CC(C)Oc1ccc(-n2cncn2)c(-c2nc3cc(-c4cnc(N)nc4)ccc3n2C(C)(C)C)c1]

5-{1-tert-Butyl-2-[5-(2-methoxy-ethoxy)-2-1,2,4-triazol-1-yl-phenyl]-1H-benzimidazol-5-yl}-pyrimidin-2-ylamine. LCMS (ESMS): m/z 485.20 (M⁺+1)

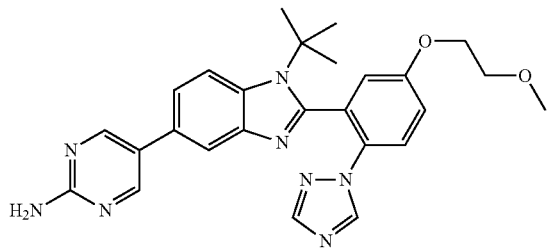 [SMILES: COCCOc1ccc(-n2cncn2)c(-c2nc3cc(-c4cnc(N)nc4)ccc3n2C(C)(C)C)c1]

5-{1-tert-Butyl-2-[5-(2-morpholin-4-yl-ethoxy)-2-1,2,4-triazol-1-yl-phenyl]-1H-benzimidazol-5-yl}-pyrimidin-2-ylamine. LCMS (ESMS): m/z 540.20 (M⁺+1)

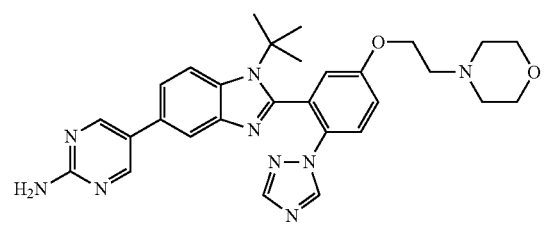 [SMILES: CC(C)(C)n1c(-c2cc(OCCN3CCOCC3)ccc2-n2cncn2)nc2cc(-c3cnc(N)nc3)ccc21]

5-[1-tert-Butyl-2-(5-cyclopropylmethoxy-2-1,2,4-triazol-1-yl-phenyl)-1H-benzimidazol-5-yl]-pyrimidin-2-ylamine. LCMS (ESMS): m/z 481.20 (M⁺+1)

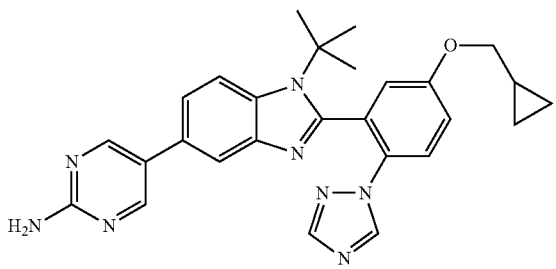 [SMILES: CC(C)(C)n1c(-c2cc(OCC3CC3)ccc2-n2cncn2)nc2cc(-c3cnc(N)nc3)ccc21]

1-(2-{3-[5-(2-Amino-pyrimidin-5-yl)-1-tert-butyl-1H-benzimidazol-2-yl]-4-1,2,4-triazol-1-yl-phenoxy}-ethyl)-pyrrolidin-2-one. LCMS (ESMS): m/z 538.20 (M⁺+1)

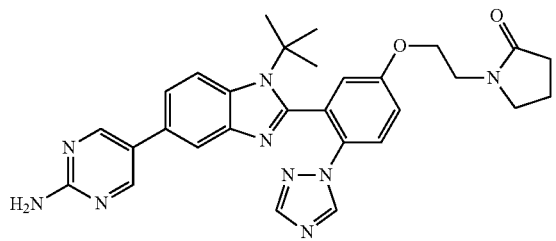 [SMILES: CC(C)(C)n1c(-c2cc(OCCN3CCCC3=O)ccc2-n2cncn2)nc2cc(-c3cnc(N)nc3)ccc21]

Example 51

5-{1-tert-Butyl-2-[2-(1-methyl-1H-[1,2,4]triazol-3-yl)-phenyl]-1H-benzimidazol-5-yl}-pyrimidin-2-ylamine

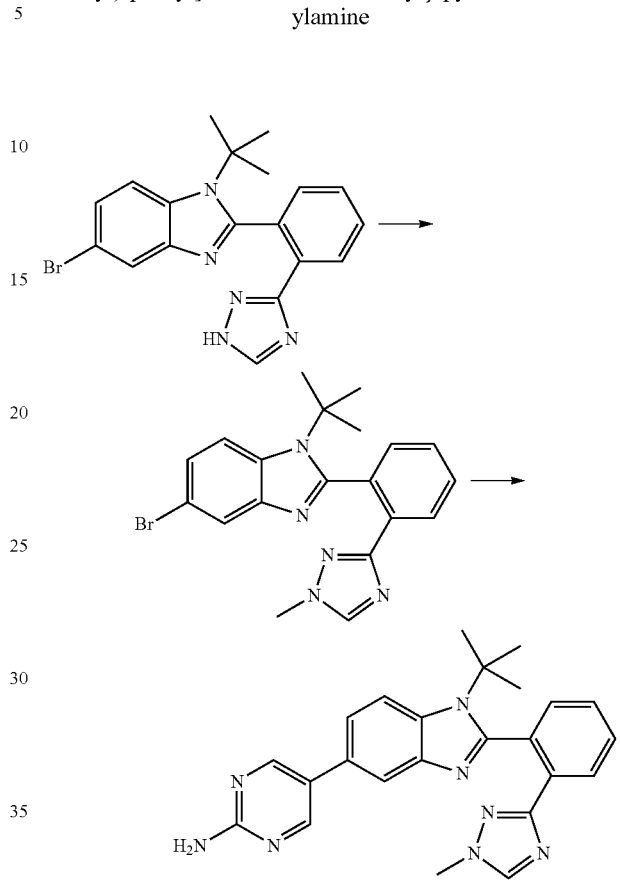

To a vial is added 5-bromo-1-tert-butyl-2-[2-(1H-[1,2,4]triazol-3-yl)-phenyl]-1H-benzimidazole (100 mg, 0.252 mmol) in DMF (1.5 mL), followed by the addition of $K_2CO_3$ (70 mg, 0.504 mmol) and MeI (60 mg, 0.423 mmol). The reaction mixture is stirred at room temperature for 1 hour. The reaction mixture is diluted with EtOAc, washed with water, brine, dried using anhydrous $Na_2SO_4$ and filtered. The filtrate is concentrated and the residue is purified by silica gel flash column chromatography with 0-3% 7M $NH_3$ in MeOH/$CH_2Cl_2$ as the eluent to afford 5-bromo-1-tert-butyl-2-[2-(1-methyl-1H-[1,2,4]-triazol-3-yl)-phenyl]-1H-benzimidazole (37 mg, 36%) as a light brown solid. LCMS (ESMS): m/z 410.58, 412.51 (M⁺+1)

To a sealed vial is added 5-bromo-1-tert-butyl-2-[2-(1-methyl-1H-[1,2,4]triazol-3-yl)-phenyl]-1H-benzimidazole (32 mg, 0.078 mmol) in DMF (2 mL), followed by the addition of 2-aminopyrimidine-5-boronic acid pinacol ester (21 mg, 0.095 mmol), tetrakis(triphenylphosphine)palladium(0) (9 mg, 0.008 mmol) and 2M aq. $Na_2CO_3$ (0.2 ml, 0.4 mmol). The reaction mixture is heated under Argon at 110° C. for 2 hours. The residue is diluted with EtOAc, washed with brine, dried under anhydrous $Na_2SO_4$, filtered and concentrated. The residue is purified by silica gel flash chromatography with 0-3% 7M $NH_3$ in MeOH/$CH_2Cl_2$ as the eluent. The product fractions are collected and concentrated to afford the title compound (27 mg, 82%) as an off-white solid. LCMS (ESMS): m/z 425.66 (M⁺+1)

The following compounds are made using the procedure described in this Example:

5-{1-tert-Butyl-2-[2-(1-ethyl-1H-[1,2,4]triazol-3-yl)-phenyl]-1H-benzimidazol-5-yl}-pyrimidin-2-ylamine. LCMS (ESMS): m/z 439.71 (M⁺+1)

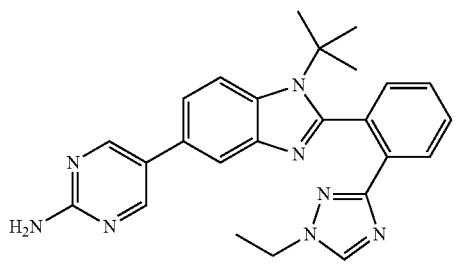 [SMILES: CCn1cnc(-c2ccccc2-c2nc3cc(-c4cnc(N)nc4)ccc3n2C(C)(C)C)n1]

5-{1-tert-Butyl-2-[2-(1-isopropyl-1H-[1,2,4]triazol-3-yl)-phenyl]-1H-benzimidazol-5-yl}-pyrimidin-2-ylamine. LCMS (ESMS): m/z 453.75 (M⁺+1)

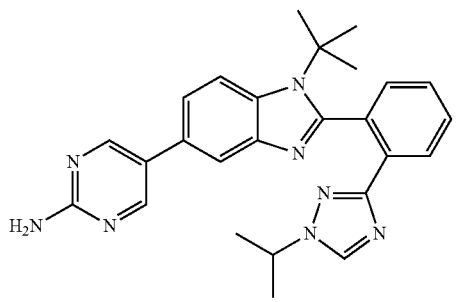 [SMILES: CC(C)n1cnc(-c2ccccc2-c2nc3cc(-c4cnc(N)nc4)ccc3n2C(C)(C)C)n1]

5-(1-tert-Butyl-2-{2-[1-(2-methoxy-ethyl)-1H-[1,2,4]triazol-3-yl]-phenyl}-1H-benzimidazol-5-yl)-pyrimidin-2-ylamine. LCMS (ESMS): m/z 469.49 (M⁺+1)

Example 52

5-{1-tert-Butyl-2-[2-(1-methyl-1H-[1,2,4]triazol-3-yl)-phenyl]-1H-benzimidazol-5-yl}-pyrimidin-2-ylamine

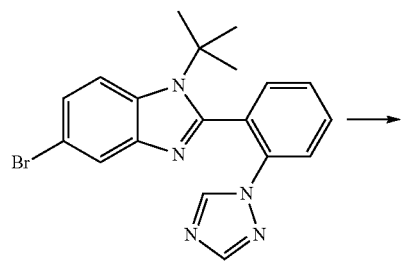

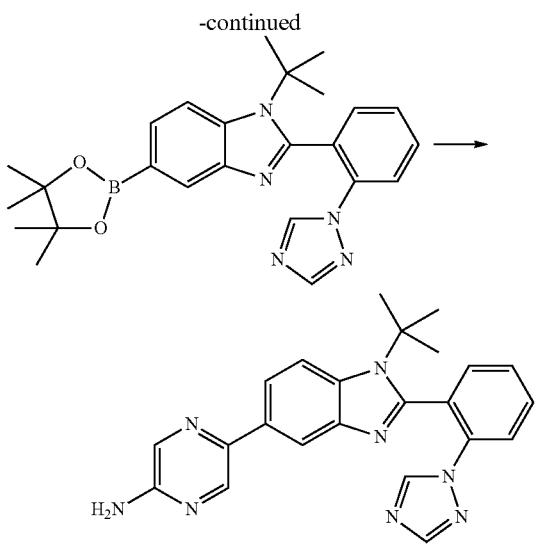

To a high pressure vessel are added 5-bromo-1-tert-butyl-2-(2-[1,2,4]triazol-1-yl-phenyl)-1H-benzimidazole (718 mg, 1.812 mmol), bis(pinacolato)diboron (552 mg, 2.174 mmol) and KOAc (712 mg, 7.254 mmol) in 1,4-dioxane (10 mL). The solution is bubbled with Argon gas for 10 minutes, followed by the addition of 1,1'-bis(diphenylphosphino)ferrocenedichloropalladium(II) CH₂Cl₂ (148 mg, 0.181 mmol). The reaction mixture is stirred at 110° C. for 4 hours. The reaction mixture is diluted with EtOAc and washed with water. The organic layer is separated, washed with brine, dried under anhydrous Na₂SO₄, filtered and concentrated. The residue is purified by silica gel flash chromatography with 0-4% MeOH/CH₂Cl₂ as the eluent. The product fractions are collected and concentrated to afford 1-tert-butyl-5-(4,4,5,5-tetramethyl-[1,3,2]dioxaborolan-2-yl)-2-(2-[1,2,4]triazol-1-yl-phenyl)-1H-benzimidazole (740 mg, 92%) as a light brown solid. LCMS (ESMS): m/z 444.57 (M⁺+1)

To a sealed vial is added 1-tert-butyl-5-(4,4,5,5-tetramethyl-[1,3,2]dioxaborolan-2-yl)-2-(2-[1,2,4]-triazol-1-yl-phenyl)-1H-benzimidazole (100 mg, 0.226 mmol) in DMF (3 mL), followed by the addition of 2-amino-5-bromopyrazine (45 mg, 0.259 mmol), tetrakis(triphenylphosphine)palladium (0) (26 mg, 0.022 mmol) and 2M aq. Na₂CO₃ (0.45 ml, 0.9 mmol). The reaction mixture is heated under Argon at 110° C. for 18 hours. The residue is diluted with EtOAc, washed with brine, dried under anhydrous Na₂SO₄, filtered and concentrated. The residue is purified by silica gel flash column chromatography with 0-5% MeOH/CH₂Cl₂ as the eluent. The product fractions are collected and concentrated to afford the title compound (40 mg, 43%) as a light brown solid. LCMS (ESMS): m/z 411.20 (M⁺+1)

The following compounds are made using the procedure described in this Example:

5-[1-tert-Butyl-2-(2-[1,2,4]triazol-1-yl-phenyl)-1H-benzimidazol-5-yl]-3-methyl-pyridin-2-ylamine. LCMS (ESMS): m/z 424.20 (M⁺+1)

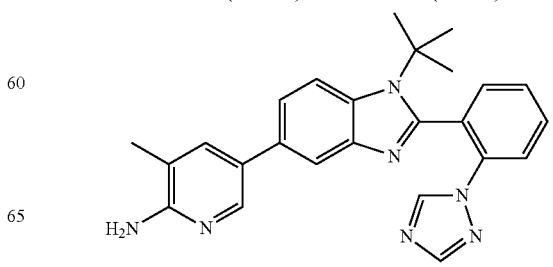

5-[1-tert-Butyl-2-(2-[1,2,4]triazol-1-yl-phenyl)-1H-benzimidazol-5-yl]-3-methyl-pyrazin-2-ylamine. LCMS (ESMS): m/z 425.66 (M⁺+1)

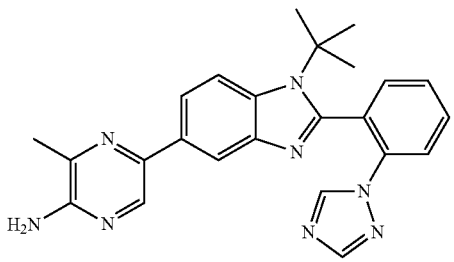

Example 53

5-{1-tert-Butyl-2-[2-(2,4-dimethyl-oxazol-5-yl)-phenyl]-1H-benzimidazol-5-yl}-pyrimidin-2-ylamine

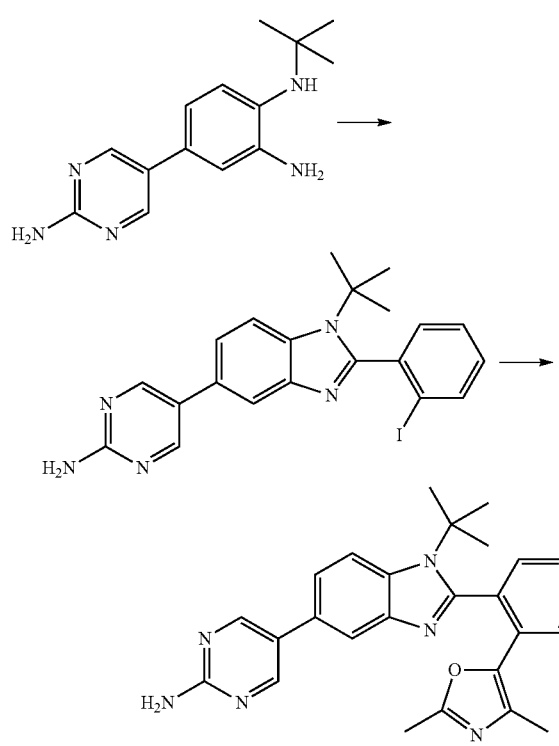

To a round bottom flask are added 4-(2-amino-pyrimidin-5-yl)-N¹-tert-butyl-benzene-1,2-diamine (430 mg, 1.67 mmol) in DMF (10 mL) and water (3 mL), followed by the addition of 2-iodobenzaldehyde (445 mg, 1.92 mmol) and oxone (1180 mg, 1.92 mmol). The reaction mixture is stirred at room temperature for 1 hour. Saturated sodium thiosulfate (10 mL) is added. The reaction mixture is diluted with EtOAc (50 mL). The organic layer is washed with water, brine, dried under anhydrous Na₂SO₄, filtered and concentrated. The residue is purified by silica gel flash column chromatography with 0-5% MeOH/CH₂Cl₂ as the eluent. The product fractions are collected and concentrated to afford 5-[1-tert-butyl-2-(2-iodo-phenyl)-1H-benzimidazol-5-yl]-pyrimidin-2-ylamine (270 mg, 34%) as a light brown solid. LCMS (ESMS): m/z 470.58 (M⁺+1)

To a vial are added 5-[1-tert-butyl-2-(2-iodo-phenyl)-1H-benzimidazol-5-yl]-pyrimidin-2-ylamine (50 mg, 0.107 mmol), 2,4-dimethyl-oxazole (21 mg, 0.216 mol), palladium (II) acetate (5 mg, 0.022 mmol), PPh₃ (6 mg, 0.023 mmol) and Cs₂CO₃ (70 mg, 0.215 mmol) in DMF (1.5 mL). The reaction mixture is stirred at 140° C. for 18 hours. The reaction mixture is diluted with EtOAc/water. The organic layer is separated, washed with brine, dried under anhydrous Na₂SO₄, filtered and concentrated. The residue is purified by silica gel flash column chromatography with 0-5% MeOH/CH₂Cl₂ as the eluent. The product fractions are collected and concentrated to afford the title compound (19 mg, 41%) as an off-white solid. LCMS (ESMS): m/z 439.86 (M⁺+1)

Example 54

5-{2-[5-(2-Amino-pyrimidin-5-yl)-1-tert-butyl-1H-benzimidazol-2-yl]-phenyl}-3H-[1,3,4]oxadiazol-2-one

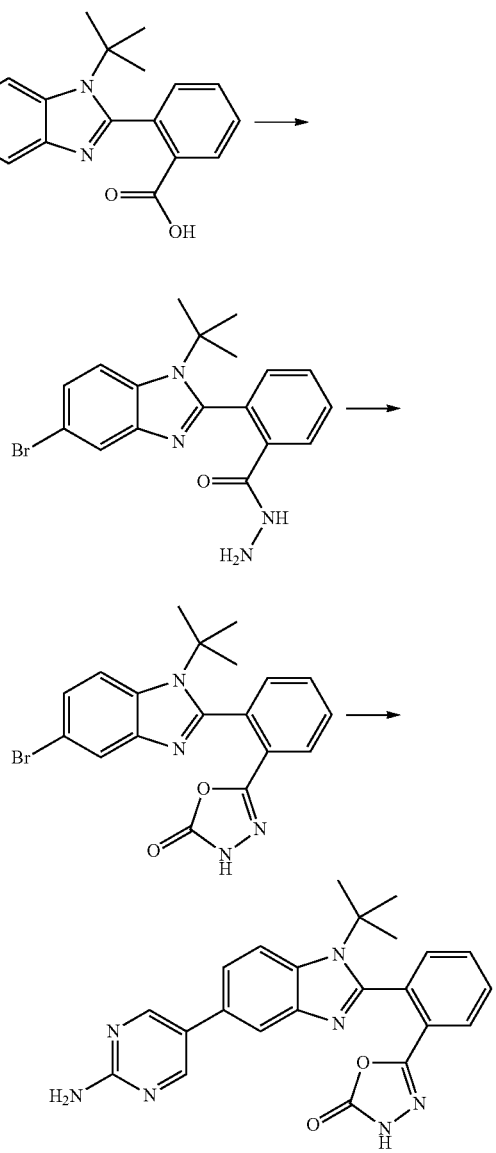

To a round bottom flask is added 2-(5-bromo-1-tert-butyl-1H-benzimidazol-2-yl)-benzoic acid (300 mg, 0.804 mmol) in DMF (8 mL), followed by the addition of HATU (611 mg, 1.607 mmol), tert-butyl carbazate (530 mg, 4.01 mmol) and iPr$_2$NEt (520 mg, 4.02 mmol). The reaction mixture is stirred at room temperature for 18 hours. The reaction mixture is diluted with EtOAc/water. The organic layer is separated, washed with brine, dried under anhydrous Na$_2$SO$_4$, filtered and concentrated. The residue is purified by silica gel flash column chromatography with 0-5% MeOH/CH$_2$Cl$_2$ as the eluent. The product fractions are collected and concentrated to afford N-[2-(5-bromo-1-tert-butyl-1H-benzimidazol-2-yl)-benzoyl]-hydrazinecarboxylic acid tert-butyl ester (390 mg). This material is dissolved in CH$_2$Cl$_2$ (3 mL), followed by the addition of trifluoroacetic acid (2 mL). The reaction mixture is stirred at room temperature for 3 hours. The reaction mixture is concentrated to afford 2-(5-bromo-1-tert-butyl-1H-benzimidazol-2-yl)-benzoic acid hydrazide (310 mg, 100%). LCMS (ESMS): m/z 387.75, 389.75 (M$^+$+1).

To a round bottom flask is added 2-(5-bromo-1-tert-butyl-1H-benzimidazol-2-yl)-benzoic acid hydrazide (310 mg, 0.8 mmol) in THF (4 mL), followed by the addition of triethylamine (2 mL) and CDI (390 mg, 2.405 mmol). The reaction mixture is stirred at room temperature for 18 hours. The reaction mixture is diluted with EtOAc/water. The organic layer is separated, washed with brine, dried under anhydrous Na$_2$SO$_4$, filtered and concentrated. The residue is purified by silica gel flash column chromatography with 0-5% MeOH/CH$_2$Cl$_2$ as the eluent to afford 5-[2-(5-bromo-1-tert-butyl-1H-benzimidazol-2-yl)-phenyl]-3H-[1,3,4]oxadiazol-2-one (140 mg, 42%) as a light brown solid. LCMS (ESMS): m/z 413.07, 415.04 (M$^+$+1).

To a sealed vial is added 5-[2-(5-bromo-1-tert-butyl-1H-benzimidazol-2-yl)-phenyl]-3H-[1,3,4]oxadiazol-2-one (40 mg, 0.097 mmol) in DMF (3 mL), followed by the addition of 2-aminopyrimidine-5-boronic acid pinacol ester (25 mg, 0.113 mmol), bis(di-tert-butyl(4-dimethylaminophenyl)phosphine)dichloropalladium(II) (8 mg, 0.011 mmol) and 2M aq. Na$_2$CO$_3$ (0.2 ml, 0.4 mmol). The reaction mixture is heated under Argon at 100° C. for 6 hours. The residue is diluted with EtOAc (20 mL), washed with brine, dried under anhydrous Na$_2$SO$_4$, filtered and concentrated. The residue is purified by silica gel flash column chromatography with 0-10% 7M NH$_3$ in MeOH/CH$_2$Cl$_2$ as the eluent to afford the title compound (4 mg, 10%) as a pale-white solid. LCMS (ESMS): m/z 428.87 (M$^+$+1).

Example 55

5-{2-[5-(2-Amino-pyrimidin-5-yl)-1-tert-butyl-1H-benzimidazol-2-yl]-phenyl}-3-methyl-3H-[1,3,4]oxadiazol-2-one

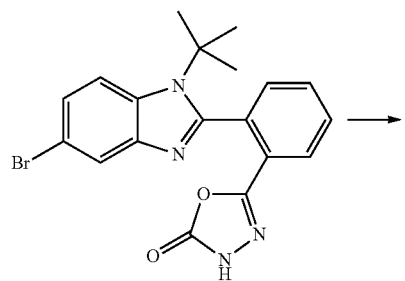

-continued

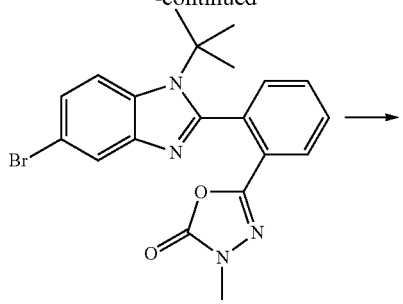

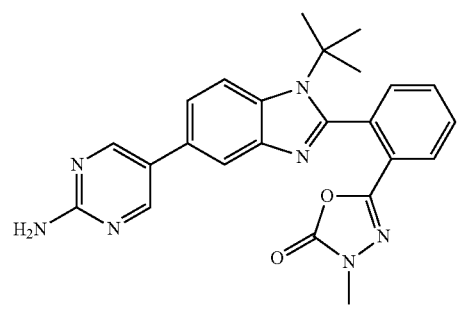

To a round bottom flask is added 5-[2-(5-bromo-1-tert-butyl-1H-benzimidazol-2-yl)-phenyl]-3H-[1,3,4]oxadiazol-2-one (100 mg, 0.242 mmol) in DMF (4 mL) at 0° C., followed by the addition of NaH (19 mg, 0.475 mmol). The reaction mixture is stirred at 0° C. for 10 minutes, followed by the addition of MeI (103 mg, 0.726 mmol). The reaction mixture is stirred at room temperature for 2 hours. The reaction mixture is quenched with saturated NH$_4$Cl (10 mL) and extracted with EtOAc (20 mL). The organic layer is separated, washed with brine, dried under anhydrous Na$_2$SO$_4$, filtered and concentrated. The residue is purified by silica gel flash chromatography with 0-5% MeOH/CH$_2$Cl$_2$ as the eluent to afford 5-[2-(5-bromo-1-tert-butyl-1H-benzimidazol-2-yl)-phenyl]-3-methyl-3H-[1,3,4]oxadiazol-2-one (92 mg, 89%) as a solid. LCMS (ESMS): m/z 427.63, 429.67 (M$^+$+1).

To a sealed vial is added 5-[2-(5-bromo-1-tert-butyl-1H-benzimidazol-2-yl)-phenyl]-3-methyl-3H-[1,3,4]oxadiazol-2-one (92 mg, 0.215 mmol) in DMF (3 mL), followed by the addition of 2-aminopyrimidine-5-boronic acid pinacol ester (57 mg, 0.258 mmol), tetrakis(triphenylphosphine)palladium (0) (25 mg, 0.022 mmol) and 2M aq. Na$_2$CO$_3$ (0.45 ml, 0.9 mmol). The reaction mixture is heated under Argon at 110° C. for 3 hours. The residue is diluted with EtOAc (20 mL), washed with brine, dried under anhydrous Na$_2$SO$_4$, filtered and concentrated. The residue is purified by silica gel flash column chromatography with 0-4% 7M NH$_3$ in MeOH/

CH$_2$Cl$_2$ as the eluent to afford the title compound (24 mg, 25%) as a off-white solid. LCMS (ESMS): m/z 442.43 (M$^+$+1).

Example 56

5-{1-tert-Butyl-2-[5-fluoro-2-(5-methyl-[1,2,4]oxadiazol-3-yl)-phenyl]-1H-benzimidazol-5-yl}-pyrimidin-2-ylamine

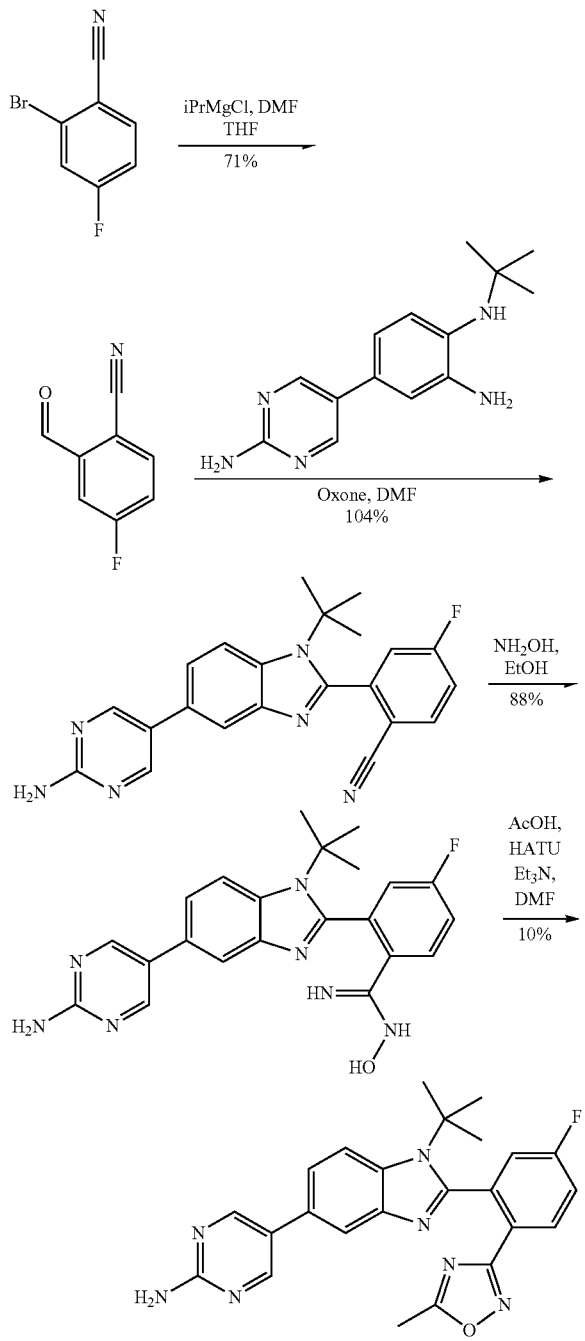

To a solution of 2-bromo-4-fluorobenzonitrile (5.0 g, 25.0 mmol) in anhydrous THF (20 mL) is added iPrMgCl 2.01\4 in THF (15.0 mL, 30.0 mmol) at −30° C. The solution is stirred at −30° C. for 3 hours and DMF (5.80 mL, 75.0 mmol) is added. The reaction mixture is allowed to warm to room temperature and is stirred for 1 hour. The solution is cooled to −10° C., 2M hydrochloric acid (37 mL) is added and the solution is stirred for 20 minutes. The solution is concentrated in vacuo to −⅓ original volume and extracted into EtOAc (3×). The combined organics are then dried (Na$_2$SO$_4$), filtered and concentrated to afford 4-fluoro-2-formyl benzonitrile (3.9 g, 71%).

To a solution of 4-(2-amino-pyrimidin-5-yl)-N-1-tert-butyl-benzene-1,2-diamine (500 mg, 1.94 mmol) in DMF (20 mL) is added 4-fluoro-2-formyl benzonitrile (627 mg, 2.53 mmol). Oxone (717 mg, 1.17 mmol) is added and the solution is stirred at the same temperature for 2 hours. The reaction mixture is poured into 0.5 M K$_2$CO$_3$ solution (30 mL). The product is extracted into EtOAc (3×) and the combined organics are then dried (Na$_2$SO$_4$), filtered, and concentrated. Purification via flash chromatography (25 g silica gel, 0-4% MeOH/CH$_2$Cl$_2$) affords 2-[5-(2-amino-pyrimidin-5-yl)-1-tert-butyl-1H-benzimidazol-2-yl]-4-fluoro-benzonitrile (1.1 g, 104%).

To a suspension of 2-[5-(2-amino-pyrimidin-5-yl)-1-tert-butyl-1H-benzimidazol-2-yl]-4-fluoro-benzonitrile (500 mg, 1.29 mmol) in EtOH (8 mL) is added hydroxylamine 50% aqueous solution (1.71 mL, 25.88 mmol) at room temperature. The solution is stirred at 75° C. for 18 hours. The reaction mixture is cooled to room temperature and the ethanol removed in vacuo. Water (30 mL) is added to the reaction mixture and the resultant precipitate is filtered and washed with 10% EtOAc/heptane (10 mL) to afford 2-[5-(2-amino-pyrimidin-5-yl)-1-tert-butyl-1H-benzimidazol-2-yl]-4-fluoro-N-hydroxy-benzamidine (485 mg, 88%).

To a solution of acetic acid (52 mg, 0.86 mmol) and HATU (326 mg, 0.86 mmol) in DMF (4 mL) is added triethylamine (0.12 mL, 0.86 mmol). The reaction mixture is stirred at room temperature for 10 minutes and 2-[5-(2-amino-pyrimidin-5-yl)-1-tert-butyl-1H-benzimidazol-2-yl]-4-fluoro-N-hydroxy-benzamidine (300 mg, 0.72 mmol) is added. The reaction mixture is stirred at room temperature for 2 hours then warmed to 80° C. and stirred for 15 hours. The reaction mixture is cooled to room temperature and concentrated in vacuo. EtOAc (30 mL) is added and the organics washed sequentially with saturated NaHCO$_3$ solution (30 mL) and H$_2$O (30 mL) then dried (Na$_2$SO$_4$), filtered and concentrated. Purification via flash chromatography (10 g silica gel, 1.5-3% MeOH/CH$_2$Cl$_2$) affords the title compound (43 mg, 10%). LCMS (ESMS): m/z 444.32 (M$^+$+1)

The following compound is made using the procedure described in this Example:

5-{1-tert-Butyl-2-[5-methyl-2-(5-methyl-[1,2,4]oxadiazol-3-yl)-phenyl]-1H-benzimidazol-5-yl}-pyrimidin-2-ylamine. LCMS (ESMS): m/z 440.29 (M$^+$+1)

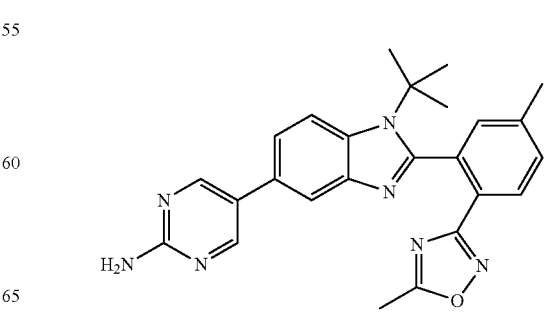

Example 57

3-{2-[5-(2-Amino-pyrimidin-5-yl)-1-tert-butyl-1H-benzimidazol-2-yl]-4-methyl-phenyl}-[1,2,4]oxadiazole-5-carboxylic acid methylamide

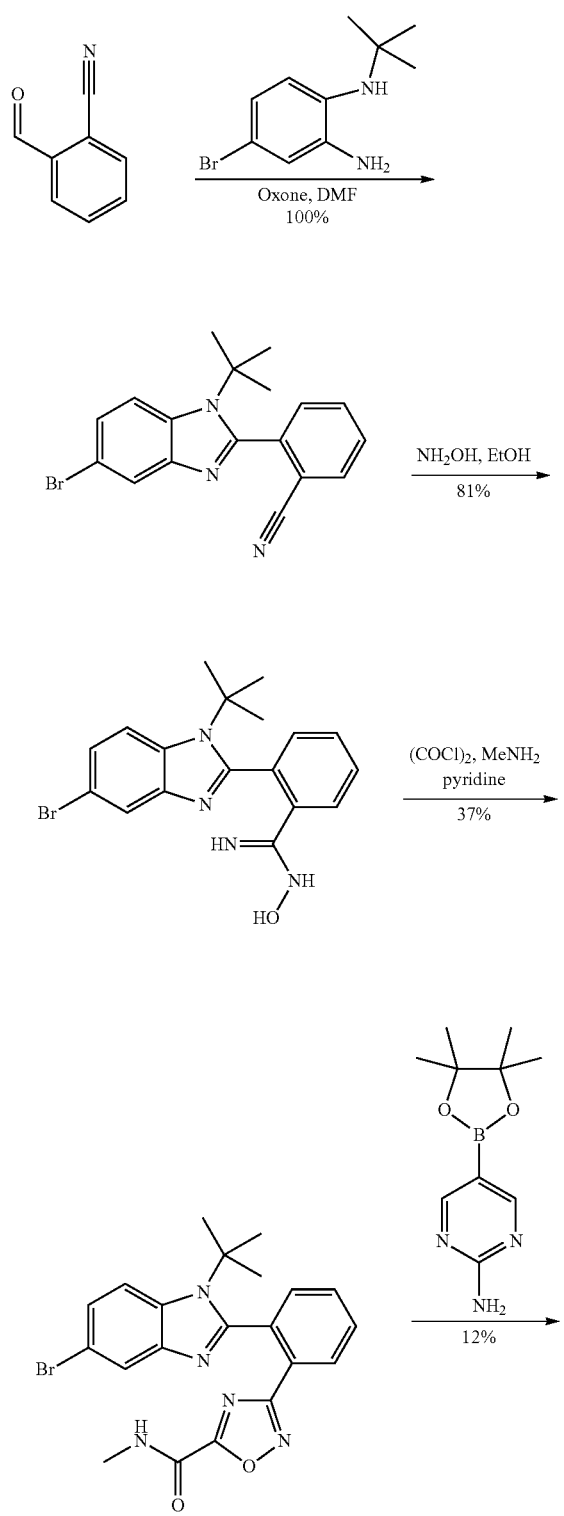

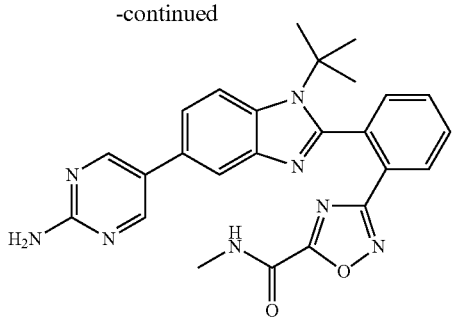

To a solution of 4-bromo-N$^1$-tert-butyl-benzene-1,2-diamine (500 mg, 2.06 mmol) in DMF (20 mL) is added 2-formyl-benzonitrile (270 mg, 2.06 mmol) at room temperature. Oxone (758 mg, 1.23 mmol) is added and the solution is stirred at the same temperature for 2 hours. The reaction mixture is poured into 0.5 M K$_2$CO$_3$ solution (30 mL). The product is extracted into EtOAc (3×) and the combined organics are then dried (Na$_2$SO$_4$), filtered, and concentrated. Purification via flash chromatography (25 g silica gel, 0-4% MeOH/CH$_2$Cl$_2$) affords 2-(5-bromo-1-tert-butyl-1H-benzimidazol-2-yl)-benzonitrile (765 mg, 100%).

To a suspension of 2-(5-bromo-1-tert-butyl-1H-benzimidazol-2-yl)-benzonitrile (765 mg, 2.16 mmol) in EtOH (15 mL) is added hydroxylamine 50% aqueous solution (2.85 mL, 43.19 mmol) at room temperature. The solution is heated to 80° C. for 2 hours. The reaction mixture is cooled to room temperature and the ethanol removed in vacuo. Water (30 mL) is added to the reaction mixture and the resultant precipitate is filtered and washed with 10% EtOAc/heptane (10 mL) to afford 2-(5-bromo-1-tert-butyl-1H-benzimidazol-2-yl)-N-hydroxy-benzamidine (716 mg, 81%).

To a solution of oxalyl chloride (0.17 mL, 1.99 mmol) in anhydrous THF (20 mL) is added methylamine 2.0M in THF (0.99 mL, 1.99 mmol) at 0° C. The solution is stirred at 0° C. to room temperature for 0.5 hours and added to a stirred solution of 2-(5-bromo-1-tert-butyl-1H-benzimidazol-2-yl)-N-hydroxy-benzamidine (350 mg, 0.9 mmol) in anhydrous pyridine (5 mL). The reaction mixture is stirred at room temperature for 1 hour and then heated to 50° C. and stirred for 16 hours. The reaction mixture is cooled to room temperature and concentrated in vacuo. Dichloromethane is added and the organics washed sequentially with saturated NaHCO$_3$ (20 mL) solution and H$_2$O (20 mL) then dried (Na$_2$SO$_4$), filtered and concentrated. Purification via flash chromatography (25 g silica gel, 50-60% EtOAc/heptane) affords 3-[2-(5-bromo-1-tert-butyl-1H-benzimidazol-2-yl)-phenyl]-[1,2,4]oxadiazole-5-carboxylic acid methylamide (150 mg, 37%)

To a solution of 3-[2-(5-bromo-1-tert-butyl-1H-benzimidazol-2-yl)-phenyl]-[1,2,4]oxadiazole-5-carboxylic acid methylamide (150 mg, 0.32 mmol) in DMF (2 mL) in a sealed vessel are added 5-(4,4,5,5-tetramethyl-[1,3,2]dioxaborolan-2-yl)-pyrimidin-2-ylamine (85 mg, 0.38 mmol), 2 M Na$_2$CO$_3$ solution (0.48 mL, 0.96 mmol) and PdCl$_2$(PPh$_3$)$_2$ (11 mg, 0.02 mmol) at room temperature. The solution is heated to 80° C. for 2 hours. The reaction mixture is cooled to room temperature and filtered through diatomaceous earth and concentrated in vacuo. Purification via flash chromatography (10 g silica gel, 2-3.5% MeOH/CH$_2$Cl$_2$) affords the title compound (18.4 mg, 12%). LCMS (ESMS): m/z 469.30 (M$^+$+1)

Example 58

5-{1-tert-Butyl-2-[2-(5-methyl-[1,2,4]oxadiazol-3-yl)-phenyl]-1H-benzimidazol-5-yl}-pyrimidin-2-ylamine

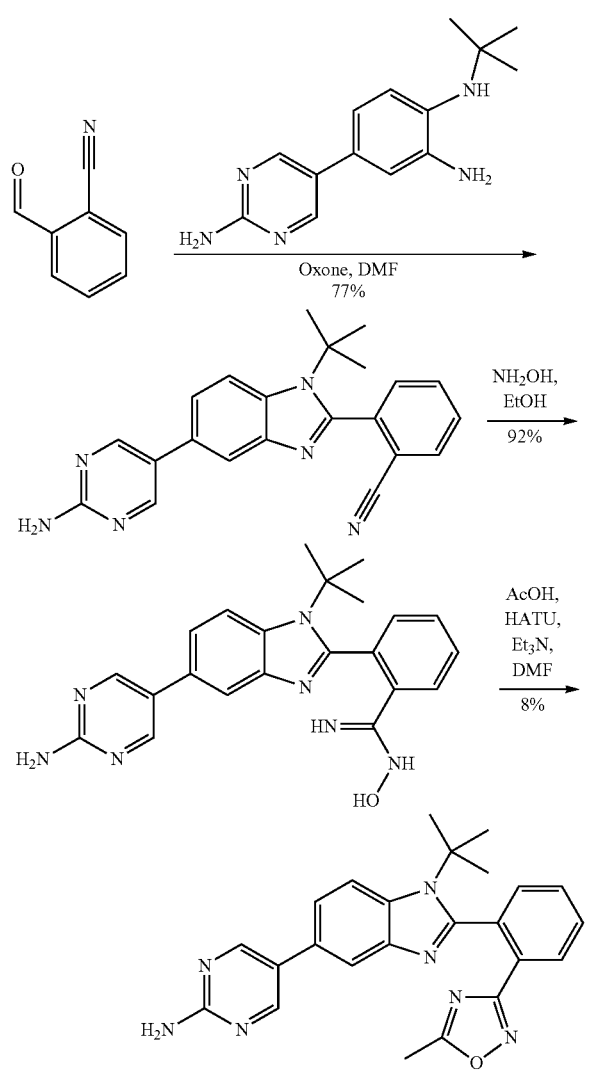

To a solution of 4-(2-amino-pyrimidin-5-yl)-N-1-tert-butyl-benzene-1,2-diamine (1 g, 3.89 mmol) in DMF (50 mL) is added 2-formyl-benzonitrile (510 mg, 3.89 mmol) at room temperature. Oxone (1.4 g, 2.33 mmol) is added and the solution is stirred at the same temperature for 1 hour. The reaction mixture is poured into 0.5 M K$_2$CO$_3$ solution (30 mL). The product is extracted into EtOAc (3×) and the combined organics are then dried (Na$_2$SO$_4$), filtered, and concentrated to afford 2-[5-(2-amino-pyrimidin-5-yl)-1-tert-butyl-1H-benzimidazol-2-yl]-benzonitrile (1.1 g, 77%).

To a suspension of 2-[5-(2-amino-pyrimidin-5-yl)-1-tert-butyl-1H-benzimidazol-2-yl]-benzonitrile (1.1 mg, 2.99 mmol) in EtOH (20 mL) is added hydroxylamine 50% aqueous solution (3.94 mL 59.71 mmol) at room temperature. The solution is stirred at 80° C. for 2 hours. The reaction mixture is cooled to room temperature and the ethanol removed in vacuo. EtOAc (50 mL) is added and the organics washed with H$_2$O then dried (Na$_2$SO$_4$), filtered and concentrated to afford 2-[5-(2-amino-pyrimidin-5-yl)-1-tert-butyl-1H-benzimidazol-2-yl]-N-hydroxy-benzamidine (1.1 g, 92%).

To a solution of acetic acid (30 mg, 0.5 mmol) and HATU (189 mg, 0.5 mmol) in DMF (2 mL) is added triethylamine (0.07 mL, 0.5 mmol). The reaction mixture is stirred at room temperature for 10 minutes and 2-[5-(2-amino-pyrimidin-5-yl)-1-tert-butyl-1H-benzimidazol-2-yl]-N-hydroxy-benzamidine (200 mg, 0.5 mmol) is added. The reaction mixture is stirred at room temperature for 0.5 hours then warmed to 80° C. and stirred for 15 hours. The reaction mixture is cooled to room temperature and concentrated in vacuo. EtOAc (20 mL) is added and the organics washed with H$_2$O (30 mL) then dried (Na$_2$SO$_4$), filtered and concentrated. Purification via prep HPLC (0.1% TFA/MeCN) affords the title compound (27 mg, 8%) as 2TFA salt. LCMS (ESMS): m/z 426.20 (M$^+$+1)

Example 59

5-{2-[2-(5-Amino-[1,2,4]oxadiazol-3-yl)-phenyl]-1-tert-butyl-1H-benzimidazol-5-yl}-pyrimidin-2-ylamine

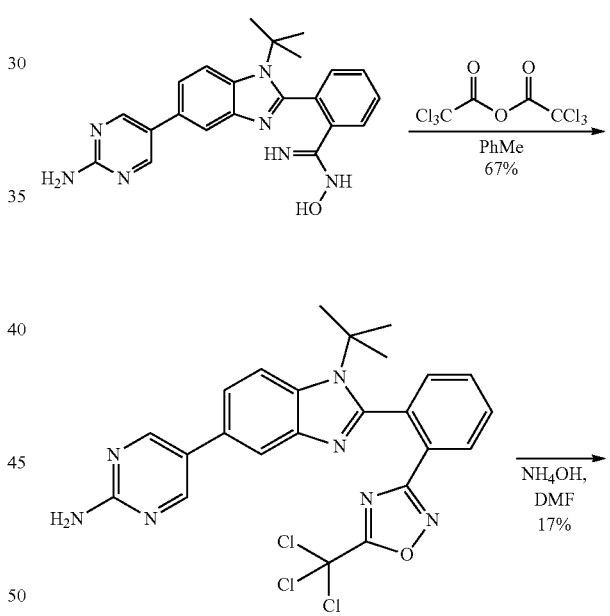

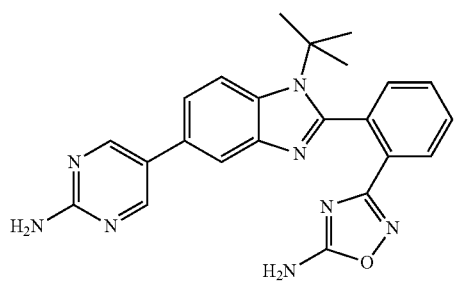

To a suspension of 2-[5-(2-amino-pyrimidin-5-yl)-1-tert-butyl-1H-benzimidazol-2-yl]-N-hydroxy-benzamidine (440 mg, 1.10 mmol) in toluene (20 mL) at room temperature is added trichloroacetic anhydride (0.24 mL, 1.32 mmol). The reaction mixture is stirred at 80° C. for 2 h. The reaction mixture is cooled to room temperature. EtOAc is added and the organics are washed sequentially with saturated NaHCO$_3$ (30 mL) solution and H$_2$O (30 mL) then dried (Na$_2$SO$_4$), filtered and concentrated to afford 5-{1-tert-butyl-2-[2-(5-trichloromethyl-[1,2,4]oxadiazol-3-yl)-phenyl]-1H-benzimidazol-5-yl}-pyrimidin-2-ylamine (0.39 g, 67%)

To a stirred solution of ammonium hydroxide (0.02 mL, 0.39 mmol) in DMF (2 mL) at room temperature is added 5-{1-tert-butyl-2-[2-(5-trichloromethyl-[1,2,4]oxadiazol-3-yl)-phenyl]-1H-benzimidazol-5-yl}-pyrimidin-2-ylamine (395 mg, 0.26 mmol). The reaction mixture is stirred at room temperature for 0.5 hours. Water is added to the reaction mixture and the product is extracted into EtOAc (3×) and the combined organics are then dried (Na$_2$SO$_4$), filtered, and concentrated. Purification via flash chromatography (10 g silica gel, 3-6% MeOH/CH$_2$Cl$_2$) affords the title compound (20.6 mg, 17%). LCMS (ESMS): m/z 427.29 (M$^+$+1)

The following compounds are made using the procedure described in this Example:

5-{1-tert-Butyl-2-[2-(5-methylamino-[1,2,4]oxadiazol-3-yl)-phenyl]-1H-benzimidazol-5-yl}-pyrimidin-2-ylamine. LCMS (ESMS): m/z 441.30 (M$^+$+1)

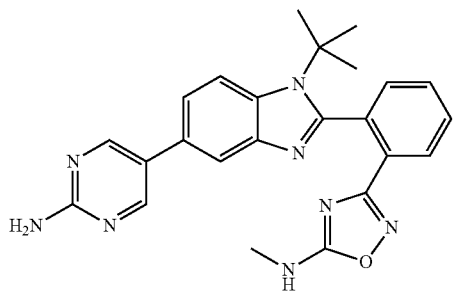 [SMILES: CNc1nc(-c2ccccc2-c2nc3cc(-c4cnc(N)nc4)ccc3n2C(C)(C)C)no1]

5-{1-tert-Butyl-2-[2-(5-dimethylamino-[1,2,4]oxadiazol-3-yl)-phenyl]-1H-benzimidazol-5-yl}-pyrimidin-2-ylamine. LCMS (ESMS): m/z 455.35 (M$^+$+1)

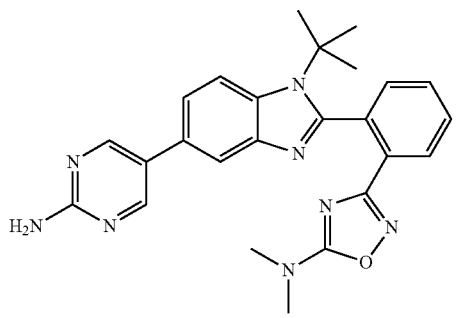 [SMILES: CN(C)c1nc(-c2ccccc2-c2nc3cc(-c4cnc(N)nc4)ccc3n2C(C)(C)C)no1]

Example 60

5-{1-tert-Butyl-2-[2-(1,5-dimethyl-1H-[1,2,4]triazol-3-yl)-phenyl]-1H-benzimidazol-5-yl}-pyrimidin-2-ylamine

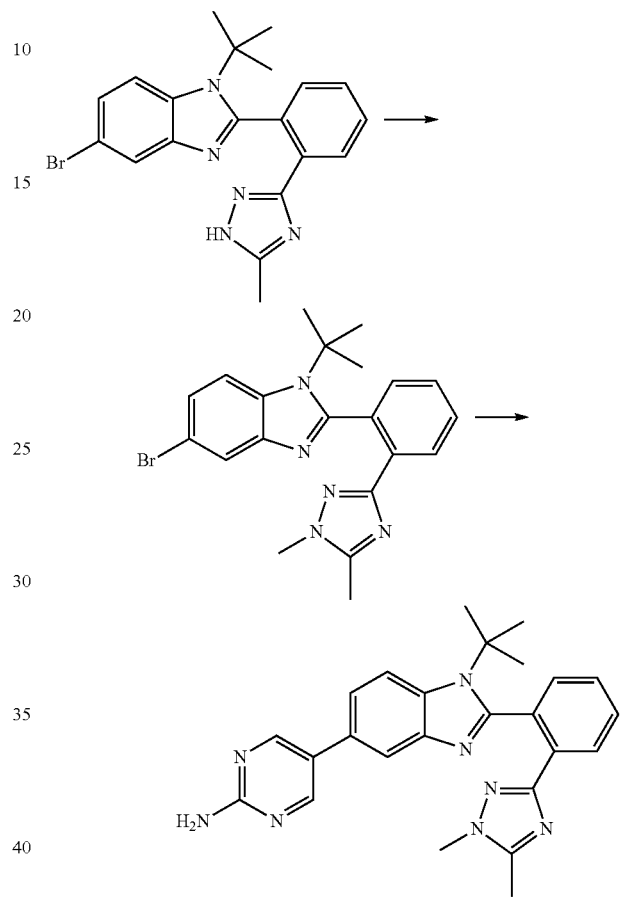

To a vial is added 5-bromo-1-tert-butyl-2-[2-(5-methyl-1H-[1,2,4]triazol-3-yl)-phenyl]-1H-benzimidazole (73 mg, 0.178 mmol) in DMF (1.5 mL), followed by the addition of MeI (40 mg, 0.282 mmol) and K$_2$CO$_3$ (49 mg, 0.355 mmol). The reaction mixture is stirred at room temperature for 1 hour. The reaction mixture is diluted with EtOAc (20 mL), washed with water, brine, dried under anhydrous Na$_2$SO$_4$, filtered and concentrated. The residue is purified by silica gel flash column chromatography with 0-3% 7M NH$_3$ in MeOH/CH$_2$Cl$_2$ as the eluent to afford 5-bromo-1-tert-butyl-2-[2-(1,5-dimethyl-1H-[1,2,4]triazol-3-yl)-phenyl]-1H-benzimidazole (44 mg, 58%) as an off-white solid. LCMS (ESMS): m/z 424.58, 426.51 (M$^+$+1).

To a sealed vial is added 5-bromo-1-tert-butyl-2-[2-(1,5-dimethyl-1H-[1,2,4]triazol-3-yl)-phenyl]-1H-benzimidazole (38 mg, 0.09 mmol) in DMF (2 mL), followed by the addition of 2-aminopyrimidine-5-boronic acid pinacol ester (24 mg, 0.109 mmol), tetrakis(triphenylphosphine)palladium (0) (11 mg, 0.01 mmol) and 2 M aqueous Na$_2$CO$_3$ (0.2 mL, 0.4 mmol). The reaction mixture is heated under Argon at 110° C. for 3 hours. The residue is diluted with EtOAc (20 mL), washed with brine, dried under anhydrous Na$_2$SO$_4$, filtered and concentrated. The residue is purified by silica gel flash column chromatography with 0-10% MeOH/CH$_2$Cl$_2$ as the eluent to afford the title compound (30 mg, 76%) as an off-white solid. LCMS (ESMS): m/z 439.72 (M⁺+1).

Example 61 and 62

5-{1-tert-Butyl-2-[4-fluoro-2-(2-methyl-2H-1,2,4-triazol-3-yl)-phenyl]-1H-benzimidazol-5-yl}-pyrimidin-2-ylamine and 5-[1-tert-Butyl-2-[5-fluoro-2-(2-methyl-2H-1,2,4-triazol-3-yl)-phenyl]-1H-benzimidazol-5-yl]-pyrimidin-2-ylamine

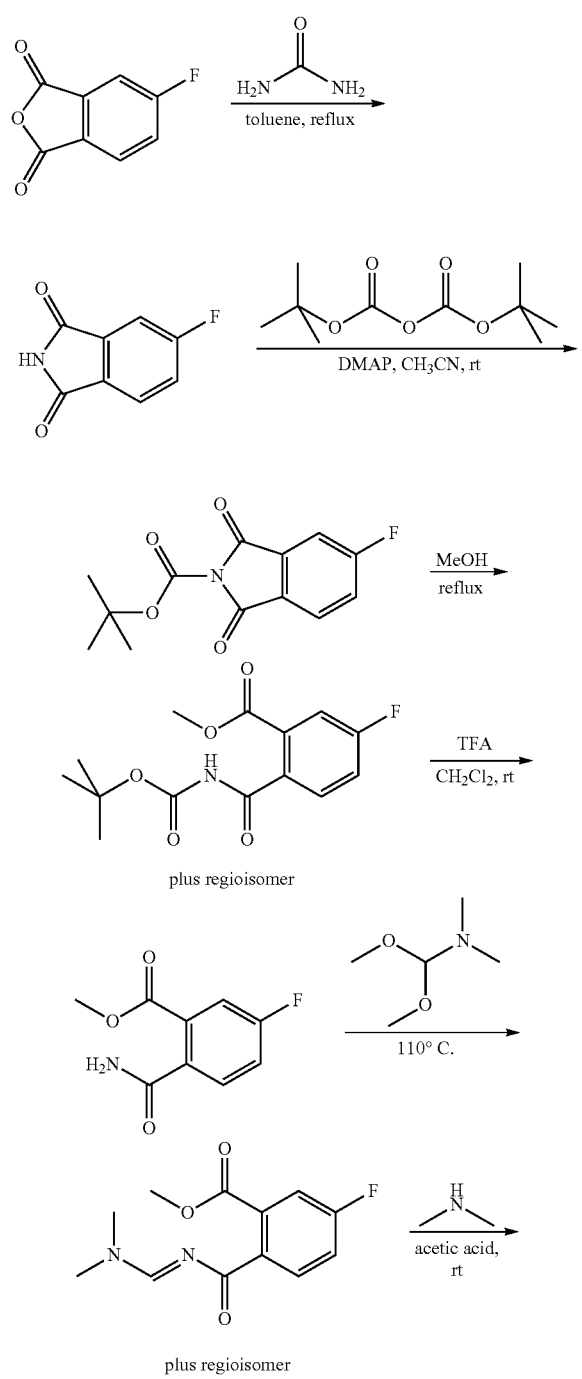

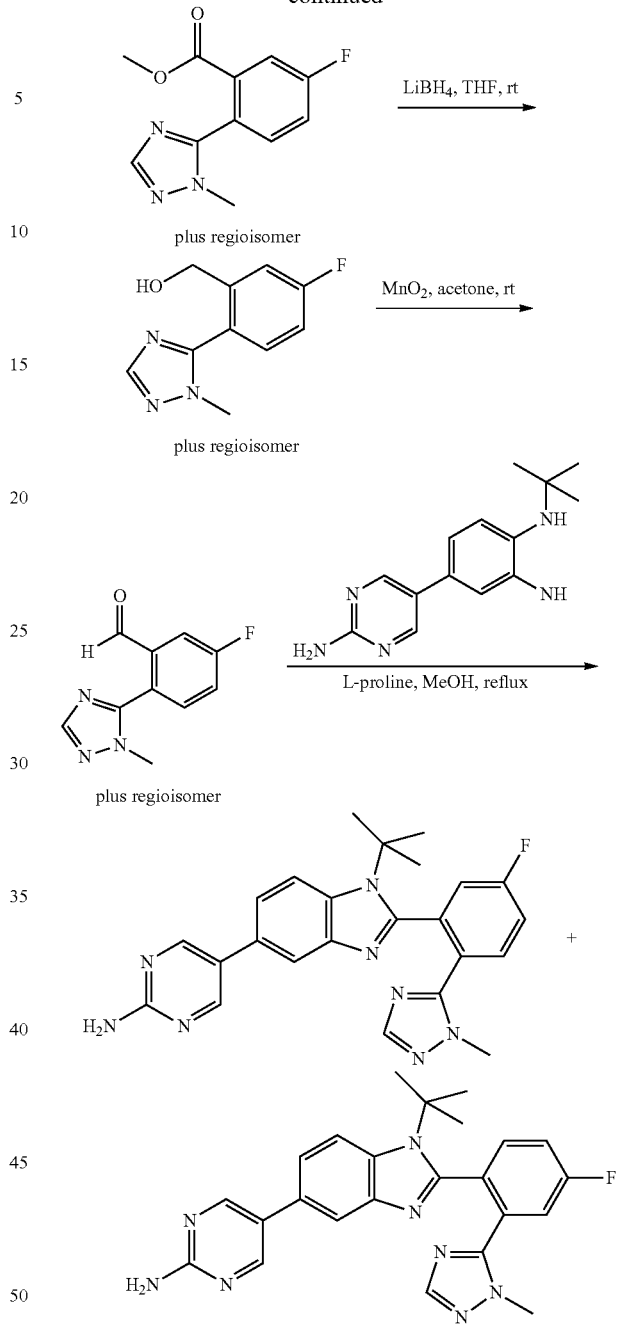

To 4-fluorophthalic anhydride (5.0 g, 30.10 mmol) in toluene (15 mL) is added urea (2.1 g). The reaction mixture is stirred at refluxed for 16 h. The reaction mixture is allowed to cool to room temperature, concentrated under reduced pressure and triturated with H₂O (250 mL) to afford 5-fluoro-isoindole-1,3-dione (5.0 g, 100%) as a white solid.

To a solution of 5-fluoro-isoindole-1,3-dione (2.5 g, 15.14 mmol), DMAP (20 mg), in CH₃CN (50 mL) is added di-tertbutyl dicarbonate (3.5 g, 16.04 mmol). The reaction mixture is stirred at room temperature for 3 hours. The reaction mixture is concentrated under reduced pressure to afford 5-fluoro-1,3-dioxo-1,3-dihydro-isoindole-2-carboxylic acid tert-butyl ester (4.0 g, 99%) as a white solid.

A solution of 5-fluoro-1,3-dioxo-1,3-dihydro-isoindole-2-carboxylic acid tert-butyl ester (4.0 g, 15.08 mmol) in MeOH (20 mL) is refluxed for 1 hour. The reaction mixture is allowed to cool to room temperature and then concentrated under reduced pressure to afford 2-tert-butoxycarbonylaminocarbonyl-5-fluoro-benzoic acid methyl ester plus regioisomer (4.5 g, 100%) as a white solid.

To a solution of 2-tert-butoxycarbonylaminocarbonyl-5-fluoro-benzoic acid methyl ester (4.5 g, 15.13 mmol) plus regioisomer in $CH_2Cl_2$ (25 mL) is added TFA (2.0 mL, 25.96 mmol). The reaction mixture is stirred at room temperature for 3 hours and concentrated under reduced pressure to afford 5-fluoro-phthalamic acid methyl ester plus regioisomer (2.24 g, 75%).

A solution of 5-fluoro-phthalamic acid methyl ester plus regioisomer (2.24 g, 11.36 mmol) in N,N-dimethylformamide dimethyl acetal (10 mL) is heated at 110° C. for 3 hours. The reaction mixture is allowed to cool to room temperature and is concentrated under reduced pressure to afford crude N-[1-dimethylamino-meth-(E)-ylidene]-5-fluoro-phthalamic acid methyl ester plus regioisomer (2.9 g).

To a solution of N-[1-dimethylamino-meth-(E)-ylidene]-5-fluoro-phthalamic acid methyl ester plus regioiosmer (2.9 g, 11.50 mmol) in acetic acid (10 mL) is added methyl hydrazine (6.0 mL, 113.95 mmol). The reaction mixture is stirred at room temperature for 1 hour. The reaction mixture is diluted with EtOAc (250 mL) and the organic layer is washed with $H_2O$ (150 mL×2), dried with $Na_2SO_4$ and filtered. The filtrate is concentrated under reduced pressure. The residue is triturated with 1:1 EtOAc:hexanes (200 mL), and filtered to remove the white solid. The mother liquor is concentrated under reduced pressure and the residue is purified by silica gel flash column chromatography with 7.5% MeOH in $CH_2Cl_2$ as the eluent to afford 5-fluoro-2-(2-methyl-2H-1,2,4-triazol-3-yl)-benzoic acid methyl ester plus regioisomer (1.5 g, 55%).

To a mixture of 5-fluoro-2-(2-methyl-2H-1,2,4-triazol-3-yl)-benzoic acid methyl ester plus regioisomer (1.5 g, 6.38 mmol) in THF (50.0 mL) is added a solution of 2 M $LiBH_4$ in THF (10.0 mL, 20 mmol). The reaction mixture is stirred at room temperature for 16 hours and is then quenched with 4 M HCl in dioxane to give an acidic solution and concentrated under reduced pressure. The resulting residue is diluted with 1 M aqueous NaOH (100 mL), extracted with EtOAc (10 mL×3) and the combined organic layers are dried with $Na_2SO_4$ and filtered. The filtrate is concentrated under reduced pressure and the residue is purified by silica gel flash column chromatography with 6% MeOH in $CH_2Cl_2$ as the eluent to afford [5-fluoro-2-(2-methyl-2H-1,2,4-triazol-3-yl)-phenyl]-methanol plus regiosiomer (1.0 g, 75%).

To a solution of [5-fluoro-2-(2-methyl-2H-1,2,4-triazol-3-yl)-phenyl]-methanol plus regiosiomer (600 mg, 2.90 mmol) in $CH_2Cl_2$ (20.0 mL) is added $MnO_2$ (750 mg, 8.63 mmol). The reaction mixture is stirred at room temperature for 72 hours and is filtered through diatomaceous earth. The filtrate is concentrated under reduced pressure and the residue is purified by silica gel flash column chromatography with 6% MeOH in $CH_2Cl_2$ as the eluent to afford 5-fluoro-2-(2-methyl-2H-1,2,4-triazol-3-yl)-benzaldehyde plus regioisomer (475 mg, 80%).

A reaction mixture of 4-(2-amino-pyrimidin-5-yl)-N1-tert-butyl-benzene-1,2-diamine (450 mg, 1.75 mmol), 5-fluoro-2-(2-methyl-2H-1,2,4-triazol-3-yl)-benzaldehyde plus regioisomer (475 mg, 2.32 mmol), L-proline (10 mg) in MeOH (25 mL) is refluxed for 16 hours. The reaction mixture is allowed to cool to room temperature and is concentrated under reduced pressure. The residue is purified by silica gel flash column chromatography with 5% MeOH in $CH_2Cl_2$ as the eluent followed by further purification using HPLC C-18 column with $CH_3CN$ (0.1% TFA) in $H_2O$ (0.1% TFA) as the eluent to afford 5-{1-tert-butyl-2-[5-fluoro-2-(2-methyl-2H-1,2,4-triazol-3-yl)-phenyl]-1H-benzimidazol-5-yl}-pyrimidin-2-ylamine (Example 61) (140 mg, 38%) and 5-{1-tert-butyl-2-[4-fluoro-2-(2-methyl-2H-1,2,4-triazol-3-yl)-phenyl]-1H-benzimidazol-5-yl}-pyrimidin-2-ylamine (Example 62) (65 mg, 17%). Data for both titled compounds LCMS (ESMS): m/z 443.20 ($M^+$+1)

The following compounds are made using the procedure described in this Example:

5-{1-tert-Butyl-2-[4-chloro-2-(2-methyl-2H-1,2,4-triazol-3-yl)-phenyl]-1H-benzimidazol-5-yl}-pyrimidin-2-ylamine. LCMS (ESMS): m/z 459.20 ($M^+$+1)

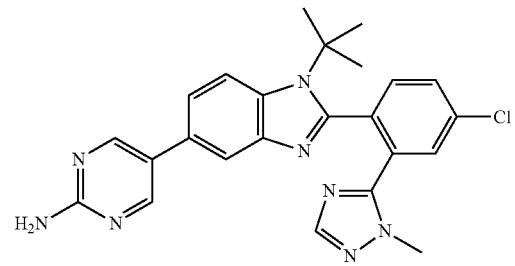 [SMILES: Cn1ncnc1-c1cc(Cl)ccc1-c1nc2cc(-c3cnc(N)nc3)ccc2n1C(C)(C)C]

5-{1-tert-Butyl-2-[5-chloro-2-(2-methyl-2H-1,2,4-triazol-3-yl)-phenyl]-1H-benzimidazol-5-yl}-pyrimidin-2-ylamine. LCMS (ESMS): m/z 459.20 ($M^+$+1)

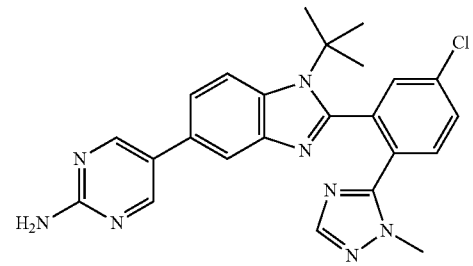 [SMILES: Cn1ncnc1-c1ccc(Cl)cc1-c1nc2cc(-c3cnc(N)nc3)ccc2n1C(C)(C)C]

5-{1-tert-Butyl-2-[4-methyl-2-(2-methyl-2H-1,2,4-triazol-3-yl)-phenyl]-1H-benzimidazol-5-yl}-pyrimidin-2-ylamine. LCMS (ESMS): m/z 439.86 ($M^+$+1)

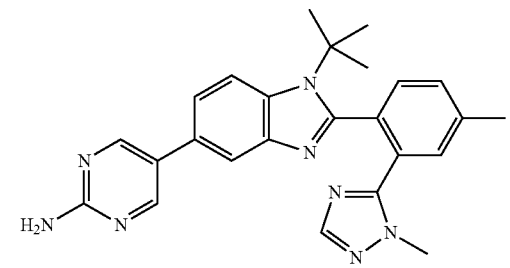 [SMILES: Cc1ccc(-c2nc3cc(-c4cnc(N)nc4)ccc3n2C(C)(C)C)c(-c2ncnn2C)c1]

5-{1-tert-Butyl-2-[5-methyl-2-(2-methyl-2H-1,2,4-triazol-3-yl)-phenyl]-1H-benzimidazol-5-yl}-pyrimidin-2-ylamine. LCMS (ESMS): m/z 439.86 (M$^+$+1)

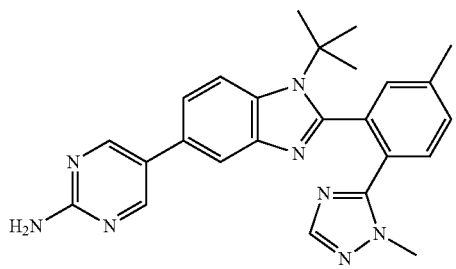 [SMILES: Cc1ccc(-c2ncnn2C)c(-c2nc3cc(-c4cnc(N)nc4)ccc3n2C(C)(C)C)c1]

Example 63

5-[1-(1,1-Dimethyl-propyl)-2-(2-1,2,4-triazol-1-yl-phenyl)-1H-benzimidazol-5-yl]-pyrimidin-2-ylamine

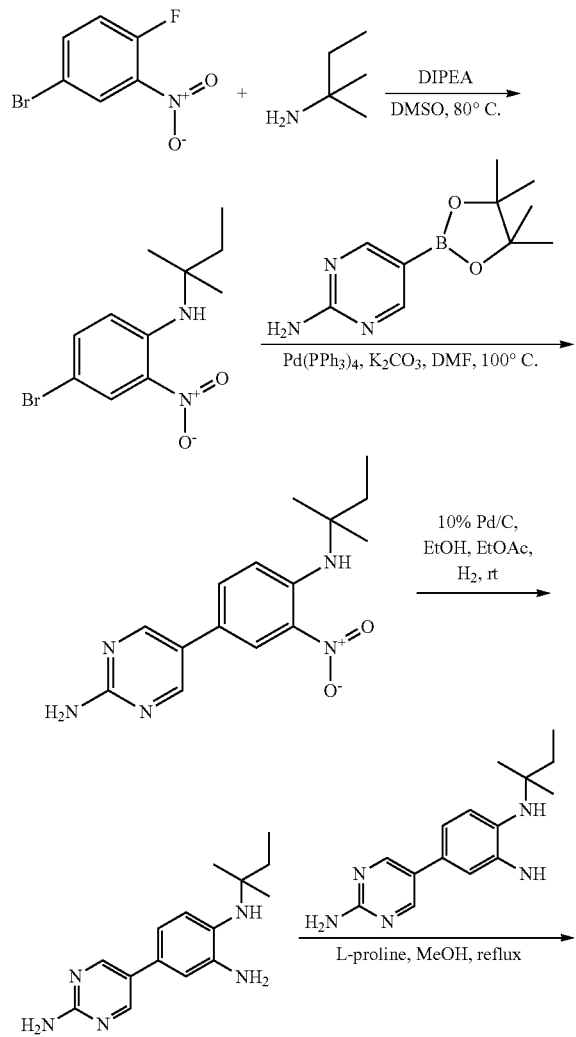

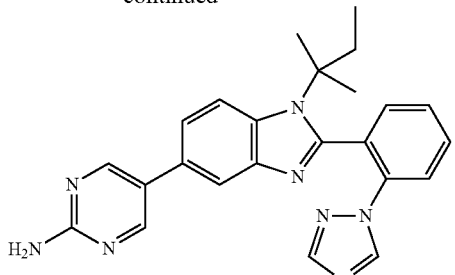

To a solution of 4-bromo-1-fluoro-2-nitrobenzene (200 μL, 1.62 mmol) and tert-amyamine (170 mg, 1.95 mmol) in THF (5.0 mL) is added diisopropylethyl amine (500 μL, 2.87 mmol). The reaction mixture is allowed to cool to room temperature and is concentrated under reduced pressure to afford crude (4-bromo-2-nitro-phenyl)-(1,1-dimethyl-propyl)-amine (600 mg).

A reaction mixture of crude (4-bromo-2-nitro-phenyl)-(1,1-dimethyl-propyl)-amine (600 mg, 2.09 mmol), 2-aminopyrimidine-5-boronic acid pinacol ester (330 mg, 1.49 mmol), Pd(PPh$_3$)$_4$ (160 mg), K$_2$CO$_3$ (600 mg, 4.34 mmol) in DMF (7.0 mL) and H$_2$O (2.0 mL) is heated under microwave conditions at 100° C. for 1 hour. The reaction mixture is allowed to cool to room temperature, diluted with EtOAc (100 mL), washed with H$_2$O (75 mL×2), dried with Na$_2$SO$_4$ and filtered. The filtrate is concentrated under reduced pressure and the residue is purified by silica gel flash column chromatography with 50% EtOAc in heptane as the eluent to afford 5-[4-(1,1-dimethyl-propylamino)-3-nitro-phenyl]-pyrimidin-2-ylamine (370 mg, 82%).

A reaction mixture of 5-[4-(1,1-dimethyl-propylamino)-3-nitro-phenyl]-pyrimidin-2-ylamine (370 mg, 1.23 mmol), 10% Pd/C (60 mg) in EtOH (5.0 mL) and EtOAc (5.0 mL) is stirred under H$_2$ (1 atm) at room temperature for 16 hours. The reaction is filtered through diatomaceous earth and is concentrated under reduced pressure to 4-(2-amino-pyrimidin-5-yl)-N1-(1,1-dimethyl-propyl)-benzene-1,2-diamine (260 mg, 78%).

A reaction mixture of 4-(2-amino-pyrimidin-5-yl)-N$^1$-(1,1-dimethyl-propyl)-benzene-1,2-diamine (130 mg, 0.48 mmol), 2-1,2,4-triazol-1-yl-benzaldehyde (110 mg, 0.64 mmol) and L-proline (5 mg) in MeOH (25 mL) is refluxed for 16 hours. The reaction mixture is allowed to cool to room temperature and is concentrated under reduced pressure. The residue is purified by silica gel flash column chromatography with 8% MeOH in CH$_2$Cl$_2$ as the eluent to afford 5-[1-(1,1-dimethyl-propyl)-2-(2-1,2,4-triazol-1-yl-phenyl)-1H-benzimidazol-5-yl]-pyrimidin-2-ylamine. LCMS (ESMS): m/z 425.20 (M$^+$+1)

The following compounds are made using the procedure described in this Example:

5-[2-[5-Chloro-2-(3-methyl-1,2,4-triazol-1-yl)-phenyl]-1-(1,1-dimethyl-propyl)-1H-benzimidazol-5-yl]-pyrimidin-2-ylamine. LCMS (ESMS): m/z 473.20 (M$^+$+1)

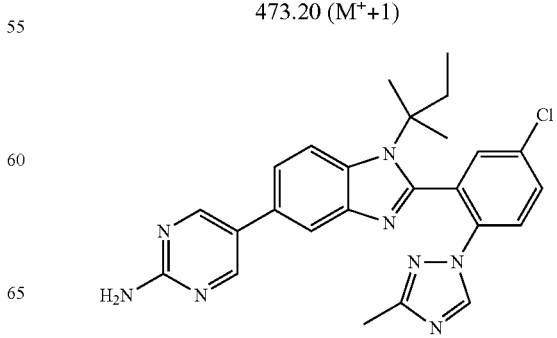

5-[1-(1,2-Dimethyl-propyl)-2-(2-1,2,4-triazol-1-yl-phenyl)-1H-benzimidazol-5-yl]-pyrimidin-2-ylamine. LCMS (ESMS): m/z 425.20 (M$^+$+1)

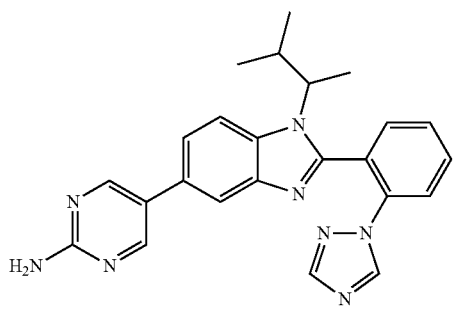 [SMILES: CC(C)C(C)n1c(-c2ccccc2-n2cncn2)nc2cc(-c3cnc(N)nc3)ccc21]

Example 64

3-[5-(2-Amino-pyrimidin-5-yl)-1-tert-butyl-1H-benzimidazol-2-yl]-4-(3-methyl-1,2,4-triazol-1-yl)-benzonitrile

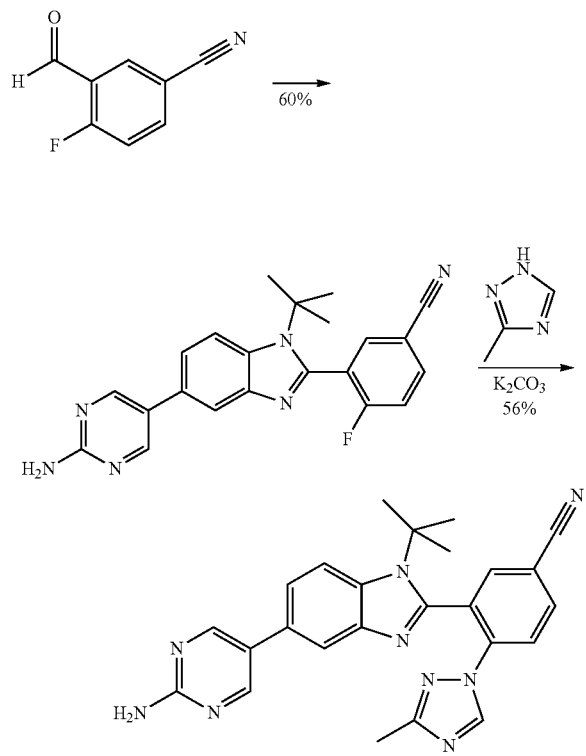

To a solution of 4-(2-amino-pyrimidin-5-yl)-N$^1$-tert-butyl-benzene-1,2-diamine (2 g, 0.008 mol) in DMF (20 mL) is added 5-cyano-2-fluorobenzaldehyde (1.4 g, 0.009 mol) at room temperature. Oxone (4.9 g, 0.008 mol) in H$_2$O (5 mL) is added and the solution is stirred at the same temperature for 3 hours. Saturated sodium thiosulfate solution (15 mL) is added and the mixture is extracted with EtOAc (3×15 mL) and H$_2$O (20 mL). The combined organic layer is dried with MgSO$_4$ (1 g) and is filtered. The filtrate is concentrated and the residue is re-dissolved in AcCN (10 mL). The solid that precipitates out from the solution is collected by filtration. The resulting white solid is dried under vacuum and is used in the next step of the synthesis without further purification.

To a solution of 3-[5-(2-amino-pyrimidin-5-yl)-1-tert-butyl-1H-benzimidazol-2-yl]-4-fluoro-benzonitrile (200 mg, 0.52 mmol) in DMSO (6 mL) are added 2-methyl-1H-1,2,4-triazole (65 mg, 0.78 mmol) and K$_2$CO$_3$ (143 mg, 1.04 mmol) at room temperature. The solution is heated at 100° C. for 12 hours. The solution is cooled down and extracted with EtOAc (2×15 mL) and H$_2$O (20 mL). The combined organic layer is dried with MgSO$_4$ (500 mg) and filtered. The filtrate is concentrated and the residue is purified by silica gel flash column chromatography with 5% MeOH in CH$_2$Cl$_2$ as the eluent to afford the title compound (130 mg, 56%) as a white solid. LCMS (ESMS): m/z: 450.20 (M$^+$+1)

Example 65

5-{1-tert-Butyl-2-[5-(2H-tetrazol-5-yl)-2-[1,2,4]triazol-1-yl-phenyl]-1H-benzoimidazol-5-yl}-pyrimidin-2-ylamine

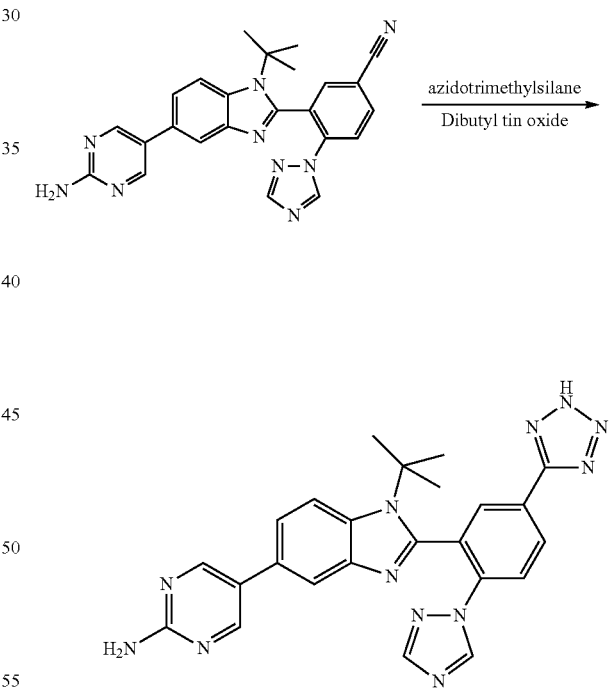

To a solution of 3-[5-(2-Amino-pyrimidin-5-yl)-1-tert-butyl-1H-benzimidazol-2-yl]-4-1,2,4-triazol-1-yl-benzonitrile (example 7) (100 mg, 0.23 mmol) in DMF (5 mL) are added azidotrimethylsilane (0.06 mL, 0.46 mmol) and dibutyltin oxide (175 mg, 0.69 mmol) at room temperature. The solution is heated up to 100° C. for 5 hours in a microwave reactor. The solution is cooled down and is extracted with Sat. NH$_4$Cl (10 mL) and EtOAc (3×10 mL). The combined organic layer is dried with MgSO$_4$ (500 mg) and is filtered. The filtrate is concentrated and the residue is purified by preparative HPLC to afford the title compound (10 mg, 9%) LCMS (ESMS): m/z: 479.40 (M⁺+1).

Example 66

3-{4-[5-(2-Amino-pyrimidin-5-yl)-1-tert-butyl-1H-benzoimidazol-2-yl]-3-[1,2,4]triazol-1-yl-phenoxy}-2,2-dimethyl-propionic acid ethyl ester

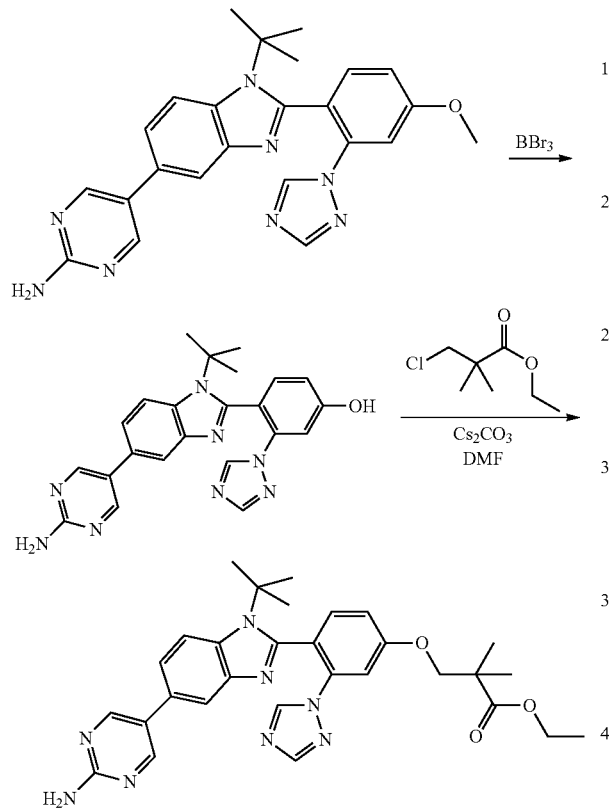

To a solution of the 5-[1-tert-Butyl-2-(4-methoxy-2-1,2,4-triazol-1-yl-phenyl)-1H-benzimidazol-5-yl]-pyrimidin-2-ylamine (example 3) (330 mg, 0.75 mmol) in CH₂Cl₂ (20 mL) is added BBr₃ (1 M hexane solution) (3.7 mL, 3.7 mmol) at room temperature under nitrogen atmosphere. The solution is stirred at room temperature for 48 hours. After this time the reaction is cooled in an ice bath and quenched with saturated. NaHCO₃ solution (10 mL). The solid is collected by filtration and is washed with water. The solid is purified by silica gel flash chromatography with 10% MeOH in CH₂Cl₂ as the eluent to afford 4-[5-(2-Amino-pyrimidin-5-yl)-1-tert-butyl-1H-benzoimidazol-2-yl]-3-[1,2,4]triazol-1-yl-phenol (150 mg, 47%).

To a stirred solution of 4-[5-(2-Amino-pyrimidin-5-yl)-1-tert-butyl-1H-benzoimidazol-2-yl]-3-[1,2,4]-triazol-1-yl-phenol (300 mg, 0.7 mmol) in DMF (10 mL) is added cesium carbonate (687 mg, 2.1 mmol) followed by Ethyl 3-chloro-2,2-dimethylpropanoate (231 mg, 1.4 mmol) at room temperature. The solution is heated to 90° C. for 72 hours. The solution is cooled to room temperature and is extracted with H₂O (10 mL) and EtOAc (3×10 mL). The combined organic layer is dried with Mg₂SO₄ (500 mg) and is filtered. The filtrate is concentrated and the residue is purified by silica gel flash column chromatography with 10% MeOH in CH₂Cl₂ as the eluent to afford the title compound (200 mg, 51%). LCMS (ESMS): m/z: 555.40 (M⁺+1).

The following compounds are made using the procedure described in this Example:

2-{4-[5-(2-Amino-pyrimidin-5-yl)-1-tert-butyl-1H-benzoimidazol-2-yl]-3-[1,2,4]triazol-1-yl-phenoxy}-2-methyl-propionic acid methyl ester. LCMS (ESMS): m/z 527.40 (M⁺+1)

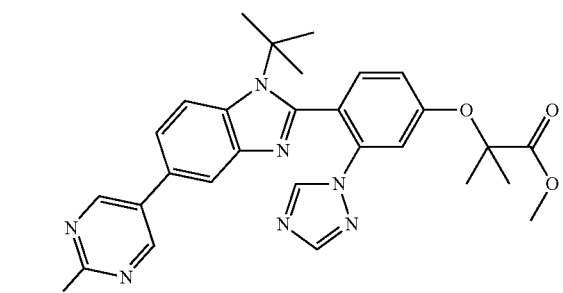

Example 67

3-{4-[5-(2-Amino-pyrimidin-5-yl)-1-tert-butyl-1H-benzoimidazol-2-yl]-3-[1,2,4]triazol-1-yl-phenoxy}-2,2-dimethyl-propionic acid

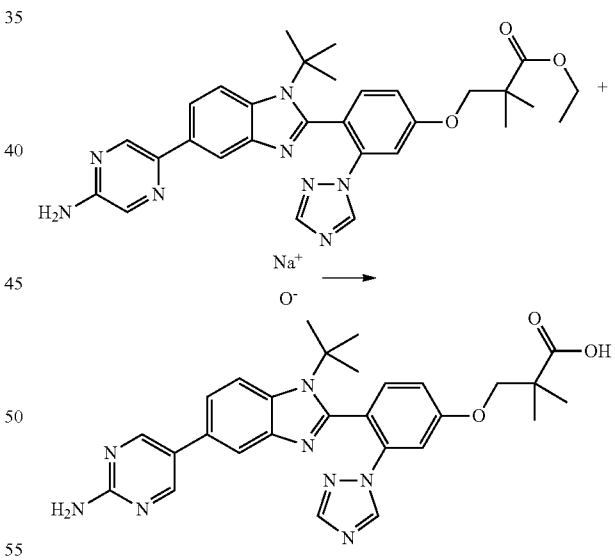

To a solution of 3-{4-[5-(2-Amino-pyrimidin-5-yl)-1-tert-butyl-1H-benzoimidazol-2-yl]-3-[1,2,4]triazol-1-yl-phenoxy}-2,2-dimethyl-propionic acid ethyl ester (example 66) (95 mg, 0.17 mmol) in 1,4-dioxane (10 mL) and H₂O (2 mL) is added 3 M NaOH solution (0.17 mL, 0.52 mmol) at room temperature. The solution is stirred at 65° C. for 6 days. The solution is concentrated and the residue is re-dissolved in H₂O (5 mL). The pH of the solution is adjusted to 5 with 12N HCl solution. The milky solution is extracted with EtOAc (3×10 mL). The combined organic layer is dried with MgSO₄ (500 mg) and is filtered. The filtrate is concentrated and the residue is purified by silica gel flash column chromatography with 10% MeOH in $CH_2Cl_2$ as the eluent to afford the title compound (63 mg, 70%). LCMS (ESMS): m/z: 527.40 ($M^+$+1).

The following compounds are made using the procedure described in this Example:

4-{3-[5-(2-Amino-pyrimidin-5-yl)-1-tert-butyl-1H-benzoimidazol-2-yl]-4-[1,2,4]triazol-1-yl-phenyl}-thiophene-2-carboxylic acid. LCMS (ESMS): m/z 537.40 ($M^+$+1)

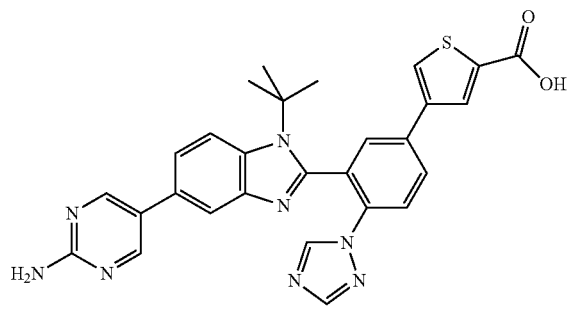 [SMILES: CC(C)(C)n1c(-c2cc(-c3csc(C(=O)O)c3)ccc2-n2cncn2)nc2cc(-c3cnc(N)nc3)ccc21]

2-{4-[5-(2-Amino-pyrimidin-5-yl)-1-tert-butyl-1H-benzoimidazol-2-yl]-3-[1,2,4]triazol-1-yl-phenoxy}-2-methyl-propionic acid. LCMS (ESMS): m/z 513.40 ($M^+$+1)

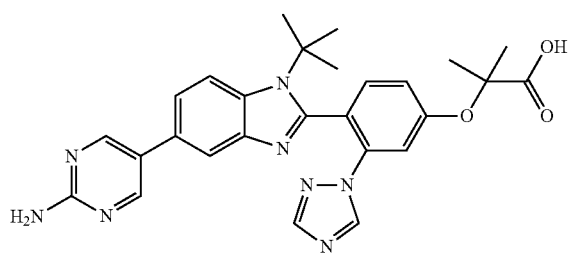 [SMILES: CC(C)(Oc1ccc(-c2nc3cc(-c4cnc(N)nc4)ccc3n2C(C)(C)C)c(-n2cncn2)c1)C(=O)O]

(E)-3-{3-[5-(2-Amino-pyrimidin-5-yl)-1-tert-butyl-1H-benzoimidazol-2-yl]-4-[1,2,4]triazol-1-yl-phenyl}-oct-2-enoic acid. LCMS (ESMS): m/z 551.40 ($M^+$+1)

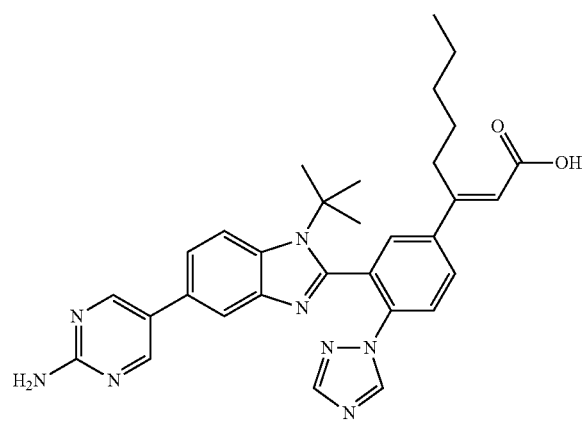 [SMILES: CCCCC/C(=C\C(=O)O)c1ccc(-n2cncn2)c(-c2nc3cc(-c4cnc(N)nc4)ccc3n2C(C)(C)C)c1]

Example 68

5-{1-tert-Butyl-2-[5-(1,5-dimethyl-1H-pyrazol-4-yl)-2-[1,2,4]triazol-1-yl-phenyl]-1H-benzoimidazol-5-yl}-pyrimidin-2-ylamine

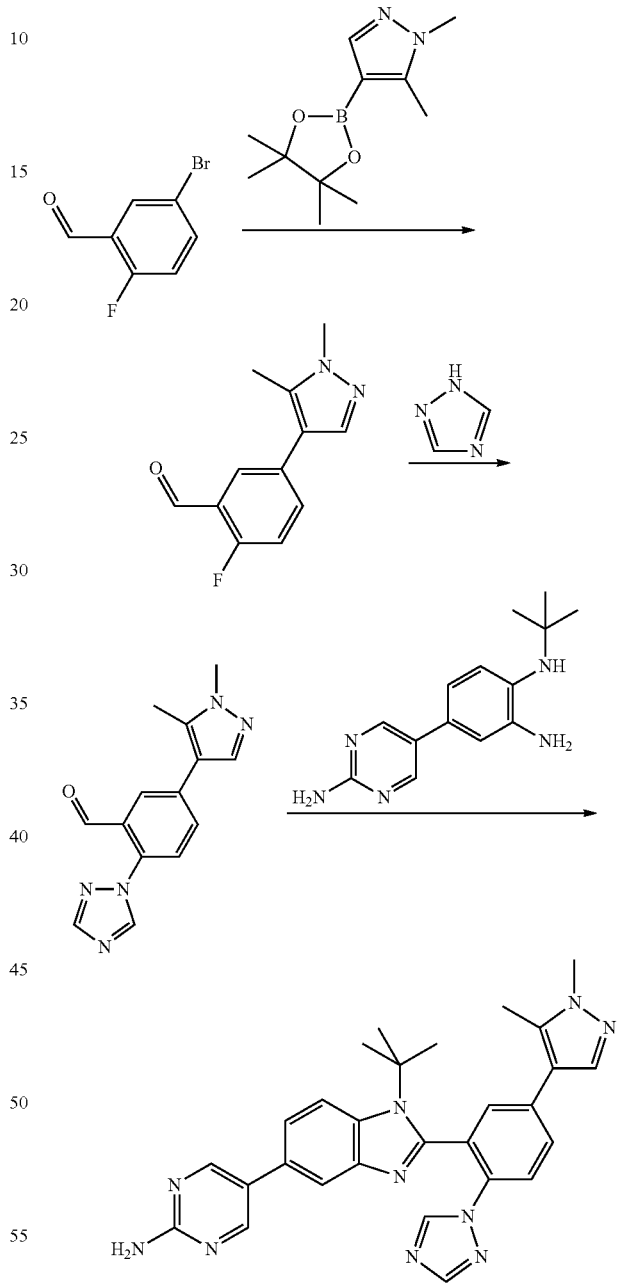

To a solution of 5-bromo-2-fluorobenzaldehyde (200 mg, 0.99 mmol) in DMF (5 mL) and $H_2O$ (1 mL) are added 1,5-dimethyl-1H-pyrazole-4-boronic acid pinacol ester (328 mg, 1.5 mmol), $Pd(PPh_3)_4$ (113 mg, 0.099 mmol) and $K_2CO_3$ (204 mg, 1.5 mmol) at room temperature. The solution is heated to 100° C. for 1 hour in a microwave reactor. The solution is cooled down and 3-mercaptopropyl-functionalized silica gel (500 mg) is added. The solution is stirred for 15 minutes and is filtered. The filtrate is washed with $H_2O$ (10 mL) and is extracted with EtOAc (3×10 mL). The combined organic layer is dried with MgSO₄ (500 mg) and is filtered. The filtrate is concentrated and the residue is purified by silica gel flash chromatography with 20% EtOAc in Hepthane as the eluent to afford 5-(1,5-dimethyl-1H-pyrazol-4-yl)-2-fluoro-benzaldehyde (160 mg, 74%).

To a solution of 5-(1,5-dimethyl-1H-pyrazol-4-yl)-2-fluoro-benzaldehyde (151 mg, 0.69 mmol) in DMSO (10 mL) are added 1,2,4-triazole (72 mg, 1.0 mmol) and K₂CO₃ (191 mg, 1.4 mmol) at room temperature. The solution is heated to 100° C. for 30 minutes in a microwave reactor. The solution is cooled down and is extracted with H₂O (10 mL) and EtOAc (3×10 mL). The combined organic layer is dried with MgSO₄ (500 mg) and is filtered. The filtrate is concentrated and the residue (112 mg. 61%) is used in the next step of the synthesis without further purification.

To a solution of 4-(2-amino-pyrimidin-5-yl)-N1-tert-butyl-benzene-1,2-diamine (100 mg, 0.39 mmol) in DMF (10 mL) is added crude 5-(1,5-dimethyl-1H-pyrazol-4-yl)-2-[1,2,4]triazole-1-yl-benzaldehyde (112 mg, 0.42 mmol) at room temperature. Oxone (239 mg, 0.39 mmol) in H₂O (1 mL) is added and the solution is stirred at the same temperature for 3 hours. Sat. sodium thiosulfate (10 mL) is added and the mixture is extracted with EtOAc (3×10 mL) and H₂O (10 mL). The combined organic layer is dried with MgSO₄ (1 g) and is filtered. The filtrate is concentrated and the residue is purified by silica gel flash column chromatography with 10% MeOH in CH₂Cl₂ as the eluent to afford the title compound (81 mg, 41%). LCMS (ESMS): m/z: 505.40 (M⁺+1).

The following compounds are made using the procedure described in this Example:

4-{3-[5-(2-Amino-pyrimidin-5-yl)-1-tert-butyl-1H-benzoimidazol-2-yl]-4-[1,2,4]triazol-1-yl-phenyl}-thiophene-2-carboxylic acid methyl ester. LCMS (ESMS): m/z 551.40 (M⁺+1)

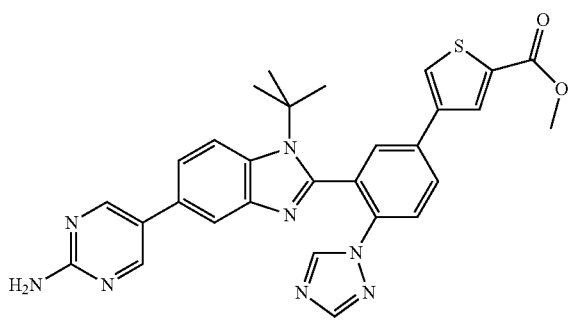 [SMILES: COC(=O)c1cc(-c2ccc(-n3cncn3)c(-c3nc4cc(-c5cnc(N)nc5)ccc4n3C(C)(C)C)c2)cs1]

(E)-3-{3-[5-(2-Amino-pyrimidin-5-yl)-1-tert-butyl-1H-benzoimidazol-2-yl]-4-[1,2,4]triazol-1-yl-phenyl}-oct-2-enoic acid methyl ester. LCMS (ESMS): m/z 565.40 (M⁺+1)

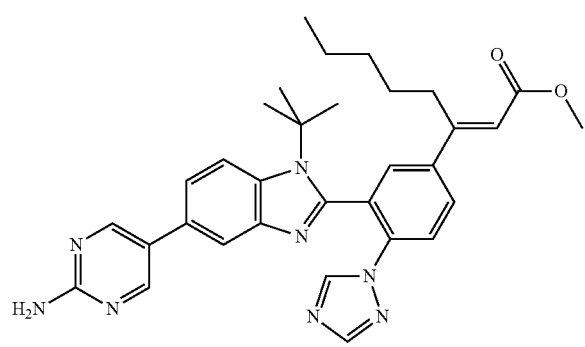 [SMILES: CCCCC/C(=C\C(=O)OC)c1ccc(-n2cncn2)c(-c2nc3cc(-c4cnc(N)nc4)ccc3n2C(C)(C)C)c1]

5-{1-tert-Butyl-2-[5-(1-methyl-1H-pyrazol-4-yl)-2-[1,2,4]triazol-1-yl-phenyl]-1H-benzoimidazol-5-yl}-pyrimidin-2-ylamine. LCMS (ESMS): m/z 491.52 (M⁺+1)

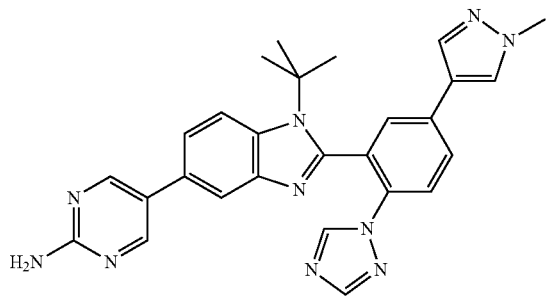 [SMILES: Cn1cc(-c2ccc(-n3cncn3)c(-c3nc4cc(-c5cnc(N)nc5)ccc4n3C(C)(C)C)c2)cn1]

Example 69

3-[5-(2-Amino-pyrimidin-5-yl)-1-tert-butyl-1H-benzoimidazol-2-yl]-N-methyl-4-[1,2,4]triazol-1-yl-benzamide

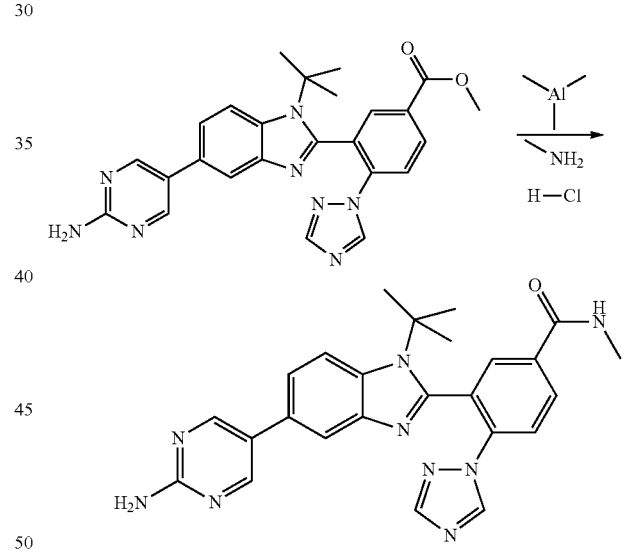

To a solution of dimethylamine hydrochloride (20 mg, 0.3 mmol) in dry toluene (8 mL) is added AlMe₃ (0.22 mL, 0.45 mmol) at room temperature. The solution is stirred at the same temperature for 15 minutes. 3-[5-(2-Amino-pyrimidin-5-yl)-1-tert-butyl-1H-benzoimidazol-2-yl]-4-[1,2,4]triazol-1-yl-benzoic acid methyl ester (example 7) (70 mg, 0.15 mmol) is added to the solution and it is heated to 90° C. for 12 hours. The mixture is cooled down to room temperature and water (10 mL) is added. The mixture is extracted with EtOAc (3×10 mL) and the combined organic layer is dried by Mg₂SO₄ (300 mg) and is filtered. The filtrate is concentrated and the residue is purified by silica gel flash column chromatography with 10% MeOH in CH₂Cl₂ as the eluent to afford the title compound (17 mg, 25%). LCMS (ESMS): m/z 468.20 (M⁺+1)

The following compounds are made using the procedure described in this Example:

3-[5-(2-Amino-pyrimidin-5-yl)-1-tert-butyl-1H-benzoimidazol-2-yl]-N,N-dimethyl-4-[1,2,4]triazol-1-yl-benzamide. LCMS (ESMS): m/z 482.20 (M⁺+1)

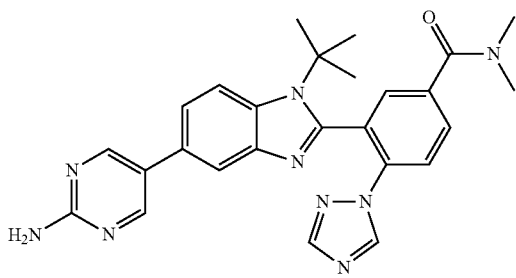 [SMILES: CN(C)C(=O)c1ccc(-n2cncn2)c(-c2nc3cc(-c4cnc(N)nc4)ccc3n2C(C)(C)C)c1]

1-{2-[5-(2-Amino-pyrimidin-5-yl)-1-tert-butyl-1H-benzoimidazol-2-yl]-4-cyano-phenyl}-1H-[1,2,4]triazole-3-carboxylic acid dimethylamide. LCMS (ESMS): m/z 507.40 (M⁺+1)

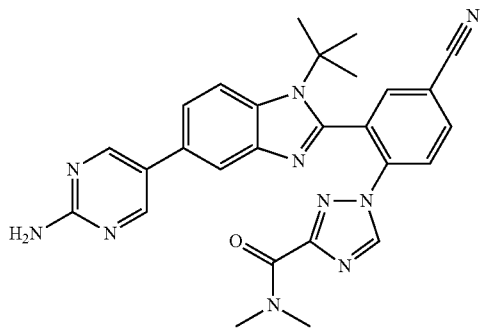 [SMILES: CN(C)C(=O)c1ncn(-c2ccc(C#N)cc2-c2nc3cc(-c4cnc(N)nc4)ccc3n2C(C)(C)C)n1]

1-{2-[5-(2-Amino-pyrimidin-5-yl)-1-tert-butyl-1H-benzoimidazol-2-yl]-4-cyano-phenyl}-1H-[1,2,4]triazole-3-carboxylic acid ethylamide. LCMS (ESMS): m/z 507.40 (M⁺+1)

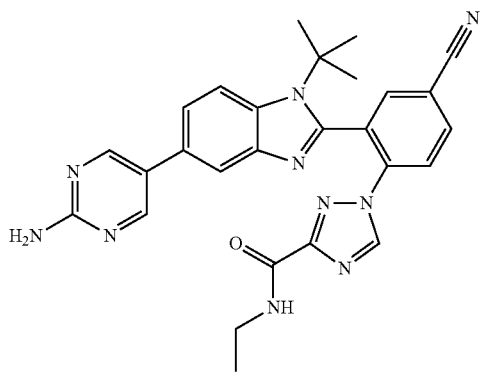 [SMILES: CCNC(=O)c1ncn(-c2ccc(C#N)cc2-c2nc3cc(-c4cnc(N)nc4)ccc3n2C(C)(C)C)n1]

Example 70

1-[2-[5-(2-Amino-pyrimidin-5-yl)-1-tert-butyl-1H-benzoimidazol-2-yl]-4-cyano-phenyl]-1H-[1,2,4]triazole-3-carboxylic acid isobutyl ester

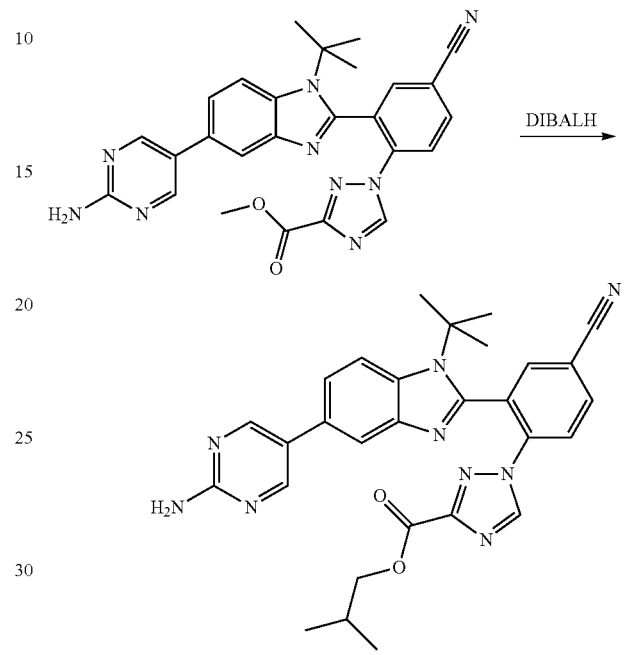

To a solution of 1-{2-[5-(2-Amino-pyrimidin-5-yl)-1-tert-butyl-1H-benzoimidazol-2-yl]-4-cyano-phenyl}-1H-[1,2,4]triazole-3-carboxylic acid methyl ester (example 64) (100 mg, 0.2 mmol) in dry THF (10 mL) is added Diisobutyl aluminium hydride (DIBALH) (1 M THF solution) (0.4 mL, 0.4 mmol) at 0° C. under nitrogen atmosphere. The solution is warmed to room temperature for 24 hours. Sat. NH₄Cl solution (10 mL) is added and the mixture is extracted with EtOAc (3×10 mL). The combined organic layer is dried with Mg₂SO₄ (500 mg) and is filtered. The filtrate is concentrated and the residue is purified by silica gel flash column chromatography with 10% MeOH in CH₂Cl₂ as the eluent to afford the title compound (29 mg, 26%). LCMS (ESMS): m/z 536.40 (M⁺+1)

Example 71

{3-[5-(2-Amino-pyrimidin-5-yl)-1-tert-butyl-1H-benzoimidazol-2-yl]-4-[1,2,4]triazol-1-yl-phenyl}-methanol

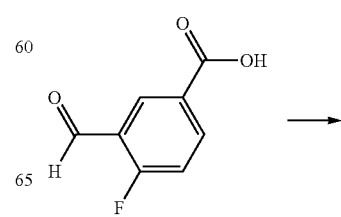

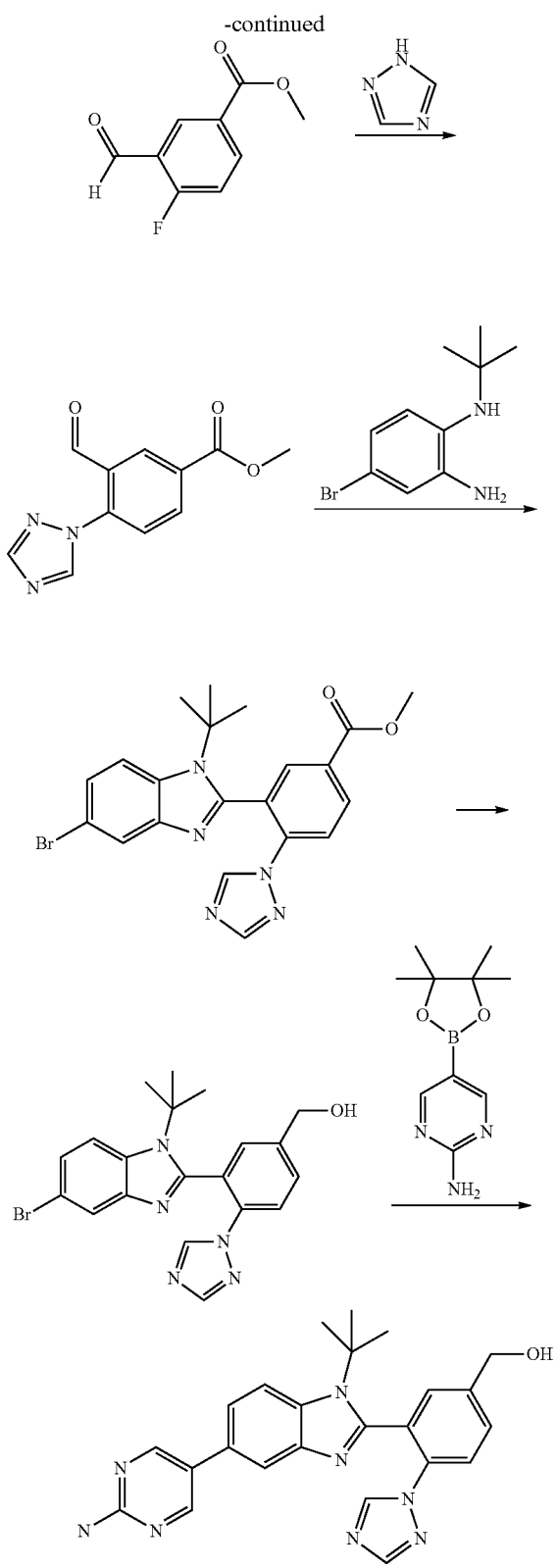

To a solution of 4-fluoro-3-formyl-benzoic acid (800 mg, 4.8 mmol) in DMF (10 mL), are added MeI (0.35 mL, 5.7 mmol) and K$_2$CO$_3$ (790 mg, 5.7 mmol). The reaction mixture is stirred at room temperature for 18 hours. The reaction mixture is diluted with EtOAc (20 mL) and water (10 mL). The organic layer is separated, washed with brine, dried under anhy. Na$_2$SO$_4$ (500 mg), filtered and is concentrated. The residue is purified by silica gel flash chromatography with 0-20% EtOAc/heptane as the eluent. The product fractions are collected and concentrated to afford 4-fluoro-3-formyl-benzoic acid methyl ester (710 mg, 82%).

To a solution of 4-fluoro-3-formyl-benzoic acid methyl ester (710 mg, 3.9 mmol) in ACN (6 mL) and DMSO (3 mL) are added 1,2,4-triazole (323 mg, 4.7 mmol) and potassium carbonate (646 mg, 4.7 mmol). The reaction mixture is stirred at 90° C. for 1 hour. The reaction mixture is diluted with EtOAc (20 mL), washed with water (10 mL), brine (10 mL), dried under anhyhydrous Na$_2$SO$_4$ (500 mg), and is filtered and concentrated to afford 3-formyl-4-[1,2,4]trizol-1-yl-benzoic acid methyl ester (828 mg, 92%).

To a solution of 4-bromo-N-1-tert-butyl-benzene-1,2-diamine (720 mg, 2.9 mmol) in DMF (10 mL), are added 3-formyl-4-[1,2,4]trizol-1-yl-benzoic acid methyl ester (828 mg, 3.6 mmol), oxone (2.2 g, 3.5 mmol) in water (3 mL). The reaction mixture is stirred at room temperature for 1 hour. The reaction mixture is quenched with aqueous sodium thiosulfate (10 mL) and EtOAc (20 mL). The organic layer is separated, washed with brine (10 mL), dried under anhydrous Na$_2$SO$_4$ (500 mg) and is filtered and concentrated. The residue is purified by silica gel flash chromatography with 0-3% MeOH/CH$_2$Cl$_2$ as the eluent. The product fractions are collected and concentrated to afford 3-(5-bromo-1-tert-butyl-1H-benzoimidazol-2-yl)-4-[1,2,4]triazol-1-yl-benzoic acid methyl ester (840 mg, 62%).

To a solution of 3-(5-bromo-1-tert-butyl-1H-benzoimidazol-2-yl)-4-[1,2,4]triazol-1-yl-benzoic acid methyl ester (100 mg, 0.22 mmol) in dry THF (2 mL) is added Lithium aluminium hydride (LiAlH) (17 mg, 0.45 mmol). The reaction mixture is stirred at room temperature for 1 hour. The reaction mixture is quenched with saturated NaHCO$_3$ (10 mL), extracted with EtOAc (3×10 mL). The organic layer is separated, washed with brine (10 mL), dried under anhydrous Na$_2$SO$_4$ (500 mg), and is filtered and concentrated. The residue is purified by silica gel flash chromatography with 0-5% MeOH/CH$_2$Cl$_2$ as the eluent. The product fractions are collected and concentrated to afford [3-(5-bromo-1-tert-butyl-1H-benzoimidazol-2-yl)-4-[1,2,4]triazol-1-yl-phenyl]-methanol (47 mg, 50%).

To a sealed vial is added [3-(5-bromo-1-tert-butyl-1H-benzoimidazol-2-yl)-4-[1,2,4]triazol-1-yl-phenyl]methanol (47 mg, 0.11 mmol) in DMF (2 mL), followed by the addition of 2-aminopyrimidine-5-boronic acid pinacol ester (29 mg, 0.13 mmol) and tetrakis(triphenylphosphine)palladium(0) (13 mg, 0.011 mmol) and 2M aqueous Na$_2$CO$_3$ (0.25 mL, 0.5 mmol). The reaction mixture is heated under argon at 110° C. for 2 hours. The residue is diluted with EtOAc (10 mL), washed with brine (10 mL), and dried under anhydrous Na$_2$SO$_4$ (500 mg). The mixture is filtered and is concentrated. The residue is purified by silica gel flash chromatography with 0-10% 2M NH$_3$ in MeOH/CH$_2$Cl$_2$ as the eluent. The product fractions are collected and concentrated to afford the title compound (30 mg, 62%). LCMS (ESMS): m/z 441.32 (M$^+$+1)

Example 72

2-{3-[5-(2-Amino-pyrimidin-5-yl)-1-tert-butyl-1H-benzoimidazol-2-yl]-4-[1,2,4]triazol-1-yl-phenyl}-propan-2-ol

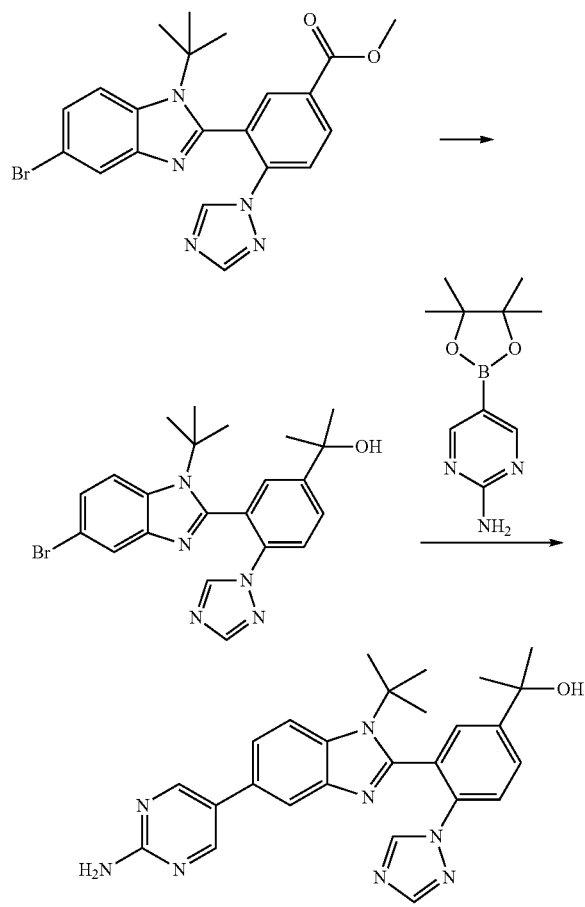

To a solution of 3-(5-bromo-1-tert-butyl-1H-benzoimidazol-2-yl)-4-[1,2,4]triazol-1-yl-benzoic acid methyl ester (100 mg, 0.22 mmol) in THF (2 mL) at 0° C., is added methylmagnesium bromide (3M Et$_2$O solution) (0.3 mL, 0.9 mmol). The reaction mixture is stirred at room temperature for 1 hour. The reaction mixture is quenched with saturated NH$_4$Cl (10 mL) and is diluted with EtOAc (20 mL). The organic layer is separated, washed with brine (10 mL), and is dried under anhydrous Na$_2$SO$_4$ (500 mg). The mixture is filtered and concentrated. The residue is purified by silica gel flash chromatography with 0-4% MeOH/CH$_2$Cl$_2$ as the eluent. The product fractions are collected and concentrated to afford 2-[3-(5-bromo-1-tert-butyl-1H-benzoimidazol-2-yl)-4-[1,2,4]triazol-1-yl-phenyl]propan-2-ol (60 mg, 60%).

To a sealed vial is added 2-[3-(5-bromo-1-tert-butyl-1H-benzoimidazol-2-yl)-4-[1,2,4]triazol-1-yl-phenyl]propan-2-ol (60 mg, 0.13 mmol) in DMF (2 mL), followed by the addition of 2-aminopyrimidine-5-boronic acid pinacol ester (35 mg, 0.16 mmol), tetrakis(triphenylphosphine)palladium (0) (15 mg, 0.013 mmol) and 2M aqueous Na$_2$CO$_3$ (0.3 mL, 0.6 mmol). The reaction mixture is heated under Ar at 110° C. for 2 hours. The residue is diluted with EtOAc (20 mL), washed with brine (10 mL), dried under anhydrous Na$_2$SO$_4$ (500 mg). The mixture is filtered and concentrated. The residue is purified by silica gel flash chromatography with 0-7% 2M NH$_3$ in MeOH/CH$_2$Cl$_2$ as the eluent. The product fractions are collected and concentrated to afford the title compound (42 mg, 68%). LCMS (ESMS): m/z 469.50 (M$^+$+1)

Example 73

5-[1-tert-Butyl-2-(5-methoxymethyl-2-[1,2,4]triazol-1-yl-phenyl)-1H-benzoimidazol-5-yl]-pyrimidin-2-ylamine

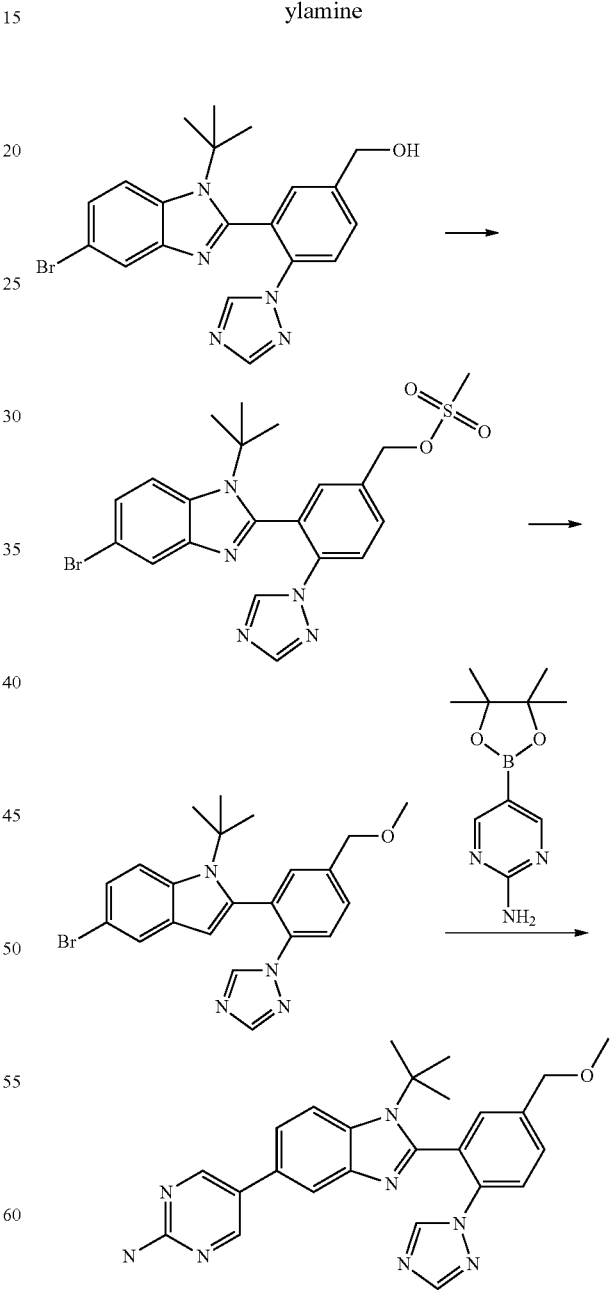

To a round bottom flask is added [3-(5-bromo-1-tert-butyl-1H-benzoimidazol-2-yl)-4-[1,2,4]triazol-1-yl-phenyl]methanol (583 mg, 1.4 mmol) in CH$_2$Cl$_2$ (5 mL), followed by the addition of methansulfonyl chloride (0.15 mL, 1.9 mmol) and triethylamine (0.4 mL, 2.9 mmol). The reaction mixture is stirred at room temperature for 1 hour. The reaction mixture is quenched with saturated NaHCO₃ (10 mL), extracted with EtOAc (3×10 mL). The organic layer is separated, washed with brine, dried under anhydrous Na₂SO₄ (500 mg), filtered and concentrated to afford methanesulfonic acid 3-(5-bromo-1-tert-butyl-1H-benzoimidazol-2-yl)-4-[1,2,4]-triazol-1-yl-benzyl ester (690 mg, 100%).

To a round bottom flask is added 3-(5-bromo-1-tert-butyl-1H-benzoimidazol-2-yl)-4-[1,2,4]triazol-1-yl-benzyl ester (85 mg, 0.17 mmol), followed by the addition of 0.5 M MeOH solution of NaOMe (3 mL, 1.5 mmol). The reaction mixture is stirred at 80° C. for 1 hour. The reaction mixture is diluted with EtOAc (20 mL) and water (10 mL). The organic layer is separated, washed with brine (10 mL), dried under anhydrous Na₂SO₄ (500 mg). The mixture is filtered and concentrated. The residue is purified by silica gel flash chromatography with 0-5% MeOH/CH₂Cl₂ as the eluent. The product fractions are collected and concentrated to afford 5-bromo-1-tert-butyl-2-(5-methoxymethyl-2-[1,2,4]triazol-1-yl-phenyl)-1H-benzoimidazole (34 mg, 46%).

To a sealed vial is added 5-bromo-1-tert-butyl-2-(5-methoxymethyl-2-[1,2,4]triazol-1-yl-phenyl)-1H-benzoimidazole (34 mg, 0.08 mmol) in DMF (1.5 mL), followed by the addition of 2-aminopyrimidine-5-boronic acid pinacol ester (20 mg, 0.09 mmol), tetrakis(triphenylphosphine)palladium (0) (9 mg, 0.008 mmol) and 2M aqueous Na₂CO₃ (0.15 mL). The reaction mixture is heated under argon at 110° C. for 2 hours. The residue is diluted with EtOAc (20 mL), washed with brine (10 mL), dried under anhydrous Na₂SO₄ (500 mg). The mixture is filtered and concentrated. The residue is purified by silica gel flash chromatography with 0-4% 2M NH₃ in MeOH/CH₂Cl₂ as the eluent. The product fractions are collected and concentrated to afford the title compound (29 mg, 83%). LCMS (ESMS): m/z 455.44 (M⁺+1)

The following compounds are made using the procedure described in this Example:

5-[1-tert-Butyl-2-(5-dimethylaminomethyl-2-[1,2,4]triazol-1-yl-phenyl)-1H-benzoimidazol-5-yl]-pyrimidin-2-ylamine. LCMS (ESMS): m/z 468.90 (M⁺+1)

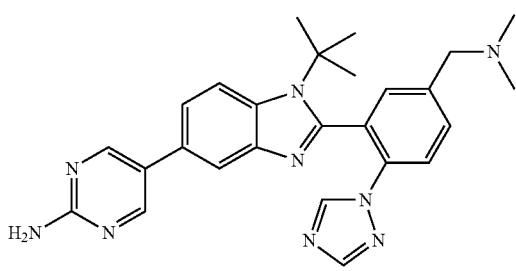

5-[1-tert-Butyl-2-(5-ethoxymethyl-2-[1,2,4]triazol-1-yl-phenyl)-1H-benzoimidazol-5-yl]-pyrimidin-2-ylamine. LCMS (ESMS): m/z 469.55 (M⁺+1)

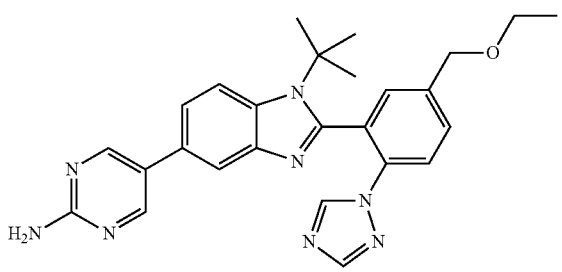 [SMILES: CCOCc1ccc(-n2cncn2)c(-c2nc3cc(-c4cnc(N)nc4)ccc3n2C(C)(C)C)c1]

5-[2-(5-Azetidin-1-ylmethyl-2-[1,2,4]triazol-1-yl-phenyl)-1-tert-butyl-1H-benzoimidazol-5-yl]-pyrimidin-2-ylamine. LCMS (ESMS): m/z 480.55 (M⁺+1)

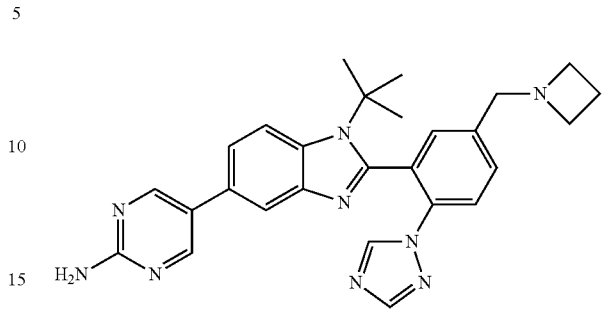

Example 74

5-[1-tert-Butyl-2-(5-methanesulfonyl-2-[1,2,4]triazol-1-yl-phenyl)-1H-benzoimidazol-5-yl]-pyrimidin-2-ylamine

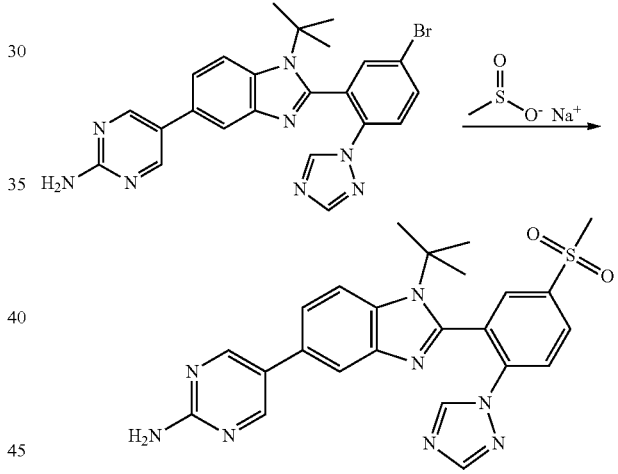

To a microwave vial is added 5-[2-(5-bromo-2-[1,2,4]triazol-1-yl-phenyl)-1-tert-butyl-1H-benzoimidazol-5-yl]-pyrimidin-2-ylamine (example 6) (237 mg, 0.48 mmol) in DMSO (10 mL), followed by the addition of methanesulfinic acid sodium salt (123 mg, 0.96 mmol), copper(II) trifluoromethanesulphonate (175 mg, 0.48 mmol) and N,N'-dimethylethylenediamine (85 mg, 0.96 mmol). The reaction mixture is heated in microwave reactor at 120° C. for 1.5 hours. The reaction mixture is diluted with EtOAc (20 mL) and water (10 mL). The organic layer is separated, washed with brine (10 mL), dried under anhydrous Na₂SO₄ (500 mg). The mixture is filtered and concentrated. The residue is purified by silica gel flash chromatography with 0-8% MeOH/CH₂Cl₂ as the eluent. The product fractions are collected and concentrated to afford the title compound (233 mg, 99%). LCMS (ESMS): m/z 489.52 (M⁺+1)

Example 75

5-[1-tert-butyl-2-(2-isoxazol-5-yl-phenyl)-1H-benzoimidazol-5-yl]-pyrimidin-2-ylamine

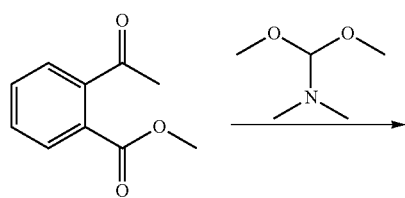

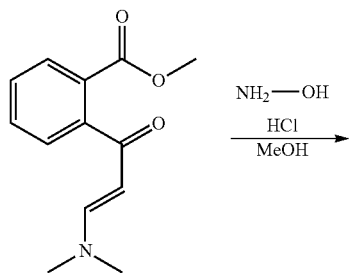

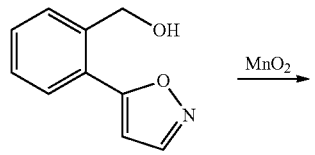

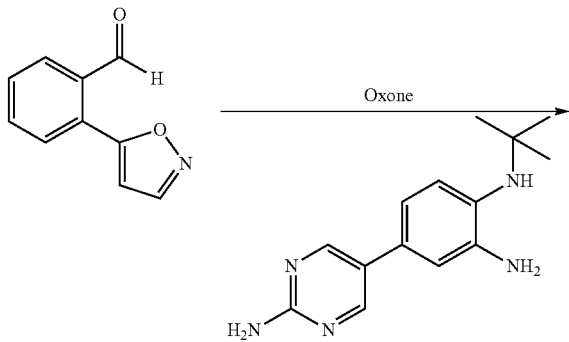

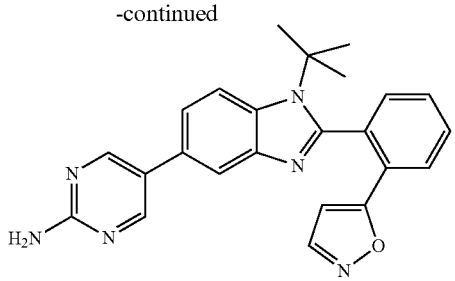

2-Acetyl-benzoic acid methyl eater (419.5 mg, 2.354 mmol) and dimethoxymethyl-dimethyl-amine (0.345 mL, 2.589 mmol) are mixed and heated at 100° C. for 1 hour and addition dimethoxymethyl-dimethyl-amine (0.314 mL, 2.354 mmol) is added to the reaction mixture and the mixture is heated at 100° C. for 65 hours. After this time, the reaction mixture is concentrated in vacuo and the residue is purified using silica gel flash column chromatography with 1-10% MeOH in $CH_2Cl_2$ as the eluent to give 2-((E)-3-dimethylamino-acryloyl)-benzoic acid methyl ester (537 mg, 97.8%).

To a solution of 2-((E)-3-dimethylamino-acryloyl)-benzoic acid methyl ester (1.295 mg, 5.552 mmol) in methanol (21 mL) is added hydroxylamine hydrochloride (964.5 mg, 13.88 mmol). The reaction mixture is heated to reflux for 1.5 hours. After this time, the reaction mixture is loaded onto silica gel and purified using silica gel flash column chromatography with 1-10% MeOH in $CH_2Cl_2$ as the eluent to give 2-isoxazol-5-yl-benzoic acid methyl ester (587 mg, 52%).

To a stirred solution of 2-isoxazol-5-yl-benzoic acid methyl ester (385 mg, 1.895 mmol) in THF (4 mL) is added lithium borohydride (82.5 mg, 3.790 mmol). The reaction mixture is stirred at room temperature for 42 hours. After this time, the reaction mixture is quenched with 1N hydrochloric acid aqueous solution and is extracted with EtOAc (2×10 mL). The organics are combined and washed with brine, dried over $Na_2SO_4$ (500 mg), filtered and concentrated in vacuo. The residue is purified using silica gel flash column chromatography with 1-10% MeOH in $CH_2Cl_2$ as the eluent to give (2-isoxazol-5-yl-phenyl)-methanol (170 mg, 51%).

To a solution of (2-isoxazol-5-yl-phenyl)-methanol (170 mg, 0.97 mmol) in THF (9 mL) is added manganese dioxide (1.29 g, 14.55 mmol). The reaction mixture is stirred at room temperature for 18 hours. After this time, the reaction mixture is filtered through celite and the filtrate is concentrated in vacuo and is redissolved in THF (11 mL) and more manganese dioxide (1.07 g, 10.46 mmol) is added. The reaction mixture is stirred at room temperature for 65 hours. After this time, the reaction mixture is filtered through celite and the celite is washed with EtOAc (20 mL). The filtrate is concentrated in vacuo and the residue is purified using silica gel flash column chromatography with 20-100% EtOAc in heptane as the eluent to give 2-isoxazol-5-yl-benzaldehyde (50 mg, 30%).

To a solution of 4-(2-amino-pyrimidin-5-yl)-N1-tert-butyl-benzene-1,2-diamine (74 mg, 029 mmol) in DMF (10 mL) is added 2-isoxazol-5-yl-benzaldehyde (60 mg, 0.29 mmol) at room temperature. Oxone (177 mg, 0.29 mmol) in $H_2O$ (1 mL) is added and the solution is stirred at the same temperature for 3 hours. Saturated sodium thiosulfate (10 mL) is added and the mixture is extracted with EtOAc (3×10 mL) and $H_2O$ (10 mL). The combined organic layer is dried with $MgSO_4$ (1 g) and is filtered. The filtrate is concentrated and the residue is purified by silica gel flash column chromatography with 10% MeOH in $CH_2Cl_2$ as the eluent to afford the title compound (37 mg, 31%). LCMS (ESMS): m/z: 411.40 (M$^+$+1).

Example 76

Isopropyl-carbamic acid 3-[5-(2-amino-pyrimidin-5-yl)-1-tert-butyl-1H-benzimidazol-2-yl]-4-1,2,4-triazol-1-yl-phenyl ester

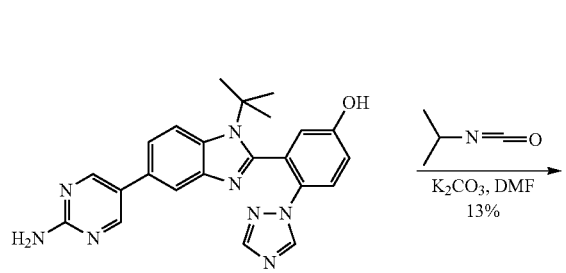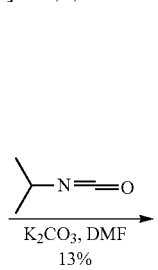

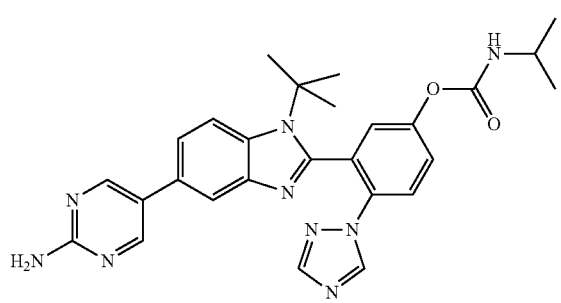

To a stirred solution of 3-[5-(2-amino-pyrimidin-5-yl)-1-tert-butyl-1H-benzimidazol-2-yl]-4-1,2,4-triazol-1-yl-phenol (100 mg, 0.23 mmol) in THF (3 mL) is added potassium carbonate (65 mg, 0.47 mmol) followed by isopropyl isocyanate (25 ul, 0.26 mmol). The resulting mixture is stirred at room temperature for 3 hours and then is warmed to 60° C. for 18 hours. The reaction is cooled to room temperature, poured into water and the product extracted into EtOAc (2×10 mL). The combined organics are dried with MgSO₄ (500 mg), filtered, and concentrated. The remaining residue is purified by silica gel flash column chromatography (12 g silica gel, 0-5% MeOH/DCM). Product-containing fractions are combined and concentrated to give the title compound (15 mg, 13%). LCMS (ESMS): m/z 512.5 (M$^+$+1)

The following compound is made using the procedure described in this Example:

Ethyl-carbamic acid 3-[5-(2-amino-pyrimidin-5-yl)-1-tert-butyl-1H-benzimidazol-2-yl]-4-1,2,4-triazol-1-yl-phenyl ester. LCMS (ESMS): m/z 498.4 (M$^+$+1)

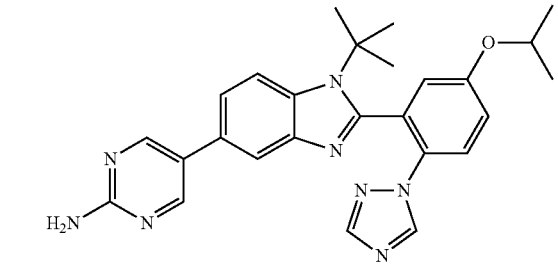 [SMILES: CC(C)Oc1ccc(-n2cncn2)c(-c2nc3cc(-c4cnc(N)nc4)ccc3n2C(C)(C)C)c1]

Assessment of Biological Properties

Compounds are assessed for the ability to bind to FLAP in a binding assay that measures compound-specific displacement of an iodinated ($^{125}$I) FLAP inhibitor via a Scintillation Proximity Assay format (adapted from S. Charleson et al., Mol. Pharmacol., 1992, 41, 873-879).

Cell pellets produced from sf9 insect cells expressing recombinant human FLAP protein are resuspended in buffer A [15 mM Tris-HCl (pH 7.5), 2 mM MgCl₂, 0.3 mM EDTA, 1 mM PMSF]. The cells are lysed with a Dounce homogenizer and the material is centrifuged at 10,000×g for 10 minutes. The supernatant is then collected and centrifuged at 100,000×g for 60 minutes. To prepare membrane protein for an assay, an aliquot of the 100,000×g pellet is resuspended in 1 ml of buffer A, Dounce homogenized, and finally subjected to polytron mixing (30 seconds). Membrane protein (25 μl, 5 μg) is mixed with WGA SPA beads (Amersham) and stirred for 1 h. To an assay plate (Perkin Elmer FlexiPlate) is added 25 μl of test compound prepared in Binding buffer [100 mM Tris (pH 7.5), 140 mM NaCl, 5% glycerol, 2 mM EDTA, 0.5 mM TCEP, 0.05% Tween 20], 25 μl of [$^{125}$I]L-691,831 (an iodinated analog of MK-591, Charleson et al. Mol. Pharmacol., 41, 873-879, 1992) and finally 50 μl of the bead/protein mixture. (final concentrations: beads, 200 μg/well; protein, 5 μg/well; [$^{125}$I] probe, 0 08 nM/well (17 nCi/well). The plates are shaken for 2 h before reading on a Microbeta plate reader. Non-specific binding is determined by the addition of 10 μM cold L-691,831 compound.

In general, the preferred potency range (IC$_{50}$) of compounds in the above assay is between 0.1 nM to 10 μM, the more preferred potency range is 0.1 nM to 1 μM, and the most preferred potency range is 0.1 nM to 100 nM.

Representative compounds of the invention have been tested in the above assay and have shown activity as FLAP inhibitors as shown in Table 2.

TABLE 2

| Name | hFLAP binding IC$_{50}$ (nM) |
|---|---|
| 5-[1-tert-Butyl-2-(2-1,2,4-triazol-1-yl-phenyl)-1H-benzimidazol-5-yl]-pyrimidin-2-ylamine | 2.7 |
| 5-[1-tert-Butyl-2-(5-methoxy-2-pyrazol-1-yl-phenyl)-1H-benzimidazol-5-yl]-pyrimidin-2-ylamine | 5.2 |
| 5-[1-tert-Butyl-2-(5-fluoro-2-pyrazol-1-yl-phenyl)-1H-benzimidazol-5-yl]-pyrimidin-2-ylamine | 1.7 |
| 5-[1-tert-Butyl-2-(5-methoxy-2-1,2,4-triazol-1-yl-phenyl)-1H-benzimidazol-5-yl]-pyrimidin-2-ylamine | 1.7 |
| 5-[1-tert-Butyl-2-(5-fluoro-2-1,2,4-triazol-1-yl-phenyl)-1H-benzimidazol-5-yl]-pyrimidin-2-ylamine | 1.4 |
| 5-[1-tert-Butyl-2-(5-methyl-2-1,2,4-triazol-1-yl-phenyl)-1H-benzimidazol-5-yl]-pyrimidine-2-ylamine | 1.6 |

TABLE 2-continued

| Name | hFLAP binding IC$_{50}$ (nM) |
|---|---|
| 5-[1-tert-Butyl-2-(4-methoxy-2-1,2,4-triazol-1-yl-phenyl)-1H-benzimidazol-5-yl]-pyrimidin-2-ylamine | 2.9 |
| 5-[1-tert-Butyl-2-(2-1,2,4-triazol-1-yl-5-trifluoromethyl-phenyl)-1H-benzimidazol-5-yl]-pyrimidin-2-ylamine | 2.4 |
| 5-[1-tert-Butyl-2-(2-1,2,4-triazol-1-yl-5-vinyl-phenyl)-1H-benzimidazol-5-yl]-pyrimidin-2-ylamine | 1.3 |
| 5-[1-tert-Butyl-2-(5-ethyl-2-1,2,4-triazol-1-yl-phenyl)-1H-benzimidazol-5-yl]-pyrimidin-2-ylamine | 2.4 |
| 5-[2-(5-Bromo-2-1,2,4-triazol-1-yl-phenyl)-1-tert-butyl-1H-benzimidazol-5-yl]-pyrimidin-2-ylamine | 4.5 |
| 3-[5-(2-Amino-pyrimidin-5-yl)-1-tert-butyl-1H-benzimidazol-2-yl]-4-1,2,4-triazol-1-yl-benzonitrile | 3.1 |
| 5-[1-tert-Butyl-2-(5-chloro-2-1,2,4-triazol-1-yl-phenyl)-1H-benzimidazol-5-yl]-pyrimidin-2-ylamine | 3 |
| 1-tert-Butyl-2-[2-(3-methyl-1,2,4-oxadiazol-5-yl)-phenyl]-5-(1H-pyrrolo[2,3-b]pyridin-5-yl)-1H-benzimidazole | 1.2 |
| 5-[1-tert-Butyl-2-(5-chloro-2-pyrazol-1-yl-phenyl)-1H-benzimidazol-5-yl]-pyrimidin-2-ylamine | 1.3 |
| 5-{1-tert-Butyl-2-[5-methoxy-2-(2-methyl-thiazol-4-yl)-phenyl]-1H-benzimidazol-5-yl}-pyrimidin-2-ylamine | 1.7 |
| 5-{1-tert-Butyl-2-[2-(3-methyl-1,2,4-triazol-1-yl)-phenyl]-1H-benzimidazol-5-yl}-pyrimidin-2-ylamine | 1.6 |
| 5-{1-tert-Butyl-2-[2-(5-methyl-1,2,4-triazol-1-yl)-phenyl]-1H-benzimidazol-5-yl}-pyrimidin-2-ylamine | 3.3 |
| 1-tert-Butyl-5-(2,3-dihydro-1H-pyrrolo[2,3-b]pyridin-5-yl)-2-(2-1,2,4-triazol-1-yl-phenyl)-1H-benzimidazole | 2.1 |
| 5-{1-tert-Butyl-2-[2-(3-methyl-pyrazol-1-yl)-phenyl]-1H-benzimidazol-5-yl}-pyrimidin-2-ylamine | 1.1 |
| 1-tert-Butyl-5-(2,3-dihydro-1H-pyrrolo[2,3-b]pyridin-5-yl)-2-(5-methoxy-2-pyrazol-1-yl-phenyl)-1H-benzimidazole | 1.5 |
| 1-tert-Butyl-2-(5-methoxy-2-pyrazol-1-yl-phenyl)-5-(1H-pyrrolo[2,3-b]pyridin-5-yl)-1H-benzimidazole | 1.1 |
| 5-{1-tert-Butyl-2-[5-methoxy-2-(3-methyl-pyrazol-1-yl)-phenyl]-1H-benzimidazol-5-yl}-pyrimidin-2-ylamine | 8.8 |
| 5-{1-tert-Butyl-2-[5-methoxy-2-(3-methyl-1,2,4-thiadiazol-5-yl)-phenyl]-1H-benzimidazol-5-yl}-pyrimidin-2-ylamine | 4.3 |
| 5-{1-tert-Butyl-2-[2-(4-chloro-pyrazol-1-yl)-phenyl]-1H-benzimidazol-5-yl}-pyrimidin-2-ylamine | 4.1 |
| 5-{1-tert-Butyl-2-[2-(3-trifluoromethyl-pyrazol-1-yl)-phenyl]-1H-benzimidazol-5-yl}-pyrimidin-2-ylamine | 4.5 |
| 5-{1-tert-Butyl-2-[2-(4-chloro-pyrazol-1-yl)-5-methoxy-phenyl]-1H-benzimidazol-5-yl}-pyrimidin-2-ylamine | 1.6 |
| 5-{1-tert-Butyl-2-[5-chloro-2-(3-methyl-pyrazol-1-yl)-phenyl]-1H-benzimidazol-5-yl}-pyrimidin-2-ylamine | 0.71 |
| 5-[1-tert-Butyl-2-(3-fluoro-2-1,2,4-triazol-1-yl-phenyl)-1H-benzimidazol-5-yl]-pyrimidin-2-ylamine | 1.7 |
| 5-[1-tert-Butyl-2-(4-chloro-2-1,2,4-triazol-1-yl-phenyl)-1H-benzimidazol-5-yl]-pyrimidin-2-ylamine | 1.7 |
| 5-{1-tert-Butyl-2-[5-chloro-2-(3-methyl-1,2,4-oxadiazol-5-yl)-phenyl]-1H-benzimidazol-5-yl}-pyrimidin-2-ylamine | 1.9 |
| 5-{1-tert-Butyl-2-[5-methyl-2-(3-methyl-1,2,4-oxadiazol-5-yl)-phenyl]-1H-benzimidazol-5-yl}-pyrimidin-2-ylamine | 1.8 |
| 5-{1-tert-Butyl-2-[5-methoxy-2-(3-methyl-1,2,4-oxadiazol-5-yl)-phenyl]-1H-benzimidazol-5-yl}-pyrimidin-2-ylamine | 24 |
| 5-{1-tert-Butyl-2-[5-chloro-2-(3-methyl-1,2,4-triazol-1-yl)-phenyl]-1H-benzimidazol-5-yl}-pyrimidin-2-ylamine | 1.4 |
| 5-{1-tert-Butyl-2-[5-methoxy-2-(3-methyl-1,2,4-triazol-1-yl)-phenyl]-1H-benzimidazol-5-yl}-pyrimidin-2-ylamine | 2.2 |
| 5-{1-tert-Butyl-2-[5-methoxy-2-(5-methyl-1,2,4-triazol-1-yl)-phenyl]-1H-benzimidazol-5-yl}-pyrimidin-2-ylamine | 1.5 |
| 5-{1-tert-butyl-2-[5-chloro-2-(5-methyl-1,2,4-triazol-1-yl)-phenyl]-1H-benzimidazol-5-yl}-pyrimidin-2-ylamine | 6.9 |
| 5-{1-tert-Butyl-2-[2-(2-methyl-2H-1,2,4-triazol-3-yl)-phenyl]-1H-benzimidazol-5-yl}-pyrimidin-2-ylamine | 6.1 |
| 5-{1-tert-Butyl-2-[2-(2,5-dimethyl-2H-1,2,4-triazol-3-yl)-phenyl]-1H-benzimidazol-5-yl}-pyrimidin-2-ylamine | 1.8 |
| 5-{1-tert-Butyl-2-[2-(2-methyl-2H-tetrazol-5-yl)-phenyl]-1H-benzimidazol-5-yl}-pyrimidin-2-ylamine | 1.3 |
| 5-{1-tert-Butyl-2-[5-fluoro-2-(2-methyl-2H-1,2,4-triazol-3-yl)-phenyl]-1H-benzimidazol-5-yl}-pyrimidin-2-ylamine | 1.6 |
| 5-{1-tert-Butyl-2-[5-fluoro-2-(3-methyl-1,2,4-triazol-1-yl)-phenyl]-1H-benzimidazol-5-yl}-pyrimidin-2-ylamine | 1.4 |
| 3-[5-(2-Amino-pyrimidin-5-yl)-1-tert-butyl-1H-benzimidazol-2-yl]-4-(3-methyl-1,2,4-triazol-1-yl)-benzonitrile | 3.0 |
| 5-{1-tert-Butyl-2-[5-chloro-2-(2-methyl-2H-1,2,4-triazol-3-yl)-phenyl]-1H-benzimidazol-5-yl}-pyrimidin-2-ylamine | 1.2 |

TABLE 2-continued

| Name | hFLAP binding IC$_{50}$ (nM) |
|---|---|
| 5-{1-tert-Butyl-2-[5-methyl-2-(3-methyl-1,2,4-triazol-1-yl)-phenyl]-1H-benzimidazol-5-yl}-pyrimidin-2-ylamine | 1.7 |
| 5-[1-tert-Butyl-2-(5-isopropoxy-2-1,2,4-triazol-1-yl-phenyl)-1H-benzimidazol-5-yl]-pyrimidin-2-ylamine | 2.2 |
| 5-(1-tert-Butyl-2-{2-[1-(2-methoxy-ethyl)-1H-[1,2,4]triazol-3-yl]-phenyl}-1H-benzoimidazol-5-yl)-pyrimidin-2-ylamine | 3.3 |
| 2-(3-{2-[5-(2-Amino-pyrimidin-5-yl)-1-tert-butyl-1H-benzoimidazol-2-yl]-phenyl}-[1,2,4]triazol-1-yl)-ethanol | 5.8 |
| (3-{2-[5-(2-Amino-pyrimidin-5-yl)-1-tert-butyl-1H-benzoimidazol-2-yl]-phenyl}-[1,2,4]triazol-1-yl)-acetonitrile | 4.2 |
| {3-[5-(2-Amino-pyrimidin-5-yl)-1-tert-butyl-1H-benzoimidazol-2-yl]-4-[1,2,4]triazol-1-yl-phenyl}-methanol | 10.4 |
| 5-[1-tert-Butyl-2-(5-methoxymethyl-2-[1,2,4]triazol-1-yl-phenyl)-1H-benzoimidazol-5-yl]-pyrimidin-2-ylamine | 13.9 |
| 5-[1-tert-Butyl-2-(5-ethoxymethyl-2-[1,2,4]triazol-1-yl-phenyl)-1H-benzoimidazol-5-yl]-pyrimidin-2-ylamine | 10 |
| 5-{1-tert-Butyl-2-[5-(1-methyl-1H-pyrazol-4-yl)-2-[1,2,4]triazol-1-yl-phenyl]-1H-benzoimidazol-5-yl}-pyrimidin-2-ylamine | 2.4 |
| 3-[5-(2-Amino-pyrimidin-5-yl)-1-tert-butyl-1H-benzoimidazol-2-yl]-4-(3-bromo-[1,2,4]triazol-1-yl)-benzonitrile | 0.83 |
| 5-[1-tert-Butyl-2-(5-methanesulfonyl-2-[1,2,4]triazol-1-yl-phenyl)-1H-benzoimidazol-5-yl]-pyrimidin-2-ylamine | 36.8 |
| 5-{1-tert-Butyl-2-[5-(2H-tetrazol-5-yl)-2-[1,2,4]triazol-1-yl-phenyl]-1H-benzoimidazol-5-yl}-pyrimidin-2-ylamine | 4.6 |
| 3-{4-[5-(2-Amino-pyrimidin-5-yl)-1-tert-butyl-1H-benzoimidazol-2-yl]-3-[1,2,4]triazol-1-yl-phenoxy}-2,2-dimethyl-propionic acid ethyl ester | 2.7 |
| 3-{4-[5-(2-Amino-pyrimidin-5-yl)-1-tert-butyl-1H-benzoimidazol-2-yl]-3-[1,2,4]triazol-1-yl-phenoxy}-2,2-dimethyl-propionic acid | 4.0 |
| 5-{1-tert-Butyl-2-[5-(1,5-dimethyl-1H-pyrazol-4-yl)-2-[1,2,4]triazol-1-yl-phenyl]-1H-benzoimidazol-5-yl}-pyrimidin-2-ylamine | 4.0 |
| 4-{3-[5-(2-Amino-pyrimidin-5-yl)-1-tert-butyl-1H-benzoimidazol-2-yl]-4-[1,2,4]triazol-1-yl-phenyl}-thiophene-2-carboxylic acid methyl ester | 5.2 |
| 4-{3-[5-(2-Amino-pyrimidin-5-yl)-1-tert-butyl-1H-benzoimidazol-2-yl]-4-[1,2,4]triazol-1-yl-phenyl}-thiophene-2-carboxylic acid | 10.6 |
| (E)-3-{3-[5-(2-Amino-pyrimidin-5-yl)-1-tert-butyl-1H-benzoimidazol-2-yl]-4-[1,2,4]triazol-1-yl-phenyl}-oct-2-enoic acid methyl ester | 28 |
| 2-{4-[5-(2-Amino-pyrimidin-5-yl)-1-tert-butyl-1H-benzoimidazol-2-yl]-3-[1,2,4]triazol-1-yl-phenoxy}-2-methyl-propionic acid methyl ester | 7.2 |
| 2-{4-[5-(2-Amino-pyrimidin-5-yl)-1-tert-butyl-1H-benzoimidazol-2-yl]-3-[1,2,4]triazol-1-yl-phenoxy}-2-methyl-propionic acid | 5.5 |
| 3-[5-(2-Amino-pyrimidin-5-yl)-1-tert-butyl-1H-benzoimidazol-2-yl]-4-[3-(2-chloro-phenyl)-[1,2,4]triazol-1-yl]-benzonitrile | 4.4 |
| (E)-3-{3-[5-(2-Amino-pyrimidin-5-yl)-1-tert-butyl-1H-benzoimidazol-2-yl]-4-[1,2,4]triazol-1-yl-phenyl}-oct-2-enoic acid | 6.0 |
| 3-[5-(2-Amino-pyrimidin-5-yl)-1-tert-butyl-1H-benzoimidazol-2-yl]-4-(3-methyl-pyrazol-1-yl)-benzonitrile | 1.8 |
| 3-[5-(2-Amino-pyrimidin-5-yl)-1-tert-butyl-1H-benzoimidazol-2-yl]-4-(5-methyl-pyrazol-1-yl)-benzonitrile | 1.3 |
| 3-[5-(2-Amino-pyrimidin-5-yl)-1-tert-butyl-1H-benzoimidazol-2-yl]-4-[1,2,4]triazol-1-yl-benzoic acid methyl ester | 2.7 |
| 3-[5-(2-Amino-pyrimidin-5-yl)-1-tert-butyl-1H-benzoimidazol-2-yl]-N-methyl-4-[1,2,4]triazol-1-yl-benzamide | 20 |
| 1-{2-[5-(2-Amino-pyrimidin-5-yl)-1-tert-butyl-1H-benzoimidazol-2-yl]-4-cyano-phenyl}-1H-[1,2,4]triazole-3-carboxylic acid methyl ester | 15.9 |
| 3-[5-(2-Amino-pyrimidin-5-yl)-1-tert-butyl-1H-benzoimidazol-2-yl]-4-(3,5-dimethyl-[1,2,4]triazol-1-yl)-benzonitrile | 2.5 |
| 1-{2-[5-(2-Amino-pyrimidin-5-yl)-1-tert-butyl-1H-benzoimidazol-2-yl]-4-cyano-phenyl}-1H-[1,2,4]triazole-3-carboxylic acid ethylamide | 29.5 |
| 1-{2-[5-(2-Amino-pyrimidin-5-yl)-1-tert-butyl-1H-benzoimidazol-2-yl]-4-cyano-phenyl}-1H-[1,2,4]triazole-3-carboxylic acid isobutyl ester | 12.4 |
| 3-{3-[5-(2-Amino-pyrimidin-5-yl)-1-tert-butyl-1H-benzimidazol-2-yl]-4-1,2,4-triazol-1-yl-phenoxy}-2,2-dimethyl-propionic acid | 5.9 |
| 5-{1-tert-Butyl-2-[5-(tetrahydro-furan-3-yloxy)-2-1,2,4-triazol-1-yl-phenyl]-1H-benzimidazol-5-yl}-pyrimidin-2-ylamine | 6.9 |
| Dimethyl-carbamic acid 3-[5-(2-amino-pyrimidin-5-yl)-1-tert-butyl-1H-benzimidazol-2-yl]-4-1,2,4-triazol-1-yl-phenyl ester | 15.5 |
| Isopropyl-carbamic acid 3-[5-(2-amino-pyrimidin-5-yl)-1-tert-butyl-1H-benzimidazol-2-yl]-4-1,2,4-triazol-1-yl-phenyl ester | 1.5 |

TABLE 2-continued

| Name | hFLAP binding IC$_{50}$ (nM) |
|---|---|
| Ethyl-carbamic acid 3-[5-(2-amino-pyrimidin-5-yl)-1-tert-butyl-1H-benzimidazol-2-yl]-4-1,2,4-triazol-1-yl-phenyl ester | 1.1 |
| Diethyl-carbamic acid 3-[5-(2-amino-pyrimidin-5-yl)-1-tert-butyl-1H-benzimidazol-2-yl]-4-1,2,4-triazol-1-yl-phenyl ester | 8.8 |
| 5-{1-tert-Butyl-2-[4-(tetrahydro-furan-3-yloxy)-2-1,2,4-triazol-1-yl-phenyl]-1H-benzimidazol-5-yl}-pyrimidin-2-ylamine | 10.6 |
| 5-[1-tert-Butyl-2-(5-iodo-2-1,2,4-triazol-1-yl-phenyl)-1H-benzimidazol-5-yl]-pyrimidin-2-ylamine | 2.7 |
| 5-[1-tert-butyl-2-(2-isoxazol-5-yl-phenyl)-1H-benzoimidazol-5-yl]-pyrimidin-2-ylamine | 2.4 |

METHOD OF USE

The compounds of the invention are effective inhibitors of 5-lipoxygenase activating protein (FLAP) and thus inhibit leukotriene production. Therefore, in one embodiment of the invention, there is provided methods of treating leukotriene-mediated disorders using compounds of the invention. In another embodiment, there is provided methods of treating cardiovascular, inflammatory, allergic, pulmonary and fibrotic diseases, renal diseases and cancer using compounds of the invention.

Without wishing to be bound by theory, by inhibiting the activity of FLAP, the compounds of the invention block the production of LTs resulting from the oxidation of arachidonic acid by 5-LO and subsequent metabolism. Thus, the inhibition of FLAP activity is an attractive means for preventing and treating a variety of diseases mediated by LTs. These include:
Cardiovascular diseases including atherosclerosis, myocardial infarction, stroke, aortic aneurysm, sickle cell crisis, ischemia-reperfusion injury, pulmonary arterial hypertension and sepsis;
Allergic diseases including asthma, allergic rhinitis, rhinosinusitis, atopic dermatitis and urticaria;
Fibrotic diseases including airway remodeling in asthma, idiopathic pulmonary fibrosis, scleroderma, asbestosis;
Pulmonary syndromes including adult respiratory distress syndrome, viral bronchiolitis, obstructive sleep apnea, chronic obstructive pulmonary disease, cystic fibrosis, and bronchopulmonary dysplasia;
Inflammatory diseases including rheumatoid arthritis, osteoarthritis, gout, glomerulonephritis, interstitial cystitis, psoriasis, inflammatory bowel disease systemic lupus erythematosus, transplant rejection, multiple sclerosis, inflammatory pain, inflammatory and allergic ocular diseases;
Cancer including solid tumors, leukemias and lymphomas; and
Renal diseases such as glomerulonephritis.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems*, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

What is claimed is:

1. A compound of Formula I:

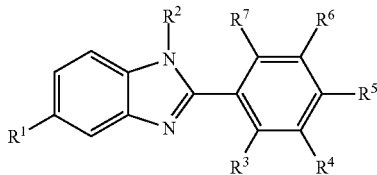

or pharmaceutically acceptable salts thereof, wherein:
$R^1$ is selected from

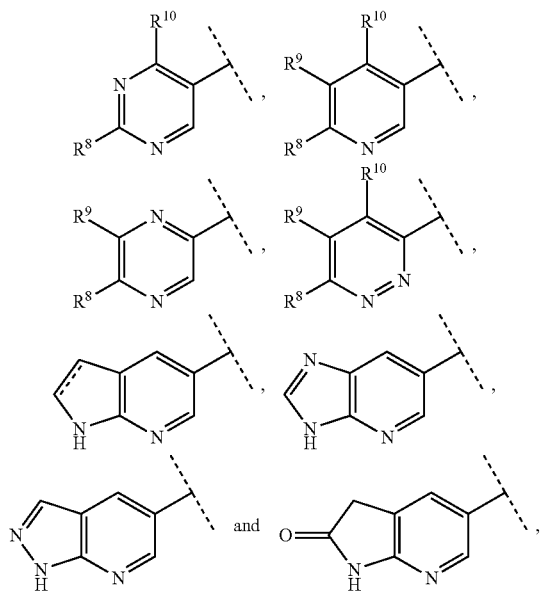

wherein --- indicates a single or double bond;
$R^2$ is —$(C_1$-$C_6)$alkyl;
$R^3$, $R^4$, $R^5$, $R^6$ and $R^7$ are each independently selected from
 (a) —H,
 (b) —OH,
 (c) halogen,
 (d) —CN,
 (e) —$CF_3$,
 (f) $C_{1-6}$alkyl optionally substituted with one to three —OH, fluorine, $C_{1-6}$alkoxyl-$N(R^{11})(R^{12})$, or —$C(O)N(R^{11})(R^{12})$,
 (g) $C_{1-8}$alkenyl optionally substituted with —$CO_2R^{11}$,
 (h) $C_{1-6}$alkoxy optionally substituted with one to three —OH, fluorine, —$OC_{1-6}$alkyl, —$OC_{3-6}$cycloalkyl, —$CO_2H$, —$CO_2R^{11}$, $C_{3-6}$cycloalkyl, $C_{3-6}$ heterocyclyl, $N(R^{11})(R^{12})$, or —$C(O)N(R^{11})(R^{12})$,
 (i) —$S(O)_nC_{1-6}$alkyl,
 (j) —$SCF_3$,
 (k) —$CO_2R^{11}$,
 (l) —$C(O)N(R^{11})(R^{12})$,
 (m) —NH—$S(O)_2$—$C_{1-6}$alkyl,
 (n) —$S(O)_2N(R^{11})(R^{12})$,
 (o) —$OCF_3$,
 (p) —$OCHF_2$,
 (q) a 5-membered heteroaryl group optionally substituted with one to three groups selected from $C_{1-6}$alkyl, $C_{3-6}$cycloalkyl, halogen, —$CF_3$, —OH, —$(CH_2)_nCO_2R^{11}$, —$SCF_3$, —$C(O)N(R^{11})(R^{12})$, —NH—$SO_2C_{1-6}$alkyl, $C_{1-6}$alkoxyl, $C_{1-6}$alkyl-O—$C_{1-3}$ alkyl, $C_{1-6}$alkylhydroxyl, $C_{1-3}$alkyl-CN, phenyl optionally substituted with halogen and —$S(O)_nC_{1-6}$alkyl,
 with the proviso that one of $R^3$, $R^4$, $R^6$ or $R^7$ must be (q);
$R^8$, $R^9$ and $R^{10}$ are each independently selected from —H, —OH, —$NR^{12}R^{13}$, —$NR^{12}C(O)C_{1-6}$alkyl, —$CH_2NH_2$, $CO_2C_{1-6}$alkyl, —CN, $C_{1-6}$alkyl, —$C_{1-6}$alkoxy, —$OC_{3-6}$cycloalkyl, —$SC_{1-6}$alkyl, —$S(O)_n$alkyl and —$CH_2OH$;
$R^{11}$, $R^{12}$ and $R^{13}$ are each independently selected from —H and —$(C_1$-$C_6)$alkyl, or $R^{11}$ and $R^{12}$ together with the nitrogen they are bonded to may form a azetidine, piperidine, pyrrolidine, piperazine or morpholine ring;
n is 0, 1 or 2.

2. A compound of claim 1, or a pharmaceutically acceptable salt thereof, wherein $R^1$ is selected from

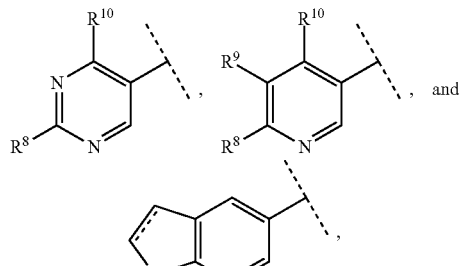

wherein --- indicates a single or double bond.

3. A compound of claim 1, or a pharmaceutically acceptable salt thereof, wherein $R^3$ is a 5-membered heteroaryl group optionally substituted with one to three groups selected from $C_{1-6}$alkyl, $C_{3-6}$cycloalkyl, halogen, —$CF_3$, —OH, —$(CH_2)_nCO_2R^{11}$, —$SCF_3$, —$C(O)N(R^{11})(R^{12})$, $N(R^{11})(R^{12})$, —NH—$SO_2C_{1-6}$alkyl, $C_{1-6}$alkoxyl, $C_{1-6}$alkyl-O—$C_{1-3}$ alkyl, $C_{1-6}$alkylhydroxyl, $C_{1-3}$alkyl-CN, phenyl optionally substituted with halogen and —$S(O)_nC_{1-6}$alkyl.

4. A compound of claim 1, or a pharmaceutically acceptable salt thereof, wherein: $R^1$ is selected from

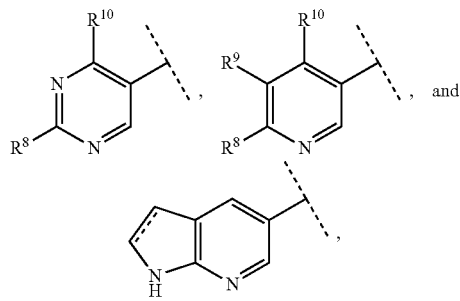

wherein --- indicates a single or double bond;
$R^2$ is —$(C_1$-$C_6)$alkyl;
$R^3$ is a 5-membered heteroaryl group optionally substituted with one to three groups selected from $C_{1-6}$alkyl, $C_{3-6}$cycloalkyl, halogen, —$CF_3$, —OH, —$CO_2R_{11}$, —$SCF_3$, —$C(O)NHR^{11}$, —$N(R^{11})(R^{12})$, —NH—$SO_2C_{1-6}$alkyl, $C_{1-6}$alkoxyl, $C_{1-6}$alkyl-O—$C_{1-3}$ alkyl, C$_{1-6}$alkylhydroxyl, C$_{1-3}$alkyl-CN, phenyl optionally substituted with halogen and —S(O)$_n$C$_{1-6}$alkyl;

R$^4$, R$^5$ and R$^6$ are each independently selected from
(a) —H,
(b) —OH,
(c) halogen,
(d) —CN,
(e) —CF$_3$,
(f) C$_{1-6}$alkyl optionally substituted with C$_{1-6}$alkoxyl,
(g) C$_{1-6}$alkenyl,
(h) C$_{1-6}$alkoxy optionally substituted with —CO$_2$R$^{11}$,
(i) —O(CH$_2$)$_2$(morpholin-4-yl),
(j) —O(CH$_2$)$_2$OCH$_3$, and
(k) —OCH$_2$C$_{3-6}$cycloalkyl;

R$^7$ is H;

R$^8$, R$^9$ and R$^{10}$ are selected from —H, —OH, —NR$^{12}$R$^{13}$, —NR$^{12}$C(O)C$_{1-6}$alkyl, —CH$_2$NH$_2$, —CO$_2$C$_{1-6}$alkyl, —CN, C$_{1-6}$alkyl, —C$_{1-6}$alkoxy, —OC$_{3-6}$cycloalkyl, —SC$_{1-6}$alkyl, —S(O)$_n$alkyl and —CH$_2$OH;

R$^{11}$, R$^{12}$ and R$^{13}$ are each independently selected from —H and —(C$_1$-C$_6$)alkyl;

n is 0, 1 or 2.

5. A compound of claim 4, or a pharmaceutically acceptable salt thereof, wherein R$^3$ is a 5-membered heteroaryl group selected from imidazolyl, [1,2,4]oxadiazolyl, [[1,3,4]oxadiazolyl, pyrazolyl, tetrazolyl, thiazolyl, [1,2,4]thiadiazolyl, [1,3,4]thiadiazolyl, [1,2,4]triazolyl and [1,2,3]triazolyl, wherein said heteroaryl group is optionally substituted with one to three groups selected from C$_{1-6}$alkyl, C$_{3-6}$cycloalkyl, halogen, —CF$_3$, —OH, —CO$_2$R$_{11}$, —SCF$_3$, —C(O)N(R$^{11}$)(R$^{12}$), —N(R$^{11}$)(R$^{12}$), —NH—SO$_2$C$_{1-6}$alkyl, C$_{1-6}$alkoxyl, C$_{1-6}$alkyl-O—C$_{1-3}$ alkyl, C$_{1-3}$alkylhydroxyl, C$_{1-3}$alkyl-CN, phenyl optionally substituted with halogen and —S(O)$_n$C$_{1-6}$alkyl.

6. A compound of claim 1, or a pharmaceutically acceptable salt thereof, wherein:

R$^1$ is selected from

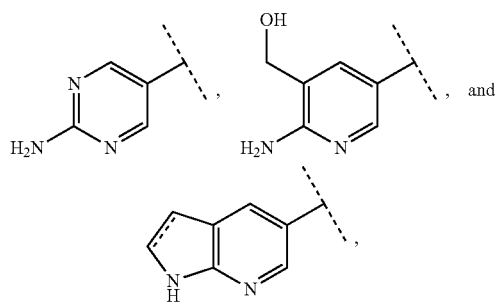

wherein --- indicates a single or double bond;

R$^2$ is —C(CH$_3$)$_3$;

R$^3$ is a 5-membered heteroaryl group selected from imidazolyl, [1,2,4]oxadiazolyl, [[1,3,4]oxadiazolyl, pyrazolyl, tetrazolyl, thiazolyl, [1,2,4]thiadiazolyl, [1,3,4]thiadiazolyl, [1,2,4]triazolyl and [1,2,3]triazolyl, wherein said heteroaryl group is optionally substituted with one to three groups selected from C$_{1-6}$alkyl, C$_{3-6}$cycloalkyl, halogen, —CF$_3$, —OH, —CO$_2$R$_{11}$, —SCF$_3$, —C(O)NHR$^{11}$, —N(R$^{11}$)(R$^{12}$), —NH—SO$_2$C$_{1-6}$alkyl, C$_{1-6}$alkoxyl, C$_{1-6}$alkyl-O—C$_{1-3}$ alkyl, C$_{1-3}$alkylhydroxyl, C$_{1-3}$alkyl-CN, phenyl substituted with chloro and —S(O)$_n$C$_{1-6}$alkyl;

R$^4$, R$^5$ and R$^6$ are each independently selected from
(a) —H,
(b) —OH,
(c) -halogen selected from —F, —Cl and —Br,
(d) —CN,
(e) —CF$_3$,
(f) —CH$_3$ optionally substituted with C$_{1-2}$alkoxyl,
(g) —CH$_2$CH=CH$_2$,
(h) —OCH$_3$,
(i) —O(CH$_2$)$_2$(morpholin-4-yl),
(j) —O(CH$_2$)$_2$OCH$_3$, and
(k) —OCH$_2$cyclopropyl;

R$^7$ is H;

R$^8$, R$^9$ and R$^{10}$ are selected from —H, —OH, —NH$_2$, —CH$_3$, and —CH$_2$OH.

7. A compound of claim 6, or a pharmaceutically acceptable salt thereof, wherein R$^1$ is selected from

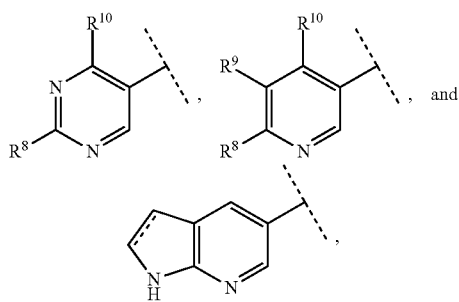

wherein --- indicates a single or double bond.

8. A compound of claim 7, or a pharmaceutically acceptable salt thereof, wherein R$^3$ is a 5-membered heteroaryl group selected from imidazolyl, [1,2,4]oxadiazolyl, [1,3,4]oxadiazolyl, pyrazolyl, tetrazolyl, thiazolyl, [1,2,4]thiadiazolyl, [1,3,4]thiadiazolyl, [1,2,4]triazolyl and [1,2,3]triazolyl, wherein said heteroaryl group is optionally substituted with one to three groups selected from C$_{1-4}$alkyl, cyclopropyl, —Cl, —CF$_3$, —CO$_2$C$_{1-2}$alkyl, —OCH$_3$, —C(O)_NHR$^{11}$, —N(R$^{11}$)(R$^{12}$) and —S(O)$_2$CH$_3$; and R$^{11}$ and R$^{12}$ are selected from H and —CH$_3$.

9. A compound according to claim 1, selected from the group consisting of:
1-tert-Butyl-2-[2-(3-methyl-[1,2,4]oxadiazol-5-yl)-phenyl]-5-(1H-pyrrolo[2,3-b]pyridin-5-yl)-1H-benzimidazole;
1-tert-Butyl-2-(5-methoxy-2-pyrazol-1-yl-phenyl)-5-(1H-pyrrolo[2,3-b]pyridin-5-yl)-1H-benzimidazole;
1-tert-Butyl-5-(2,3-dihydro-1H-pyrrolo[2,3-b]pyridin-5-yl)-2-(5-methoxy-2-pyrazol-1-yl-phenyl)-1H-benzimidazole;
5-{1-tert-Butyl-2-[5-chloro-2-(2-methyl-thiazol-4-yl)-phenyl]-1H-benzimidazol-5-yl}-pyrimidin-2-ylamine;
5-[1-tert-Butyl-2-(5-methyl-2-pyrazol-1-yl-phenyl)-1H-benzimidazol-5-yl]-pyrimidin-2-ylamine;
5-[1-tert-Butyl-2-(5-chloro-2-pyrazol-1-yl-phenyl)-1H-benzimidazol-5-yl]-pyrimidin-2-ylamine;
1-tert-Butyl-5-(2,3-dihydro-1H-pyrrolo[2,3-b]pyridin-5-yl)-2-(2-[1,2,4]triazol-1-yl-phenyl)-1H-benzimidazole;
5-{1-tert-Butyl-2-[5-methoxy-2-(5-methyl-thiazol-2-yl)-phenyl]-1H-benzimidazol-5-yl}-pyrimidin-2-ylamine;
5-[1-tert-Butyl-2-(5-methoxy-2-pyrazol-1-yl-phenyl)-1H-benzimidazol-5-yl]-pyrimidin-2-ylamine;
5-[1-tert-Butyl-2-(5-fluoro-2-pyrazol-1-yl-phenyl)-1H-benzimidazol-5-yl]-pyrimidin-2-ylamine;

5-{1-tert-Butyl-2-[5-methoxy-2-(2-methyl-thiazol-4-yl)-phenyl]-1H-benzimidazol-5-yl}-pyrimidin-2-ylamine;
5-{1-tert-Butyl-2-[5-methoxy-2-(3-methyl-[1,2,4]thiadiazol-5-yl)-phenyl]-1H-benzimidazol-5-yl}-pyrimidin-2-ylamine;
5-{1-tert-Butyl-2-[2-(4-chloro-pyrazol-1-yl)-phenyl]-1H-benzimidazol-5-yl}-pyrimidin-2-ylamine;
5-[2-(5-Bromo-2-[1,2,4]triazol-1-yl-phenyl)-1-tert-butyl-1H-benzimidazol-5-yl]-pyrimidin-2-ylamine;
5-{1-tert-Butyl-2-[2-(2-methyl-2H-[1,2,4]triazol-3-yl)-phenyl]-1H-benzimidazol-5-yl}-pyrimidin-2-ylamine;
5-{1-tert-Butyl-2-[2-(3-trifluoromethyl-pyrazol-1-yl)-phenyl]-1H-benzimidazol-5-yl}-pyrimidin-2-ylamine;
5-[1-tert-Butyl-2-(5-methyl-2-[1,2,4]triazol-1-yl-phenyl)-1H-benzimidazol-5-yl]-pyrimidin-2-ylamine;
5-[1-tert-Butyl-2-(5-chloro-2-[1,2,4]triazol-1-yl-phenyl)-1H-benzimidazol-5-yl]-pyrimidin-2-ylamine;
5-{1-tert-Butyl-2-[5-chloro-2-(3-methyl-pyrazol-1-yl)-phenyl]-1H-benzimidazol-5-yl}-pyrimidin-2-ylamine;
5-{1-tert-Butyl-2-[5-methoxy-2-(3-methyl-pyrazol-1-yl)-phenyl]-1H-benzimidazol-5-yl}-pyrimidin-2-ylamine;
5-[1-tert-Butyl-2-(2-[1,2,3]triazol-2-yl-phenyl)-1H-benzimidazol-5-yl]-pyrimidin-2-ylamine;
5-[1-tert-Butyl-2-(2-thiazol-2-yl-phenyl)-1H-benzimidazol-5-yl]-pyrimidin-2-ylamine;
5-{1-tert-Butyl-2-[2-(4-chloro-pyrazol-1-yl)-5-methoxy-phenyl]-1H-benzimidazol-5-yl}-pyrimidin-2-ylamine;
5-{1-tert-Butyl-2-[5-methoxy-2-(4-methyl-pyrazol-1-yl)-phenyl]-1H-benzimidazol-5-yl}-pyrimidin-2-ylamine;
5-{1-tert-Butyl-2-[5-methoxy-2-(3-trifluoromethyl-pyrazol-1-yl)-phenyl]-1H-benzimidazol-5-yl}-pyrimidin-2-ylamine;
5-{1-tert-Butyl-2-[5-methyl-2-(3-methyl-[1,2,4]oxadiazol-5-yl)-phenyl]-1H-benzimidazol-5-yl}-pyrimidin-2-ylamine;
5-{1-tert-Butyl-2-[2-(3-methyl-pyrazol-1-yl)-phenyl]-1H-benzimidazol-5-yl}-pyrimidin-2-ylamine;
5-[1-tert-Butyl-2-(2-pyrazol-1-yl-5-trifluoromethyl-phenyl)-1H-benzimidazol-5-yl]-pyrimidin-2-ylamine;
5-[1-tert-Butyl-2-(5-fluoro-2-[1,2,4]triazol-1-yl-phenyl)-1H-benzimidazol-5-yl]-pyrimidin-2-ylamine;
5-{1-tert-Butyl-2-[2-(4-methyl-pyrazol-1-yl)-phenyl]-1H-benzimidazol-5-yl}-pyrimidin-2-ylamine;
5-[1-tert-Butyl-2-(5-methoxy-2-[1,2,4]triazol-1-yl-phenyl)-1H-benzimidazol-5-yl]-pyrimidin-2-ylamine;
5-[1-tert-Butyl-2-(2-pyrazol-1-yl-phenyl)-1H-benzimidazol-5-yl]-pyrimidin-2-ylamine;
5-{1-tert-Butyl-2-[2-(3-methyl-[1,2,4]triazol-1-yl)-phenyl]-1H-benzimidazol-5-yl}-pyrimidin-2-ylamine;
5-[1-tert-Butyl-2-(2-[1,2,4]triazol-1-yl-phenyl)-1H-benzimidazol-5-yl]-pyrimidin-2-ylamine;
5-{1-tert-Butyl-2-[2-(3-cyclopropyl-[1,2,4]oxadiazol-5-yl)-phenyl]-1H-benzimidazol-5-yl}-pyrimidin-2-ylamine;
5-{1-tert-Butyl-2-[2-(2-methyl-thiazol-4-yl)-phenyl]-1H-benzimidazol-5-yl}-pyrimidin-2-ylamine;
5-{1-tert-Butyl-2-[2-(3-methyl-[1,2,4]oxadiazol-5-yl)-phenyl]-1H-benzimidazol-5-yl}-pyrimidin-2-ylamine;
5-{1-tert-Butyl-2-[2-(2,4-dimethyl-thiazol-5-yl)-5-methoxy-phenyl]-1H-benzimidazol-5-yl}-pyrimidin-2-ylamine;
5-{1-tert-Butyl-2-[2-(3-methyl-[1,2,4]thiadiazol-5-yl)-phenyl]-1H-benzimidazol-5-yl}-pyrimidin-2-ylamine;
5-[1-tert-Butyl-2-(2-[1,2,4]triazol-1-yl-5-trifluoromethyl-phenyl)-1H-benzimidazol-5-yl]-pyrimidin-2-ylamine;
5-[1-tert-Butyl-2-(4-methoxy-2-[1,2,4]triazol-1-yl-phenyl)-1H-benzimidazol-5-yl]-pyrimidin-2-ylamine;
5-{1-tert-Butyl-2-[2-(5-methyl-[1,2,4]triazol-1-yl)-phenyl]-1H-benzimidazol-5-yl}-pyrimidin-2-ylamine;
5-{1-tert-Butyl-2-[5-methoxy-2-(3-methyl-[1,2,4]triazol-1-yl)-phenyl]-1H-benzimidazol-5-yl}-pyrimidin-2-ylamine;
5-{1-tert-Butyl-2-[5-chloro-2-(2,4-dimethyl-thiazol-5-yl)-phenyl]-1H-benzimidazol-5-yl}-pyrimidin-2-ylamine;
5-[1-tert-Butyl-2-(3-methoxy-2-[1,2,4]triazol-1-yl-phenyl)-1H-benzimidazol-5-yl]-pyrimidin-2-ylamine;
5-{1-tert-Butyl-2-[2-(2,4-dimethyl-thiazol-5-yl)-phenyl]-1H-benzimidazol-5-yl}-pyrimidin-2-ylamine;
5-[1-tert-Butyl-2-(2-[1,2,3]triazol-1-yl-phenyl)-1H-benzimidazol-5-yl]-pyrimidin-2-ylamine; and
5-{1-tert-Butyl-2-[5-methoxy-2-(5-methyl-[1,2,4]triazol-1-yl)-phenyl]-1H-benzimidazol-5-yl}-yrimidin-2-ylamine;
5-{1-tert-Butyl-2-[5-methoxy-2-(3-methyl-[1,2,4]oxadiazol-5-yl)-phenyl]-1H-benzimidazol-5-yl}-pyrimidin-2-ylamine;
5-{1-tert-Butyl-2-[5-chloro-2-(3-methyl-[1,2,4]oxadiazol-5-yl)-phenyl]-1H-benzimidazol-5-yl}-pyrimidin-2-ylamine;
5-[1-tert-Butyl-2-(2-[1,2,4]triazol-1-yl-5-vinyl-phenyl)-1H-benzimidazol-5-yl]-pyrimidin-2-ylamine;
5-{1-tert-Butyl-2-[2-(2-methyl-2H-tetrazol-5-yl)-phenyl]-1H-benzimidazol-5-yl}-pyrimidin-2-ylamine;
5-{1-tert-Butyl-2-[2-(1,5-dimethyl-1H-[1,2,4]triazol-3-yl)-phenyl]-1H-benzimidazol-5-yl}-pyrimidin-2-ylamine;
5-{1-tert-Butyl-2-[5-chloro-2-(3-methyl-[1,2,4]triazol-1-yl)-phenyl]-1H-benzimidazol-5-yl}-pyrimidin-2-ylamine;
5-{1-tert-Butyl-2-[5-chloro-2-(5-methyl-[1,2,4]triazol-1-yl)-phenyl]-1H-benzimidazol-5-yl}-pyrimidin-2-ylamine;
5-{1-tert-Butyl-2-[4-chloro-2-(3-methyl-[1,2,4]oxadiazol-5-yl)-phenyl]-1H-benzimidazol-5-yl}-pyrimidin-2-ylamine;
3-[5-(2-Amino-pyrimidin-5-yl)-1-tert-butyl-1H-benzimidazol-2-yl]-4-[1,2,4]triazol-1-yl-benzonitrile;
5-[1-tert-Butyl-2-(4-chloro-2-[1,2,4]triazol-1-yl-phenyl)-1H-benzimidazol-5-yl]-pyrimidin-2-ylamine;
5-[1-tert-Butyl-2-(3-fluoro-2-[1,2,4]triazol-1-yl-phenyl)-1H-benzimidazol-5-yl]-pyrimidin-2-ylamine;
5-{1-tert-Butyl-2-[2-(1-ethyl-1H-[1,2,4]triazol-3-yl)-phenyl]-1H-benzimidazol-5-yl}-pyrimidin-2-ylamine;
5-[1-tert-Butyl-2-(3-chloro-2-[1,2,4]triazol-1-yl-phenyl)-1H-benzimidazol-5-yl]-pyrimidin-2-ylamine;
5-[1-tert-Butyl-2-(5-ethyl-2-1,2,4-triazol-1-yl-phenyl)-1H-benzimidazol-5-yl]-pyrimidin-2-ylamine;
5-(1-tert-Butyl-2-{2-[1-(2-methoxy-ethyl)-1H-[1,2,4]triazol-3-yl]-phenyl}-1H-benzoimidazol-5-yl)-pyrimidin-2-ylamine;
2-(3-{2-[5-(2-Amino-pyrimidin-5-yl)-1-tert-butyl-1H-benzoimidazol-2-yl]-phenyl}-[1,2,4]triazol-1-yl)-ethanol;
(3-{2-[5-(2-Amino-pyrimidin-5-yl)-1-tert-butyl-1H-benzoimidazol-2-yl]-phenyl}-[1,2,4]triazol-1-yl)-acetonitrile;
{3-[5-(2-Amino-pyrimidin-5-yl)-1-tert-butyl-1H-benzoimidazol-2-yl]-4-[1,2,4]triazol-1-yl-phenyl}-methanol;
2-{3-[5-(2-Amino-pyrimidin-5-yl)-1-tert-butyl-1H-benzoimidazol-2-yl]-4-[1,2,4]triazol-1-yl-phenyl}-propan-2-ol;

5-[1-tert-Butyl-2-(5-methoxymethyl-2-[1,2,4]triazol-1-yl-phenyl)-1H-benzoimidazol-5-yl]-pyrimidin-2-ylamine;

5-[1-tert-Butyl-2-(5-dimethylaminomethyl-2-[1,2,4]triazol-1-yl-phenyl)-1H-benzoimidazol-5-yl]-pyrimidin-2-ylamine;

5-[1-tert-Butyl-2-(5-ethoxymethyl-2-[1,2,4]triazol-1-yl-phenyl)-1H-benzoimidazol-5-yl]-pyrimidin-2-ylamine;

5-[2-(5-Azetidin-1-ylmethyl-2-[1,2,4]triazol-1-yl-phenyl)-1-tert-butyl-1H-benzoimidazol-5-yl]-pyrimidin-2-ylamine;

5-{1-tert-Butyl-2-[5-(1-methyl-1H-pyrazol-4-yl)-2-[1,2,4]triazol-1-yl-phenyl]-1H-benzoimidazol-5-yl}-pyrimidin-2-ylamine;

3-[5-(2-Amino-pyrimidin-5-yl)-1-tert-butyl-1H-benzoimidazol-2-yl]-4-(3-bromo-[1,2,4]triazol-1-yl)-benzonitrile;

5-[1-tert-Butyl-2-(5-methanesulfonyl-2-[1,2,4]triazol-1-yl-phenyl)-1H-benzoimidazol-5-yl]-pyrimidin-2-ylamine;

5-{1-tert-Butyl-2-[5-(2H-tetrazol-5-yl)-2-[1,2,4]triazol-1-yl-phenyl]-1H-benzoimidazol-5-yl}-pyrimidin-2-ylamine;

3-{4-[5-(2-Amino-pyrimidin-5-yl)-1-tert-butyl-1H-benzoimidazol-2-yl]-3-[1,2,4]triazol-1-yl-phenoxy}-2,2-dimethyl-propionic acid ethyl ester;

3-{4-[5-(2-Amino-pyrimidin-5-yl)-1-tert-butyl-1H-benzoimidazol-2-yl]-3-[1,2,4]triazol-1-yl-phenoxy}-2,2-dimethyl-propionic acid;

5-{1-tert-Butyl-2-[5-(1,5-dimethyl-1H-pyrazol-4-yl)-2-[1,2,4]triazol-1-yl-phenyl]-1H-benzoimidazol-5-yl}-pyrimidin-2-ylamine;

4-{3-[5-(2-Amino-pyrimidin-5-yl)-1-tert-butyl-1H-benzoimidazol-2-yl]-4-[1,2,4]triazol-1-yl-phenyl}-thiophene-2-carboxylic acid methyl ester;

4-{3-[5-(2-Amino-pyrimidin-5-yl)-1-tert-butyl-1H-benzoimidazol-2-yl]-4-[1,2,4]triazol-1-yl-phenyl}-thiophene-2-carboxylic acid;

(E)-3-{3-[5-(2-Amino-pyrimidin-5-yl)-1-tert-butyl-1H-benzoimidazol-2-yl]-4-[1,2,4]triazol-1-yl-phenyl}-oct-2-enoic acid methyl ester;

2-{4-[5-(2-Amino-pyrimidin-5-yl)-1-tert-butyl-1H-benzoimidazol-2-yl]-3-[1,2,4]triazol-1-yl-phenoxy}-2-methyl-propionic acid methyl ester;

2-{4-[5-(2-Amino-pyrimidin-5-yl)-1-tert-butyl-1H-benzoimidazol-2-yl]-3-[1,2,4]triazol-1-yl-phenoxy}-2-methyl-propionic acid;

3-[5-(2-Amino-pyrimidin-5-yl)-1-tert-butyl-1H-benzoimidazol-2-yl]-4-[3-(2-chloro-phenyl)-[1,2,4]triazol-1-yl]-benzonitrile;

(E)-3-{3-[5-(2-Amino-pyrimidin-5-yl)-1-tert-butyl-1H-benzoimidazol-2-yl]-4-[1,2,4]triazol-1-yl-phenyl}-oct-2-enoic acid;

3-[5-(2-Amino-pyrimidin-5-yl)-1-tert-butyl-1H-benzoimidazol-2-yl]-4-(3-methyl-pyrazol-1-yl)-benzonitrile;

3-[5-(2-Amino-pyrimidin-5-yl)-1-tert-butyl-1H-benzoimidazol-2-yl]-4-(5-methyl-pyrazol-1-yl)-benzonitrile;

3-[5-(2-Amino-pyrimidin-5-yl)-1-tert-butyl-1H-benzoimidazol-2-yl]-4-[1,2,4]triazol-1-yl-benzoic acid methyl ester;

3-[5-(2-Amino-pyrimidin-5-yl)-1-tert-butyl-1H-benzoimidazol-2-yl]-N-methyl-4-[1,2,4]triazol-1-yl-benzamide;

3-[5-(2-Amino-pyrimidin-5-yl)-1-tert-butyl-1H-benzoimidazol-2-yl]-N,N-dimethyl-4-[1,2,4]triazol-1-yl-benzamide;

1-{2-[5-(2-Amino-pyrimidin-5-yl)-1-tert-butyl-1H-benzoimidazol-2-yl]-4-cyano-phenyl}-1H-[1,2,4]triazole-3-carboxylic acid methyl ester;

1-{2-[5-(2-Amino-pyrimidin-5-yl)-1-tert-butyl-1H-benzoimidazol-2-yl]-4-cyano-phenyl}-1H-[1,2,4]triazole-3-carboxylic acid dimethylamide;

3-[5-(2-Amino-pyrimidin-5-yl)-1-tert-butyl-1H-benzoimidazol-2-yl]-4-(3,5-dimethyl-[1,2,4]triazol-1-yl)-benzonitrile;

1-{2-[5-(2-Amino-pyrimidin-5-yl)-1-tert-butyl-1H-benzoimidazol-2-yl]-4-cyano-phenyl}-1H-[1,2,4]triazole-3-carboxylic acid ethylamide;

1-{2-[5-(2-Amino-pyrimidin-5-yl)-1-tert-butyl-1H-benzoimidazol-2-yl]-4-cyano-phenyl}-1H-[1,2,4]triazole-3-carboxylic acid isobutyl ester;

3-{3-[5-(2-Amino-pyrimidin-5-yl)-1-tert-butyl-1H-benzimidazol-2-yl]-4-1,2,4-triazol-1-yl-phenoxy}-2,2-dimethyl-propionic acid;

2-{3-[5-(2-Amino-pyrimidin-5-yl)-1-tert-butyl-1H-benzimidazol-2-yl]-4-1,2,4-triazol-1-yl-phenoxy}-N,N-dimethyl-acetamide;

5-{1-tert-Butyl-2-[5-(tetrahydro-furan-3-yloxy)-2-1,2,4-triazol-1-yl-phenyl]-1H-benzimidazol-5-yl}-pyrimidin-2-ylamine;

Dimethyl-carbamic acid 3-[5-(2-amino-pyrimidin-5-yl)-1-tert-butyl-1H-benzimidazol-2-yl]-4-1,2,4-triazol-1-yl-phenyl ester;

Isopropyl-carbamic acid 3-[5-(2-amino-pyrimidin-5-yl)-1-tert-butyl-1H-benzimidazol-2-yl]-4-1,2,4-triazol-1-yl-phenyl ester;

Ethyl-carbamic acid 3-[5-(2-amino-pyrimidin-5-yl)-1-tert-butyl-1H-benzimidazol-2-yl]-4-1,2,4-triazol-1-yl-phenyl ester;

Diethyl-carbamic acid 3-[5-(2-amino-pyrimidin-5-yl)-1-tert-butyl-1H-benzimidazol-2-yl]-4-1,2,4-triazol-1-yl-phenyl ester;

5-{1-tert-Butyl-2-[4-(tetrahydro-furan-3-yloxy)-2-1,2,4-triazol-1-yl-phenyl]-1H-benzimidazol-5-yl}-pyrimidin-2-ylamine;

5-[1-tert-Butyl-2-(5-iodo-2-1,2,4-triazol-1-yl-phenyl)-1H-benzimidazol-5-yl]-pyrimidin-2-ylamine;

5-[1-tert-butyl-2-(2-isoxazol-5-yl-phenyl)-1H-benzoimidazol-5-yl]-pyrimidin-2-ylamine;

or the pharmaceutically acceptable salts thereof.

10. A pharmaceutical composition comprising a compound according to claim 1, or a pharmaceutically acceptable salt thereof, and a pharmaceutically acceptable excipient and/or carrier.

* * * * *